US012617834B2

(12) United States Patent
Witte et al.

(10) Patent No.: US 12,617,834 B2
(45) Date of Patent: May 5, 2026

(54) COMPOSITION OF NY-ESO-1-SPECIFIC T CELL RECEPTORS RESTRICTED ON MULTIPLE MAJOR HISTOCOMPATIBILITY COMPLEX MOLECULES

(71) Applicants: The Regents of the University of California, Oakland, CA (US); California Institute of Technology, Pasadena, CA (US); Ludwig Institute for Cancer Research Ltd, Zurich (CH)

(72) Inventors: Owen N. Witte, Sherman Oaks, CA (US); Jami McLaughlin Witte, Sherman Oaks, CA (US); Antoni Ribas, Los Angeles, CA (US); Lili Yang, Los Angeles, CA (US); Michael T. Bethune, Castro Valley, CA (US); Jonathan Cebon, New York, NY (US); Katherine Woods, New York, NY (US); Ashley J. Knights, Chadstone (AU); David Baltimore, Pasadena, CA (US)

(73) Assignees: THE REGENT'S OF THE UNIVERSITY OF CALIFORNIA, Oakland, CA (US); CALIFORNIA INSTITUTE OF TECHNOLOGY, Pasadena, CA (US); LUDWIG INSTITUTE FOR CANCER RESEARCH LTD, Zurich (CH)

( * ) Notice: Subject to any disclaimer, the term of this patent is extended or adjusted under 35 U.S.C. 154(b) by 1374 days.

(21) Appl. No.: 17/273,192

(22) PCT Filed: Sep. 4, 2019

(86) PCT No.: PCT/US2019/049484
§ 371 (c)(1),
(2) Date: Mar. 3, 2021

(87) PCT Pub. No.: WO2020/086158
PCT Pub. Date: Apr. 30, 2020

(65) Prior Publication Data
US 2021/0324035 A1 Oct. 21, 2021

Related U.S. Application Data

(60) Provisional application No. 62/727,485, filed on Sep. 5, 2018.

(51) Int. Cl.
| | |
|---|---|
| *C07K 14/725* | (2006.01) |
| *A61K 40/11* | (2025.01) |
| *A61K 40/32* | (2025.01) |
| *A61K 40/42* | (2025.01) |
| *A61P 35/00* | (2006.01) |
| *C12N 5/0783* | (2010.01) |
| *C12N 15/86* | (2006.01) |
| *A61K 48/00* | (2006.01) |

(52) U.S. Cl.
CPC .......... *C07K 14/7051* (2013.01); *A61K 40/11* (2025.01); *A61K 40/32* (2025.01); *A61K 40/4269* (2025.01); *A61P 35/00* (2018.01); *C12N 5/0636* (2013.01); *C12N 15/86* (2013.01); *A61K 48/00* (2013.01); *A61K 2239/31* (2023.05); *A61K 2239/58* (2023.05); *C12N 2740/10043* (2013.01)

(58) Field of Classification Search
None
See application file for complete search history.

(56) References Cited

U.S. PATENT DOCUMENTS

| | | | |
|---|---|---|---|
| 4,645,738 A | 2/1987 | Knowles et al. | |
| 2002/0193329 A1 | 12/2002 | Hand-Zimmermann et al. | |
| 2008/0085266 A1 | 4/2008 | Santin | |
| 2014/0356398 A1 | 12/2014 | Riddell et al. | |
| 2015/0141347 A1* | 5/2015 | Parkhurst ......... | G01N 33/57492 |
| | | | 514/19.5 |

(Continued)

FOREIGN PATENT DOCUMENTS

| | | |
|---|---|---|
| CN | 106632658 | 5/2017 |
| JP | 2003111595 | 4/2003 |

(Continued)

OTHER PUBLICATIONS

Garcia, K. Christopher, and Erin J. Adams. "How the T cell receptor sees antigen-a structural view." Cell 122.3 (2005): 333-336 (Year: 2005).*

(Continued)

*Primary Examiner* — Michael Szperka
*Assistant Examiner* — Lia E Taylor
(74) *Attorney, Agent, or Firm* — GATES & COOPER LLP

(57) ABSTRACT

Tumor-specific T cell receptor (TCR) gene transfer enables specific and potent immune targeting of tumor antigens. The canonical cancer-testis antigen, NY-ESO-1, is not expressed in normal tissues but is aberrantly expressed across a broad array of cancer types. It has also been targeted with A2-restricted TCR gene therapy without adverse events or notable side effects. To enable the targeting of NY-ESO-1 in a broader array of HLA haplotypes, we isolated TCRs specific for NY-ESO-1 epitopes presented by four MHC molecules: HLA-A2, -B07, -B18, and -C03. Using these TCRs, we have developed an approach to extend TCR gene therapies targeting NY-ESO-1 to patient populations beyond those expressing HLA-A2.

7 Claims, 34 Drawing Sheets
Specification includes a Sequence Listing.

(56) References Cited

U.S. PATENT DOCUMENTS

2016/0152681 A1      6/2016   Hinrichs et al.

FOREIGN PATENT DOCUMENTS

WO          2017/109496          6/2017
WO          WO-2018132739 A2 *   7/2018   .............. A61P 43/00

OTHER PUBLICATIONS

Canadian Examiner's Report dated May 15, 2024 for Canadian Patent Application No. 3,111,381.
Japanese Office Action (with English translation) dated May 6, 2022 for Japanese Patent Application No. 2021-513255.
Canadian Examination Report dated Jan. 14, 2023 for Canadian Patent Application No. 3,111,381.
PCT Search Reportand Written Opinion dated May 27, 2020 for PCT Application No. PCT/US2019/049484.
Extended European Search Report dated Jan. 12, 2023 for European Patent Application No. 19877170.1.
Bethune, M.T., et al., "Isolation and characterization of NY-ESO-1-specific T cell receptors restricted on various MHC molecules", Proceedings of The National Academy of Sciences, National Academy of Sciences, Nov. 2018, pp. E10702-E10711, vol. 115, No. 45.
Klippel, Z.K., et al., "Immune escape from NY-ESO-1-specific T cell therapy via loss of heterozygosity in the MHC", Gene Ther., Mar. 2014, pp. 337-342, vol. 21, No. 3.
Robbin, P.F., et al., "Tumor Regression in Patients With Metastatic Synovial Cell Sarcoma and Melanoma Using Genetically Engineered Lymphocytes Reactive With NY-ESO-1", Journal of Clinical Oncology, Mar. 2011, pp. 917-924, vol. 29, No. 7.
Robbin, P.F., et al., "A Pilot Trial Using Lymphocytes Genetically Engineered with an NY-ESO-1-Reactive T-cell Receptor: Long-term Follow-up and Correlates with Response", Clinical Cancer Research, Mar. 2015, pp. 1019-1027, vol. 21, No. 5.
Rapoport, A.P., et al., "NY-ESO-1 specific TCR engineered T-cells mediate sustained antigen-specific antitumor effects in myeloma", Nat Med, Aug. 2015, pp. 914-921, vol. 21, No. 8.
Database EMBL, "*Homo sapiens* (human) partial T-cell receptor beta-chain (V14-D-J-C) precursor ID-AAA61022; SV 1; linear; mRNA; STD; Hum; 394 BP.", Apr. 1988, retrieved from EBI accession No. EMBL:AAA61022, p. 1.
Chinese First Office Action (with English translation) dated Sep. 29, 2023 for Chinese Patent Application No. 201980064425.X.
Rosati, S.F., et al., "A Novel Murine T Cell Receptor Targeting NY-ESO-1", J Immunother, Apr. 2014, pp. 135-146, vol. 37, No. 3.
Gu, N., et al., "Construction and identification of lentiviral vector for NY-ESO-1 antigen T cell receptor gene", Beijing Medical Journal, 2010, pp. 1-19, vol. 32, No. 12.
Chinese Third Office Action (English translation) dated Nov. 23, 2024 for Chinese Patent Application No. 201980064425.X.

* cited by examiner

SEQUENCE LISTING

```
<160> NUMBER OF SEQ ID NOS: 37

<210> SEQ ID NO 1
<211> LENGTH: 336
<212> TYPE: DNA
<213> ORGANISM: Homo sapiens

<400> SEQUENCE: 1
ggtcaacagc tgaatcagag tcctcaatct atgtttatcc aggaaggaga agatgtctcc      60
```

```
atgaactgca cttcttcaag catatttaac acctggctat ggtacaagca ggaccctggg      120
gaaggtcctg tcctcttgat agccttatat aaggctggtg aattgacctc aaatggaaga      180
ctgactgctc agtttggtat aaccagaaag gacagcttcc tgaatatctc agcatccata      240
cctagtgatg taggcatcta cttctgtgct ggatttctgg atagcaacta tcagttaatc      300
tggggcgctg ggaccaagct aattataaag ccagat                                336

<210> SEQ ID NO 2
<211> LENGTH: 345
<212> TYPE: DNA
<213> ORGANISM: Homo sapiens

<400> SEQUENCE: 2
gaagcccaag tgacccagaa cccaagatac ctcatcacag tgactggaaa gaagttaaca       60
gtgacttgtt ctcagaatat gaaccatgag tatatgtcct ggtatcgaca gacccaggg      120 ctgggcttaa ggcagatcta ctattcaatg aatgttgagg tgactgataa gggagatgtt      180
cctgaagggt acaaagtctc tcgaaaagag aagaggaatt ccccctgat cctggagtcg      240 cccagcccca accagacctc tctgtacttc tgtgccagcg ctagcgggta ccgcacagat      300
acgcagtatt ttggcccagg cacccggctg acagtgctcg aggac                     345

<210> SEQ ID NO 3
<211> LENGTH: 112
<212> TYPE: PRT
<213> ORGANISM: Homo sapiens

<400> SEQUENCE: 3

Gly Gln Gln Leu Asn Gln Ser Pro Gln Ser Met Phe Ile Gln Glu Gly
1               5                   10                  15

Glu Asp Val Ser Met Asn Cys Thr Ser Ser Ser Ile Phe Asn Thr Trp
            20                  25                  30

Leu Trp Tyr Lys Gln Asp Pro Gly Glu Gly Pro Val Leu Leu Ile Ala
        35                  40                  45

Leu Tyr Lys Ala Gly Glu Leu Thr Ser Asn Gly Arg Leu Thr Ala Gln
    50                  55                  60

Phe Gly Ile Thr Arg Lys Asp Ser Phe Leu Asn Ile Ser Ala Ser Ile
65                  70                  75                  80

Pro Ser Asp Val Gly Ile Tyr Phe Cys Ala Gly Phe Leu Asp Ser Asn
                85                  90                  95

Tyr Gln Leu Ile Trp Gly Ala Gly Thr Lys Leu Ile Ile Lys Pro Asp
            100                 105                 110

<210> SEQ ID NO 4
<211> LENGTH: 115
<212> TYPE: PRT
<213> ORGANISM: Homo sapiens

<400> SEQUENCE: 4

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
            20                  25                  30

Ser Trp Tyr Arg Gln Asp Pro Gly Leu Gly Leu Arg Gln Ile Tyr Tyr
        35                  40                  45

Ser Met Asn Val Glu Val Thr Asp Lys Gly Asp Val Pro Glu Gly Tyr
    50                  55                  60
```

```
Lys Val Ser Arg Lys Glu Lys Arg Asn Phe Pro Leu Ile Leu Glu Ser
65                  70                  75                  80

Pro Ser Pro Asn Gln Thr Ser Leu Tyr Phe Cys Ala Ser Ala Ser Gly
                    85                  90                  95

Tyr Arg Thr Asp Thr Gln Tyr Phe Gly Pro Gly Thr Arg Leu Thr Val
                100                 105                 110

Leu Glu Asp
        115

<210> SEQ ID NO 5
<211> LENGTH: 354
<212> TYPE: DNA
<213> ORGANISM: Homo sapiens

<400> SEQUENCE: 5
gctcagtcag tggctcagcc ggaagatcag gtcaacgttg ctgaagggaa tcctctgact        60
gtgaaatgca cctattcagt ctctggaaac ccttatcttt tttggtatgt tcaataccccc       120 aaccgaggcc tccagttcct tctgaaatac atcacagggg ataacctggt taaaggcagc       180
tatggctttg aagctgaatt taacaagagc caaacctcct tccacctgaa gaaaccatct       240
gcccttgtga gcgactccgc tttgtacttc tgtgctgtga gagacagtcg gtctggggct       300
gggagttacc aactcacttt cgggaagggg accaaactct cggtcatacc aaat            354

<210> SEQ ID NO 6
<211> LENGTH: 357
<212> TYPE: DNA
<213> ORGANISM: Homo sapiens

<400> SEQUENCE: 6
ggtgctgtcg tctctcaaca tccgagctgg gttatctgta agagtggaac ctctgtgaag        60
atcgagtgcc gttccctgga ctttcaggcc acaactatgt tttggtatcg tcagttcccg       120
aaacagagtc tcatgctgat ggcaacttcc aatgagggcc ccaaggccac atacgagcaa       180
ggcgtcgaga aggacaagtt tctcatcaac catgcaagcc tgaccttgtc cactctgaca       240
gtgaccagtg cccatcctga agacagcagc ttctacatct gcagtgctcc ccaaggttat       300
gggggcacag atacgcagta ttttggccca ggcacccggc tgacagtgct cgaggac        357

<210> SEQ ID NO 7
<211> LENGTH: 118
<212> TYPE: PRT
<213> ORGANISM: Homo sapiens

<400> SEQUENCE: 7

Ala Gln Ser Val Ala Gln Pro Glu Asp Gln Val Asn Val Ala Glu Gly
1                   5                   10                  15

Asn Pro Leu Thr Val Lys Cys Thr Tyr Ser Val Ser Gly Asn Pro Tyr
                    20                  25                  30

Leu Phe Trp Tyr Val Gln Tyr Pro Asn Arg Gly Leu Gln Phe Leu Leu
                35                  40                  45

Lys Tyr Ile Thr Gly Asp Asn Leu Val Lys Gly Ser Tyr Gly Phe Glu
        50                  55                  60

Ala Glu Phe Asn Lys Ser Gln Thr Ser Phe His Leu Lys Lys Pro Ser
65                  70                  75                  80

Ala Leu Val Ser Asp Ser Ala Leu Tyr Phe Cys Ala Val Arg Asp Ser
                85                  90                  95
```

-continued

```
Arg Ser Gly Ala Gly Ser Tyr Gln Leu Thr Phe Gly Lys Gly Thr Lys
            100                 105                 110

Leu Ser Val Ile Pro Asn
        115

<210> SEQ ID NO 8
<211> LENGTH: 339
<212> TYPE: DNA
<213> ORGANISM: Homo sapiens

<400> SEQUENCE: 8
gatgctaaga ccacacagcc aaattcaatg gagagtaacg aagaagagcc tgttcacttg       60
ccttgtaacc actccacaat cagtggaact gattacatac attggtatcg acagcttccc      120
tcccagggtc cagagtacgt gattcatggt cttacaagca atgtgaacaa cagaatggcc      180
tctctggcaa tcgctgaaga cagaaagtcc agtaccttga tcctgcaccg tgctaccttg      240
agagatgctg ctgtgtacta ctgcatcctg agaacctctg gggctgggag ttaccaactc      300
actttcggga aggggaccaa actctcggtc ataccaaat                             339

<210> SEQ ID NO 9
<211> LENGTH: 351
<212> TYPE: DNA
<213> ORGANISM: Homo sapiens

<400> SEQUENCE: 9
agtgctgtca tctctcaaaa gccaagcagg gatatctgtc aacgtggaac ctccctgacg       60
atccagtgtc aagtcgatag ccaagtcacc atgatgttct ggtaccgtca gcaacctgga      120
cagagcctga cactgatcgc aactgcaaat cagggctctg aggccacata tgagagtgga      180
tttgtcattg acaagtttcc catcagccgc ccaaacctaa cattctcaac tctgactgtg      240
agcaacatga gccctgaaga cagcagcata tatctctgca gcgcgggagg agcgggagcg      300
tcagatacgc agtattttgg cccaggcacc cggctgacag tgctcgagga c              351

<210> SEQ ID NO 10
<211> LENGTH: 113
<212> TYPE: PRT
<213> ORGANISM: Homo sapiens

<400> SEQUENCE: 10

Asp Ala Lys Thr Thr Gln Pro Asn Ser Met Glu Ser Asn Glu Glu Glu
1               5                   10                  15

Pro Val His Leu Pro Cys Asn His Ser Thr Ile Ser Gly Thr Asp Tyr
            20                  25                  30

Ile His Trp Tyr Arg Gln Leu Pro Ser Gln Gly Pro Glu Tyr Val Ile
        35                  40                  45

His Gly Leu Thr Ser Asn Val Asn Asn Arg Met Ala Ser Leu Ala Ile
    50                  55                  60

Ala Glu Asp Arg Lys Ser Ser Thr Leu Ile Leu His Arg Ala Thr Leu
65                  70                  75                  80

Arg Asp Ala Ala Val Tyr Tyr Cys Ile Leu Arg Thr Ser Gly Ala Gly
                85                  90                  95

Ser Tyr Gln Leu Thr Phe Gly Lys Gly Thr Lys Leu Ser Val Ile Pro
            100                 105                 110

Asn

<210> SEQ ID NO 11
```

-continued

```
<211> LENGTH: 117
<212> TYPE: PRT
<213> ORGANISM: Homo sapiens

<400> SEQUENCE: 11

Ser Ala Val Ile Ser Gln Lys Pro Ser Arg Asp Ile Cys Gln Arg Gly
1               5                   10                  15

Thr Ser Leu Thr Ile Gln Cys Gln Val Asp Ser Gln Val Thr Met Met
            20                  25                  30

Phe Trp Tyr Arg Gln Gln Pro Gly Gln Ser Leu Thr Leu Ile Ala Thr
        35                  40                  45

Ala Asn Gln Gly Ser Glu Ala Thr Tyr Glu Ser Gly Phe Val Ile Asp
    50                  55                  60

Lys Phe Pro Ile Ser Arg Pro Asn Leu Thr Phe Ser Thr Leu Thr Val
65                  70                  75                  80

Ser Asn Met Ser Pro Glu Asp Ser Ser Ile Tyr Leu Cys Ser Ala Gly
                85                  90                  95

Gly Ala Gly Ala Ser Asp Thr Gln Tyr Phe Gly Pro Gly Thr Arg Leu
            100                 105                 110

Thr Val Leu Glu Asp
        115

<210> SEQ ID NO 12
<211> LENGTH: 324
<212> TYPE: DNA
<213> ORGANISM: Homo sapiens

<400> SEQUENCE: 12
cagaaggagg tggagcagaa ttctggaccc ctcagtgttc cagagggagc cattgcctct      60
ctcaactgca cttacagtga ccgaggttcc cagtccttct tctggtacag acaatattct     120
gggaaaagcc ctgagttgat aatgttcata tactccaatg gtgacaaaga agatggaagg     180
tttacagcac agctcaataa agccagccag tatgtttctc tgctcatcag agactcccag     240
cccagtgatt cagccaccta cctctgtgcc gtagatgaca agatcatctt tggaaaaggg     300
acacgacttc atattctccc caat                                           324

<210> SEQ ID NO 13
<211> LENGTH: 351
<212> TYPE: DNA
<213> ORGANISM: Homo sapiens

<400> SEQUENCE: 13
gatgctggag ttatccagtc accccggcac gaggtgacag agatgggaca agaagtgact      60
ctgagatgta aaccaatttc aggacacgac taccttttct ggtacagaca gaccatgatg     120
cggggactgg agttgctcat ttactttaac aacaacgttc gatagatga ttcagggatg      180 cccgaggatc gattctcagc taagatgcct aatgcatcat ctccactct gaagatccag       240 ccctcagaac ccaggggactc agctgtgtac ttctgtgcca gcagtttggg acagccaagc     300
acagatacgc agtattttgg cccaggcacc cggctgacag tgctcgagga c               351

<210> SEQ ID NO 14
<211> LENGTH: 108
<212> TYPE: PRT
<213> ORGANISM: Homo sapiens

<400> SEQUENCE: 14

Gln Lys Glu Val Glu Gln Asn Ser Gly Pro Leu Ser Val Pro Glu Gly
```

```
1            5              10             15

Ala Ile Ala Ser Leu Asn Cys Thr Tyr Ser Asp Arg Gly Ser Gln Ser
         20             25             30

Phe Phe Trp Tyr Arg Gln Tyr Ser Gly Lys Ser Pro Glu Leu Ile Met
     35             40             45

Phe Ile Tyr Ser Asn Gly Asp Lys Glu Asp Gly Arg Phe Thr Ala Gln
     50             55             60

Leu Asn Lys Ala Ser Gln Tyr Val Ser Leu Leu Ile Arg Asp Ser Gln
65             70             75             80

Pro Ser Asp Ser Ala Thr Tyr Leu Cys Ala Val Asp Asp Lys Ile Ile
             85             90             95

Phe Gly Lys Gly Thr Arg Leu His Ile Leu Pro Asn
             100            105
```

<210> SEQ ID NO 15
<211> LENGTH: 117
<212> TYPE: PRT
<213> ORGANISM: Homo sapiens

<400> SEQUENCE: 15

```
Asp Ala Gly Val Ile Gln Ser Pro Arg His Glu Val Thr Glu Met Gly
1            5              10             15

Gln Glu Val Thr Leu Arg Cys Lys Pro Ile Ser Gly His Asp Tyr Leu
         20             25             30

Phe Trp Tyr Arg Gln Thr Met Met Arg Gly Leu Glu Leu Leu Ile Tyr
     35             40             45

Phe Asn Asn Asn Val Pro Ile Asp Asp Ser Gly Met Pro Glu Asp Arg
     50             55             60

Phe Ser Ala Lys Met Pro Asn Ala Ser Phe Ser Thr Leu Lys Ile Gln
65             70             75             80

Pro Ser Glu Pro Arg Asp Ser Ala Val Tyr Phe Cys Ala Ser Ser Leu
             85             90             95

Gly Gln Pro Ser Thr Asp Thr Gln Tyr Phe Gly Pro Gly Thr Arg Leu
             100            105            110

Thr Val Leu Glu Asp
         115
```

<210> SEQ ID NO 16
<211> LENGTH: 351
<212> TYPE: DNA
<213> ORGANISM: Homo sapiens

<400> SEQUENCE: 16

```
aaacaggagg tgacgcagat tcctgcagct ctgagtgtcc cagaaggaga aaacttggtt      60
ctcaactgca gtttcactga tagcgctatt tacaacctcc agtggtttag gcaggaccct     120
gggaaaggtc tcacatctct gttgcttatt cagtcaagtc agagagagca aacaagtgga     180
agacttaatg cctcgctgga taaatcatca ggacgtagta ctttatacat tgcagcttct     240
cagcctggtg actcagccac ctacctctgt gctgtgagta ctgcgtattc aggaggaggt     300
gctgacggac tcacctttgg caaagggact catctaatca tccagcccta t              351
```

<210> SEQ ID NO 17
<211> LENGTH: 351
<212> TYPE: DNA
<213> ORGANISM: Homo sapiens

<400> SEQUENCE: 17

-continued

```
gatactggag tctcccagaa ccccagacac aagatcacaa agaggggaca gaatgtaact      60
ttcaggtgtg atccaatttc tgaacacaac cgcctttatt ggtaccgaca gaccctgggg     120
cagggcccag agtttctgac ttacttccag aatgaagctc aactagaaaa atcaaggctg     180
ctcagtgatc ggttctctgc agagaggcct aagggatctt tctccacctt ggagatccag     240
cgcacagagc aggggactc ggccatgtat ctctgtgcca gcagcccccc gactgttcgg     300
gtctatggct acaccttcgg ttcggggacc aggttaaccg ttgtagagga c             351
```

```
<210> SEQ ID NO 18
<211> LENGTH: 117
<212> TYPE: PRT
<213> ORGANISM: Homo sapiens

<400> SEQUENCE: 18

Lys Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Ser Thr Ala Tyr
                85                  90                  95

Ser Gly Gly Gly Ala Asp Gly Leu Thr Phe Gly Lys Gly Thr His Leu
            100                 105                 110

Ile Ile Gln Pro Tyr
            115

<210> SEQ ID NO 19
<211> LENGTH: 117
<212> TYPE: PRT
<213> ORGANISM: Homo sapiens

<400> SEQUENCE: 19

Asp Thr Gly Val Ser Gln Asn Pro Arg His Lys Ile Thr Lys Arg Gly
1               5                   10                  15

Gln Asn Val Thr Phe Arg Cys Asp Pro Ile Ser Glu His Asn Arg Leu
            20                  25                  30

Tyr Trp Tyr Arg Gln Thr Leu Gly Gln Gly Pro Glu Phe Leu Thr Tyr
        35                  40                  45

Phe Gln Asn Glu Ala Gln Leu Glu Lys Ser Arg Leu Leu Ser Asp Arg
    50                  55                  60

Phe Ser Ala Glu Arg Pro Lys Gly Ser Phe Ser Thr Leu Glu Ile Gln
65                  70                  75                  80

Arg Thr Glu Gln Gly Asp Ser Ala Met Tyr Leu Cys Ala Ser Ser Pro
                85                  90                  95

Pro Thr Val Arg Val Tyr Gly Tyr Thr Phe Gly Ser Gly Thr Arg Leu
            100                 105                 110

Thr Val Val Glu Asp
        115

<210> SEQ ID NO 20
```

-continued

```
<211> LENGTH: 336
<212> TYPE: DNA
<213> ORGANISM: Homo sapiens

<400> SEQUENCE: 20
ggacaacagg taatgcaaat tcctcagtac cagcatgtac aagaaggaga agacttcacc        60
acgtactgca attcctcaac tactttaagc aatatacagt ggtataagca aaggcctggt       120
ggacatcccg ttttttgat acagttagtg aagagtggag aagtgaagaa gcagaaaaga       180
ctgacatttc agtttggaga agcaaaaaag aacagctccc tgcacatcac agccacccag       240
actacagatg taggaaccta cttctgtgcg gaccctaact ttggaaatga gaaattaacc       300
tttgggactg gaacaagact caccatcata cccaat                                 336

<210> SEQ ID NO 21
<211> LENGTH: 351
<212> TYPE: DNA
<213> ORGANISM: Homo sapiens

<400> SEQUENCE: 21
gaagcccaag tgacccagaa cccaagatac ctcatcacag tgactggaaa gaagttaaca        60
gtgacttgtt ctcagaatat gaaccatgag tatatgtcct ggtatcgaca agacccaggg       120
ctgggcttaa ggcagatcta ctattcaatg aatgttgagg tgactgataa gggagatgtt       180
cctgaagggt acaaagtctc tcgaaaagag aagaggaatt ccccctgat cctggagtcg        240 cccagcccca accagacctc tctgtacttc tgtgccagca gtttgaatcc ctttgcaact       300
aatgaaaaac tgtttttgg cagtggaacc cagctctctg tcttggagga c                 351

<210> SEQ ID NO 22
<211> LENGTH: 112
<212> TYPE: PRT
<213> ORGANISM: Homo sapiens

<400> SEQUENCE: 22

Gly Gln Gln Val Met Gln Ile Pro Gln Tyr Gln His Val Gln Glu Gly
1               5                   10                  15

Glu Asp Phe Thr Thr Tyr Cys Asn Ser Ser Thr Thr Leu Ser Asn Ile
            20                  25                  30

Gln Trp Tyr Lys Gln Arg Pro Gly Gly His Pro Val Phe Leu Ile Gln
        35                  40                  45

Leu Val Lys Ser Gly Glu Val Lys Lys Gln Lys Arg Leu Thr Phe Gln
    50                  55                  60

Phe Gly Glu Ala Lys Lys Asn Ser Ser Leu His Ile Thr Ala Thr Gln
65                  70                  75                  80

Thr Thr Asp Val Gly Thr Tyr Phe Cys Ala Asp Pro Asn Phe Gly Asn
                85                  90                  95

Glu Lys Leu Thr Phe Gly Thr Gly Thr Arg Leu Thr Ile Ile Pro Asn
            100                 105                 110

<210> SEQ ID NO 23
<211> LENGTH: 117
<212> TYPE: PRT
<213> ORGANISM: Homo sapiens

<400> SEQUENCE: 23

Glu Ala Gln Val Thr Gln Asn Pro Arg Tyr Leu Ile Thr Val Thr Gly
1               5                   10                  15

Lys Lys Leu Thr Val Thr Cys Ser Gln Asn Met Asn His Glu Tyr Met
```

-continued

```
            20                25                30
Ser Trp Tyr Arg Gln Asp Pro Gly Leu Gly Leu Arg Gln Ile Tyr Tyr
        35                40                45

Ser Met Asn Val Glu Val Thr Asp Lys Gly Asp Val Pro Glu Gly Tyr
    50                55                60

Lys Val Ser Arg Lys Glu Lys Arg Asn Phe Pro Leu Ile Leu Glu Ser
65                70                75                80

Pro Ser Pro Asn Gln Thr Ser Leu Tyr Phe Cys Ala Ser Ser Leu Asn
                85                90                95

Pro Phe Ala Thr Asn Glu Lys Leu Phe Phe Gly Ser Gly Thr Gln Leu
                100               105               110

Ser Val Leu Glu Asp
        115

<210> SEQ ID NO 24
<211> LENGTH: 327
<212> TYPE: DNA
<213> ORGANISM: Homo sapiens

<400> SEQUENCE: 24
ggacaaaaca ttgaccagcc cactgagatg acagctacgg aaggtgccat tgtccagatc      60
aactgcacgt accagacatc tgggttcaac gggctgttct ggtaccagca acatgctggc     120
gaagcaccta catttctgtc ttacaatgtt ctggatggtt tggaggagaa aggtcgtttt     180
tcttcattcc ttagtcggtc taaagggtac agttacctcc ttttgaagga gctccagatg     240
aaagactctg cctcttacct ctgtgctgtg agaggcgact acaagctcag ctttggagcc     300
ggaaccacag taactgtaag agcaaat                                         327

<210> SEQ ID NO 25
<211> LENGTH: 354
<212> TYPE: DNA
<213> ORGANISM: Homo sapiens

<400> SEQUENCE: 25
gattctggag tcacacaaac cccaaagcac ctgatcacag caactggaca gcgagtgacg      60
ctgagatgct cccctaggtc tggagacctc tctgtgtact ggtaccaaca gagcctggac     120
cagggcctcc agttcctcat tcagtattat aatggagaag agagagcaaa ggaaacatt      180 cttgaacgat tctccgcaca acagttccct gacttgcact ctgaactaaa cctgagctct     240
ctggagctgg gggactcagc tttgtatttc tgtgccagca gctcgataca cggtgtctct     300
ggggccaacg tcctgacttt cggggccggc agcaggctga ccgtgctgga ggac           354

<210> SEQ ID NO 26
<211> LENGTH: 109
<212> TYPE: PRT
<213> ORGANISM: Homo sapiens

<400> SEQUENCE: 26

Gly Gln Asn Ile Asp Gln Pro Thr Glu Met Thr Ala Thr Glu Gly Ala
1               5                 10                15

Ile Val Gln Ile Asn Cys Thr Tyr Gln Thr Ser Gly Phe Asn Gly Leu
                20                25                30

Phe Trp Tyr Gln Gln His Ala Gly Glu Ala Pro Thr Phe Leu Ser Tyr
        35                40                45

Asn Val Leu Asp Gly Leu Glu Glu Lys Gly Arg Phe Ser Ser Phe Leu
    50                55                60
```

```
Ser Arg Ser Lys Gly Tyr Ser Tyr Leu Leu Leu Lys Glu Leu Gln Met
65                  70                  75                  80

Lys Asp Ser Ala Ser Tyr Leu Cys Ala Val Arg Gly Asp Tyr Lys Leu
                85                  90                  95

Ser Phe Gly Ala Gly Thr Thr Val Thr Val Arg Ala Asn
            100                 105

<210> SEQ ID NO 27
<211> LENGTH: 118
<212> TYPE: PRT
<213> ORGANISM: Homo sapiens

<400> SEQUENCE: 27

Asp Ser Gly Val Thr Gln Thr Pro Lys His Leu Ile Thr Ala Thr Gly
1               5                   10                  15

Gln Arg Val Thr Leu Arg Cys Ser Pro Arg Ser Gly Asp Leu Ser Val
                20                  25                  30

Tyr Trp Tyr Gln Gln Ser Leu Asp Gln Gly Leu Gln Phe Leu Ile Gln
            35                  40                  45

Tyr Tyr Asn Gly Glu Glu Arg Ala Lys Gly Asn Ile Leu Glu Arg Phe
        50                  55                  60

Ser Ala Gln Gln Phe Pro Asp Leu His Ser Glu Leu Asn Leu Ser Ser
65                  70                  75                  80

Leu Glu Leu Gly Asp Ser Ala Leu Tyr Phe Cys Ala Ser Ser Ser Ile
                85                  90                  95

His Gly Val Ser Gly Ala Asn Val Leu Thr Phe Gly Ala Gly Ser Arg
            100                 105                 110

Leu Thr Val Leu Glu Asp
        115

<210> SEQ ID NO 28
<211> LENGTH: 180
<212> TYPE: PRT
<213> ORGANISM: Homo sapiens

<400> SEQUENCE: 28

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Gly Asn Ala Gly
                20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Gly Ala Pro Arg Gly Pro
        50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
        130                 135                 140

Leu Gln Leu Ser Ile Ser Ser Cys Leu Gln Gln Leu Ser Leu Leu Met
145                 150                 155                 160
```

-continued

```
Trp Ile Thr Gln Cys Phe Leu Pro Val Phe Leu Ala Gln Pro Pro Ser
            165                 170                 175

Gly Gln Arg Arg
            180
```

```
<210> SEQ ID NO 29
<211> LENGTH: 8347
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
tgaaagaccc cacctgtagg tttggcaagc tagcttaagt aacgccattt tgcaaggcat        60
ggaaaataca taactgagaa tagagaagtt cagatcaagg ttaggaacag agagacagca       120
gaatatgggc caaacaggat atctgtggta agcagttcct gccccggctc agggccaaga       180
acagatggtc cccagatgcg gtcccgccct cagcagtttc tagagaacca tcagatgttt       240
ccagggtgcc ccaaggacct gaaaatgacc ctgtgcctta tttgaactaa ccaatcagtt       300
cgcttctcgc ttctgttcgc gcgcttctgc tccccgagct caataaaaga gcccacaacc       360
cctcactcgg cgcgccagtc ctccgataga ctgcgtcgcc cgggtacccg tattcccaat       420
aaagcctctt gctgtttgca tccgaatcgt ggactcgctg atccttggga gggtctcctc       480
agattgattg actgcccacc tcgggggtct ttcatttgga ggttccaccg agatttggag       540 accctgcct agggaccacc gacccccccg ccgggaggta agctggccag cggtcgtttc       600
gtgtctgtct ctgtctttgt gcgtgtttgt gccggcatct aatgtttgcg cctgcgtctg       660
tactagttag ctaactagct ctgtatctgg cggacccgtg gtggaactga cgagttcgga       720
acacccggcc gcaaccctgg gagacgtccc agggacttcg ggggccgttt ttgtggcccg       780
acctgagtcc taaaatcccg atcgtttagg actctttggt gcaccccct tagaggaggg       840 atatgtggtt ctggtaggag acgagaacct aaaacagttc ccgcctccgt ctgaatttt        900 gctttcggtt tgggaccgaa gccgcgccgc gcgtcttgtc tgctgcagca tcgttctgtg       960
ttgtctctgt ctgactgtgt ttctgtattt gtctgaaaat atgggcccgg gctagcctgt      1020
taccactccc ttaagtttga ccttaggtca ctggaaagat gtcgagcgga tcgctcacaa      1080
ccagtcggta gatgtcaaga agagacgttg ggttaccttc tgctctgcag aatggccaac      1140
ctttaacgtc ggatggccgc gagacggcac ctttaaccga gacctcatca cccaggttaa      1200
gatcaaggtc ttttcacctg gcccgcatgg acacccagac caggtcccct acatcgtgac      1260
ctgggaagcc ttggcttttg accccctcc ctgggtcaag ccctttgtac accctaagcc      1320
tccgcctcct cttcctccat ccgccccgtc tctcccctt gaacctcctc gttcgacccc      1380
gcctcgatcc tcccttatc cagccctcac tccttctcta ggcgccccca tatggccata      1440
tgagatctta tatgggcac ccccgcccct tgtaaacttc cctgaccctg acatgacaag      1500
agttactaac agcccctctc tccaagctca cttacaggct ctctacttag tccagcacga      1560
agtctggaga cctctggcgg cagcctacca agaacaactg gaccgaccgg tggtacctca      1620
cccttaccga gtcggcgaca cagtgtgggt ccgccgacac cagactaaga acctagaacc      1680
tcgctggaaa ggaccttaca cagtcctgct gaccacccc accgccctca aagtagacgg      1740
catcgcagct tggatacacg ccgccacgt gaaggctgcc gaccccgggg gtggaccatc      1800
ctctagaccg ccatgtcggg ggcaggtgcc accggccgcg ccatggacgg gccgcgcctg      1860
```

-continued

```
ctgctgttgc tgcttctggg ggtgtccctt ggaggtgcca aggaggcatg ccccacaggc    1920
ctgtacacac acagcggtga gtgctgcaaa gcctgcaacc tgggcgaggg tgtggcccag    1980
ccttgtggag ccaaccagac cgtgtgtgag ccctgcctgg acagcgtgac gttctccgac    2040
gtggtgagcg cgaccgagcc gtgcaagccg tgcaccgagt gcgtggggct ccagagcatg    2100
tcggcgccat gcgtggaggc cgacgacgcc gtgtgccgct gcgcctacgg ctactaccag    2160
gatgagacga ctgggcgctg cgaggcgtgc cgcgtgtgcg aggcgggctc gggcctcgtg    2220
ttctcctgcc aggacaagca gaacaccgtg tgcgaggagt gccccgacgg cacgtattcc    2280
gacgaggcca accacgtgga cccgtgcctg ccctgcaccg tgtgcgagga caccgagcgc    2340
cagctccgcg agtgcacacg ctgggccgac gccgagtgcg aggagatccc tggccgttgg    2400
attacacggt ccacacccc agagggctcg gacagcacag cccccagcac ccaggagcct    2460
gaggcacctc cagaacaaga cctcatagcc agcacggtgg caggtgtggt gaccacagtg    2520
atgggcagct cccagcccgt ggtgacccga ggcaccaccg acaacctcat ccctgtctat    2580
tgctccatcc tggctgctgt ggttgtgggt cttgtggcct acatagcctt caagaggtgg    2640
aacagctccg gctccggagc caccaacttc agcctgctga agcaggccgg cgacgtggag    2700
gagaaccccg gccccgcggc cgccatggcg acgggttcaa gaacttccct acttcttgca    2760
tttggcctgc tttgtttgcc gtggttacag gaagcctcag cagctcagtc agtggctcag    2820
ccggaagatc aggtcaacgt tgctgaaggg aatcctctga ctgtgaaatg cacctattca    2880
gtctctggaa acccttatct tttttggtat gttcaataccc ccaaccgagg cctccagttc    2940
cttctgaaat acatcacagg ggataacctg gttaaaggca gctatggctt tgaagctgaa    3000
tttaacaaga gccaaacctc cttccacctg aagaaaccat ctgcccttgt gagcgactcc    3060
gctttgtact tctgtgctgt gagagacagt cggtctgggg ctgggagtta ccaactcact    3120
ttcgggaagg ggaccaaact ctcggtcata ccaaatatcc agaaccccga gcccgccgtg    3180
taccagctga aggaccccag aagccaggac agcaccctgt gcctgttcac cgacttcgac    3240
agccagatca cgtgcccaa gaccatggag agcggcacct tcatcaccga caagaccgtg    3300
ctggacatga aggccatgga cagcaagagc aacggcgcca tcgcctggtc caaccagacc    3360
agcttcacat gccaggacat cttcaaggag accaacgcca cctacccag cagcgacgtg    3420 ccctgcgacg ccaccctgac cgagaagagc ttcgagaccg acatgaacct gaacttccag    3480
aacctgagcg tgatgggcct gagaatcctg ctgctgaagg tggccggctt caacctgctg    3540
atgaccctga ggctgtggag cagcagggca aaacgttcgg gttcgggtgc gccagtaaag    3600
cagacattaa actttgattt gctgaaactt gcaggtgatg tagagtcaaa tccaggtcca    3660
atggcaacag ggagccgaac ctctctgctc cttgctttcg ggctcctttg cctaccgtgc    3720
ctgcaggagg gctcggcagg tgctgtcgtc tctcaacatc cgagctgggt tatctgtaag    3780
agtggaacct ctgtgaagat cgagtgccgt tccctggact tcaggccac aactatgttt    3840 tggtatcgtc agttcccgaa acagagtctc atgctgatgg caacttccaa tgagggctcc    3900
aaggccacat acgagcaagg cgtcgagaag gacaagtttc tcatcaacca tgcaagcctg    3960
accttgtcca ctctgacagt gaccagtgcc catcctgaag acagcagctt ctacatctgc    4020
agtgctcccc aaggttatgg gggcacagat acgcagtatt ttggcccagg caccgggctg    4080
acagtgctcg aggacctgag gaacgtgacc cccccaagg tgtccctgtt cgagcccagc    4140
aaggccgaga tcgccaacaa gcagaaggcc accctggtgt gcctggccag gggcttcttc    4200
```

-continued

```
cccgaccacg tggagctgtc ttggtgggtg aacggcaagg aggtgcacag cggcgtgagc    4260 accgacccc aggcctacaa ggagagcaac tacagctact gcctgagcag caggctgaga      4320
gtgagcgcca ccttctggca caaccccagg aaccacttcc gctgtcaggt gcagttccac     4380
ggcctgagcg aggaggacaa gtggcccgag ggcagcccca agcccgtgac ccagaacatc     4440
agcgccgagg cctggggcag agccgactgc ggcatcacca gcgccagcta ccaccagggc     4500
gtgctgtccg ccaccatcct gtacgagatc ctgctgggca aggccacact gtacgccgtg     4560
ctggtgtccg gcctggtgct gatggccatg gtgaagaaga agaacagcta aaggatccga     4620
taaaataaaa gattttattt agtctccaga aaaaggggg aatgaaagac cccacctgta      4680
ggtttggcaa gctagcttaa gtaacgccat tttgcaaggc atggaaaata cataactgag     4740
aatagagaag ttcagatcaa ggttaggaac agagagacag cagaatatgg gccaaacagg     4800
atatctgtgg taagcagttc ctgccccggc tcagggccaa gaacagatgg tccccagatg     4860
cggtcccgcc ctcagcagtt tctagagaac catcagatgt ttccagggtg ccccaaggac     4920
ctgaaatgac cctgtgcctt atttgaacta accaatcagt tcgcttctcg cttctgttcg     4980
cgcgcttctg ctccccgagc tcaataaaag agcccacaac ccctcactcg gcgcgccagt     5040
cctccgatag actgcgtcgc ccgggtaccc gtgtatccaa taaaccctct tgcagttgca     5100
tccgacttgt ggtctcgctg ttccttggga gggtctcctc tgagtgattg actacccgtc     5160
agcgggggtc tttcatgggt aacagtttct tgaagttgga gaacaacatt ctgagggtag     5220
gagtcgaata ttaagtaatc ctgactcaat tagccactgt tttgaatcca catactccaa     5280
tactcctgaa atccatcgat ggagttcatt atggacagcg cagaaagagc tggggagaat     5340
tgtgaaattg ttatccgctc acaattccac acaacatacg agccggaagc ataaagtgta     5400
aagcctgggt gcctaatga gtgagctaac tcacattaat tgcgttgcgc tcactgcccg      5460
ctttccagtc gggaaacctg tcgtgccagc tgcattaatg aatcggccaa cgcgcgggga     5520
gaggcggttt gcgtattggg cgctcttccg cttcctcgct cactgactcg ctgcgctcgg     5580
tcgttcggct gcggcgagcg gtatcagctc actcaaaggc ggtaatacgg ttatccacag     5640 aatcaggggga taacgcagga aagaacatgt gagcaaaagg ccagcaaaag gccaggaacc    5700
gtaaaaaggc cgcgttgctg gcgtttttcc ataggctccg cccccctgac gagcatcaca     5760
aaaatcgacg ctcaagtcag aggtggcgaa acccgacagg actataaaga taccaggcgt     5820
ttccccctgg aagctccctc gtgcgctctc ctgttccgac cctgccgctt accggatacc     5880
tgtccgcctt tctcccttcg ggaagcgtgg cgctttctca tagctcacgc tgtaggtatc     5940
tcagttcggt gtaggtcgtt cgctccaagc tgggctgtgt gcacgaaccc cccgttcagc     6000
ccgaccgctg cgccttatcc ggtaactatc gtcttgagtc caacccggta agacacgact     6060
tatcgccact ggcagcagcc actggtaaca ggattagcag agcgaggtat gtaggcggtg     6120
ctacagagtt cttgaagtgg tggcctaact acggctacac tagaaggaca gtatttggta     6180
tctgcgctct gctgaagcca gttaccttcg gaaaaagagt tggtagctct tgatccggca     6240
aacaaaccac cgctggtagc ggtggttttt ttgtttgcaa gcagcagatt acgcgcagaa     6300
aaaaaggatc tcaagaagat cctttgatct tttctacggg gtctgacgct cagtggaacg     6360
aaaactcacg ttaagggatt ttggtcatga gattatcaaa aaggatcttc acctagatcc     6420 tttaaatta aaaatgaagt tttaaatcaa tctaaagtat atatgagtaa acttggtctg      6480
acagttacca atgcttaatc agtgaggcac ctatctcagc gatctgtcta tttcgttcat     6540
ccatagttgc ctgactcccc gtcgtgtaga taactacgat acgggagggc ttaccatctg     6600
```

```
gccccagtgc tgcaatgata ccgcgagacc cacgctcacc ggctccagat ttatcagcaa    6660
taaaccagcc agccggaagg gccgagcgca gaagtggtcc tgcaacttta tccgcctcca    6720
tccagtctat taattgttgc cgggaagcta gagtaagtag ttcgccagtt aatagtttgc    6780
gcaacgttgt tgccattgct acaggcatcg tggtgtcacg ctcgtcgttt ggtatggctt    6840
cattcagctc cggttcccaa cgatcaaggc gagttacatg atcccccatg ttgtgcaaaa    6900
aagcggttag ctccttcggt cctccgatcg ttgtcagaag taagttggcc gcagtgttat    6960
cactcatggt tatggcagca ctgcataatt ctcttactgt catgccatcc gtaagatgct    7020
tttctgtgac tggtgagtac tcaaccaagt cattctgaga atagtgtatg cggcgaccga    7080
gttgctcttg cccggcgtca atacgggata ataccgcgcc acatagcaga actttaaaag    7140
tgctcatcat tggaaaacgt tcttcggggc gaaaactctc aaggatctta ccgctgttga    7200
gatccagttc gatgtaaccc actcgtgcac ccaactgatc ttcagcatct tttactttca    7260
ccagcgtttc tgggtgagca aaaacaggaa ggcaaaatgc cgcaaaaaag ggaataaggg    7320
cgacacggaa atgttgaata ctcatactct tcctttttca atattattga agcatttatc    7380
agggttattg tctcatgagc ggatacatat ttgaatgtat ttagaaaaat aaacaaatag    7440
gggttccgcg cacatttccc cgaaaagtgc cacctgacgt ctaagaaacc attattatca    7500
tgacattaac ctataaaaat aggcgtatca cgaggccctt tcgtctcgcg cgtttcggtg    7560
atgacggtga aaacctctga cacatgcagc tcccggagac ggtcacagct tgtctgtaag    7620
cggatgccgg gagcagacaa gcccgtcagg gcgcgtcagc gggtgttggc gggtgtcggg    7680
gctggcttaa ctatgcggca tcagagcaga ttgtactgag agtgcaccat atgcggtgtg    7740
aaataccgca cagatgcgta aggagaaaat accgcatcag gcgccattcg ccattcaggc    7800
tgcgcaactg ttgggaaggg cgatcggtgc gggcctcttc gctattacgc cagctggcga    7860 aaggggggatg tgctgcaagg cgattaagtt gggtaacgcc agggtttttcc cagtcacgac   7920 gttgtaaaac gacggccagt gccacgctct cccttatgcg actcctgcat taggaagcag    7980
cccagtagta ggttgaggcc gttgagcacc gccgccgcaa ggaatggtgc atgcaaggag    8040
atggcgccca acagtccccc ggccacgggg cctgccacca tacccacgcc gaaacaagcg    8100
ctcatgagcc cgaagtggcg agcccgatct tccccatcgg tgatgtcggc gatataggcg    8160
ccagcaaccg cacctgtggc gccggtgatg ccggccacga tgcgtccggc gtagaggcga    8220
tttaaagaca ggatatcagt ggtccaggct ctagttttga ctcaacaata tcaccagctg    8280
aagcctatag agtacgagcc atagataaaa taaaagattt tatttagtct ccagaaaaag    8340
gggggaa                                                                8347
```

```
<210> SEQ ID NO 30
<211> LENGTH: 8326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
```

```
tgaaagaccc cacctgtagg tttggcaagc tagcttaagt aacgccattt tgcaaggcat    60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
```

-continued

```
ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcactcgg cgcgccagtc ctccgataga ctgcgtcgcc cgggtacccg tattcccaat     420
aaagcctctt gctgtttgca tccgaatcgt ggactcgctg atccttggga gggtctcctc     480
agattgattg actgcccacc tcgggggtct ttcatttgga ggttccaccg agatttggag     540
acccctgcct agggaccacc gaccccccg ccgggaggta agctggccag cggtcgtttc      600
gtgtctgtct ctgtctttgt gcgtgtttgt gccggcatct aatgtttgcg cctgcgtctg     660
tactagttag ctaactagct ctgtatctgg cggacccgtg gtggaactga cgagttcgga     720
acacccggcc gcaaccctgg gagacgtccc agggacttcg ggggccgttt ttgtggcccg     780
acctgagtcc taaaatcccg atcgtttagg actctttggt gcacccccct tagaggaggg     840
atatgtggtt ctggtaggag acgagaacct aaaacagttc ccgcctccgt ctgaattttt     900
gctttcggtt tgggaccgaa gccgcgccgc gcgtcttgtc tgctgcagca tcgttctgtg     960
ttgtctctgt ctgactgtgt ttctgtattt gtctgaaaat atgggcccgg gctagcctgt    1020
taccactccc ttaagtttga ccttaggtca ctggaaagat gtcgagcgga tcgctcacaa    1080
ccagtcggta gatgtcaaga agagacgttg ggttaccttc tgctctgcag aatggccaac    1140
ctttaacgtc ggatggccgc gagacggcac ctttaaccga gacctcatca cccaggttaa    1200
gatcaaggtc ttttcacctg gcccgcatgg acacccagac caggtcccct acatcgtgac    1260
ctgggaagcc ttggcttttg accccccctcc ctgggtcaag ccctttgtac accctaagcc    1320
tccgcctcct cttcctccat ccgccccgtc tctcccctt gaacctcctc gttcgacccc     1380
gcctcgatcc tccctttatc cagccctcac tccttctcta ggcgccccca tatggccata    1440
tgagatctta tatgggcac ccccgcccct tgtaaacttc cctgaccctg acatgacaag     1500
agttactaac agcccctctc tccaagctca cttacaggct ctctacttag tccagcacga    1560
agtctggaga cctctggcgg cagcctacca agaacaactg gaccgaccgg tggtacctca    1620
cccttaccga gtcggcgaca cagtgtgggt ccgccgacac cagactaaga acctagaacc    1680
tcgctggaaa ggaccttaca cagtcctgct gaccacccc accgccctca aagtagacgg     1740
catcgcagct tggatacacg ccgcccacgt gaaggctgcc gaccccgggg gtggaccatc    1800
ctctagaccg ccatgtcggg ggcaggtgcc accggccgcg ccatgacgg gccgcgcctg      1860 ctgctgttgc tgcttctggg ggtgtccctt ggaggtgcca aggaggcatg ccccacaggc    1920
ctgtacacac acagcggtga gtgctgcaaa gcctgcaacc tgggcgaggg tgtggcccag    1980
ccttgtggag ccaaccagac cgtgtgtgag ccctgcctgg acagcgtgac gttctccgac    2040
gtggtgagcg cgaccgagcc gtgcaagccg tgcaccgagt gcgtgggct ccagagcatg     2100 tcggcgccat gcgtggaggc cgacgacgcc gtgtgccgct gcgcctacgg ctactaccag    2160
gatgagacga ctgggcgctg cgaggcgtgc cgcgtgtgcg aggcgggctc gggcctcgtg    2220
ttctcctgcc aggacaagca gaacaccgtg tgcgaggagt gccccgacgg cacgtattcc    2280
gacgaggcca accacgtgga cccgtgcctg ccctgcaccg tgtgcgagga caccgagcgc    2340
cagctccgcg agtgcacacg ctgggccgac gccgagtgcg aggagatccc tggccgttgg    2400
attacacggt ccacacccccc agagggctcg gacagcacag cccccagcac ccaggagcct    2460
gaggcacctc cagaacaaga cctcatagcc agcacggtgg caggtgtggt gaccacagtg    2520
atgggcagct cccagcccgt ggtgacccga ggcaccaccg acaacctcat ccctgtctat    2580
```

-continued

```
tgctccatcc tggctgctgt ggttgtgggt cttgtggcct acatagcctt caagaggtgg   2640
aacagctccg gctccggagc caccaacttc agcctgctga agcaggccgg cgacgtggag   2700
gagaaccccg gccccgcggc cgccatggcg acgggttcaa gaacttccct acttcttgca   2760
tttggcctgc tttgtttgcc gtggttacag gaagcctcag cagatgctaa gaccacacag   2820
ccaaattcaa tggagagtaa cgaagaagag cctgttcact tgccttgtaa ccactccaca   2880
atcagtggaa ctgattacat acattggtat cgacagcttc cctcccaggg tccagagtac   2940
gtgattcatg gtcttacaag caatgtgaac aacagaatgg cctctctggc aatcgctgaa   3000
gacagaaagt ccagtacctt gatcctgcac cgtgctacct tgagagatgc tgctgtgtac   3060
tactgcatcc tgagaacctc tggggctggg agttaccaac tcactttcgg gaaggggacc   3120
aaactctcgg tcataccaaa tatccagaac cccgagcccg ccgtgtacca gctgaaggac   3180
cccagaagcc aggacagcac cctgtgcctg ttcaccgact tcgacagcca gatcaacgtg   3240
cccaagacca tggagagcgg caccttcatc accgacaaga ccgtgctgga catgaaggcc   3300
atggacagca agagcaacgg cgccatcgcc tggtccaacc agaccagctt cacatgccag   3360
gacatcttca aggagaccaa cgccacctac cccagcagcg acgtgccctg cgacgccacc   3420
ctgaccgaga agagcttcga gaccgacatg aacctgaact ccagaacct gagcgtgatg   3480 ggcctgagaa tcctgctgct gaaggtggcc ggcttcaacc tgctgatgac cctgaggctg   3540
tggagcagca gggcaaaacg ttcgggttcg ggtgcgccag taaagcagac attaaacttt   3600
gatttgctga aacttgcagg tgatgtagag tcaaatccag gtccaatggc aacagggagc   3660
cgaacctctc tgctccttgc tttcgggctc ctttgcctac cgtgcctgca ggagggctcg   3720
gcaagtgctg tcatctctca aaagccaagc agggatatct gtcaacgtgg aacctccctg   3780
acgatccagt gtcaagtcga tagccaagtc accatgatgt tctggtaccg tcagcaacct   3840
ggacagagcc tgacactgat cgcaactgca aatcagggct ctgaggccac atatgagagt   3900
ggatttgtca ttgacaagtt tcccatcagc cgcccaaacc taacattctc aactctgact   3960
gtgagcaaca tgagccctga agacagcagc atatatctct gcagcgcggg aggagcggga   4020
gcgtcagata cgcagtattt tggcccaggc acccggctga cagtgctcga ggacctgagg   4080
aacgtgaccc cccccaaggt gtccctgttc gagcccagca aggccgagat cgccaacaag   4140
cagaaggcca ccctggtgtg cctggccagg ggcttcttcc ccgaccacgt ggagctgtct   4200
tggtgggtga cggcaagga ggtgcacagc ggcgtgagca ccgacccca ggcctacaag   4260 gagagcaact acagctactg cctgagcagc aggctgagag tgagcgccac cttctggcac   4320
aaccccagga accacttccg ctgtcaggtg cagttccacg gcctgagcga ggaggacaag   4380
tggcccgagg gcagccccaa gcccgtgacc cagaacatca cgccgaggc ctggggcaga   4440 gccgactgcg gcatcaccag cgccagctac caccagggcg tgctgtccgc caccatcctg   4500
tacgagatcc tgctgggcaa ggccacactg tacgccgtgc tggtgtccgg cctggtgctg   4560
atggccatgg tgaagaagaa gaacagctaa aggatccgat aaaataaaag attttatta   4620 gtctccagaa aaaggggga atgaaagacc ccacctgtag gtttggcaag ctagcttaag   4680
taacgccatt ttgcaaggca tggaaaatac ataactgaga atagagaagt tcagatcaag   4740
gttaggaaca gagagacagc agaatatggg ccaaacagga tatctgtggt aagcagttcc   4800
tgccccggct cagggccaag aacagatggt ccccagatgc ggtcccgccc tcagcagttt   4860
ctagagaacc atcagatgtt ccagggtgc cccaaggacc tgaaatgacc ctgtgcctta   4920
tttgaactaa ccaatcagtt cgcttctcgc ttctgttcgc gcgcttctgc tccccgagct   4980
```

-continued

```
caataaaaga gcccacaacc cctcactcgg cgcgccagtc ctccgataga ctgcgtcgcc    5040
cgggtacccg tgtatccaat aaaccctctt gcagttgcat ccgacttgtg gtctcgctgt    5100
tccttgggag ggtctcctct gagtgattga ctacccgtca gcgggggtct ttcatgggta    5160
acagtttctt gaagttggag aacaacattc tgagggtagg agtcgaatat taagtaatcc    5220
tgactcaatt agccactgtt ttgaatccac atactccaat actcctgaaa tccatcgatg    5280
gagttcatta tggacagcgc agaaagagct ggggagaatt gtgaaattgt tatccgctca    5340
caattccaca caacatacga gccggaagca taaagtgtaa agcctggggt gcctaatgag    5400
tgagctaact cacattaatt gcgttgcgct cactgcccgc tttccagtcg ggaaacctgt    5460
cgtgccagct gcattaatga atcggccaac gcgcggggag aggcggtttg cgtattgggc    5520
gctcttccgc ttcctcgctc actgactcgc tgcgctcggt cgttcggctg cggcgagcgg    5580
tatcagctca ctcaaaggcg gtaatacggt tatccacaga atcaggggat aacgcaggaa    5640
agaacatgtg agcaaaaggc cagcaaaagg ccaggaaccg taaaaaggcc gcgttgctgg    5700 cgttttttcca taggctccgc ccccctgacg agcatcacaa aaatcgacgc tcaagtcaga    5760
ggtggcgaaa cccgacagga ctataaagat accaggcgtt tcccccctgga agctccctcg    5820 tgcgctctcc tgttccgacc ctgccgctta ccggatacct gtccgccttt ctcccttcgg    5880
gaagcgtggc gctttctcat agctcacgct gtaggtatct cagttcggtg taggtcgttc    5940
gctccaagct gggctgtgtg cacgaacccc ccgttcagcc cgaccgctgc gccttatccg    6000
gtaactatcg tcttgagtcc aacccggtaa gacacgactt atcgccactg gcagcagcca    6060
ctggtaacag gattagcaga gcgaggtatg taggcggtgc tacagagttc ttgaagtggt    6120
ggcctaacta cggctacact agaaggacag tatttggtat ctgcgctctg ctgaagccag    6180
ttaccttcgg aaaaagagtt ggtagctctt gatccggcaa acaaaccacc gctggtagcg    6240
gtggtttttt tgtttgcaag cagcagatta cgcgcagaaa aaaaggatct caagaagatc    6300
ctttgatctt ttctacgggg tctgacgctc agtggaacga aaactcacgt taagggattt    6360
tggtcatgag attatcaaaa aggatcttca cctagatcct tttaaattaa aaatgaagtt    6420
ttaaatcaat ctaaagtata tatgagtaaa cttggtctga cagttaccaa tgcttaatca    6480
gtgaggcacc tatctcagcg atctgtctat ttcgttcatc catagttgcc tgactccccg    6540
tcgtgtagat aactacgata cgggagggct taccatctgg ccccagtgct gcaatgatac    6600
cgcgagaccc acgctcaccg gctccagatt tatcagcaat aaaccagcca gccggaaggg    6660
ccgagcgcag aagtggtcct gcaactttat ccgcctccat ccagtctatt aattgttgcc    6720
gggaagctag agtaagtagt tcgccagtta atagtttgcg caacgttgtt gccattgcta    6780
caggcatcgt ggtgtcacgc tcgtcgtttg gtatggcttc attcagctcc ggttcccaac    6840
gatcaaggcg agttacatga tcccccatgt tgtgcaaaaa agcggttagc tccttcggtc    6900
ctccgatcgt tgtcagaagt aagttggccg cagtgttatc actcatggtt atggcagcac    6960
tgcataattc tcttactgtc atgccatccg taagatgctt ttctgtgact ggtgagtact    7020
caaccaagtc attctgagaa tagtgtatgc ggcgaccgag ttgctcttgc ccggcgtcaa    7080
tacgggataa taccgcgcca catagcagaa ctttaaaagt gctcatcatt ggaaaacgtt    7140
cttcggggcg aaaactctca aggatcttac cgctgttgag atccagttcg atgtaaccca    7200
ctcgtgcacc caactgatct tcagcatctt ttactttcac cagcgtttct gggtgagcaa    7260
aaacaggaag gcaaaatgcc gcaaaaaagg gaataagggc gacacggaaa tgttgaatac    7320
```

-continued

```
tcatactctt cctttttcaa tattattgaa gcatttatca gggttattgt ctcatgagcg   7380
gatacatatt tgaatgtatt tagaaaaata aacaaatagg ggttccgcgc acatttcccc   7440
gaaaagtgcc acctgacgtc taagaaacca ttattatcat gacattaacc tataaaaata   7500
ggcgtatcac gaggcccttt cgtctcgcgc gtttcggtga tgacggtgaa aacctctgac   7560
acatgcagct cccggagacg gtcacagctt gtctgtaagc ggatgccggg agcagacaag   7620
cccgtcaggg cgcgtcagcg ggtgttggcg ggtgtcgggg ctggcttaac tatgcggcat   7680
cagagcagat tgtactgaga gtgcaccata tgcggtgtga ataccgcac agatgcgtaa     7740 ggagaaaata ccgcatcagg cgccattcgc cattcaggct gcgcaactgt tgggaagggc   7800
gatcggtgcg ggcctcttcg ctattacgcc agctggcgaa aggggggatgt gctgcaaggc   7860 gattaagttg ggtaacgcca gggttttccc agtcacgacg ttgtaaaacg acggccagtg   7920
ccacgctctc ccttatgcga ctcctgcatt aggaagcagc ccagtagtag gttgaggccg   7980
ttgagcaccg ccgccgcaag gaatggtgca tgcaaggaga tggcgcccaa cagtcccccg   8040
gccacggggc ctgccaccat acccacgccg aaacaagcgc tcatgagccc gaagtggcga   8100
gcccgatctt ccccatcggt gatgtcggcg atataggcgc cagcaaccgc acctgtggcg   8160
ccggtgatgc cggccacgat gcgtccggcg tagaggcgat ttaaagacag gatatcagtg   8220
gtccaggctc tagttttgac tcaacaatat caccagctga agcctataga gtacgagcca   8280
tagataaaat aaaagatttt atttagtctc cagaaaaagg ggggaa                  8326
```

<210> SEQ ID NO 31
<211> LENGTH: 8311
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
tgaaagaccc cacctgtagg tttggcaagc tagcttaagt aacgccattt tgcaaggcat     60
ggaaaataca taactgagaa tagagaagtt cagatcaagg ttaggaacag agagacagca    120
gaatatgggc caaacaggat atctgtggta agcagttcct gccccggctc agggccaaga    180
acagatggtc cccagatgcg gtcccgccct cagcagtttc tagagaacca tcagatgttt    240
ccagggtgcc ccaaggacct gaaatgacc ctgtgcctta tttgaactaa ccaatcagtt     300
cgcttctcgc ttctgttcgc gcgcttctgc tccccgagct caataaaaga gcccacaacc    360
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcgggggtct ttcatttgga ggttccaccg agatttggag    540
acccctgcct agggaccacc gacccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggacccgtg gtggaactga cgagttcgga    720
acacccggcc gcaaccctgg gagacgtccc agggacttcg ggggccgttt ttgtggcccg    780
acctgagtcc taaaatcccg atcgtttagg actctttggt gcacccccct tagaggaggg    840
atatgtggtt ctggtaggag acgagaacct aaaacagttc ccgcctccgt ctgaattttt    900
gctttcggtt tgggaccgaa gccgcgcgc gcgtcttgtc tgctgcagca tcgttctgtg    960
ttgtctctgt ctgactgtgt ttctgtattt gtctgaaaat atgggcccgg gctagcctgt   1020
```

-continued

```
taccactccc ttaagtttga ccttaggtca ctggaaagat gtcgagcgga tcgctcacaa    1080
ccagtcggta gatgtcaaga agagacgttg ggttaccttc tgctctgcag aatggccaac    1140
ctttaacgtc ggatggccgc gagacggcac ctttaaccga gacctcatca cccaggttaa    1200
gatcaaggtc tttttcacctg gcccgcatgg acacccagac caggtcccct acatcgtgac    1260
ctgggaagcc ttggctttttg acccccctcc ctgggtcaag ccctttgtac accctaagcc    1320
tccgcctcct cttcctccat ccgccccgtc tctcccccctt gaacctcctc gttcgacccc    1380
gcctcgatcc tcccttttatc cagccctcac tccttctcta ggcgccccca tatggccata    1440
tgagatctta tatggggcac ccccgccccct tgtaaacttc cctgaccctg acatgacaag    1500
agttactaac agcccctctc tccaagctca cttacaggct ctctacttag tccagcacga    1560
agtctggaga cctctggcgg cagcctacca agaacaactg gaccgaccgg tggtacctca    1620
cccttaccga gtcggcgaca cagtgtgggt ccgccgacac cagactaaga acctagaacc    1680
tcgctggaaa ggaccttaca cagtcctgct gaccacccccc accgccctca aagtagacgg    1740
catcgcagct tggatacacg ccgcccacgt gaaggctgcc gaccccgggg gtggaccatc    1800
ctctagaccg ccatgtcggg ggcaggtgcc accggccgcg ccatggacgg gccgcgcctg    1860
ctgctgttgc tgcttctggg ggtgtccctt ggaggtgcca aggaggcatg ccccacaggc    1920
ctgtacacac acagcggtga gtgctgcaaa gcctgcaacc tgggcgaggg tgtggcccag    1980
ccttgtggag ccaaccagac cgtgtgtgag ccctgcctgg acagcgtgac gttctccgac    2040
gtggtgagcg cgaccgagcc gtgcaagccg tgcaccgagt gcgtggggct ccagagcatg    2100
tcggcgccat gcgtggaggc cgacgacgcc gtgtgccgct gcgcctacgg ctactaccag    2160
gatgagacga ctgggcgctg cgaggcgtgc cgcgtgtgcg aggcgggctc gggcctcgtg    2220
ttctcctgcc aggacaagca gaacaccgtg tgcgaggagt gccccgacgg cacgtattcc    2280
gacgaggcca accacgtgga cccgtgcctg cctgcaccg tgtgcgagga caccgagcgc    2340
cagctccgcg agtgcacacg ctgggccgac gccgagtgcg aggagatccc tggccgttgg    2400
attacacggt ccacacccccc agagggctcg gacagcacag cccccagcac ccaggagcct    2460
gaggcacctc cagaacaaga cctcatagcc agcacggtgg caggtgtggt gaccacagtg    2520
atgggcagct cccagcccgt ggtgacccga ggcaccaccg acaacctcat ccctgtctat    2580
tgctccatcc tggctgctgt ggttgtgggt cttgtggcct acatagcctt caagaggtgg    2640
aacagctccg gctccggagc caccaacttc agcctgctga agcaggccgg cgacgtggag    2700
gagaaccccg gccccgcggc cgccatggcg acgggttcaa gaacttccct acttcttgca    2760
tttggcctgc tttgtttgcc gtggttacag gaagcctcag cacagaagga ggtggagcag    2820
aattctggac ccctcagtgt tccagaggga gccattgcct ctctcaactg cacttacagt    2880
gaccgaggtt cccagtcctt cttctggtac agacaatatt ctgggaaaag ccctgagttg    2940
ataatgttca tatactccaa tggtgacaaa gaagatggaa ggtttacagc acagctcaat    3000
aaagccagcc agtatgtttc tctgctcatc agagactccc agcccagtga ttcagccacc    3060
tacctctgtg ccgtagatga caagatcatc tttggaaaag ggacacgact tcatattctc    3120
cccaatatcc agaaccccga gcccgccgtg taccagctga aggaccccag aagccaggac    3180
agcaccctgt gcctgttcac cgacttcgac agccagatca acgtgcccaa gaccatggag    3240
agcggcacct tcatcaccga caagaccgtg ctggacatga aggccatgga cagcaagagc    3300
aacggcgcca tcgcctggtc caaccagacc agcttcacat gccaggacat cttcaaggag    3360
accaacgcca cctaccccag cagcgacgtg ccctgcgacg ccaccctgac cgagaagagc    3420
```

```
ttcgagaccg acatgaacct gaacttccag aacctgagcg tgatgggcct gagaatcctg      3480
ctgctgaagg tggccggctt caacctgctg atgaccctga ggctgtggag cagcagggca      3540
aaacgttcgg gttcgggtgc gccagtaaag cagacattaa actttgattt gctgaaactt      3600
gcaggtgatg tagagtcaaa tccaggtcca atggcaacag ggagccgaac ctctctgctc      3660
cttgctttcg ggctcctttg cctaccgtgc ctgcaggagg gctcggcaga tgctggagtt      3720
atccagtcac cccggcacga ggtgacagag atgggacaag aagtgactct gagatgtaaa      3780
ccaatttcag gacacgacta cctttttctgg tacagacaga ccatgatgcg gggactggag      3840
ttgctcattt actttaacaa caacgttccg atagatgatt cagggatgcc cgaggatcga      3900
ttctcagcta agatgcctaa tgcatcattc tccactctga agatccagcc ctcagaaccc      3960
agggactcag ctgtgtactt ctgtgccagc agtttgggac agccaagcac agatacgcag      4020
tattttggcc caggcacccg gctgacagtg ctcgaggacc tgaggaacgt gacccccccc      4080
aaggtgtccc tgttcgagcc cagcaaggcc gagatcgcca acaagcagaa ggccaccctg      4140
gtgtgcctgg ccaggggctt cttccccgac cacgtggagc tgtcttggtg ggtgaacggc      4200
aaggaggtgc acagcggcgt gagcaccgac ccccaggcct acaaggagag caactacagc      4260
tactgcctga gcagcaggct gagagtgagc gccaccttct ggcacaaccc caggaaccac      4320
ttccgctgtc aggtgcagtt ccacggcctg agcgaggagg acaagtggcc cgagggcagc      4380
cccaagcccg tgacccagaa catcagcgcc gaggcctggg gcagagccga ctgcggcatc      4440
accagcgcca gctaccacca gggcgtgctg tccgccacca tcctgtacga gatcctgctg      4500
ggcaaggcca cactgtacgc cgtgctggtg tccggcctgg tgctgatggc catggtgaag      4560
aagaagaaca gctaaaggat ccgataaaat aaaagatttt atttagtctc cagaaaaagg      4620
ggggaatgaa agaccccacc tgtaggtttg gcaagctagc ttaagtaacg ccattttgca      4680
aggcatggaa aatacataac tgagaataga gaagttcaga tcaaggttag gaacagagag      4740
acagcagaat atgggccaaa caggatatct gtggtaagca gttcctgccc cggctcaggg      4800
ccaagaacag atggtcccca gatgcggtcc cgccctcagc agtttctaga gaaccatcag      4860
atgtttccag ggtgccccaa ggacctgaaa tgaccctgtg ccttatttga actaaccaat      4920
cagttcgctt ctcgcttctg ttcgcgcgct tctgctcccc gagctcaata aaagagccca      4980
caacccctca ctcggcgcgc cagtcctccg atagactgcg tcgcccgggt acccgtgtat      5040
ccaataaacc ctcttgcagt tgcatccgac ttgtggtctc gctgttcctt gggagggtct      5100
cctctgagtg attgactacc cgtcagcggg ggtctttcat gggtaacagt ttcttgaagt      5160
tggagaacaa cattctgagg gtaggagtcg aatattaagt aatcctgact caattagcca      5220 ctgtttttgaa tccacatact ccaatactcc tgaaatccat cgatggagtt cattatggac      5280
agcgcagaaa gagctgggga gaattgtgaa attgttatcc gctcacaatt ccacacaaca      5340
tacgagccgg aagcataaag tgtaaagcct ggggtgccta atgagtgagc taactcacat      5400
taattgcgtt gcgctcactg cccgctttcc agtcgggaaa cctgtcgtgc cagctgcatt      5460
aatgaatcgg ccaacgcgcg gggagaggcg gtttgcgtat tgggcgctct tccgcttcct      5520
cgctcactga ctcgctgcgc tcggtcgttc ggctgcggcg agcggtatca gctcactcaa      5580
aggcggtaat acggttatcc acagaatcag gggataacgc aggaaagaac atgtgagcaa      5640
aaggccagca aaaggccagg aaccgtaaaa aggccgcgtt gctggcgttt ttccataggc      5700
tccgcccccc tgacgagcat cacaaaaatc gacgctcaag tcagaggtgg cgaaacccga      5760
```

-continued

```
caggactata aagataccag gcgtttcccc ctggaagctc cctcgtgcgc tctcctgttc    5820
cgaccctgcc gcttaccgga tacctgtccg cctttctccc ttcgggaagc gtggcgcttt    5880
ctcatagctc acgctgtagg tatctcagtt cggtgtaggt cgttcgctcc aagctgggct    5940
gtgtgcacga acccccgtt cagcccgacc gctgcgcctt atccggtaac tatcgtcttg     6000
agtccaaccc ggtaagacac gacttatcgc cactggcagc agccactggt aacaggatta    6060
gcagagcgag gtatgtaggc ggtgctacag agttcttgaa gtggtggcct aactacggct    6120
acactagaag gacagtattt ggtatctgcg ctctgctgaa gccagttacc ttcggaaaaa    6180
gagttggtag ctcttgatcc ggcaaacaaa ccaccgctgg tagcggtggt tttttgttt     6240 gcaagcagca gattacgcgc agaaaaaaag gatctcaaga agatcctttg atcttttcta    6300
cggggtctga cgctcagtgg aacgaaaact cacgttaagg gattttggtc atgagattat    6360
caaaaaggat cttcacctag atccttttaa attaaaaatg aagttttaaa tcaatctaaa    6420
gtatatatga gtaaacttgg tctgacagtt accaatgctt aatcagtgag gcacctatct    6480
cagcgatctg tctatttcgt tcatccatag ttgcctgact ccccgtcgtg tagataacta    6540
cgatacggga gggcttacca tctggcccca gtgctgcaat gataccgcga gacccacgct    6600
caccggctcc agatttatca gcaataaacc agccagccgg aagggccgag cgcagaagtg    6660
gtcctgcaac tttatccgcc tccatccagt ctattaattg ttgccgggaa gctagagtaa    6720
gtagttcgcc agttaatagt ttgcgcaacg ttgttgccat tgctacaggc atcgtggtgt    6780
cacgctcgtc gtttggtatg gcttcattca gctccggttc ccaacgatca aggcgagtta    6840
catgatcccc catgttgtgc aaaaaagcgg ttagctcctt cggtcctccg atcgttgtca    6900
gaagtaagtt ggccgcagtg ttatcactca tggttatggc agcactgcat aattctctta    6960
ctgtcatgcc atccgtaaga tgcttttctg tgactggtga gtactcaacc aagtcattct    7020
gagaatagtg tatgcggcga ccgagttgct cttgcccggc gtcaatacgg gataataccg    7080
cgccacatag cagaacttta aaagtgctca tcattggaaa acgttcttcg gggcgaaaac    7140
tctcaaggat cttaccgctg ttgagatcca gttcgatgta acccactcgt gcacccaact    7200
gatcttcagc atcttttact ttcaccagcg tttctgggtg agcaaaaaca ggaaggcaaa    7260
atgccgcaaa aaagggaata agggcgacac ggaaatgttg aatactcata ctcttccttt    7320
ttcaatatta ttgaagcatt tatcagggtt attgtctcat gagcggatac atatttgaat    7380
gtatttagaa aaataaacaa ataggggttc cgcgcacatt tccccgaaaa gtgccacctg    7440
acgtctaaga aaccattatt atcatgacat taacctataa aaataggcgt atcacgaggc    7500
cctttcgtct cgcgcgtttc ggtgatgacg gtgaaaacct ctgacacatg cagctcccgg    7560
agacggtcac agcttgtctg taagcggatg ccgggagcag acaagcccgt cagggcgcgt    7620
cagcgggtgt tggcgggtgt cggggctggc ttaactatgc ggcatcagag cagattgtac    7680
tgagagtgca ccatatgcgg tgtgaaatac cgcacagatg cgtaaggaga aaataccgca    7740
tcaggcgcca ttcgccattc aggctgcgca actgttggga agggcgatcg gtgcgggcct    7800
cttcgctatt acgccagctg gcgaaagggg gatgtgctgc aaggcgatta agttgggtaa    7860
cgccagggtt ttcccagtca cgacgttgta aaacgacggc cagtgccacg ctctccctta    7920
tgcgactcct gcattaggaa gcagcccagt agtaggttga ggccgttgag caccgccgcc    7980
gcaaggaatg gtgcatgcaa ggagatggcg cccaacagtc cccggccac ggggcctgcc     8040 accataccca cgccgaaaca gcgctcatg agcccgaagt ggcgagcccg atcttcccca     8100
tcggtgatgt cggcgatata ggcgccagca accgcacctg tggcgccggt gatgccggcc    8160
```

-continued

```
acgatgcgtc cggcgtagag gcgatttaaa gacaggatat cagtggtcca ggctctagtt    8220
ttgactcaac aatatcacca gctgaagcct atagagtacg agccatagat aaaataaaag    8280
attttattta gtctccagaa aaagggggga a                                  8311

<210> SEQ ID NO 32
<211> LENGTH: 8338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaaatgacc ctgtgcctta tttgaactaa ccaatcagtt     300
cgcttctcgc ttctgttcgc gcgcttctgc tccccgagct caataaaaga gcccacaacc     360
cctcactcgg cgcgccagtc ctccgataga ctgcgtcgcc cgggtacccg tattcccaat     420
aaagcctctt gctgtttgca tccgaatcgt ggactcgctg atccttggga gggtctcctc     480
agattgattg actgcccacc tcgggggtct ttcatttgga ggttccaccg agatttggag     540
acccctgcct agggaccacc gacccccccg ccgggaggta agctggccag cggtcgtttc     600
gtgtctgtct ctgtctttgt gcgtgtttgt gccggcatct aatgtttgcg cctgcgtctg     660
tactagttag ctaactagct ctgtatctgg cggacccgtg gtggaactga cgagttcgga     720
acacccggcc gcaaccctgg gagacgtccc agggacttcg ggggccgttt ttgtggcccg     780
acctgagtcc taaaatcccg atcgtttagg actctttggt gcaccccct tagaggaggg     840 atatgtggtt ctggtaggag acgagaacct aaaacagttc ccgcctccgt ctgaatttt     900 gctttcggtt tgggaccgaa gccgcgccgc gcgtcttgtc tgctgcagca tcgttctgtg     960
ttgtctctgt ctgactgtgt ttctgtattt gtctgaaaat atgggcccgg gctagcctgt    1020
taccactccc ttaagtttga ccttaggtca ctggaaagat gtcgagcgga tcgctcacaa    1080
ccagtcggta gatgtcaaga agagacgttg ggttaccttc tgctctgcag aatggccaac    1140
ctttaacgtc ggatggccgc gagacggcac ctttaaccga gacctcatca cccaggttaa    1200
gatcaaggtc ttttcacctg gcccgcatgg acacccagac caggtcccct acatcgtgac    1260
ctgggaagcc ttggctttttg acccccctcc ctgggtcaag ccctttgtac accctaagcc    1320
tccgcctcct cttcctccat ccgccccgtc tctcccctt gaacctcctc gttcgacccc    1380
gcctcgatcc tccctttatc cagccctcac tccttctcta ggcgccccca tatggccata    1440
tgagatctta tatgggggcac ccccgcccct tgtaaacttc cctgaccctg acatgacaag    1500
agttactaac agcccctctc tccaagctca cttacaggct ctctacttag tccagcacga    1560
agtctggaga cctctggcgg cagcctacca agaacaactg gaccgaccgg tggtacctca    1620
cccttaccga gtcggcgaca cagtgtgggt ccgccgacac cagactaaga acctagaacc    1680
tcgctggaaa ggaccttaca cagtcctgct gaccacccc accgccctca aagtagacgg    1740
catcgcagct tggatacacg ccgccacgt gaaggctgcc gaccccgggg gtggaccatc    1800
ctctagaccg ccatgtcggg ggcaggtgcc accggccgcg ccatggacgg gccgcgcctg    1860
```

```
ctgctgttgc tgcttctggg ggtgtccctt ggaggtgcca aggaggcatg ccccacaggc   1920
ctgtacacac acagcggtga gtgctgcaaa gcctgcaacc tgggcgaggg tgtggcccag   1980
ccttgtggag ccaaccagac cgtgtgtgag ccctgcctgg acagcgtgac gttctccgac   2040
gtggtgagcg cgaccgagcc gtgcaagccg tgcaccgagt gcgtggggct ccagagcatg   2100
tcggcgccat gcgtggaggc cgacgacgcc gtgtgccgct gcgcctacgg ctactaccag   2160
gatgagacga ctgggcgctg cgaggcgtgc cgcgtgtgcg aggcgggctc gggcctcgtg   2220
ttctcctgcc aggacaagca gaacaccgtg tgcgaggagt gccccgacgg cacgtattcc   2280
gacgaggcca accacgtgga cccgtgcctg ccctgcaccg tgtgcgagga caccgagcgc   2340
cagctccgcg agtgcacacg ctgggccgac gccgagtgcg aggagatccc tggccgttgg   2400
attacacggt ccacaccccc agagggctcg gacagcacag cccccagcac ccaggagcct   2460
gaggcacctc cagaacaaga cctcatagcc agcacggtgg caggtgtggt gaccacagtg   2520
atgggcagct cccagcccgt ggtgacccga ggcaccaccg acaacctcat ccctgtctat   2580
tgctccatcc tggctgctgt ggttgtgggt cttgtggcct acatagcctt caagaggtgg   2640
aacagctccg gctccggagc caccaacttc agcctgctga agcaggccgg cgacgtggag   2700 gagaacccg gcccgcggc cgccatggcg acgggttcaa gaacttccct acttcttgca   2760
tttggcctgc tttgtttgcc gtggttacag gaagcctcag caaaacagga ggtgacgcag   2820
attcctgcag ctctgagtgt cccagaagga gaaaacttgg ttctcaactg cagtttcact   2880
gatagcgcta tttacaacct ccagtggttt aggcaggacc ctgggaaagg tctcacatct   2940
ctgttgctta ttcagtcaag tcagagagag caaacaagtg gaagacttaa tgcctcgctg   3000
gataaatcat caggacgtag tactttatac attgcagctt ctcagcctgg tgactcagcc   3060
acctacctct gtgctgtgag tactgcgtat tcaggaggag gtgctgacgg actcacctttt   3120 ggcaaaggga ctcatctaat catccagccc tatatccaga accccgagcc cgccgtgtac   3180
cagctgaagg accccagaag ccaggacagc accctgtgcc tgttcaccga cttcgacagc   3240
cagatcaacg tgcccaagac catggagagc ggcaccttca tcaccgacaa gaccgtgctg   3300
gacatgaagg ccatggacag caagagcaac ggcgccatcg cctggtccaa ccagaccagc   3360
ttcacatgcc aggacatctt caaggagacc aacgccacct accccagcag cgacgtgccc   3420
tgcgacgcca ccctgaccga gaagagcttc gagaccgaca tgaacctgaa cttccagaac   3480
ctgagcgtga tgggcctgag aatcctgctg ctgaaggtgg ccggcttcaa cctgctgatg   3540
accctgaggc tgtggagcag cagggcaaaa cgttcgggtt cgggtgcgcc agtaaagcag   3600
acattaaact ttgatttgct gaaacttgca ggtgatgtag agtcaaatcc aggtccaatg   3660
gcaacaggga gccgaacctc tctgctcctt gctttcgggc tcctttgcct accgtgcctg   3720
caggagggct cggcagatac tggagtctcc cagaacccca gacacaagat cacaaagagg   3780
ggacagaatg taactttcag gtgtgatcca atttctgaac acaaccgcct ttattggtac   3840
cgacagaccc tggggcaggg cccagagttt ctgacttact ccagaatga agctcaacta   3900 gaaaaatcaa ggctgctcag tgatcggttc tctgcagaga ggcctaaggg atctttctcc   3960
accttggaga tccagcgcac agagcagggg gactcggcca tgtatctctg tgccagcagc   4020 ccccgactg ttcgggtcta tggctacacc ttcggttcgg ggaccaggtt aaccgttgta   4080
gaggacctga ggaacgtgac cccccccaag gtgtccctgt tcgagcccag caaggccgag   4140
atcgccaaca agcagaaggc caccctggtg tgcctggcca ggggcttctt ccccgaccac   4200
```

-continued

```
gtggagctgt cttggtgggt gaacggcaag gaggtgcaca gcggcgtgag caccgacccc   4260
caggcctaca aggagagcaa ctacagctac tgcctgagca gcaggctgag agtgagcgcc   4320
accttctggc acaaccccag gaaccacttc cgctgtcagg tgcagttcca cggcctgagc   4380
gaggaggaca agtggcccga gggcagcccc aagcccgtga cccagaacat cagcgccgag   4440
gcctggggca gagccgactg cggcatcacc agcgccagct accaccaggg cgtgctgtcc   4500
gccaccatcc tgtacgagat cctgctgggc aaggccacac tgtacgccgt gctggtgtcc   4560
ggcctggtgc tgatggccat ggtgaagaag aagaacagct aaaggatccg ataaaataaa   4620
agattttatt tagtctccag aaaaaggggg gaatgaaaga ccccacctgt aggtttggca   4680
agctagctta agtaacgcca ttttgcaagg catggaaaat acataactga gaatagagaa   4740
gttcagatca aggttaggaa cagagagaca gcagaatatg ggccaaacag gatatctgtg   4800
gtaagcagtt cctgccccgg ctcagggcca agaacagatg gtccccagat gcggtcccgc   4860
cctcagcagt ttctagagaa ccatcagatg tttccagggt gccccaagga cctgaaatga   4920
ccctgtgcct tatttgaact aaccaatcag ttcgcttctc gcttctgttc gcgcgcttct   4980
gctccccgag ctcaataaaa gagcccacaa cccctcactc ggcgcgccag tcctccgata   5040
gactgcgtcg cccgggtacc cgtgtatcca ataaaccctc ttgcagttgc atccgacttg   5100
tggtctcgct gttccttggg agggtctcct ctgagtgatt gactacccgt cagcgggggt   5160
ctttcatggg taacagtttc ttgaagttgg agaacaacat tctgagggta ggagtcgaat   5220
attaagtaat cctgactcaa ttagccactg ttttgaatcc acatactcca atactcctga   5280
aatccatcga tggagttcat tatggacagc gcagaaagag ctggggagaa ttgtgaaatt   5340
gttatccgct cacaattcca cacaacatac gagccggaag cataaagtgt aaagcctggg   5400
gtgcctaatg agtgagctaa ctcacattaa ttgcgttgcg ctcactgccc gctttccagt   5460
cgggaaacct gtcgtgccag ctgcattaat gaatcggcca acgcgcgggg agaggcggtt   5520
tgcgtattgg cgctcttccg cttcctcgc tcactgactc gctgcgctcg tcgttcggc   5580 tgcggcgagc ggtatcagct cactcaaagg cggtaatacg gttatccaca gaatcagggg   5640
ataacgcagg aaagaacatg tgagcaaaag gccagcaaaa ggccaggaac cgtaaaaagg   5700
ccgcgttgct ggcgtttttc cataggctcc gcccccctga cgagcatcac aaaaatcgac   5760
gctcaagtca gaggtggcga aacccgacag gactataaag ataccaggcg tttccccctg   5820
gaagctccct cgtgcgctct cctgttccga ccctgccgct taccggatac ctgtccgcct   5880
ttctcccttc gggaagcgtg cgctttctc atagctcacg ctgtaggtat ctcagttcgg   5940
tgtaggtcgt tcgctccaag ctgggctgtg tgcacgaacc ccccgttcag cccgaccgct   6000
gcgccttatc cggtaactat cgtcttgagt ccaacccggt aagacacgac ttatcgccac   6060
tggcagcagc cactggtaac aggattagca gagcgaggta tgtaggcggt gctacagagt   6120
tcttgaagtg gtggcctaac tacggctaca ctagaaggac agtatttggt atctgcgctc   6180
tgctgaagcc agttaccttc ggaaaaagag ttggtagctc ttgatccggc aaacaaacca   6240
ccgctggtag cggtggtttt tttgtttgca agcagcagat tacgcgcaga aaaaaggat   6300 ctcaagaaga tcctttgatc ttttctacgg ggtctgacgc tcagtggaac gaaaactcac   6360
gttaagggat tttggtcatg agattatcaa aaaggatctt cacctagatc cttttaaatt   6420
aaaaatgaag ttttaaatca atctaaagta tatatgagta aacttggtct gacagttacc   6480
aatgcttaat cagtgaggca cctatctcag cgatctgtct atttcgttca tccatagttg   6540
cctgactccc cgtcgtgtag ataactacga tacgggaggg cttaccatct ggccccagtg   6600
```

```
ctgcaatgat accgcgagac ccacgctcac cggctccaga tttatcagca ataaaccagc    6660
cagccggaag ggccgagcgc agaagtggtc ctgcaacttt atccgcctcc atccagtcta    6720
ttaattgttg ccgggaagct agagtaagta gttcgccagt taatagtttg cgcaacgttg    6780
ttgccattgc tacaggcatc gtggtgtcac gctcgtcgtt tggtatggct tcattcagct    6840
ccggttccca acgatcaagg cgagttacat gatcccccat gttgtgcaaa aaagcggtta    6900
gctccttcgg tcctccgatc gttgtcagaa gtaagttggc cgcagtgtta tcactcatgg    6960
ttatggcagc actgcataat tctcttactg tcatgccatc cgtaagatgc ttttctgtga    7020
ctggtgagta ctcaaccaag tcattctgag aatagtgtat gcggcgaccg agttgctctt    7080
gcccggcgtc aatacgggat aataccgcgc cacatagcag aactttaaaa gtgctcatca    7140
ttggaaaacg ttcttcgggg cgaaaactct caaggatctt accgctgttg agatccagtt    7200
cgatgtaacc cactcgtgca cccaactgat cttcagcatc ttttactttc accagcgttt    7260
ctgggtgagc aaaaacagga aggcaaaatg ccgcaaaaaa gggaataagg cgacacgga    7320 aatgttgaat actcatactc ttcctttttc aatattattg aagcatttat cagggttatt    7380
gtctcatgag cggatacata tttgaatgta tttagaaaaa taaacaaata ggggttccgc    7440
gcacatttcc ccgaaaagtg ccacctgacg tctaagaaac cattattatc atgacattaa    7500
cctataaaaa taggcgtatc acgaggccct ttcgtctcgc gcgtttcggt gatgacggtg    7560
aaaacctctg acacatgcag ctcccggaga cggtcacagc ttgtctgtaa gcggatgccg    7620
ggagcagaca gcccgtcag ggcgcgtcag cgggtgttgg cgggtgtcgg ggctggctta    7680
actatgcggc atcagagcag attgtactga gagtgcacca tatgcggtgt gaaataccgc    7740
acagatgcgt aaggagaaaa taccgcatca ggcgccattc gccattcagg ctgcgcaact    7800
gttgggaagg gcgatcggtg cgggcctctt cgctattacg ccagctggcg aaagggggat    7860
gtgctgcaag gcgattaagt tgggtaacgc cagggttttc ccagtcacga cgttgtaaaa    7920
cgacggccag tgccacgctc tcccttatgc gactcctgca ttaggaagca gcccagtagt    7980
aggttgaggc cgttgagcac cgccgccgca aggaatggtg catgcaagga gatggcgccc    8040
aacagtcccc cggccacggg gcctgccacc atacccacgc cgaaacaagc gctcatgagc    8100
ccgaagtggc gagcccgatc ttccccatcg gtgatgtcgg cgatataggc gccagcaacc    8160
gcacctgtgg cgccggtgat gccggccacg atgcgtccgg cgtagaggcg atttaaagac    8220
aggatatcag tggtccaggc tctagttttg actcaacaat atcaccagct gaagcctata    8280
gagtacgagc catagataaa ataaaagatt ttatttagtc tccagaaaaa gggggga      8338
```

```
<210> SEQ ID NO 33
<211> LENGTH: 8323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
tgaaagaccc cacctgtagg tttggcaagc tagcttaagt aacgccattt tgcaaggcat      60
ggaaaataca taactgagaa tagagaagtt cagatcaagg ttaggaacag agagacagca     120
gaatatgggc caaacaggat atctgtggta agcagttcct gccccggctc agggccaaga     180
acagatggtc cccagatgcg gtcccgccct cagcagtttc tagagaacca tcagatgttt     240
ccagggtgcc ccaaggacct gaaatgacc ctgtgcctta tttgaactaa ccaatcagtt      300
```

-continued

```
cgcttctcgc ttctgttcgc gcgcttctgc tccccgagct caataaaaga gcccacaacc    360
cctcactcgg cgcgccagtc ctccgataga ctgcgtcgcc cgggtacccg tattcccaat    420
aaagcctctt gctgtttgca tccgaatcgt ggactcgctg atccttggga gggtctcctc    480
agattgattg actgcccacc tcgggggtct ttcatttgga ggttccaccg agatttggag    540
acccctgcct agggaccacc gacccccccg ccgggaggta agctggccag cggtcgtttc    600
gtgtctgtct ctgtctttgt gcgtgtttgt gccggcatct aatgtttgcg cctgcgtctg    660
tactagttag ctaactagct ctgtatctgg cggacccgtg gtggaactga cgagttcgga    720
acacccggcc gcaaccctgg gagacgtccc agggacttcg ggggccgttt ttgtggcccg    780
acctgagtcc taaaatcccg atcgtttagg actctttggt gcacccccct tagaggaggg    840
atatgtggtt ctggtaggag acgagaacct aaaacagttc ccgcctccgt ctgaattttt    900
gctttcggtt tgggaccgaa gccgcgccgc gcgtcttgtc tgctgcagca tcgttctgtg    960
ttgtctctgt ctgactgtgt ttctgtattt gtctgaaaat atgggcccgg gctagcctgt   1020
taccactccc ttaagtttga ccttaggtca ctggaaagat gtcgagcgga tcgctcacaa   1080
ccagtcggta gatgtcaaga agagacgttg ggttaccttc tgctctgcag aatggccaac   1140
ctttaacgtc ggatggccgc gagacggcac ctttaaccga gacctcatca cccaggttaa   1200
gatcaaggtc ttttcacctg gcccgcatgg acacccagac caggtcccct acatcgtgac   1260
ctgggaagcc ttggcttttg acccccctcc ctgggtcaag ccctttgtac accctaagcc   1320
tccgcctcct cttcctccat ccgccccgtc tctccccctt gaacctcctc gttcgacccc   1380
gcctcgatcc tccctttatc cagccctcac tccttctcta ggcgccccca tatggccata   1440
tgagatctta tatggggcac ccccgcccct tgtaaacttc cctgaccctg acatgacaag   1500
agttactaac agcccctctc tccaagctca cttacaggct ctctacttag tccagcacga   1560
agtctggaga cctctggcgg cagcctacca agaacaactg gaccgaccgg tggtacctca   1620
cccttaccga gtcggcgaca cagtgtgggt ccgccgacac cagactaaga acctagaacc   1680
tcgctggaaa ggaccttaca cagtcctgct gaccacccc accgccctca aagtagacgg   1740
catcgcagct tggatacacg ccgcccacgt gaaggctgcc gaccccgggg gtggaccatc   1800
ctctagaccg ccatgtcggg ggcaggtgcc accggccgcg ccatggacgg gccgcgcctg   1860
ctgctgttgc tgcttctggg ggtgtccctt ggaggtgcca aggaggcatg ccccacaggc   1920
ctgtacacac acagcggtga gtgctgcaaa gcctgcaacc tgggcgaggg tgtggcccag   1980
ccttgtggag ccaaccagac cgtgtgtgag ccctgcctgg acagcgtgac gttctccgac   2040
gtggtgagcg cgaccgagcc gtgcaagccg tgcaccgagt gcgtggggct ccagagcatg   2100
tcggcgccat gcgtggaggc cgacgacgcc gtgtgccgct gcgcctacgg ctactaccag   2160
gatgagacga ctgggcgctg cgaggcgtgc cgcgtgtgcg aggcgggctc gggcctcgtg   2220
ttctcctgcc aggacaagca gaacaccgtg tgcgaggagt cccccgacgg cacgtattcc   2280
gacgaggcca accacgtgga cccgtgcctg ccctgcaccg tgtgcgagga caccgagcgc   2340
cagctccgcg agtgcacacg ctgggccgac gccgagtgcg aggagatccc tggccgttgg   2400
attacacggt ccacacccc agagggctcg gacagcacag cccccagcac ccaggagcct   2460
gaggcacctc cagaacaaga cctcatagcc agcacggtgg caggtgtggt gaccacagtg   2520
atgggcagct cccagcccgt ggtgacccga ggcaccaccg acaacctcat ccctgtctat   2580
tgctccatcc tggctgctgt ggttgtgggt cttgtggcct acatagcctt caagaggtgg   2640
```

-continued

```
aacagctccg gctccggagc caccaacttc agcctgctga agcaggccgg cgacgtggag      2700
gagaaccccg gccccgcggc cgccatggcg acgggttcaa gaacttccct acttcttgca      2760
tttggcctgc tttgtttgcc gtggttacag gaagcctcag caggacaaca ggtaatgcaa      2820
attcctcagt accagcatgt acaagaagga gaagacttca ccacgtactg caattcctca      2880
actactttaa gcaatataca gtggtataag caaaggcctg gtggacatcc cgtttttttg      2940
atacagttag tgaagagtgg agaagtgaag aagcagaaaa gactgacatt tcagtttgga      3000
gaagcaaaaa agaacagctc cctgcacatc acagccaccc agactacaga tgtaggaacc      3060
tacttctgtg cggaccctaa ctttggaaat gagaaattaa cctttgggac tggaacaaga      3120
ctcaccatca tacccaatat ccagaacccc gagcccgccg tgtaccagct gaaggacccc      3180
agaagccagg acagcaccct gtgcctgttc accgacttcg acagccagat caacgtgccc      3240
aagaccatgg agagcggcac cttcatcacc gacaagaccg tgctggacat gaaggccatg      3300
gacagcaaga gcaacggcgc catcgcctgg tccaaccaga ccagcttcac atgccaggac      3360
atcttcaagg agaccaacgc cacctacccc agcagcgacg tgccctgcga cgccaccctg      3420
accgagaaga gcttcgagac cgacatgaac ctgaacttcc agaacctgag cgtgatgggc      3480
ctgagaatcc tgctgctgaa ggtggccggc ttcaacctgc tgatgaccct gaggctgtgg      3540
agcagcaggg caaaacgttc gggttcgggt gcgccagtaa agcagacatt aaactttgat      3600
ttgctgaaac ttgcaggtga tgtagagtca aatccaggtc caatggcaac agggagccga      3660
acctctctgc tccttgcttt cgggctcctt tgcctaccgt gcctgcagga gggctcggca      3720
gaagcccaag tgacccagaa cccaagatac ctcatcacag tgactggaaa gaagttaaca      3780
gtgacttgtt ctcagaatat gaaccatgag tatatgtcct ggtatcgaca agacccaggg      3840
ctgggcttaa ggcagatcta ctattcaatg aatgttgagg tgactgataa gggagatgtt      3900
cctgaagggt acaaagtctc tcgaaaagag aagaggaatt tcccctgat cctggagtcg      3960 cccagcccca accagacctc tctgtacttc tgtgccagca gtttgaatcc ctttgcaact      4020
aatgaaaaac tgttttttgg cagtggaacc cagctctctg tcttggagga cctgaggaac      4080 gtgaccccc ccaaggtgtc cctgttcgag cccagcaagg ccgagatcgc caacaagcag      4140
aaggccaccc tggtgtgcct ggccagggc ttcttccccg accacgtgga gctgtcttgg      4200
tgggtgaacg gcaaggaggt gcacagcggc gtgagcaccg acccccaggc ctacaaggag      4260
agcaactaca gctactgcct gagcagcagg ctgagagtga gcgccacctt ctggcacaac      4320
cccaggaacc acttccgctg tcaggtgcag ttccacggcc tgagcgagga ggacaagtgg      4380
cccgagggca gccccaagcc cgtgacccag aacatcagcg ccgaggcctg gggcagagcc      4440
gactgcggca tcaccagcgc cagctaccac caggcgtgc tgtccgccac catcctgtac      4500
gagatcctgc tgggcaaggc cacactgtac gccgtgctgg tgtccggcct ggtgctgatg      4560
gccatggtga gaagaagaa cagctaaagg atccgataaa ataaaagatt ttatttagtc      4620
tccagaaaaa gggggaatg aaagacccca cctgtaggtt tggcaagcta gcttaagtaa      4680
cgccattttg caaggcatgg aaaatacata actgagaata gagaagttca gatcaaggtt      4740
aggaacagag agacagcaga atatgggcca aacaggatat ctgtggtaag cagttcctgc      4800
cccggctcag ggccaagaac agatggtccc cagatgcggt cccgccctca gcagtttcta      4860
gagaaccatc agatgtttcc agggtgcccc aaggacctga aatgaccctg tgccttattt      4920
gaactaacca atcagttcgc ttctcgcttc tgttcgcgcg cttctgctcc ccgagctcaa      4980
taaaagagcc cacaaccct cactcggcgc gccagtcctc cgatagactg cgtcgcccgg      5040
```

-continued

```
gtacccgtgt atccaataaa ccctcttgca gttgcatccg acttgtggtc tcgctgttcc      5100
ttgggagggt ctcctctgag tgattgacta cccgtcagcg ggggtctttc atgggtaaca      5160
gtttcttgaa gttggagaac aacattctga gggtaggagt cgaatattaa gtaatcctga      5220
ctcaattagc cactgttttg aatccacata ctccaatact cctgaaatcc atcgatggag      5280
ttcattatgg acagcgcaga aagagctggg gagaattgtg aaattgttat ccgctcacaa      5340
ttccacacaa catacgagcc ggaagcataa agtgtaaagc ctggggtgcc taatgagtga      5400
gctaactcac attaattgcg ttgcgctcac tgcccgcttt ccagtcggga aacctgtcgt      5460
gccagctgca ttaatgaatc ggccaacgcg cggggagagg cggtttgcgt attgggcgct      5520
cttccgcttc ctcgctcact gactcgctgc gctcggtcgt tcggctgcgg cgagcggtat      5580
cagctcactc aaaggcggta atacggttat ccacagaatc aggggataac gcaggaaaga      5640
acatgtgagc aaaaggccag caaaaggcca ggaaccgtaa aaaggccgcg ttgctggcgt      5700
ttttccatag gctccgcccc cctgacgagc atcacaaaaa tcgacgctca agtcagaggt      5760
ggcgaaaccc gacaggacta taaagatacc aggcgtttcc ccctggaagc tccctcgtgc      5820
gctctcctgt tccgaccctg ccgcttaccg gatacctgtc cgcctttctc ccttcgggaa      5880
gcgtggcgct ttctcatagc tcacgctgta ggtatctcag ttcggtgtag gtcgttcgct      5940
ccaagctggg ctgtgtgcac gaaccccccg ttcagcccga ccgctgcgcc ttatccggta      6000
actatcgtct tgagtccaac ccggtaagac acgacttatc gccactggca gcagccactg      6060
gtaacaggat tagcagagcg aggtatgtag gcggtgctac agagttcttg aagtggtggc      6120
ctaactacgg ctacactaga aggacagtat ttggtatctg cgctctgctg aagccagtta      6180
ccttcggaaa aagagttggt agctcttgat ccggcaaaca aaccaccgct ggtagcggtg      6240
gtttttttgt ttgcaagcag cagattacgc gcagaaaaaa aggatctcaa gaagatcctt      6300
tgatcttttc tacggggtct gacgctcagt ggaacgaaaa ctcacgttaa gggattttgg      6360
tcatgagatt atcaaaaagg atcttcacct agatcctttt aaattaaaaa tgaagtttta      6420
aatcaatcta agtatatat gagtaaactt ggtctgacag ttaccaatgc ttaatcagtg      6480
aggcacctat ctcagcgatc tgtctatttc gttcatccat agttgcctga ctccccgtcg      6540
tgtagataac tacgatacgg gagggcttac catctggccc cagtgctgca atgataccgc      6600
gagacccacg ctcaccggct ccagatttat cagcaataaa ccagccagcc ggaagggccg      6660
agcgcagaag tggtcctgca actttatccg cctccatcca gtctattaat tgttgccggg      6720
aagctagagt aagtagttcg ccagttaata gtttgcgcaa cgttgttgcc attgctacag      6780
gcatcgtggt gtcacgctcg tcgtttggta tggcttcatt cagctccggt tcccaacgat      6840
caaggcgagt tacatgatcc cccatgttgt gcaaaaaagc ggttagctcc ttcggtcctc      6900
cgatcgttgt cagaagtaag ttggccgcag tgttatcact catggttatg gcagcactgc      6960
ataattctct tactgtcatg ccatccgtaa gatgcttttc tgtgactggt gagtactcaa      7020
ccaagtcatt ctgagaatag tgtatgcggc gaccgagttg ctcttgcccg gcgtcaatac      7080
gggataatac cgcgccacat agcagaactt taaaagtgct catcattgga aaacgttctt      7140
cggggcgaaa actctcaagg atcttaccgc tgttgagatc cagttcgatg taacccactc      7200
gtgcacccaa ctgatcttca gcatctttta ctttcaccag cgtttctggg tgagcaaaaa      7260
caggaaggca aaatgccgca aaaaagggaa taagggcgac acggaaatgt tgaatactca      7320
tactcttcct ttttcaatat tattgaagca tttatcaggg ttattgtctc atgagcggat      7380
```

-continued

```
acatatttga atgtatttag aaaaataaac aaataggggt tccgcgcaca tttccccgaa      7440
aagtgccacc tgacgtctaa gaaaccatta ttatcatgac attaacctat aaaaataggc      7500
gtatcacgag gccctttcgt ctcgcgcgtt tcggtgatga cggtgaaaac ctctgacaca      7560
tgcagctccc ggagacggtc acagcttgtc tgtaagcgga tgccgggagc agacaagccc      7620
gtcagggcgc gtcagcgggt gttggcgggt gtcggggctg gcttaactat gcggcatcag      7680
agcagattgt actgagagtg caccatatgc ggtgtgaaat accgcacaga tgcgtaagga      7740
gaaaataccg catcaggcgc cattcgccat tcaggctgcg caactgttgg gaagggcgat      7800
cggtgcgggc ctcttcgcta ttacgccagc tggcgaaagg gggatgtgct gcaaggcgat      7860
taagttgggt aacgccaggg ttttcccagt cacgacgttg taaaacgacg gccagtgcca      7920
cgctctccct tatgcgactc ctgcattagg aagcagccca gtagtaggtt gaggccgttg      7980
agcaccgccg ccgcaaggaa tggtgcatgc aaggagatgg cgcccaacag tcccccggcc      8040
acggggcctg ccaccatacc cacgccgaaa caagcgctca tgagcccgaa gtggcgagcc      8100
cgatcttccc catcggtgat gtcggcgata taggcgccag caaccgcacc tgtggcgccg      8160
gtgatgccgg ccacgatgcg tccggcgtag aggcgattta aagacaggat atcagtggtc      8220
caggctctag ttttgactca acaatatcac cagctgaagc ctatagagta cgagccatag      8280
ataaaataaa agattttatt tagtctccag aaaaaggggg gaa                       8323
```

```
<210> SEQ ID NO 34
<211> LENGTH: 8317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34
```

```
tgaaagaccc cacctgtagg tttggcaagc tagcttaagt aacgccattt tgcaaggcat        60
ggaaaataca taactgagaa tagagaagtt cagatcaagg ttaggaacag agagacagca       120
gaatatgggc caaacaggat atctgtggta agcagttcct gccccggctc agggccaaga       180
acagatggtc cccagatgcg gtcccgccct cagcagtttc tagagaacca tcagatgttt       240
ccagggtgcc ccaaggacct gaaaatgacc ctgtgcctta tttgaactaa ccaatcagtt       300
cgcttctcgc ttctgttcgc gcgcttctgc tccccgagct caataaaaga gcccacaacc       360
cctcactcgg cgcgccagtc ctccgataga ctgcgtcgcc cgggtacccg tattcccaat       420
aaagcctctt gctgtttgca tccgaatcgt ggactcgctg atccttggga gggtctcctc       480
agattgattg actgcccacc tcggggggtct ttcatttgga ggttccaccg agatttggag       540
acccctgcct agggaccacc gacccccccg ccgggaggta agctggccag cggtcgtttc       600
gtgtctgtct ctgtctttgt gcgtgtttgt gccggcatct aatgtttgcg cctgcgtctg       660
tactagttag ctaactagct ctgtatctgg cggacccgtg gtggaactga cgagttcgga       720
acacccggcc gcaaccctgg gagacgtccc agggacttcg ggggccgttt ttgtggcccg       780
acctgagtcc taaaatcccg atcgtttagg actctttggt gcaccccccct tagaggaggg       840 atatgtggtt ctggtaggag acgagaacct aaaacagttc ccgcctccgt ctgaattttt       900
gctttcggtt tgggaccgaa gccgcgccgc gcgtcttgtc tgctgcagca tcgttctgtg       960
ttgtctctgt ctgactgtgt ttctgtattt gtctgaaaat atgggcccgg gctagcctgt      1020
taccactccc ttaagtttga ccttaggtca ctggaaagat gtcgagcgga tcgctcacaa      1080
```

```
ccagtcggta gatgtcaaga agagacgttg ggttaccttc tgctctgcag aatggccaac    1140
ctttaacgtc ggatggccgc gagacggcac ctttaaccga gacctcatca cccaggttaa    1200
gatcaaggtc ttttcacctg gcccgcatgg acacccagac caggtcccct acatcgtgac    1260
ctgggaagcc ttggcttttg acccccctcc ctgggtcaag ccctttgtac accctaagcc    1320
tccgcctcct cttcctccat ccgccccgtc tctccccctt gaacctcctc gttcgacccc    1380
gcctcgatcc tccctttatc cagccctcac tccttctcta ggcgccccca tatggccata    1440
tgagatctta tatggggcac ccccgcccct tgtaaacttc cctgaccctg acatgacaag    1500
agttactaac agcccctctc tccaagctca cttacaggct ctctacttag tccagcacga    1560
agtctggaga cctctggcgg cagcctacca agaacaactg gaccgaccgg tggtacctca    1620
cccttaccga gtcggcgaca cagtgtgggt ccgccgacac cagactaaga acctagaacc    1680
tcgctggaaa ggaccttaca cagtcctgct gaccacccc accgccctca aagtagacgg    1740
catcgcagct tggatacacg ccgcccacgt gaaggctgcc gaccccgggg gtggaccatc    1800
ctctagaccg ccatgtcggg ggcaggtgcc accggccgcg ccatggacgg gccgcgcctg    1860
ctgctgttgc tgcttctggg ggtgtccctt ggaggtgcca aggaggcatg ccccacaggc    1920
ctgtacacac acagcggtga gtgctgcaaa gcctgcaacc tgggcgaggg tgtggcccag    1980
ccttgtggag ccaaccagac cgtgtgtgag ccctgcctgg acagcgtgac gttctccgac    2040
gtggtgagcg cgaccgagcc gtgcaagccg tgcaccgagt gcgtggggct ccagagcatg    2100
tcggcgccat gcgtggaggc cgacgacgcc gtgtgccgct gcgcctacgg ctactaccag    2160
gatgagacga ctgggcgctg cgaggcgtgc cgcgtgtgcg aggcgggctc gggcctcgtg    2220
ttctcctgcc aggacaagca gaacaccgtg tgcgaggagt gccccgacgg cacgtattcc    2280
gacgaggcca accacgtgga cccgtgcctg ccctgcaccg tgtgcgagga caccgagcgc    2340
cagctccgcg agtgcacacg ctgggccgac gccgagtgcg aggagatccc tggccgttgg    2400
attacacggt ccacacccccc agagggctcg gacagcacag cccccagcac ccaggagcct    2460
gaggcacctc cagaacaaga cctcatagcc agcacggtgg caggtgtggt gaccacagtg    2520
atgggcagct cccagcccgt ggtgacccga ggcaccaccg acaacctcat ccctgtctat    2580
tgctccatcc tggctgctgt ggttgtgggt cttgtggcct acatagcctt caagaggtgg    2640
aacagctccg gctccggagc caccaacttc agcctgctga gcaggccgg cgacgtggag    2700 gagaaccccg gccccgcggc cgccatggcg acgggttcaa gaacttccct acttcttgca    2760
tttggcctgc tttgtttgcc gtggttacag gaagcctcag caggacaaaa cattgaccag    2820
cccactgaga tgacagctac ggaaggtgcc attgtccaga tcaactgcac gtaccagaca    2880
tctgggttca acgggctgtt ctggtaccag caacatgctg cgcgaagcacc tacatttctg    2940 tcttacaatg ttctggatgg tttggaggag aaaggtcgtt tttcttcatt ccttagtcgg    3000
tctaaagggt acagttacct ccttttgaag gagctccaga tgaaagactc tgcctcttac    3060
ctctgtgctg tgagaggcga ctacaagctc agctttggag ccggaaccac agtaactgta    3120
agagcaaata tccagaaccc cgagcccgcc gtgtaccagc tgaaggaccc cagaagccag    3180
gacagcaccc tgtgcctgtt caccgacttc gacagccaga tcaacgtgcc caagaccatg    3240
gagagcggca cccttcatcac cgacaagacc gtgctggaca tgaaggccat ggacagcaag    3300
agcaacggcg ccatcgcctg gtccaaccag accagcttca catgccagga catcttcaag    3360
gagaccaacg ccacctaccc cagcagcgac gtgccctgcg acgccaccct gaccgagaag    3420
agcttcgaga ccgacatgaa cctgaacttc cagaacctga gcgtgatggg cctgagaatc    3480
```

```
ctgctgctga aggtggccgg cttcaacctg ctgatgaccc tgaggctgtg gagcagcagg      3540
gcaaaacgtt cgggttcggg tgcgccagta aagcagacat taaactttga tttgctgaaa      3600
cttgcaggtg atgtagagtc aaatccaggt ccaatggcaa cagggagccg aacctctctg      3660
ctccttgctt tcgggctcct ttgcctaccg tgcctgcagg agggctcggc agattctgga      3720
gtcacacaaa ccccaaagca cctgatcaca gcaactggac agcgagtgac gctgagatgc      3780
tcccctaggt ctggagacct ctctgtgtac tggtaccaac agagcctgga ccagggcctc      3840
cagttcctca ttcagtatta taatggagaa gagagagcaa aaggaaacat tcttgaacga      3900
ttctccgcac aacagttccc tgacttgcac tctgaactaa acctgagctc tctggagctg      3960
ggggactcag ctttgtattt ctgtgccagc agctcgatac acggtgtctc tggggccaac      4020
gtcctgactt cgggggccgg cagcaggctg accgtgctgg aggacctgag gaacgtgacc      4080
cccccaaagg tgtccctgtt cgagcccagc aaggccgaga tcgccaacaa gcagaaggcc      4140
accctggtgt gcctggccag gggcttcttc cccgaccacg tggagctgtc ttggtgggtg      4200
aacggcaagg aggtgcacag cggcgtgagc accgacccc aggcctacaa ggagagcaac      4260
tacagctact gcctgagcag caggctgaga gtgagcgcca ccttctggca caaccccagg      4320
aaccacttcc gctgtcaggt gcagttccac ggcctgagcg aggaggacaa gtggcccgag      4380
ggcagcccca gcccgtgac ccagaacatc agcgccgagg cctggggcag agccgactgc      4440
ggcatcacca gcgccagcta ccaccagggc gtgctgtccg ccaccatcct gtacgagatc      4500
ctgctgggca aggccacact gtacgccgtg ctggtgtccg gcctggtgct gatggccatg      4560
gtgaagaaga agaacagcta aaggatccga taaaataaaa gattttattt agtctccaga      4620 aaaaggggg aatgaaagac cccacctgta ggtttggcaa gctagcttaa gtaacgccat      4680
tttgcaaggc atggaaaata cataactgag aatagagaag ttcagatcaa ggttaggaac      4740
agagagacag cagaatatgg gccaaacagg atatctgtgg taagcagttc ctgccccggc      4800
tcagggccaa gaacagatgg tccccagatg cggtcccgcc ctcagcagtt tctagagaac      4860
catcagatgt ttccagggtg ccccaaggac ctgaaatgac cctgtgcctt atttgaacta      4920
accaatcagt tcgcttctcg cttctgttcg cgcgcttctg ctccccgagc tcaataaaag      4980
agcccacaac ccctcactcg gcgcgccagt cctccgatag actgcgtcgc ccgggtaccc      5040
gtgtatccaa taaaccctct tgcagttgca tccgacttgt ggtctcgctg ttccttggga      5100
gggtctcctc tgagtgattg actacccgtc agcgggggtc tttcatgggt aacagtttct      5160
tgaagttgga gaacaacatt ctgagggtag gagtcgaata ttaagtaatc ctgactcaat      5220
tagccactgt tttgaatcca catactccaa tactcctgaa atccatcgat ggagttcatt      5280
atggacagcg cagaaagagc tggggagaat tgtgaaattg ttatccgctc acaattccac      5340
acaacatacg agccggaagc ataaagtgta aagcctgggg tgcctaatga gtgagctaac      5400
tcacattaat tgcgttgcgc tcactgcccg ctttccagtc gggaaacctg tcgtgccagc      5460
tgcattaatg aatcggccaa cgcgcgggga gaggcggttt gcgtattggg cgctcttccg      5520
cttcctcgct cactgactcg ctgcgctcgg tcgttcggct gcggcgagcg gtatcagctc      5580
actcaaaggc ggtaatacgg ttatccacag aatcagggga taacgcagga aagaacatgt      5640
gagcaaaagg ccagcaaaag gccaggaacc gtaaaaaggc cgcgttgctg gcgtttttcc      5700
ataggctccg cccccctgac gagcatcaca aaaatcgacg ctcaagtcag aggtggcgaa      5760
acccgacagg actataaaga taccaggcgt ttccccctgg aagctccctc gtgcgctctc      5820
```

-continued

```
ctgttccgac cctgccgctt accggatacc tgtccgcctt tctcccttcg ggaagcgtgg    5880
cgctttctca tagctcacgc tgtaggtatc tcagttcggt gtaggtcgtt cgctccaagc    5940
tgggctgtgt gcacgaaccc cccgttcagc ccgaccgctg cgccttatcc ggtaactatc    6000
gtcttgagtc caacccggta agacacgact tatcgccact ggcagcagcc actggtaaca    6060
ggattagcag agcgaggtat gtaggcggtg ctacagagtt cttgaagtgg tggcctaact    6120
acggctacac tagaaggaca gtatttggta tctgcgctct gctgaagcca gttaccttcg    6180
gaaaaagagt tggtagctct tgatccggca aacaaaccac cgctggtagc ggtggttttt    6240
ttgtttgcaa gcagcagatt acgcgcagaa aaaaaggatc tcaagaagat cctttgatct    6300
tttctacggg gtctgacgct cagtggaacg aaaactcacg ttaagggatt ttggtcatga    6360
gattatcaaa aaggatcttc acctagatcc ttttaaatta aaaatgaagt tttaaatcaa    6420
tctaaagtat atatgagtaa acttggtctg acagttacca atgcttaatc agtgaggcac    6480
ctatctcagc gatctgtcta tttcgttcat ccatagttgc ctgactcccc gtcgtgtaga    6540
taactacgat acgggagggc ttaccatctg gccccagtgc tgcaatgata ccgcgagacc    6600
cacgctcacc ggctccagat ttatcagcaa taaaccagcc agccggaagg gccgagcgca    6660
gaagtggtcc tgcaacttta tccgcctcca tccagtctat taattgttgc cgggaagcta    6720
gagtaagtag ttcgccagtt aatagtttgc gcaacgttgt tgccattgct acaggcatcg    6780
tggtgtcacg ctcgtcgttt ggtatggctt cattcagctc cggttcccaa cgatcaaggc    6840
gagttacatg atcccccatg ttgtgcaaaa aagcggttag ctccttcggt cctccgatcg    6900
ttgtcagaag taagttggcc gcagtgttat cactcatggt tatggcagca ctgcataatt    6960
ctcttactgt catgccatcc gtaagatgct tttctgtgac tggtgagtac tcaaccaagt    7020
cattctgaga atagtgtatg cggcgaccga gttgctcttg cccggcgtca atacgggata    7080
ataccgcgcc acatagcaga actttaaaag tgctcatcat tggaaaacgt tcttcggggc    7140
gaaaactctc aaggatctta ccgctgttga tccagttc gatgtaaccc actcgtgcac     7200
ccaactgatc ttcagcatct tttactttca ccagcgtttc tgggtgagca aaaacaggaa    7260
ggcaaaatgc cgcaaaaaag ggaataaggg cgacacggaa atgttgaata ctcatactct    7320
tcctttttca atattattga agcatttatc agggttattg tctcatgagc ggatacatat    7380
ttgaatgtat ttagaaaaat aaacaaatag gggttccgcg cacatttccc cgaaaagtgc    7440
cacctgacgt ctaagaaacc attattatca tgacattaac ctataaaaat aggcgtatca    7500
cgaggccctt tcgtctcgcg cgtttcggtg atgacggtga aaacctctga cacatgcagc    7560
tcccggagac ggtcacagct tgtctgtaag cggatgccgg gagcagacaa gcccgtcagg    7620
gcgcgtcagc gggtgttggc gggtgtcggg gctggcttaa ctatgcggca tcagagcaga    7680
ttgtactgag agtgcaccat atgcggtgtg aaataccgca cagatgcgta aggagaaaat    7740
accgcatcag cgccattcg ccattcaggc tgcgcaactg ttgggaaggg cgatcggtgc     7800
gggcctcttc gctattacgc cagctggcga aggggggatg gctgcaagg cgattaagtt     7860 gggtaacgcc agggttttcc cagtcacgac gttgtaaaac gacggccagt gccacgctct    7920
cccttatgcg actcctgcat taggaagcag cccagtagta ggttgaggcc gttgagcacc    7980
gccgccgcaa ggaatggtgc atgcaaggag atggcgccca acagtccccc ggccacgggg    8040
cctgccacca tacccacgcc gaaacaagcg ctcatgagcc cgaagtggcg agcccgatct    8100
tccccatcgg tgatgtcggc gatataggcg ccagcaaccg cacctgtggc gccggtgatg    8160
ccggccacga tgcgtccggc gtagaggcga tttaaagaca ggatatcagt ggtccaggct    8220
```

-continued

```
ctagttttga ctcaacaata tcaccagctg aagcctatag agtacgagcc atagataaaa      8280
taaaagattt tatttagtct ccagaaaaag gggggaa                               8317

<210> SEQ ID NO 35
<211> LENGTH: 8317
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35
tgaaagaccc cacctgtagg tttggcaagc tagcttaagt aacgccattt tgcaaggcat        60
ggaaaataca taactgagaa tagagaagtt cagatcaagg ttaggaacag agagacagca       120
gaatatgggc caaacaggat atctgtggta agcagttcct gccccggctc agggccaaga       180
acagatggtc cccagatgcg gtcccgccct cagcagtttc tagagaacca tcagatgttt       240
ccagggtgcc ccaaggacct gaaaatgacc ctgtgcctta tttgaactaa ccaatcagtt       300
cgcttctcgc ttctgttcgc gcgcttctgc tccccgagct caataaaaga gcccacaacc       360
cctcactcgg cgcgccagtc ctccgataga ctgcgtcgcc cgggtacccg tattcccaat       420
aaagcctctt gctgtttgca tccgaatcgt ggactcgctg atccttggga gggtctcctc       480
agattgattg actgcccacc tcgggggtct ttcatttgga ggttccaccg agatttggag       540
acccctgcct agggaccacc gacccccccg ccgggaggta agctggccag cggtcgtttc       600
gtgtctgtct ctgtctttgt gcgtgtttgt gccggcatct aatgtttgcg cctgcgtctg       660
tactagttag ctaactagct ctgtatctgg cggacccgtg gtggaactga cgagttcgga       720
acacccggcc gcaaccctgg gagacgtccc agggacttcg ggggccgttt ttgtggcccg       780
acctgagtcc taaaatcccg atcgtttagg actctttggt gcaccccccct tagaggaggg       840 atatgtggtt ctggtaggag acgagaacct aaaacagttc ccgcctccgt ctgaattttt       900
gctttcggtt tgggaccgaa gccgcgccgc gcgtcttgtc tgctgcagca tcgttctgtg       960
ttgtctctgt ctgactgtgt ttctgtattt gtctgaaaat atgggcccgg gctagcctgt      1020
taccactccc ttaagtttga ccttaggtca ctggaaagat gtcgagcgga tcgctcacaa      1080
ccagtcggta gatgtcaaga agagacgttg ggttaccttc tgctctgcag aatggccaac      1140
ctttaacgtc ggatggccgc gagacggcac ctttaaccga gacctcatca cccaggttaa      1200
gatcaaggtc ttttcacctg gcccgcatgg acacccagac caggtcccct acatcgtgac      1260
ctgggaagcc ttggcttttg accccctcc ctgggtcaag ccctttgtac accctaagcc      1320
tccgcctcct cttcctccat ccgccccgtc tctcccctt gaacctcctc gttcgacccc      1380
gcctcgatcc tcctttatc cagccctcac tccttctcta ggcgcccca tatggccata      1440 tgagatctta tatggggcac ccccgcccct tgtaaacttc cctgaccctg acatgacaag      1500
agttactaac agcccctctc tccaagctca cttacaggct ctctacttag tccagcacga      1560
agtctggaga cctctggcgg cagcctacca agaacaactg gaccgaccgg tggtacctca      1620
cccttaccga gtcggcgaca cagtgtgggt ccgccgacac cagactaaga acctagaacc      1680
tcgctggaaa ggaccttaca cagtcctgct gaccacccc accgccctca aagtagacgg      1740
catcgcagct tggatacacg ccgcccacgt gaaggctgcc gaccccgggg gtggaccatc      1800
ctctagaccg ccatgtcggg ggcaggtgcc accggccgcg ccatggacgg gccgcgcctg      1860
ctgctgttgc tgcttctggg ggtgtccctt ggaggtgcca aggaggcatg ccccacaggc      1920
```

-continued

```
ctgtacacac acagcggtga gtgctgcaaa gcctgcaacc tgggcgaggg tgtggcccag    1980
ccttgtggag ccaaccagac cgtgtgtgag ccctgcctgg acagcgtgac gttctccgac    2040
gtggtgagcg cgaccgagcc gtgcaagccg tgcaccgagt gcgtggggct ccagagcatg    2100
tcggcgccat gcgtggaggc cgacgacgcc gtgtgccgct gcgcctacgg ctactaccag    2160
gatgagacga ctgggcgctg cgaggcgtgc cgcgtgtgcg aggcgggctc gggcctcgtg    2220
ttctcctgcc aggacaagca gaacaccgtg tgcgaggagt gccccgacgg cacgtattcc    2280
gacgaggcca accacgtgga cccgtgcctg ccctgcaccg tgtgcgagga caccgagcgc    2340
cagctccgcg agtgcacacg ctgggccgac gccgagtgcg aggagatccc tggccgttgg    2400
attacacggt ccacaccccc agagggctcg gacagcacag cccccagcac ccaggagcct    2460
gaggcacctc cagaacaaga cctcatagcc agcacggtgg caggtgtggt gaccacagtg    2520
atgggcagct cccagcccgt ggtgacccga ggcaccaccg acaacctcat ccctgtctat    2580
tgctccatcc tggctgctgt ggttgtgggt cttgtggcct acatagcctt caagaggtgg    2640
aacagctccg gctccggagc caccaacttc agcctgctga agcaggccgg cgacgtggag    2700
gagaaccccg gccccgcggc cgccatggcg acgggttcaa gaacttccct acttcttgca    2760
tttggcctgc tttgtttgcc gtggttacag gaagcctcag caggtcaaca gctgaatcag    2820
agtcctcaat ctatgtttat ccaggaagga gaagatgtct ccatgaactg cacttcttca    2880
agcatattta acacctggct atggtacaag caggaccctg gggaaggtcc tgtcctcttg    2940
atagccttat ataaggctgg tgaattgacc tcaaatggaa gactgactgc tcagtttggt    3000
ataaccagaa aggacagctt cctgaatatc tcagcatcca tacctagtga tgtaggcatc    3060
tacttctgtg ctggatttct ggatagcaac tatcagttaa tctggggcgc tgggaccaag    3120
ctaattataa agccagatat ccagaacccc gagcccgccg tgtaccagct gaaggacccc    3180
agaagccagg acagcaccct gtgcctgttc accgacttcg acagccagat caacgtgccc    3240
aagaccatgg agagcggcac cttcatcacc gacaagaccg tgctggacat gaaggccatg    3300
gacagcaaga gcaacggcgc catcgcctgg tccaaccaga ccagcttcac atgccaggac    3360
atcttcaagg agaccaacgc cacctacccc agcagcgacg tgccctgcga cgccaccctg    3420
accgagaaga gcttcgagac cgacatgaac ctgaacttcc agaacctgag cgtgatgggc    3480
ctgagaatcc tgctgctgaa ggtggccggc ttcaacctgc tgatgaccct gaggctgtgg    3540
agcagcaggg caaaacgttc gggttcgggt gcgccagtaa agcagacatt aaactttgat    3600
ttgctgaaac ttgcaggtga tgtagagtca aatccaggtc caatggcaac agggagccga    3660
acctctctgc tccttgcttt cgggctcctt tgcctaccgt gcctgcagga gggctcggca    3720
gaagcccaag tgacccagaa cccaagatac ctcatcacag tgactggaaa gaagttaaca    3780
gtgacttgtt ctcagaatat gaaccatgag tatatgtcct ggtatcgaca agacccaggg    3840
ctgggcttaa ggcagatcta ctattcaatg aatgttgagg tgactgataa gggagatgtt    3900
cctgaagggt acaaagtctc tcgaaaagag aagaggaatt ccccctgat cctggagtcg    3960 cccagcccca accagacctc tctgtacttc tgtgccagcg ctagcgggta ccgcacagat    4020
acgcagtatt ttggcccagg cacccggctg acagtgctcg aggacctgag gaacgtgacc    4080
ccccccaagg tgtccctgtt cgagcccagc aaggccgaga tcgccaacaa gcagaaggcc    4140
accctggtgt gcctggccag gggcttcttc cccgaccacg tggagctgtc ttggtgggtg    4200
aacggcaagg aggtgcacag cggcgtgagc accgacccccc aggcctacaa ggagagcaac    4260
```

-continued

```
tacagctact gcctgagcag caggctgaga gtgagcgcca ccttctggca caaccccagg   4320
aaccacttcc gctgtcaggt gcagttccac ggcctgagcg aggaggacaa gtggcccgag   4380
ggcagcccca agcccgtgac ccagaacatc agcgccgagg cctggggcag agccgactgc   4440
ggcatcacca gcgccagcta ccaccagggc gtgctgtccg ccaccatcct gtacgagatc   4500
ctgctgggca aggccacact gtacgccgtg ctggtgtccg gcctggtgct gatggccatg   4560
gtgaagaaga agaacagcta aaggatccga taaaataaaa gatttattt agtctccaga    4620 aaaagggggg aatgaaagac cccacctgta ggtttggcaa gctagcttaa gtaacgccat   4680
tttgcaaggc atggaaaata cataactgag aatagagaag ttcagatcaa ggttaggaac   4740
agagagacag cagaatatgg gccaaacagg atatctgtgg taagcagttc ctgccccggc   4800
tcagggccaa gaacagatgg tccccagatg cggtcccgcc ctcagcagtt tctagagaac   4860
catcagatgt ttccagggtg ccccaaggac ctgaaatgac cctgtgcctt atttgaacta   4920
accaatcagt tcgcttctcg cttctgttcg cgcgcttctg ctccccgagc tcaataaaag   4980
agcccacaac ccctcactcg gcgcgccagt cctccgatag actgcgtcgc ccgggtaccc   5040
gtgtatccaa taaaccctct tgcagttgca tccgacttgt ggtctcgctg ttccttggga   5100
gggtctcctc tgagtgattg actacccgtc agcgggggtc tttcatgggt aacagtttct   5160
tgaagttgga gaacaacatt ctgagggtag gagtcgaata ttaagtaatc ctgactcaat   5220
tagccactgt tttgaatcca catactccaa tactcctgaa atccatcgat ggagttcatt   5280
atggacagcg cagaaagagc tggggagaat tgtgaaattg ttatccgctc acaattccac   5340
acaacatacg agccggaagc ataaagtgta aagcctgggg tgcctaatga gtgagctaac   5400
tcacattaat tgcgttgcgc tcactgcccg ctttccagtc gggaaacctg tcgtgccagc   5460
tgcattaatg aatcggccaa cgcgcgggga gaggcggttt gcgtattggg cgctcttccg   5520
cttcctcgct cactgactcg ctgcgctcgg tcgttcggct gcggcgagcg gtatcagctc   5580
actcaaaggc ggtaatacgg ttatccacag aatcagggga taacgcagga aagaacatgt   5640
gagcaaaagg ccagcaaaag gccaggaacc gtaaaaaggc cgcgttgctg gcgtttttcc   5700
ataggctccg cccccctgac gagcatcaca aaaatcgacg ctcaagtcag aggtggcgaa   5760
acccgacagg actataaaga taccaggcgt ttccccctgg aagctccctc gtgcgctctc   5820
ctgttccgac cctgccgctt accggatacc tgtccgcctt tctcccttcg ggaagcgtgg   5880
cgctttctca tagctcacgc tgtaggtatc tcagttcggt gtaggtcgtt cgctccaagc   5940
tgggctgtgt gcacgaaccc cccgttcagc ccgaccgctg cgccttatcc ggtaactatc   6000
gtcttgagtc caacccggta agacacgact tatcgccact ggcagcagcc actggtaaca   6060
ggattagcag agcgaggtat gtaggcggtg ctacagagtt cttgaagtgg tggcctaact   6120
acggctacac tagaaggaca gtatttggta tctgcgctct gctgaagcca gttaccttcg   6180
gaaaaagagt tggtagctct tgatccggca acaaaccacc gctggtagc ggtggttttt    6240 ttgtttgcaa gcagcagatt acgcgcagaa aaaaaggatc tcaagaagat cctttgatct   6300
tttctacggg gtctgacgct cagtggaacg aaaactcacg ttaagggatt ttggtcatga   6360
gattatcaaa aaggatcttc acctagatcc ttttaaatta aaaatgaagt tttaaatcaa   6420
tctaaagtat atatgagtaa acttggtctg acagttacca atgcttaatc agtgaggcac   6480
ctatctcagc gatctgtcta tttcgttcat ccatagttgc ctgactcccc gtcgtgtaga   6540
taactacgat acgggagggc ttaccatctg gccccagtgc tgcaatgata ccgcgagacc   6600
cacgctcacc ggctccagat ttatcagcaa taaaccagcc agccggaagg gccgagcgca   6660
```

-continued

```
gaagtggtcc tgcaacttta tccgcctcca tccagtctat taattgttgc cgggaagcta    6720
gagtaagtag ttcgccagtt aatagtttgc gcaacgttgt tgccattgct acaggcatcg    6780
tggtgtcacg ctcgtcgttt ggtatggctt cattcagctc cggttcccaa cgatcaaggc    6840
gagttacatg atcccccatg ttgtgcaaaa aagcggttag ctccttcggt cctccgatcg    6900
ttgtcagaag taagttggcc gcagtgttat cactcatggt tatggcagca ctgcataatt    6960
ctcttactgt catgccatcc gtaagatgct tttctgtgac tggtgagtac tcaaccaagt    7020
cattctgaga atagtgtatg cggcgaccga gttgctcttg cccggcgtca atacgggata    7080
ataccgcgcc acatagcaga actttaaaag tgctcatcat tggaaaacgt tcttcggggc    7140
gaaaactctc aaggatctta ccgctgttga tccagttc gatgtaaccc actcgtgcac    7200
ccaactgatc ttcagcatct tttactttca ccagcgtttc tgggtgagca aaaacaggaa    7260
ggcaaaatgc cgcaaaaaag ggaataaggg cgacacggaa atgttgaata ctcatactct    7320
tcctttttca atattattga agcatttatc agggttattg tctcatgagc ggatacatat    7380
ttgaatgtat ttagaaaaat aaacaaatag gggttccgcg cacatttccc cgaaaagtgc    7440
cacctgacgt ctaagaaacc attattatca tgacattaac ctataaaaat aggcgtatca    7500
cgaggccctt tcgtctcgcg cgtttcggtg atgacggtga aaacctctga cacatgcagc    7560
tcccggagac ggtcacagct tgtctgtaag cggatgccgg gagcagacaa gcccgtcagg    7620
gcgcgtcagc gggtgttggc gggtgtcggg gctggcttaa ctatgcggca tcagagcaga    7680
ttgtactgag agtgcaccat atgcggtgtg aaataccgca cagatgcgta aggagaaaat    7740
accgcatcag gcgccattcg ccattcaggc tgcgcaactg ttgggaaggg cgatcggtgc    7800
gggcctcttc gctattacgc cagctggcga aggggggatg tgctgcaagg cgattaagtt    7860
gggtaacgcc agggttttcc cagtcacgac gttgtaaaac gacggccagt gccacgctct    7920
cccttatgcg actcctgcat taggaagcag cccagtagta ggttgaggcc gttgagcacc    7980
gccgccgcaa ggaatggtgc atgcaaggag atggcgccca acagtccccc ggccacgggg    8040
cctgccacca tacccacgcc gaaacaagcg ctcatgagcc cgaagtggcg agcccgatct    8100
tccccatcgg tgatgtcggc gatataggcg ccagcaaccg cacctgtggc gccggtgatg    8160
ccggccacga tgcgtccggc gtagaggcga tttaaagaca ggatatcagt ggtccaggct    8220
ctagttttga ctcaacaata tcaccagctg aagcctatag agtacgagcc atagataaaa    8280
taaaagattt tatttagtct ccagaaaaag gggggaa    8317
```

```
<210> SEQ ID NO 36
<211> LENGTH: 9
<212> TYPE: PRT
<213> ORGANISM: Homo sapiens

<400> SEQUENCE: 36

Ser Leu Leu Met Trp Ile Thr Gln Cys
1               5

<210> SEQ ID NO 37
<211> LENGTH: 119
<212> TYPE: PRT
<213> ORGANISM: Homo sapiens

<400> SEQUENCE: 37

Gly Ala Val Val Ser Gln His Pro Ser Trp Val Ile Cys Lys Ser Gly
1               5                   10                  15
```

-continued

```
Thr Ser Val Lys Ile Glu Cys Arg Ser Leu Asp Phe Gln Ala Thr Thr
            20                  25                  30

Met Phe Trp Tyr Arg Gln Phe Pro Lys Gln Ser Leu Met Leu Met Ala
            35                  40                  45

Thr Ser Asn Glu Gly Ser Lys Ala Thr Tyr Glu Gln Gly Val Glu Lys
        50                  55                  60

Asp Lys Phe Leu Ile Asn His Ala Ser Leu Thr Leu Ser Thr Leu Thr
65                  70                  75                  80

Val Thr Ser Ala His Pro Glu Asp Ser Ser Phe Tyr Ile Cys Ser Ala
                85                  90                  95

Pro Gln Gly Tyr Gly Gly Thr Asp Thr Gln Tyr Phe Gly Pro Gly Thr
            100                 105                 110

Arg Leu Thr Val Leu Glu Asp
            115
```

COMPOSITION OF NY-ESO-1-SPECIFIC T CELL RECEPTORS RESTRICTED ON MULTIPLE MAJOR HISTOCOMPATIBILITY COMPLEX MOLECULES

CROSS REFERENCE TO RELATED APPLICATIONS

This application claims the benefit under 35 U.S.C. Section 119(e) of commonly-assigned U.S. Provisional Patent Application Ser. No. 62/727,485, filed on Sep. 5, 2018, and entitled "COMPOSITION OF NY-ESO-1-SPECIFIC T CELL RECEPTORS RESTRICTED ON MULTIPLE MAJOR HISTOCOMPATIBILITY COMPLEX MOLECULES" which application is incorporated by reference herein.

STATEMENT REGARDING FEDERALLY SPONSORED RESEARCH AND DEVELOPMENT

This invention was made with government support under Grant Numbers CA132681 and CA197633, awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Aug. 28, 2019, is named 30435_364-WO-U1_SL.txt and is 101,375 bytes in size.

TECHNICAL FIELD

The present invention relates to methods and materials useful in αβ T cell receptor gene therapy.

BACKGROUND OF THE INVENTION

The αβ T cell receptor (TCR) determines the unique specificity of each naïve T cell. Upon assembly with CD3 signaling proteins on the T cell surface, the TCR surveils peptide ligands presented by major histocompatibility complex (MHC) molecules on the surface of nucleated cells. The specificity of the TCR for a peptide-MHC complex is determined by both the presenting MHC molecule and the presented peptide. The MHC locus (also known as the human leukocyte antigen (HLA) locus in humans) is the most multi-allelic locus in the human genome, comprising >18,000 MHC class I and II alleles that vary widely in frequency across ethnic subgroups (1, 2). Ligands presented by MHC class I molecules are derived primarily from proteasomal cleavage of endogenously expressed antigens. Infected and cancerous cells present peptides that are recognized by CD8+ T cells as foreign or aberrant, resulting in T cell-mediated killing of the presenting cell.

T cells can be engineered to kill tumor cells through the transfer of tumor-reactive as TCR genes (3). Key to this approach is that the patient expresses the MHC allele on which the therapeutic TCR is restricted and that the targeted peptide is derived from a tumor-associated or tumor-specific antigen. Private (patient-specific) neoantigens resulting from tumor-specific mutations are a potential source of such targets (4). However, implementation of personalized TCR gene therapy is complicated by the need to identify mutations through sequencing, to isolate mutation-reactive, patient-specific TCRs, and to genetically modify patient T cells on-demand. This is still more challenging for tumors that cannot be accessed for sequencing and for low mutational burden tumors with few or no neoantigens (5). Particularly for these last tumor types, targeting public (non-patient specific), tumor-restricted antigens with off-the-shelf TCRs remains an attractive option.

The first public antigen targeted with TCR gene therapy in the clinic was melanocyte antigen MART1/Melan-A, yielding objective responses in 2/15 patients with metastatic melanoma (6). Use of a higher affinity MART1-reactive TCR (F5) increased the response rate to 30% but also produced a variety of side effects including vitiligo, uveitis, and transient hearing loss due to MART1 expression on healthy melanocytes in the skin, eye, and middle ear (7). T cell therapies targeting other public antigens have similarly resulted in morbidity or other serious adverse events due to on-target/off-tumor reactivity. For example, targeting carcinoembryonic antigen produces severe colitis in patients with metastatic colorectal cancer due to reactivity with normal colorectal tissue (8). More seriously, T cell therapies targeted at ERBB2 or MAGE-A3 each resulted in deaths due to unappreciated expression of the target antigen (or similar variant) on vital organs (9, 10). Thus, these studies underscore the importance of identifying stringently tumor-specific public antigens (11), particularly when well-expressed, high-affinity targeting receptors necessary for therapeutic success are employed (7, 12).

NY-ESO-1—the product of the CTAG1B gene—is an attractive target for off-the-shelf TCR gene therapy. As the prototypical cancer-testis antigen, NY-ESO-1 is not expressed in normal, non-germline tissue, but it is aberrantly expressed in many tumors (13). The frequency of aberrant expression ranges from 10-50% among solid tumors, 25-50% of melanomas, and up to 80% of synovial sarcomas (13-18), with increased expression observed in higher-grade metastatic tumor tissue (14, 15, 19). Moreover, NY-ESO-1 is highly immunogenic, precipitating spontaneous and vaccine-induced T cell immune responses against multiple epitopes presented by various MHC alleles (20-23). As a result, the epitope NY-ESO-1157-165 (SLLMWITQC, (SEQ ID NO. 36)) presented by HLA-A*02:01 has been targeted with cognate 1G4 TCR in gene therapy trials, yielding an objective response rate of 55% and 61% of patients with metastatic melanoma and synovial sarcoma, respectively, and producing no adverse events related to targeting (24, 25). Targeting this same A2-restricted epitope with lentiviral-mediated TCR gene therapy in patients with multiple myeloma similarly resulted in 70% complete or near-complete responses without significant safety concerns (26). Unfortunately however, the majority of patients who respond to therapy relapse within months, and loss of heterozygosity at the MHCI locus has been reported as a mechanism by which tumors escape adoptive T cell therapy targeting HLA-A*02:01/NY-ESO-1157-165 (27). Thus, NY-ESO-1 is a tumor-specific, immunogenic public antigen that is expressed across an array of tumor types, that is safe to target in the clinic, but that is susceptible to escape when targeted through a single HLA subtype.

For the reasons noted above, there is a need in the art for additional methods and materials useful for NY-ESO-1 TCR gene therapy.

SUMMARY OF THE INVENTION

As noted above, T lymphocytes can be engineered to express tumor-specific T cell receptor (TCR) genes and thereby kill cancer cells. This approach—termed TCR gene therapy—is effective but can cause serious adverse events if the target is also expressed in healthy, non-cancerous tissue. NY-ESO-1 is a tumor-specific antigen that has been targeted successfully and safely through TCR gene therapies for melanoma, synovial sarcoma, and myeloma. However, trials to date have focused exclusively on a single NY-ESO-1-derived epitope presented on HLA-A*02:01, limiting application to patients expressing that allele. As disclosed below, we have developed new TCRs that collectively recognize multiple NY-ESO-1-derived epitopes presented by multiple MHC alleles. We thereby provide a general approach for expanding targeted immunotherapies to more diverse MHC haplotypes.

Embodiments of the present invention include methods and materials for making and using modified CD 8$^+$ T cells comprising nucleic acids encoding certain αβ T cell receptor polypeptides. Embodiments of the invention include, for example, a polynucleotide disposed in a vector, wherein the polynucleotide encodes a Vα T cell receptor polypeptide and/or a Vβ T cell receptor polypeptide. In typical embodiments, when a Vα/Vβ T cell receptor comprising the Vα T cell receptor polypeptide and/or the VP T cell receptor polypeptide is expressed in a CD 8$^+$ T cell, the heterologous Vα/Vβ T cell receptor expressed on the surface of the CD 8$^+$ T cell recognizes a NY-ESO-1 peptide associated with human leukocyte antigen A2, human leukocyte antigen B07, human leukocyte antigen B18, or human leukocyte antigen C03. In the illustrative working embodiments of this invention disclosed herein, the heterologous T cell receptor comprises a Vα/Vβ T cell receptor designated "3A1", "4A2", "5G6", 9D2", "1E4", "2B8" or "3C7".

Embodiments of the invention also include a number of different TCR nucleic acids and polypeptides that are disclosed herein (e.g. ap TCR nucleic acids and encoded polypeptides for TCRs designated "3A1", "4A2", "5G6", 9D2", "1E4", "2B8" and "3C7"). For example, embodiments of the invention include a composition of matter comprising one or more polynucleotides (polynucleotides typically disposed in one or more vectors) encoding TCR Vα and/or TCR Vβ polynucleotides including: a polynucleotide encoding at least a 3A1 TCR Vα polypeptide (SEQ ID NO: 3); a polynucleotide encoding at least a 3A1 TCR Vβ polypeptide (SEQ ID NO: 4); a polynucleotide encoding at least a 4A2 TCR Vα polypeptide (SEQ ID NO: 7); a polynucleotide encoding at least a 4A2 TCR Vβ polypeptide (SEQ ID NO: 37); a polynucleotide encoding at least a 5G6 TCR Vα polypeptide (SEQ ID NO: 10); a polynucleotide encoding at least a 5G6 TCR Vβ polypeptide (SEQ ID NO: 11); a polynucleotide encoding at least a 9D2 TCR Vα polypeptide (SEQ ID NO: 14); a polynucleotide encoding at least a 9D2 TCR Vβ polypeptide (SEQ ID NO: 15); a polynucleotide encoding at least a 1E4 TCR Vα polypeptide (SEQ ID NO: 18); a polynucleotide encoding at least a 1E4 TCR Vβ polypeptide (SEQ ID NO: 19); a polynucleotide encoding at least a 2B8 TCR Vα polypeptide (SEQ ID NO: 22); a polynucleotide encoding at least a 2B8 TCR Vβ polypeptide (SEQ ID NO: 23); a polynucleotide encoding a at least 3C7 TCR Vα polypeptide (SEQ ID NO: 26); or a polynucleotide encoding at least a 3C7 TCR Vβ polypeptide (SEQ ID NO: 27). In typical embodiments of the invention, these polynucleotides further encode additional amino acids such as a constant region of an alpha and/or beta polypeptide, a TM domain, a short cytoplasmic tail, or the like. In illustrative embodiments of the invention, the composition comprises a polynucleotide encoding a TCR Vα polypeptide in combination with a polynucleotide encoding a TCR Vβ polypeptide, wherein such polynucleotides are disposed within one or more vectors such that a Vα/Vβ TCR can be expressed on the surface of a mammalian cell (e.g. a CD8$^+$ T cell) transduced with the vector(s), with this expressed heterologous Vα/Vβ TCR recognizing a NY-ESO-1 peptide associated with a human leukocyte antigen.

In another aspect, the invention includes methods for generating a modified CD8$^+$ T cell comprising introducing nucleic acids encoding a TCR polypeptide disclosed herein into a T cell (e.g. a CD8$^+$ T cell obtained from an individual diagnosed with a cancer that expresses a NY-ESO-1 antigen). In another aspect, the invention includes a composition comprising the modified CD8$^+$ T cell generated according to the methods described herein. In another aspect, the invention includes methods of treating a disease or condition characterized by the expression of NY-ESO-1. The treatment methodology comprises administering an effective amount of the modified CD8$^+$ T cell(s) described herein to a subject in need thereof. In typical embodiments of the invention, the subject has a cancer. In certain embodiments of the invention, the cancer cells form solid tumors. In some embodiments of the invention, the cancer is a melanoma, neuroblastoma, a myeloma, a metastatic melanoma, a synovial sarcoma, a bladder cancer, a esophageal cancer, a hepatocellular cancer, a head and neck cancer, a non-small cell lung cancer, a ovarian cancer, a prostate cancer, or a breast cancer.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

FIG. 1(A) provides a schematic outlining the expansion and testing strategy to identify NY-ESO-1-reactive T cell clones. PBMCs were incubated with 28 NY-ESO-1 18mer peptides (overlapping by 12 amino acids) and then expanded for 10 days before restimulation with individual peptides in the presence of BFA. Epitopes presented by patient MHC alleles are colored red, blue, and green in those peptides containing the full epitope sequence. FIG. 1(B) provides a representative flow cytometry measurement of intracellular staining for IFN-γ in expanded PBMCs restimulated with individual NY-ESO-1-derived 18-mer peptides. FIG. 1(C) provides a schematic outlining the re-expansion strategy using individual 9-mer or 10-mer peptides verified to elicit a T cell response. FIG. 1(D) provides representative flow cytometry data showing an NY-ESO-1 reactive subpopulation of CD3$^+$CD8$^+$ T cells prior to sorting. Sorted cells were expanded in the presence of IL-2 and irradiated autologous PBMCs. FIG. 1(E) provides representative flow cytometry data showing an NY-ESO-1 reactive subpopulation of CD3$^+$CD8$^+$ T cells following sorting.

FIG. 2(A) provides a schematic of functional TCR cloning strategy. For each TCR, two constructs were prepared incorporating either human or murine TCR constant domains. FIG. 2(B) provides protein sequence of NY-ESO-1 with epitopes relevant to this study delineated (SEQ ID NO: 28). FIG. 2(C) provides flow cytometry histograms comparing HLA-A2/NY$_{157-165}$ dextramer binding by HEK 293T cells transfected with vector backbone only, previously reported 1G4 TCR, and novel A2-restricted, NY-ESO-1-specific TCRs. FIG. 2(D) provides flow cytometry histograms comparing indicated peptide-MHC dextramer binding by HEK 293T cells transfected with vector backbone only or the indicated novel NY-ESO-1-specific TCR restricted on MHC alleles other than HLA-A2. Transfection experiments were performed twice, each in duplicate. Representative histograms are presented.

FIG. 3(A) provides an overlay of representative flow cytometry plots comparing A2/NY-ESO-1$_{157-165}$ dextramer binding by Jurkat and CD8$^+$ Jurkat cells expressing A2-restricted TCRs with human or murine constant domains. FIG. 3(B) shows dextramer binding mean fluorescence intensity measurements from two independent experiments as in A. FIG. 3(C) shows the ratio of dextramer binding mean fluorescent intensity measurements from two independent experiments in B. FIG. 3(D) shows ELISA measuring secretion of IL-2 from TCR-transduced Jurkat cells following 48 hours coincubation with K562 target cells expressing A2/MART$_{26-35}$ or A2/NY-ESO-1$_{157-165}$ single-chain trimer. Experiment was repeated 3 times, each with two technical replicates. Means±SD for a representative experiment are shown. FIG. 3(E) shows ELISA measuring secretion of IFN-γ from TCR-transduced PBMCs following 48 hours coincubation with the melanoma cell line M257 or an A2$^+$ derivative. Experiment was repeated at least three times, each with two technical replicates. Means±SD for a representative experiment are shown. FIG. 3(F) shows IncuCyte measurements of total green object area over time as a measurement of TCR-transduced T cell-mediated killing of GFP$^+$ A2$^+$ M257 cells. Means±SD for four technical replicates are shown.

FIGS. 4(A and B) show schematics of the experimental designs to FIG. 4(A) generate NY-ESO-1 TCR-engineered human T cells, and to FIG. 4(B) study anti-tumor efficacy of these engineered T cells in an NSG mouse human prostate tumor xenograft model. PBMCs: peripheral blood mononuclear cells; NSG: immunodeficient NOD/SCID/γc$^{-/-}$ mice. FIG. 4(C) shows representative flow cytometry plots characterizing engineered human T cells present in the peripheral blood of experimental mice on day 14 post adoptive T cell transfer. FIG. 4(D) provides a time course showing persistence of engineered human T cells (gated as LNGFR$^+$ hCD45$^+$) in the peripheral blood of experimental mice. FIGS. 4(E and F) provide mean fluorescence intensity measurements for FIG. 4(E) murine TCR and FIG. 4(F) HLA-A2/NY-ESO-1 dextramer for engineered human T cells in the peripheral blood of experimental mice on day 14 post adoptive T cell transfer. FIGS. 4(G and H) provide measurements of cross-sectional area for FIG. 4(G) PC-3/ HLA-A2 and FIG. 4(H) PC-3/HLA-A2/NY-ESO-1 tumors. FIG. 4(I) provides immunohistology images showing representative tumor sections. CD3$^+$ cells are stained in red. Upper panel scale bar: 500 μm; lower panel scale bar: 50 μm. FIG. 4(J) shows the percentage of CD3$^+$ cell area over whole tumor section area. Representative of two experiments. Data are presented as the mean±SEM (n=4-5). ns, not significant, *P<0.05; P<0.01, *P<0.001, ****P<0.0001, by one-way ANOVA.

FIG. 5(A) provides an overlay of representative flow cytometry plots comparing specified dextramer binding by Jurkat and CD8$^+$ Jurkat cells expressing novel TCRs with human or murine constant domains. FIG. 5(B) provides indicated dextramer binding mean fluorescence intensity measurements from two independent experiments as in (A). FIG. 5(C) shows the ratio of respective dextramer binding mean fluorescent intensity measurements from two independent experiments in (B). FIGS. 5(D and E) provide ELISAs measuring FIG. 5(D) secretion of IL-2 from TCR-transduced Jurkat cells or FIG. 5(E) secretion of IFN-γ from TCR-transduced PBMCs following 48 hours coincubation with K562 target cells expressing indicated single-chain trimer. Experiments were repeated three times, each with two technical replicates. Means±SD for a representative experiment are shown.

FIGS. 6(A and B) provide ELISAs measuring secretion of IFN-γ from TCR-transduced PBMCs following 48 hours coincubation with FIG. 6(A) M257 or FIG. 6(B) PC-3 tumor cell lines engineered to express eGFP and HLA-A*02:01 or HLA-B*07:02. PC-3 lines were additionally engineered to express NY-ESO-1. M257 lines express endogenous NY-ESO-1. Experiments were repeated three times, each with four or eight replicates. Means±SD for a representative experiment are shown. FIGS. 6(C and D) show T-cell mediated killing of FIG. 6(C) M257 and FIG. 6(D) PC-3 tumor cell line derivatives measured over time using IncuCyte live-cell analysis. Total green object area (indicative of tumor cell density) at each time point measured over 48 hours was normalized for each treatment relative to treatment with LNGFR-transduced T cells. Experiments were repeated three times, each with four or eight replicates. Results from a representative 8-replicate experiment are shown.

FIGS. 7(A and B) provide ELISAs measuring secretion of IFN-γ from TCR-transduced PBMCs following 48 hours coincubation with K562 engineered to express HLA-A*02:01 and pulsed with varied concentrations of FIG. 7(A) MART126-35 or (B) NYESO1157-165 peptide. FIG. 7(C-E) provide ELISAs measuring secretion of IFN-γ from TCR-transduced PBMCs following 48 hours coincubation with K562 engineered to express FIG. 7(C) HLA-B*07:02, FIG. 7(D) HLA-B*18:01, or FIG. 7(E) HLA-C*03:04 and pulsed with varied concentrations of indicated peptides. Means±SD for two technical replicates are shown. EC50 values and associated errors determined by non-linear curve fitting are indicated.

FIG. 8(A) provides an ELISA measuring secretion of IFN-γ from TCR-transduced PBMCs following 48 hours coincubation with derivatives of the PC-3 prostate cancer cell line engineered to express (left) HLA- A*02:01 and NY-ESO-1 full protein, (middle) HLA-A*02:01 alone, or (right) NY-ESO-1 full protein alone. Means±SD for two technical replicates are shown. FIG. 8(B) provides an ELISA comparing secretion of IFN-γ from TCR-transduced PBMCs following 48 hours coincubation with indicated M257 or PC-3 target cells. On the 4th day post transduction, TCR-transduced PBMCs were sorted for CD3+/LNGFR+ and then expanded for 13 additional days prior to the co-culture/ELISA assay and the in vivo experiment. Means±SD for a representative experiment with two technical replicates is shown. FIG. 8(C) provides flow cytometry contour plots comparing the transduction (LNGFR+) levels of TCR transduced PBMCs used for the in vivo experiment.

DETAILED DESCRIPTION OF THE INVENTION

Figure 1A:
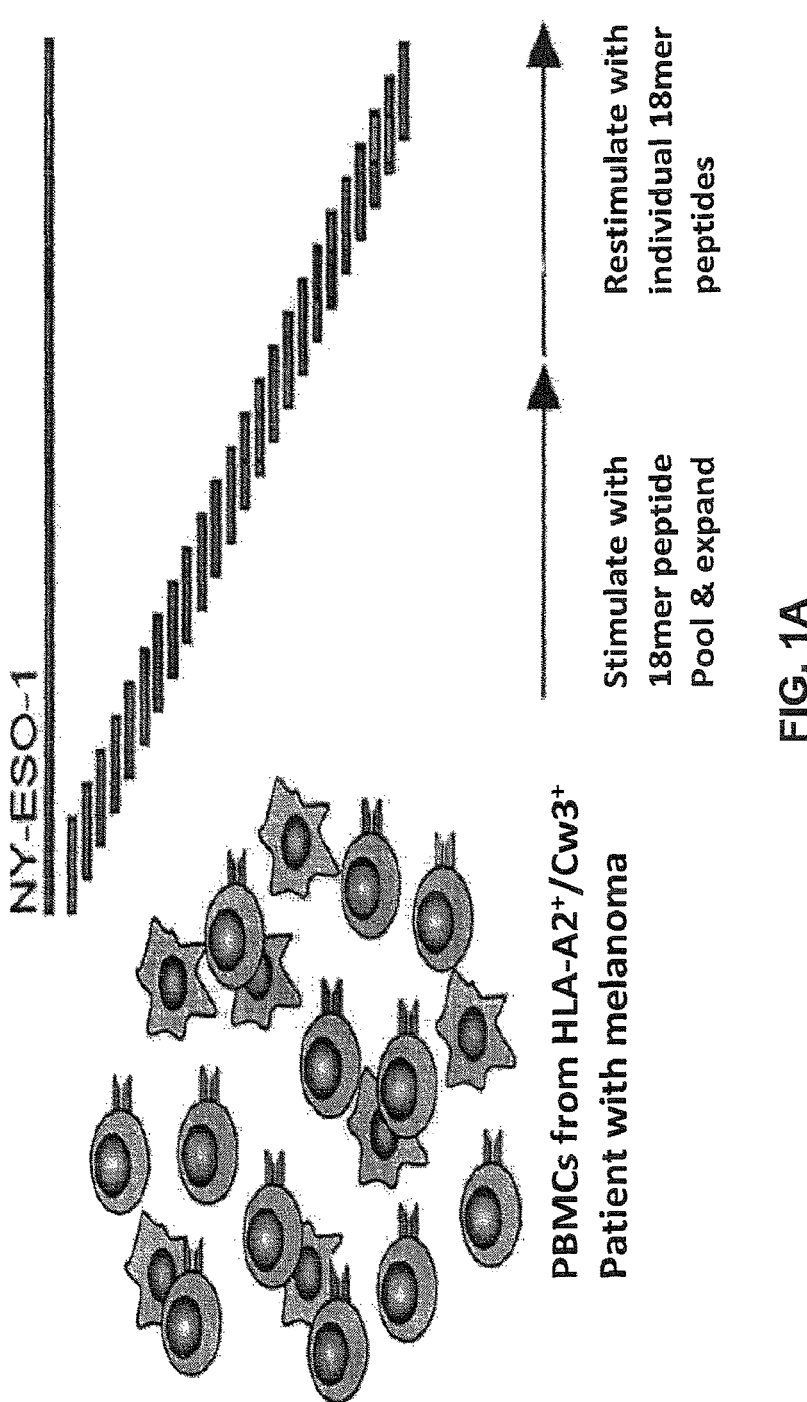
FIGS. 1A-1E show disclosure relating to the expansion and isolation of NY-ESO-1-specific T cell clones. PBMCs were obtained from patients with metastatic melanoma. T cell cloning strategy for a representative HLA-A2$^+$, HLA-Cw3$^+$ donor is shown.

In the description of embodiments, reference may be made to the accompanying figures which form a part hereof, and in which is shown by way of illustration a specific embodiment in which the invention may be practiced. It is to be understood that other embodiments may be utilized, and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

NY-ESO-1 is an archetypical example of a cancer-testis antigen with restricted expression to germ cells and placental cells and re-expression in tumor cells. NY-ESO-1 expression has been reported in a wide range of tumor types, including neuroblastoma, myeloma, metastatic melanoma, synovial sarcoma, bladder cancer, esophageal cancer, hepatocellular cancer, head and neck cancer, non-small cell lung cancer, ovarian cancer, prostate cancer, and breast cancer. Its ability to elicit spontaneous humoral and cellular immune responses, together with its restricted expression pattern, render it a good candidate target for cancer immunotherapy. See, e.g., Thomas et al., Front Immunol. 2018; 9: 947. doi: 10.3389/fimmu.2018.00947.

The disclosure herein demonstrates the accomplishment of two significant goals relating to methods and materials useful in NY-ESO-1 TCR gene therapy. First, since TCRs of higher strength and affinity are more effective, we sought to identify new TCRs that target A2/NY-ESO-1$_{157-165}$ with comparable or better sensitivity than the clinically-employed 1G4 TCR. As affinity-enhanced TCRs can be cross-reactive (28-30), we established a protocol for isolating antigen-reactive TCRs directly from patient blood. Two of these novel TCRs demonstrated comparable or greater sensitivity than 1G4 both in vitro and in vivo in tumor killing assays. Second, to broaden the clinical utility of NY-ESO-1 as a TCR gene therapy target, we used our isolation protocol to identify TCRs that target NY-ESO-1 epitopes presented by common MHC alleles other than HLA-A*02:01. Targeting multiple NY-ESO-1 epitopes will enable treatment of a larger patient set and may render treatment more robust toward tumor escape.

As described herein, the present invention provides methods and materials for making and using modified T cells comprising nucleic acids encoding certain T cell receptor polypeptides. As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta chains. TCRs may exist in alpha/beta and gamma/delta forms, which are structurally similar but have distinct anatomical locations and functions. Each chain is composed of two extracellular domains, a variable and constant domain. Embodiments of the invention include a number of different TCR alpha/beta nucleic acids and their encoded polypeptides (e.g. TCR nucleic acids and encoded polypeptides for the TCRs designated "3A1", "4A2", "5'6", "9D2", "1E4", "2B8" and "3C7").

Embodiments of the invention include compositions of matter comprising one or more vectors comprising the TCR polynucleotides disclosed herein. A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Typically, the vector is an expression vector. The term "expression" as used herein is defined as the transcription and/or translation of a particular nucleotide sequence driven by its promoter. In this context, the term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

Embodiments of the invention include, for example, a polynucleotide disposed in an expression vector, wherein the polynucleotide encodes a Vα T cell receptor polypeptide and/or a Vβ T cell receptor polypeptide. In such embodiments, when a Vα/Vβ cell receptor comprising the Vα T cell receptor polypeptide and/or the Vβ T cell receptor polypeptide is expressed in a CD 8⁺ T cell, the Vα/Vβ T cell receptor recognizes a NY-ESO-1 peptide associated with human leukocyte antigen A2, human leukocyte antigen B07, human leukocyte antigen B18 or human leukocyte antigen C03. In the working embodiments of the invention disclosed herein, the modified CD 8⁺ T cell receptor comprises a 3A1 T cell receptor, a 4A2 T cell receptor, a 5G6 T cell receptor, a 9D2 T cell receptor, a 1E4 T cell receptor, a 2B8 T cell receptor, or a 3C7 T cell receptor.

In typical embodiments of the invention, the vector comprises at least one of: a polynucleotide encoding a 3A1 TCR Vα polypeptide (SEQ ID NO: 3); a polynucleotide encoding a 3A1 TCR Vβ polypeptide (SEQ ID NO: 4); a polynucleotide encoding a 4A2 TCR Vα polypeptide (SEQ ID NO: 7); a polynucleotide encoding a 4A2 TCR VP polypeptide (SEQ ID NO: 37); a polynucleotide encoding a 5G6 TCR Vα polypeptide (SEQ ID NO: 10); a polynucleotide encoding a 5G6 TCR Vβ polypeptide (SEQ ID NO: 11); a polynucleotide encoding a 9D2 TCR Vα polypeptide (SEQ ID NO: 14); a polynucleotide encoding a 9D2 TCR Vβ polypeptide (SEQ ID NO: 15); a polynucleotide encoding a 1E4 TCR Vα polypeptide (SEQ ID NO: 18); a polynucleotide encoding a 1E4 TCR Vβ polypeptide (SEQ ID NO: 19); a polynucleotide encoding a 2B8 TCR Vα polypeptide (SEQ ID NO: 22); a polynucleotide encoding a 2B8 TCR Vβ polypeptide (SEQ ID NO: 23); a polynucleotide encoding a 3C7 TCR Vα polypeptide (SEQ ID NO: 26); or a polynucleotide encoding a 3C7 TCR Vβ polypeptide (SEQ ID NO: 27). Table 1 below discloses illustrative polynucleotide sequences that encode these TCR polypeptides.

Typically, a composition of the invention comprises one or more Vα/Vβ polynucleotides, for example a polynucleotide encoding a TCR Vα polypeptide in combination with a polynucleotide encoding a TCR Vβ polypeptide such that a Vα/Vβ TCR can be expressed on the surface of a mammalian cell (e.g. a CD8+ T cell) transduced with the vector (s), wherein the Vα/Vβ TCR recognizes a NY-ESO-1 peptide associated with a HLA. The term "transduced" or "transfected" or "transformed" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

In another aspect, the invention includes a method for generating a modified T cell comprising introducing one or more nucleic acids (e.g., nucleic acids disposed within a lentiviral vector) encoding a TCR disclosed herein into a T cell (e.g. a CD8+ T cell obtained from an individual diagnosed with a cancer that expresses a NY-ESO-1 antigen). The present invention also includes modified T cells with downregulated or knocked out gene expression (e.g., a modified T cell having a knocked out endogenous T cell receptor and an exogenous/introduced T cell receptor that recognizes a NY-ESO-1 peptide associated with a HLA). The term "knockdown" as used herein refers to a decrease in gene expression of one or more genes. The term "knockout" as used herein refers to the ablation of gene expression of one or more genes.

The modified T cells described herein may be included in a composition for use in a therapeutic regimen. The composition may include a pharmaceutical composition and further include a pharmaceutically acceptable carrier. A therapeutically effective amount of the pharmaceutical composition comprising the modified T cells may be administered. Pharmaceutical compositions of the present invention may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

Compositions of the present invention are preferably formulated for intravenous administration.

Adoptive immunotherapy with T cells harboring antigen-specific TCRs have therapeutic potential in the treatment of cancers. Gene-engineering of CD 8+ T cells with a specific TCR has the advantage of redirecting the T cell to a selected antigen such as an NY-ESO-1 antigen. In this context, in one aspect, the invention includes methods for stimulating a T cell-mediated immune response to a target cell or tissue in a subject comprising administering to a subject an effective amount of a modified CD 8+ T cell. In this embodiment, the CD8+ T cell is modified as described elsewhere herein. Embodiments of the invention also include administering multiple modified CD 8+ T cells that target multiple NY-ESO-1 epitopes. For example, embodiments of the invention include administering at least two different modified CD8+ T cells, for example a first modified CD8+ T cell that targets a NY-ESO-1 peptide associated with a first human leukocyte antigen human leukocyte antigen in combination with a second CD8+ T cells that targets a NY-ESO-1 peptide associated with second human leukocyte antigen.

Embodiments of the invention encompass methods of treating a disease or condition characterized by the expression of NY-ESO-1, a prototypical cancer-testis antigen. The treatment methodology comprises comprising administering an effective amount of a pharmaceutical composition comprising the modified T cell described herein to a subject in need thereof. The term "subject" is intended to include living organisms in which an immune response can be elicited (e.g., mammals). A "subject" or "patient", as used therein, may be a human or non-human mammal. Non-human mammals include, for example, livestock and pets, such as ovine, bovine, porcine, canine, feline and murine mammals. Preferably, the subject is human. In typical embodiments of the invention, the human has a cancer expressing NY-ESO-1 antigen. In some embodiments of the invention, the cells of the cancer form solid tumors. In illustrative embodiments of the invention, the cancer cells are neuroblastoma cells, myeloma cells, metastatic melanoma cells, synovial sarcoma cells, bladder cancer cells, esophageal cancer cells, hepatocellular cancer cells, head and neck cancer cells, non-small cell lung cancer cells, ovarian cancer cells, prostate cancer cells, or breast cancer cells.

A related embodiment of the invention includes a method for prophylaxis and/or therapy of an individual diagnosed with, suspected of having or at risk for developing or recurrence of a cancer, wherein the cancer comprises cancer cells which express NY-ESO-1 antigen. This approach comprises administering to the individual modified human T cells comprising a recombinant polynucleotide encoding a TCR, wherein the T cells are capable of direct recognition of the cancer cells expressing the NY-ESO-1 antigen, and wherein the direct recognition of the cancer cells comprises HLA class II-restricted binding of the TCR to the NY-ESO-1 antigen expressed by the cancer cells.

With respect to use of the engineered CD8+ T cells of the present invention, the method generally comprises administering an effective amount (e.g. by intravenous or intraperitoneal injections) of a composition comprising the CD8+ T cells to an individual in need thereof. An appropriate pharmaceutical composition may be adapted for administration by any appropriate route, such as parenteral (including subcutaneous, intramuscular, or intravenous), enteral (including oral or rectal), inhalation or intranasal routes. Such compositions may be prepared by any method known in the art of pharmacy, for example by mixing the active ingredient with the carrier(s) or excipient(s) under sterile conditions.

In another aspect, the invention includes use of a poly-nucleotide or a modified CD8$^+$ T cell described herein in the manufacture of a medicament for the treatment of a disease or condition characterized by the expression of NY-ESO-1, in a subject in need thereof. In illustrative embodiments of the invention, the disease is a cancer expressing NY-ESO-1 antigen, for example a melanoma, a neuroblastoma, a myeloma, a metastatic melanoma, a synovial sarcoma, a bladder cancer, an esophageal cancer, a hepatocellular cancer, a head and neck cancer, a non-small cell lung cancer, an ovarian cancer, a prostate cancer, or a breast cancer.

The technology in this area is fairly developed and a number of methods and materials know in this art can be adapted for use with the invention disclosed herein. Such methods and materials are disclosed, for example in U.S. Patent Publication Nos. 20190247432, 20190119350, 20190002523, 20190002522, 20180371050, 20180057560, 20170029483, 20160024174, and 20150141347, the contents of which are incorporated by reference.

Further aspects and embodiments of the invention are provided in the examples below.

EXAMPLES

Example 1: Expansion and Isolation of NY-ESO-1-Specific T Cell Clones

Figure 1B:
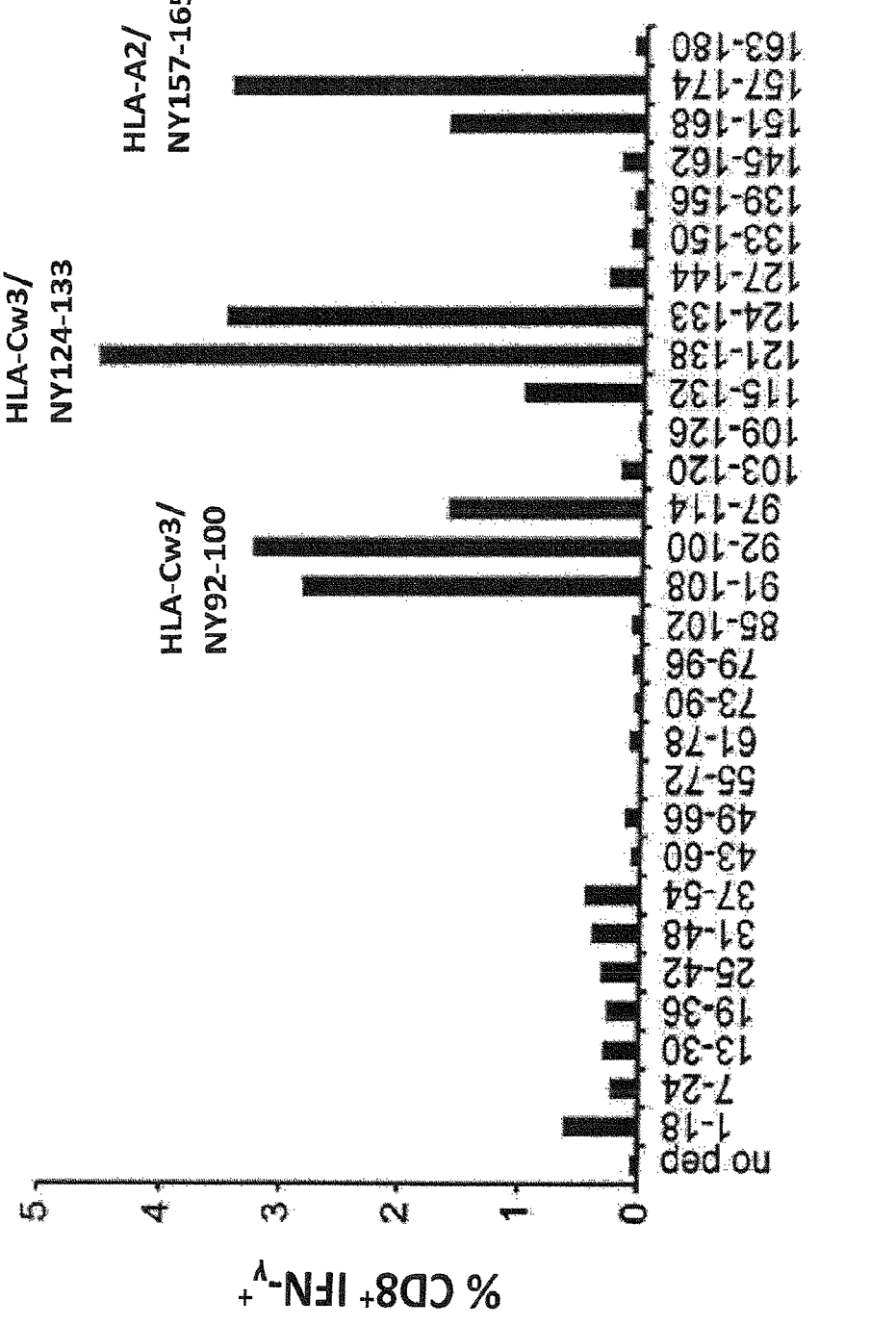
Figures 1C, 1D, 1E:
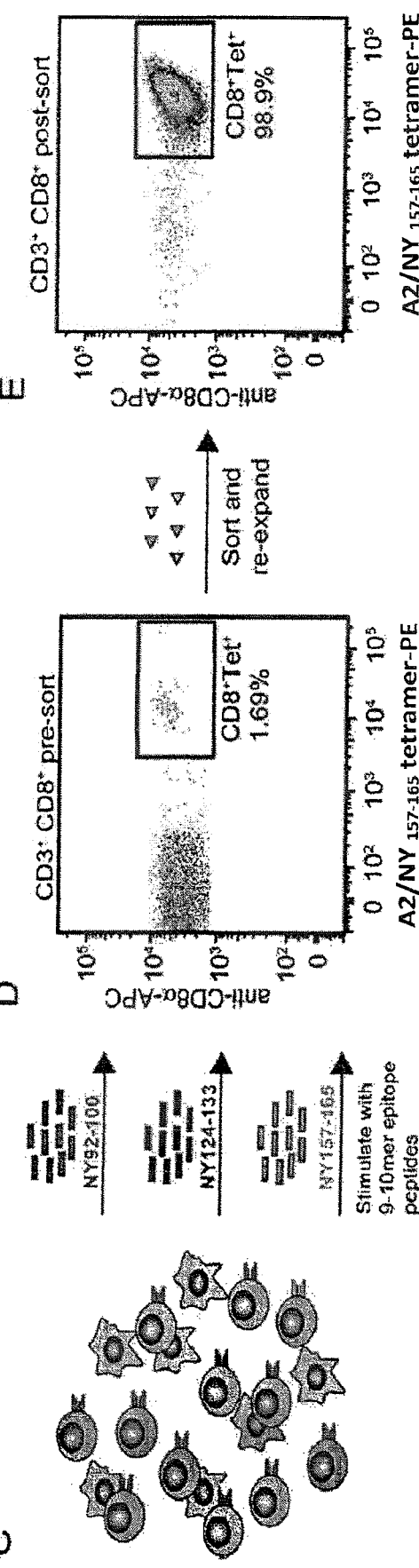

We previously reported the presence of T cells reactive with various NY-ESO-1-derived epitopes in the blood of patients with metastatic melanoma (22). To enrich for these reactive T cells, we stimulated expansion of patient peripheral blood mononuclear cells (PBMCs) with a panel of 28 overlapping 18-mers collectively constituting the full NY-ESO-1 protein sequence (FIG. 1A). We then re-stimulated the expanded cells with individual peptides, performed intracellular staining for IFN-γ to determine which peptides drove expansion, and analyzed stimulatory peptides with a predictive algorithm to identify minimal epitopes relevant to each patient's MHC haplotype (31) (FIG. 1B). Reactive T cells were re-expanded in the presence of individual 9-10-mer peptides corresponding to immunostimulatory epitopes (FIG. 1C) and sorted via fluorescence-activated cell sorting (FACS) using cognate peptide-MHC tetramers (FIG. 1D). The cell lines grown from these single cell sorts were clonal and reactive with their cognate epitopes (FIG. 1E). In total, 4 cell lines reactive with HLA-A*02:01/NY-ESO-1$_{157-165}$ and 4 cell lines reactive with epitopes presented by HLA-B and HLA-C alleles were selected for further study.

Example 2: Cloning and Screening of NY-ESO-1-Specific TCRs

Figure 2A:
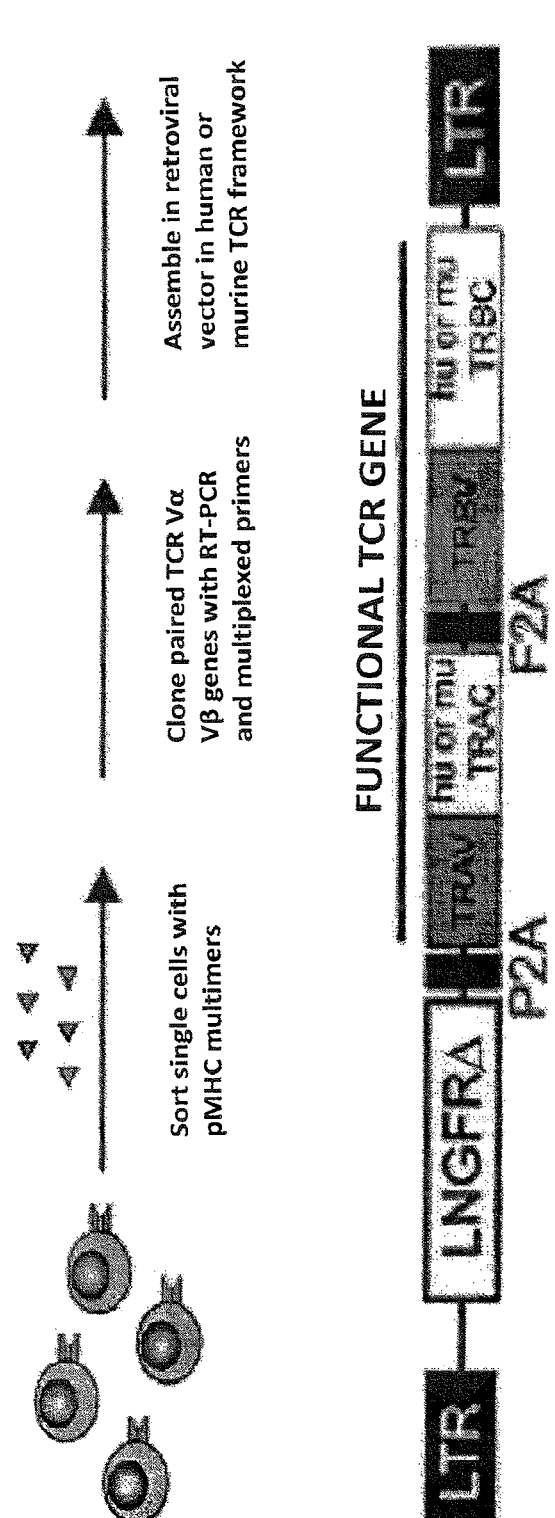
FIGS. 2A-2D provide disclosure relating to cloning and functional screening of NY-ESO-1-specific T cell receptors.
Figures 2B, 2C:
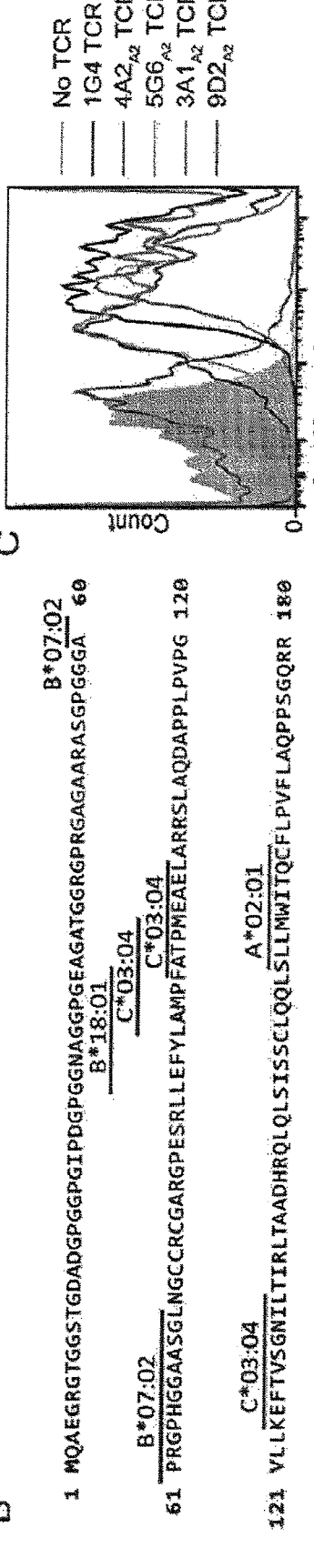

We cloned paired TCRα and TCRβ genes from sorted single cells using a commercial RT-PCR kit with custom multiplexed primers targeting all human TRAV and TRBV gene segments. The resulting V$_\alpha$ and V$_\beta$ cDNAs were sub-cloned into a retroviral vector backbone with either human or murine TCR constant regions (FIG. 2A). To verify the specificity of cloned TCRs, we transfected CD3$^+$ HEK 293T cells with each fully human TCR, and stained the transfected cells with peptide-MHC dextramer reagents for each of the targeted NY-ESO-1 epitopes (FIG. 2B). All 4 HLA-A2-restricted TCRs exhibited the expected reactivity (FIG. 2C). Although analyzed events were gated for similar transfection level, novel TCRs exhibited highly variable dextramer binding. Dextramer binding for the 9D2 TCR was barely discernible from background, whereas the 3A1 TCR exhibited superior dextramer binding compared to the clinically-employed 1G4 TCR. Dextramer binding for 4A2 and 5G6 TCRs were intermediate between 9D2 and 1G4.

Figure 2D:
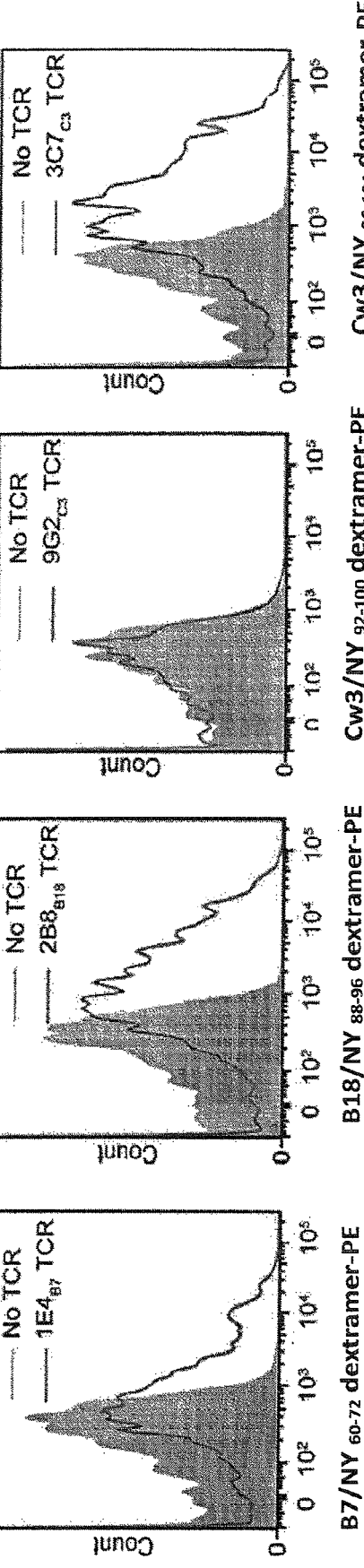

Additionally, 3 of 4 of the TCRs restricted on MHC alleles other than HLA-A2 were verified to bind their targets specifically (FIG. 2D). Transfected 293T cells expressing the B7/NY-ESO-1$_{60-72}$-specific 1E4 TCR, the B18/NY-ESO-1$_{88-96}$-specific 2B8 TCR, or the Cw3/NY-ESO-1$_{96-104}$-specific 3C7 TCR each bound their respective dextramers, whereas untransfected cells did not. Cells transfected with the 9G2 TCR—cloned from T cells that were reactive with Cw3/NY-ESO-1$_{92-100}$—did not detectably bind cognate dextramer relative to untransfected cells. A possible reason for this was that HEK 293T cells do not express the CD8 co-receptor. CD8 increases the avidity of the TCR-pMHC interaction by binding to MHCI directly, enabling lower affinity TCRs to engage (32). We therefore included this TCR for further analysis of CD8 dependency in Jurkat T cells.

Example 3: Functional Characterization of A2-Restricted, NY-ESO-1-Specific TCRs The sensitivity of a TCR-transduced T cell is a function of the monomeric affinity of the TCR for its cognate peptide-MHC (K$_d$~0.1-400 μM) (33) as well as the density of the TCR on the cell surface (12). Transduced TCRs express on the T cell surface at widely varying levels due to variation in the efficiency with which they fold, dimerize, and compete with endogenous TCRs for assembly with limiting CD3 chains (a property termed TCR "strength") (34, 35). Therefore, optimal cytotoxic function of TCR-transduced T cells correlates with TCR affinity and surface expression (3, 12), underscoring the importance of selecting high affinity, efficiently exported TCRs for gene therapy(7).

Figure 3A:
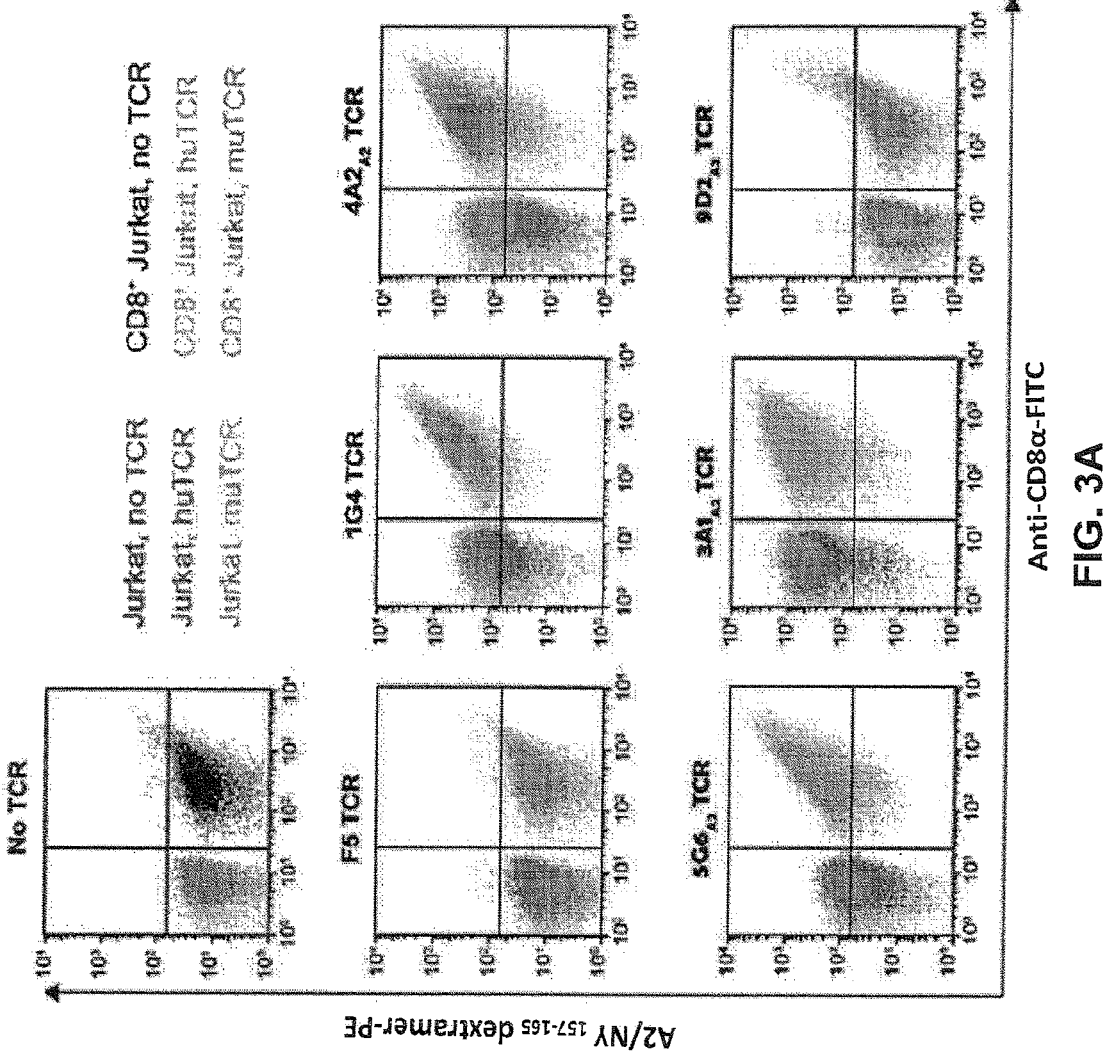
FIGS. 3A-3F provide disclosure relating to the function of A2-restricted, NY-ESO-1-specific TCRs.
Figure 3B:
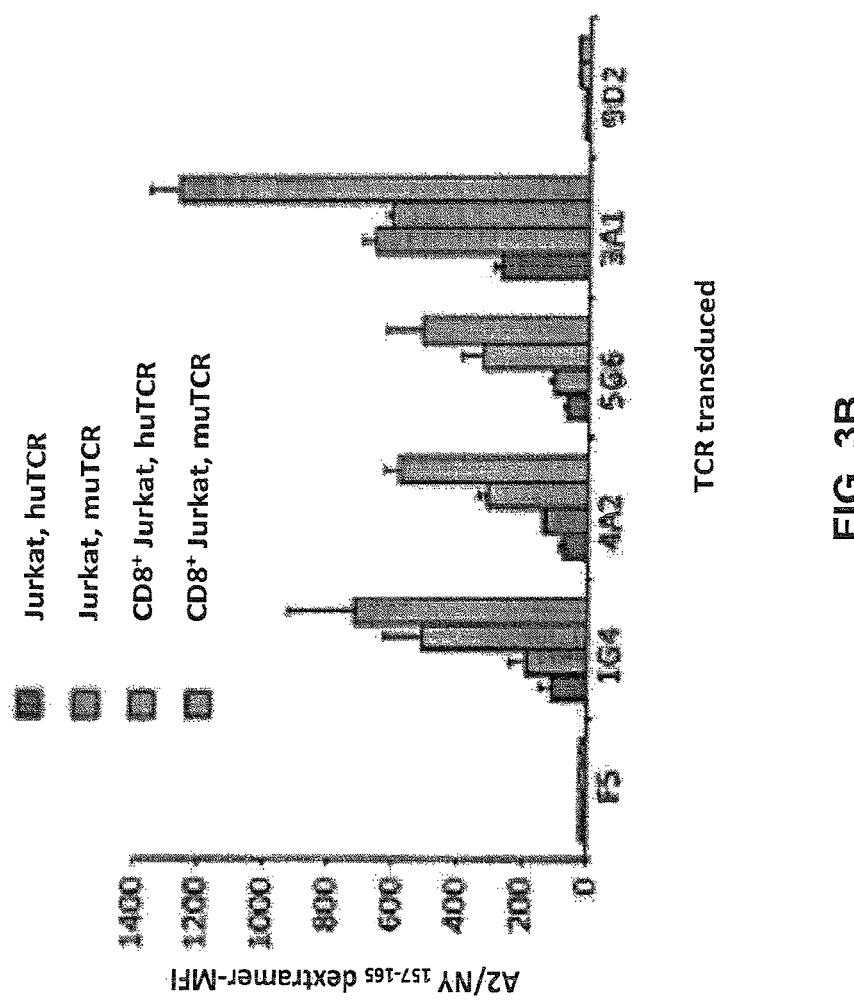
Figure 3C:
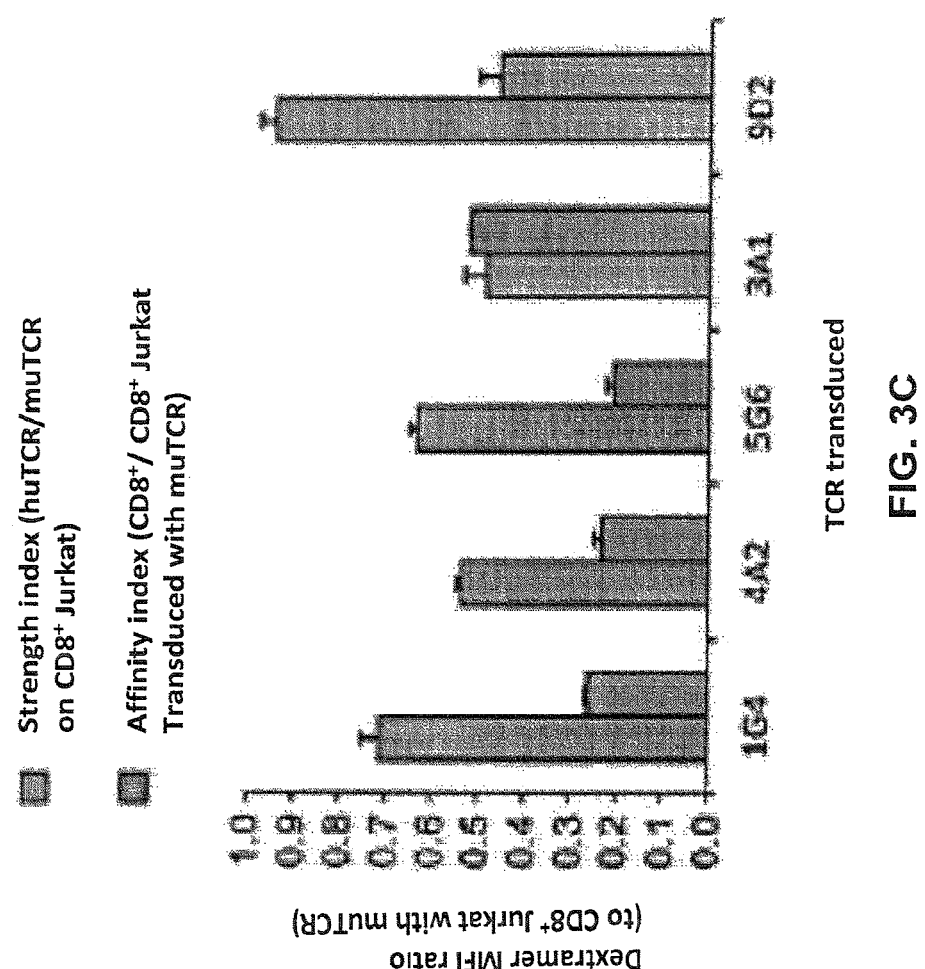

As higher affinity TCR-pMHC interactions are less dependent on CD8 participation, we reasoned that high affinity TCRs can be identified by comparing dextramer binding of TCR-transduced Jurkat T cells with or without co-expression of CD8. Additionally, because the strength of surface expression for human TCRs can be increased through substitution with murine constant domains (36), we expressed each TCR as a fully human or murinized derivative to assess each TCR's strength. Cells transduced with vehicle only or with a mismatched TCR (MART1-specific F5 TCR) did not exhibit any binding to A2/NY-ESO-1$_{157-165}$ dextramer (FIG. 3A, 3B). By contrast, cells transduced with the well-established 1G4 TCR (K$_D$=9.3 μM) (37) bound cognate dextramer whether 1G4 was fully human or murinized, and whether or not CD8 was present. Murinization of 1G4 increased the intensity of dextramer binding by the muTCR 1.4-fold over the parental huTCR, indicating a modest improvement in strength (FIG. 3B, 3C). The presence of CD8 increased dextramer binding 3.8-fold for 1G4 muTCR. Dextramer binding for novel TCRs 4A2 and 5G6 was similar in both magnitude and comparative indices to 1G4 (FIG. 3A-3C). The 3A1 TCR exhibited only a 1.9-fold increase in dextramer binding in the presence of CD8, indicating that this TCR binds A2/NY-ESO-1$_{157-165}$ with higher affinity than 1G4. This is further supported by the reduced dependence of dextramer binding on CD8 level among CD8$^+$ cells transduced with 3A1 muTCR relative to CD8$^+$ cells transduced with 1G4, 4A2, and 5G6 muTCRs (compare slopes of green populations in FIG. 3A). Finally, 9D2 exhibited no detectable binding to dextramer on Jurkat cells in the absence of CD8 and only weak binding upon co-expression of CD8. Murinization of 9D2 did not increase its binding to dextramer.

Figures 3D, 3E:
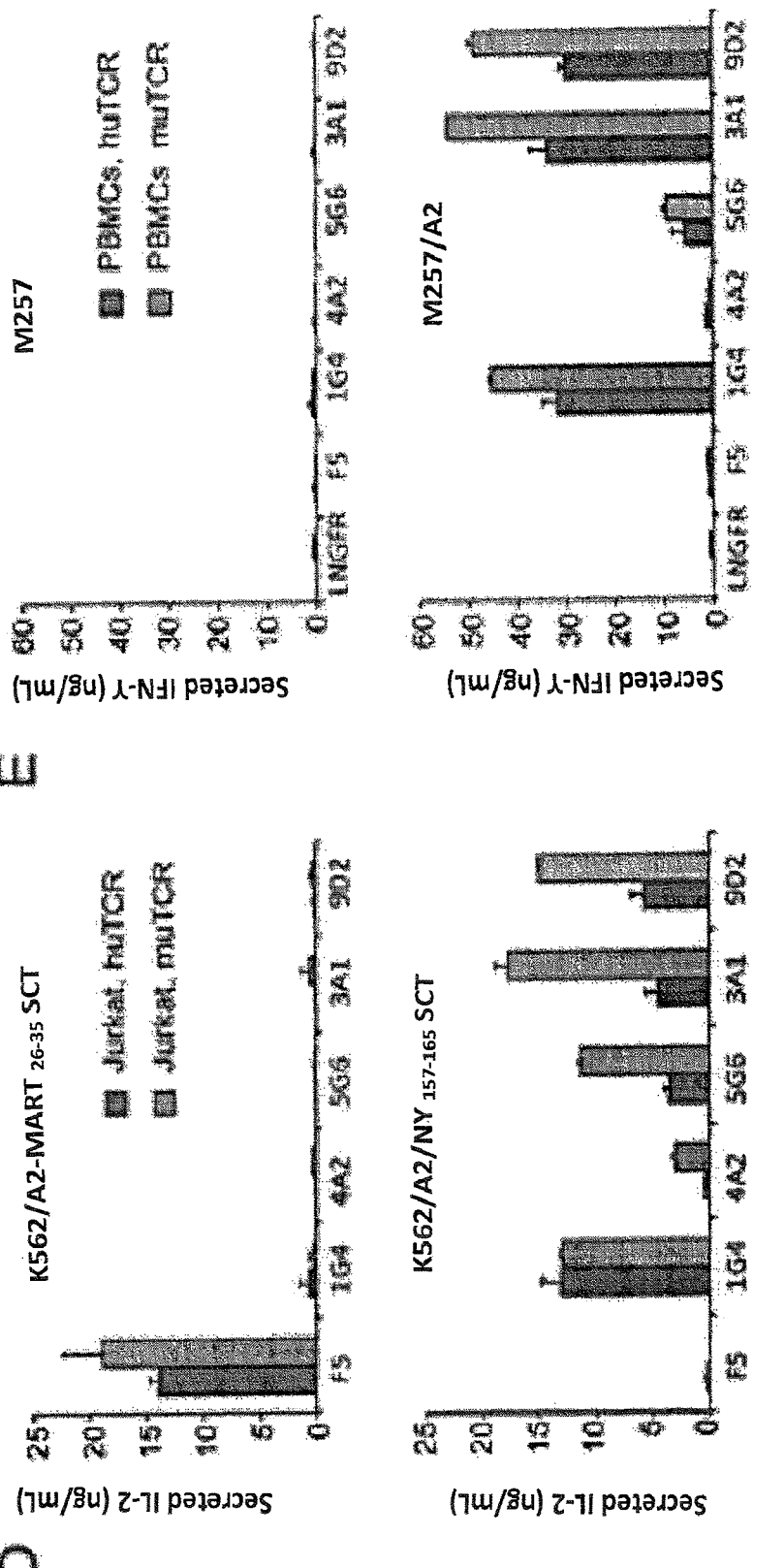
Figure 3F:
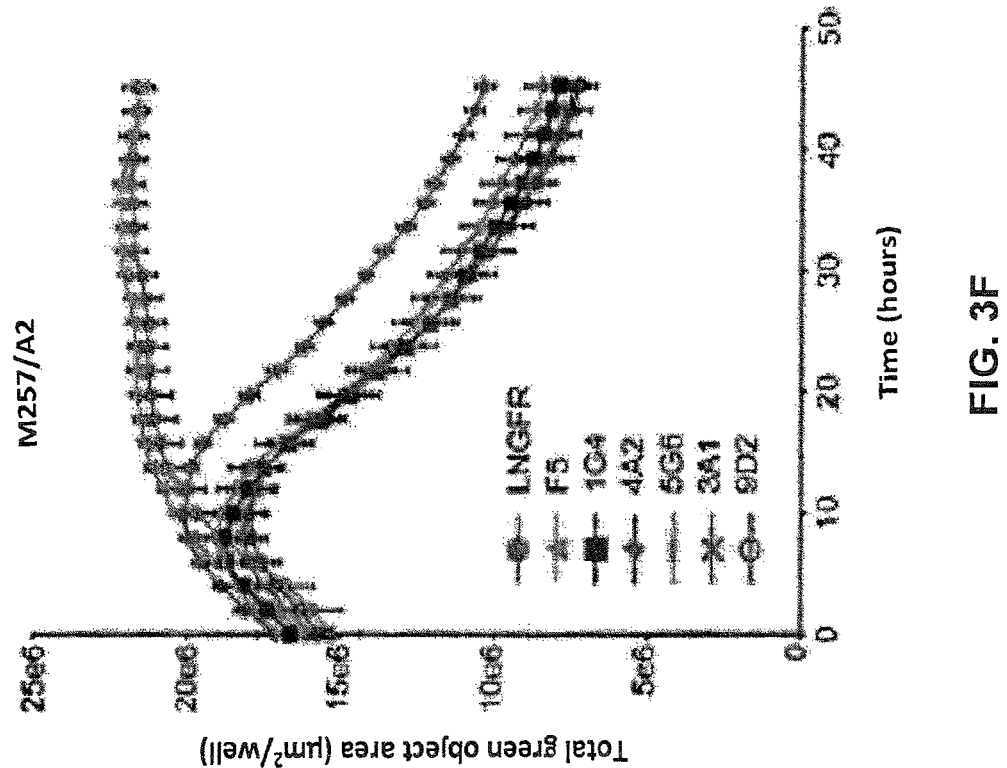
Figure 7A:
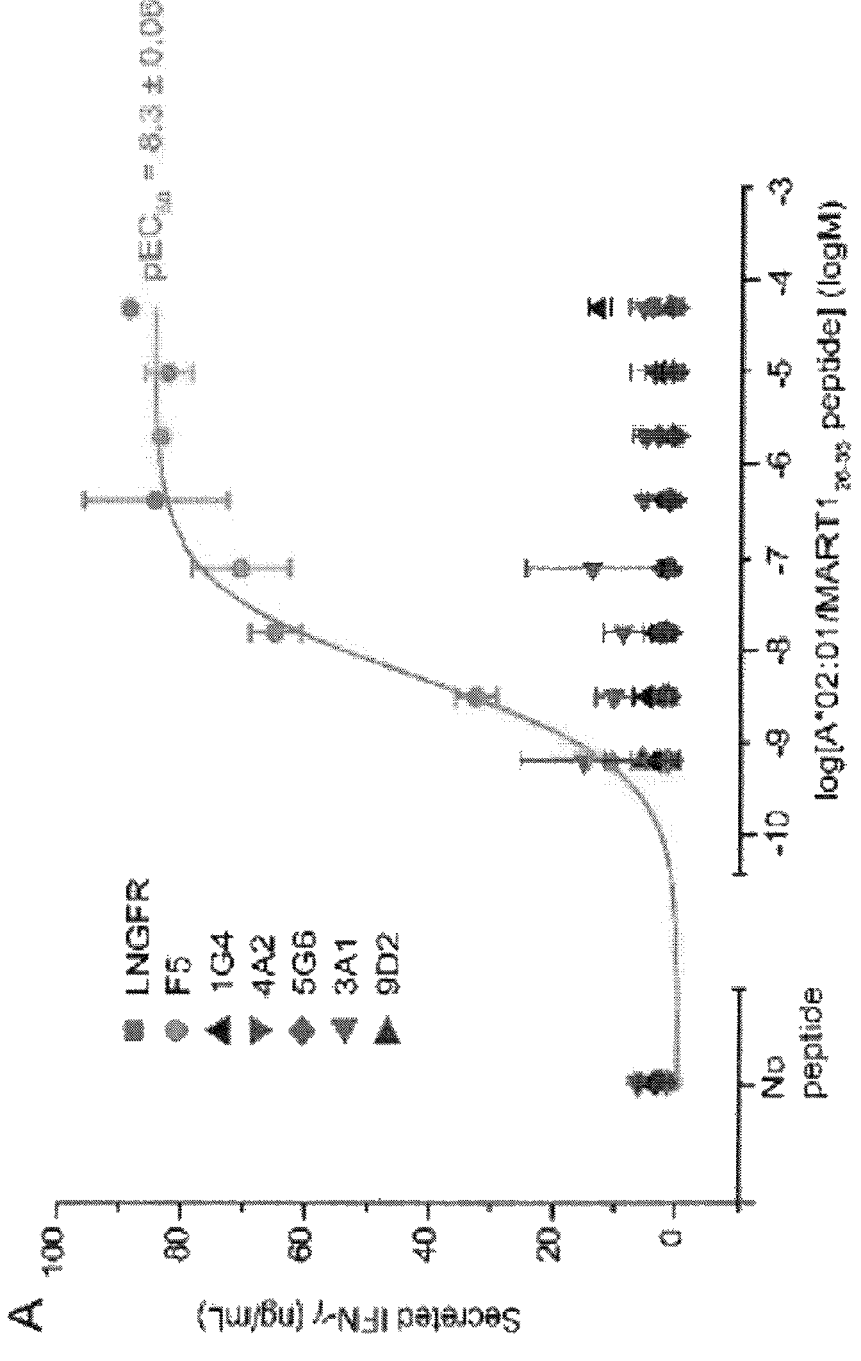
FIGS. 7A-7E provide disclosure relating to determinations of EC50 for NY-ESO-1-specific TCRs.
Figure 7B:
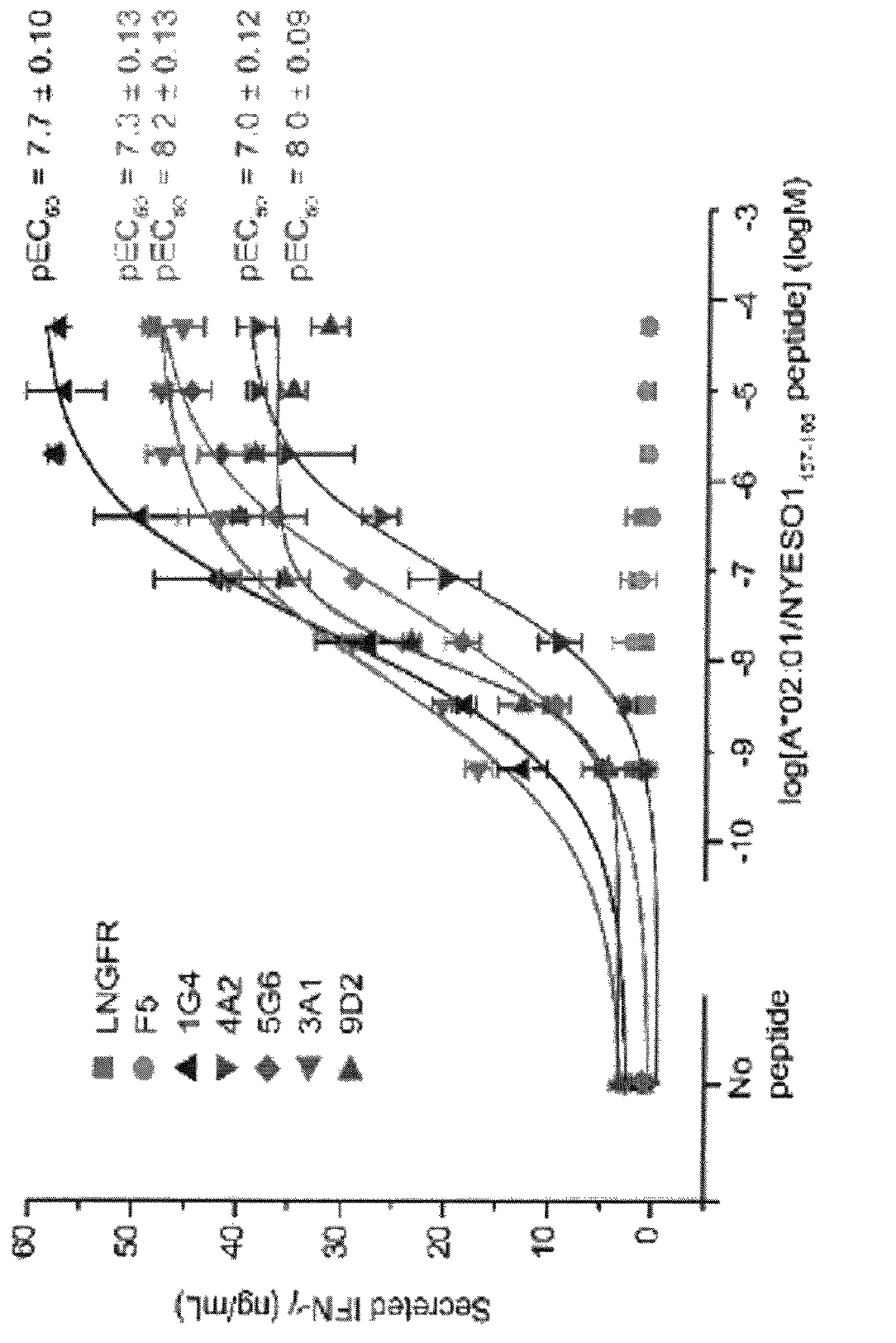

To compare the functional sensitivity of T cells expressing novel, A2/NY-ESO-1-specific TCRs, we co-incubated TCR-transduced Jurkat T cells with K562 cells expressing either A*02:01/NY-ESO-1$_{157-165}$ or A*02:01/MART1$_{27-35}$ single-chain trimers (38) and measured secreted interleukin-2 (IL-2). All TCRs exhibited their expected peptide specificity: the control MART1-specific F5 TCR mediated IL-2 release only in response to MART1 presentation and all NY-ESO-1-specific TCRs mediated IL-2 release only in response to NY-ESO-1 presentation (FIG. 3D). Murinization improved functional sensitivity for all TCRs except for 1G4. Consistent with dextramer staining results, 1G4 and 3A1 muTCRs outperformed 4A2 and 5G6 muTCRs. By contrast, despite its weak binding to dextramer, 9D2 exhibited high functional sensitivity to cognate ligand, comparable to 3A1. To quantify this observation, we pulsed A2*K562 cells with varied concentrations of NY-ESO-1$_{157-165}$ or MART1$_{27-35}$ peptide, and then measured IFN-$\gamma$ secretion from TCR-transduced primary T cells co-incubated with peptide-pulsed target cells (FIG. 7A, 7B). As observed with single-chain trimer targets, 3A1, 9D2, and 1G4 exhibited highest sensitivity to NY-ESO-1$_{157-165}$ peptide. The functional sensitivity of 9D2 was 10-fold higher than 4A2, despite 4A2 binding dextramer with 18-fold higher MFI than 9D2 (FIG. 3A, 3B). To evaluate responses to endogenously-processed and presented antigen, TCR-transduced primary T cells were co-incubated with the human melanoma cell line, A2*M257 (FIG. 3E). Again, T cells transduced with 3A1, 9D2, and 1G4 responded comparably to one another, and with higher sensitivity than did those transduced with 5G6 and 4A2. TCR-transduced T cells did not respond to the M257 line lacking HLA-A*02:01. Finally, in vitro cytotoxicity tracked closely with cytokine release: T cells expressing 9D2 or 3A1 killed A2$^+$ M257 tumor cells most efficiently, followed by T cells transduced with 1G4, 5G6, and, least efficiently, 4A2 (FIG. 3F).

Figures 4A, 4B:
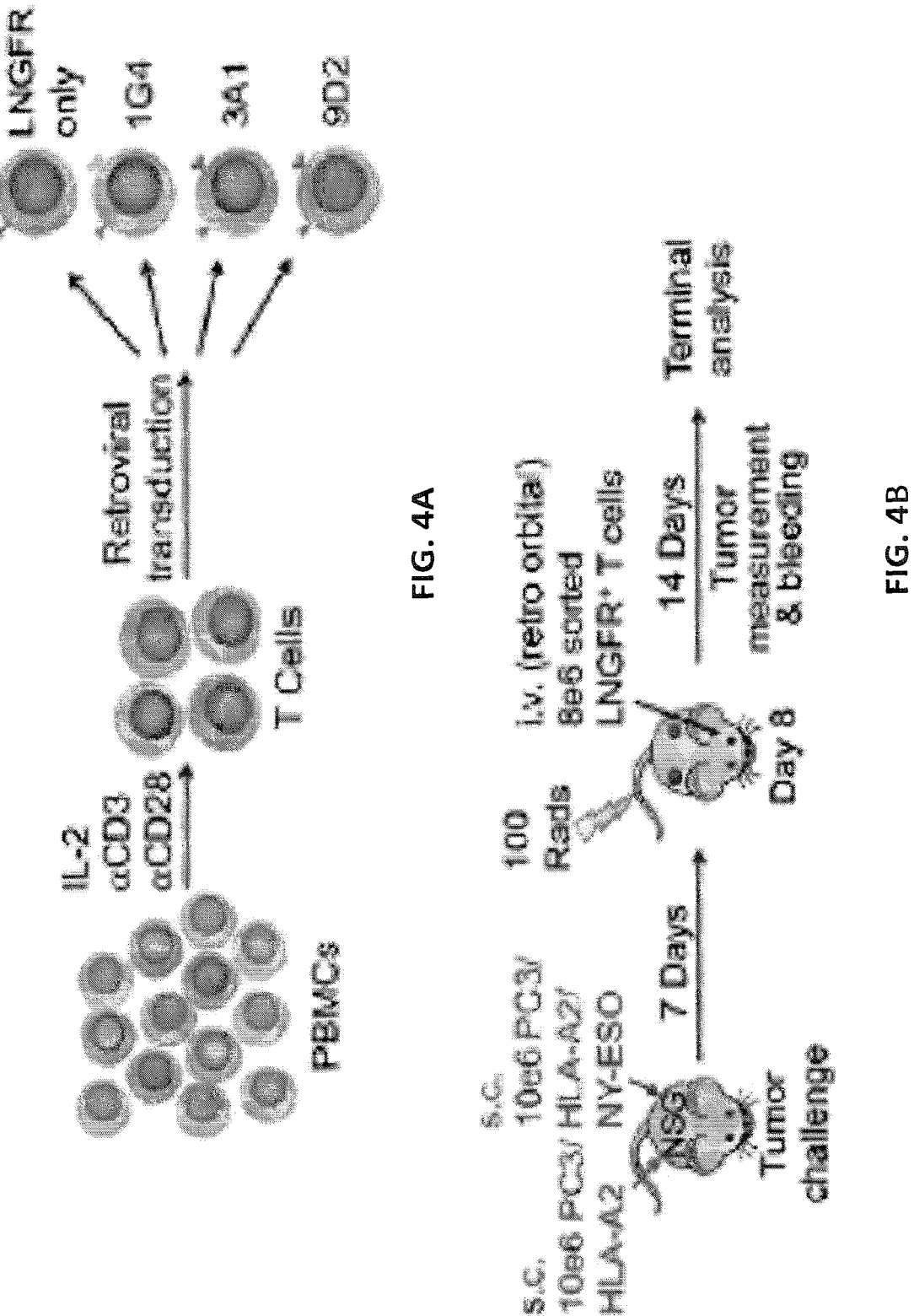
FIGS. 4A-4J provide disclosure relating to the in vivo anti-tumor efficacy of NY-ESO-1 TCR-engineered human T cells.
Figure 8A:
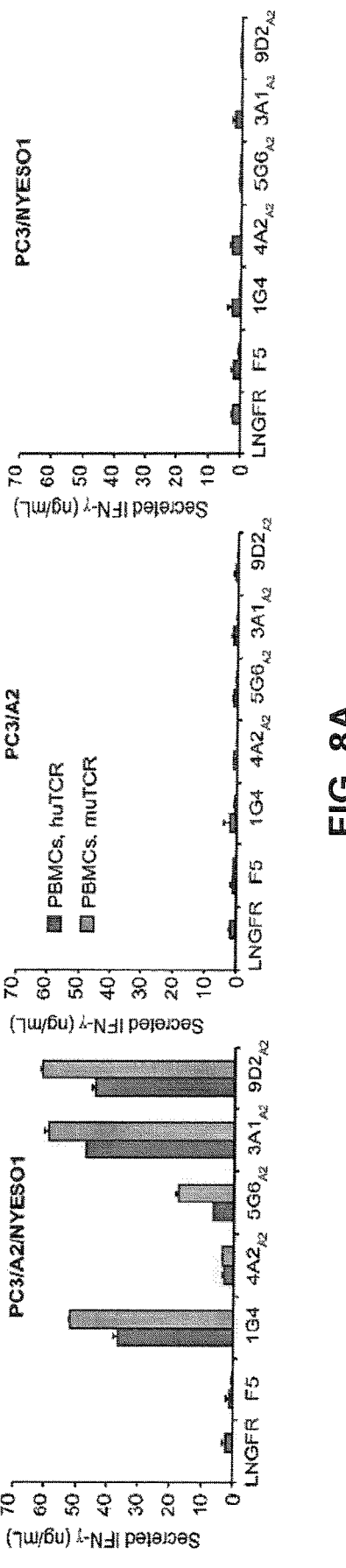
FIGS. 8A-8C provide disclosure relating to the establishment of xenograft tumor line and function of input T cells for in vivo experiments.
Figure 8B:
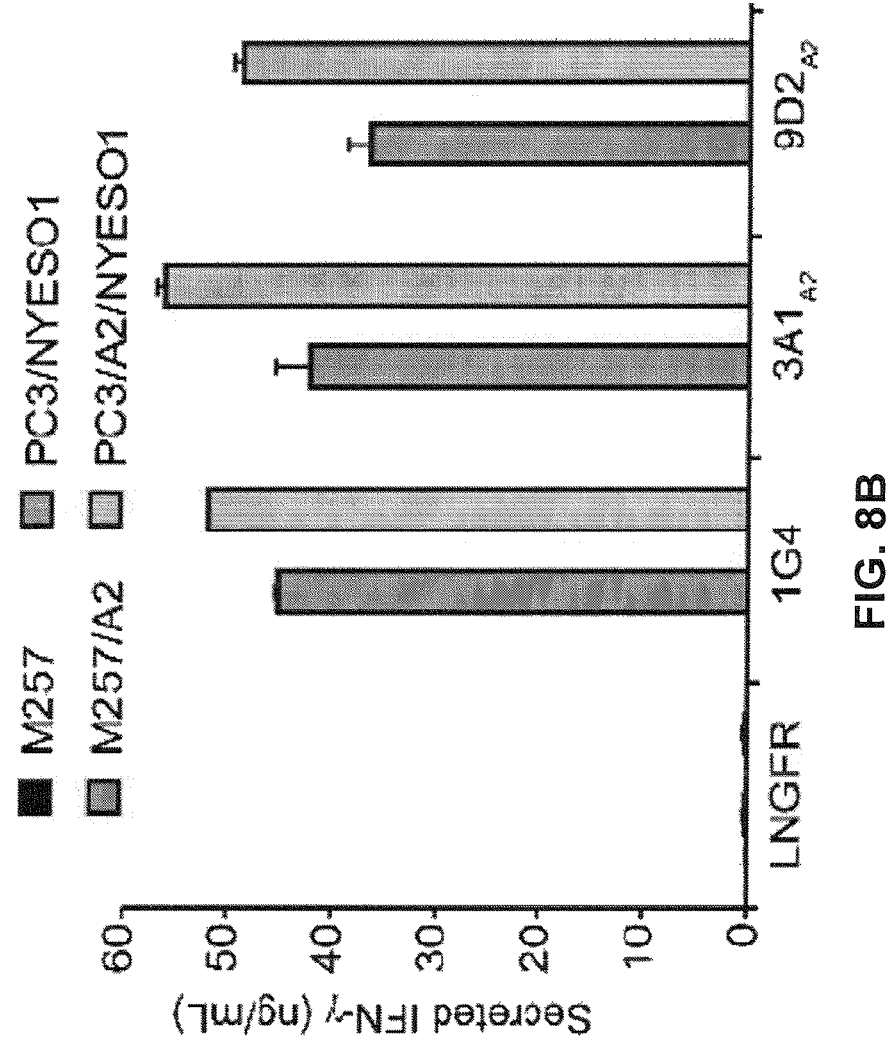
Figure 8C:
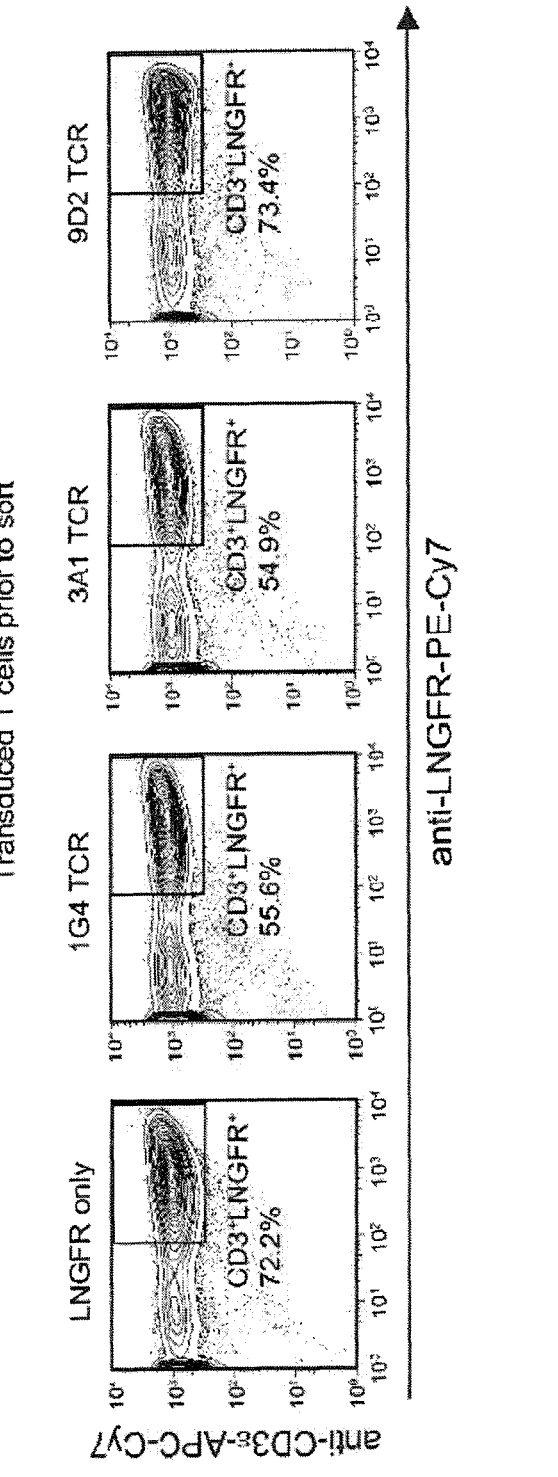

To enable evaluation of TCR function in a tumor xenograft model, we engineered the PC-3 human prostate cancer cell line to express NY-ESO-1 and HLA-A*02:01 and then verified that this line elicited functional responses from TCR-transduced T cells in an antigen-dependent and MHC-restricted manner (FIG. 8A). The relative responses to A2$^+$NY$^+$PC-3 from our panel of novel NY-ESO-1-reactive TCRs were consistent with those elicited by A2$^+$M257 (FIG. 3E and FIG. 8B). Based on these results, we selected 1G4, 3A1, and 9D2 muTCRs for further functional characterization in vivo. We transduced activated human PBMCs with a vector encoding each murinized TCR and a transduction marker (low-affinity nerve growth factor receptor (LNGFR) (FIG. 4A). We sorted transduced (CD3$^+$LNGFR$^+$) T cells (FIG. 8C) and retro-orbitally i.v. injected these T cells into irradiated NOD/SCID/$\gamma$c$^{-/-}$ (NSG) mice pre-inoculated with PC-3/HLA-A2 (control) and PC-3/HLA-A2/NYESO (target) tumors on opposing flanks (FIG. 4B). We then monitored T cell engraftment and tumor size until the conclusion of the experiment two weeks after T cell injection.

Figure 4C:
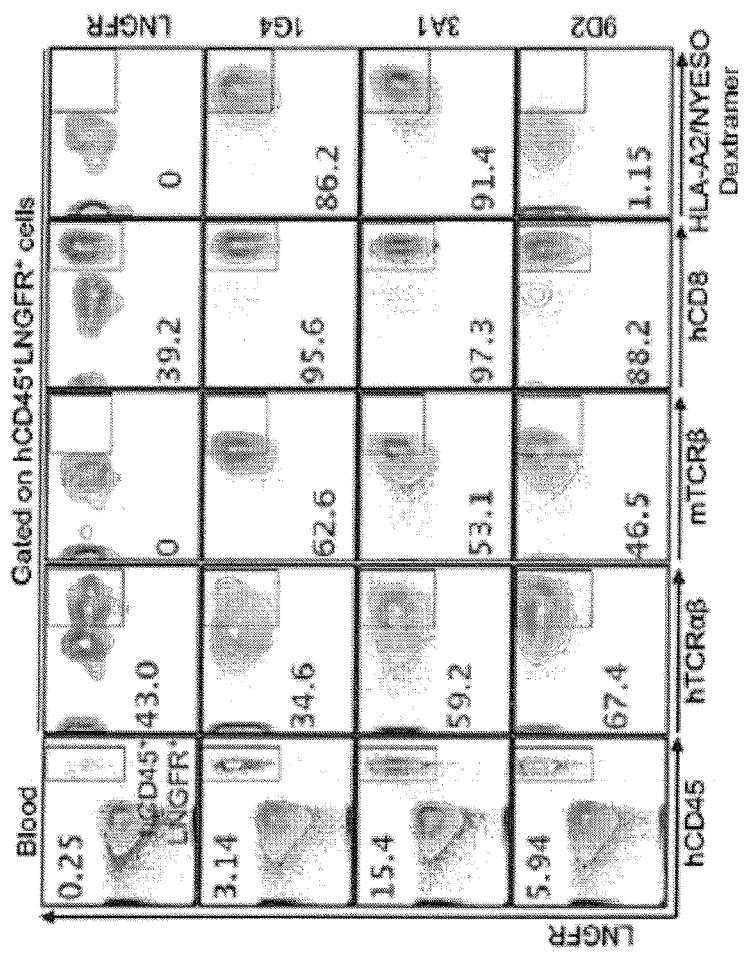
Figure 4D:
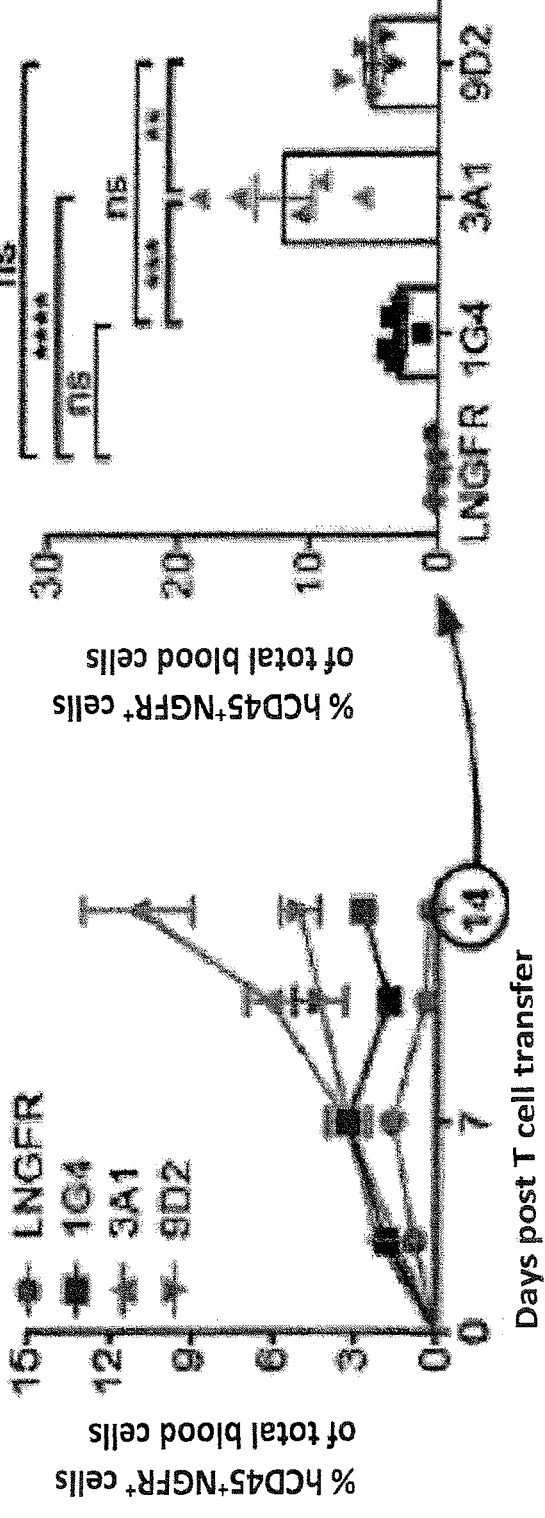
Figures 4E, 4F:
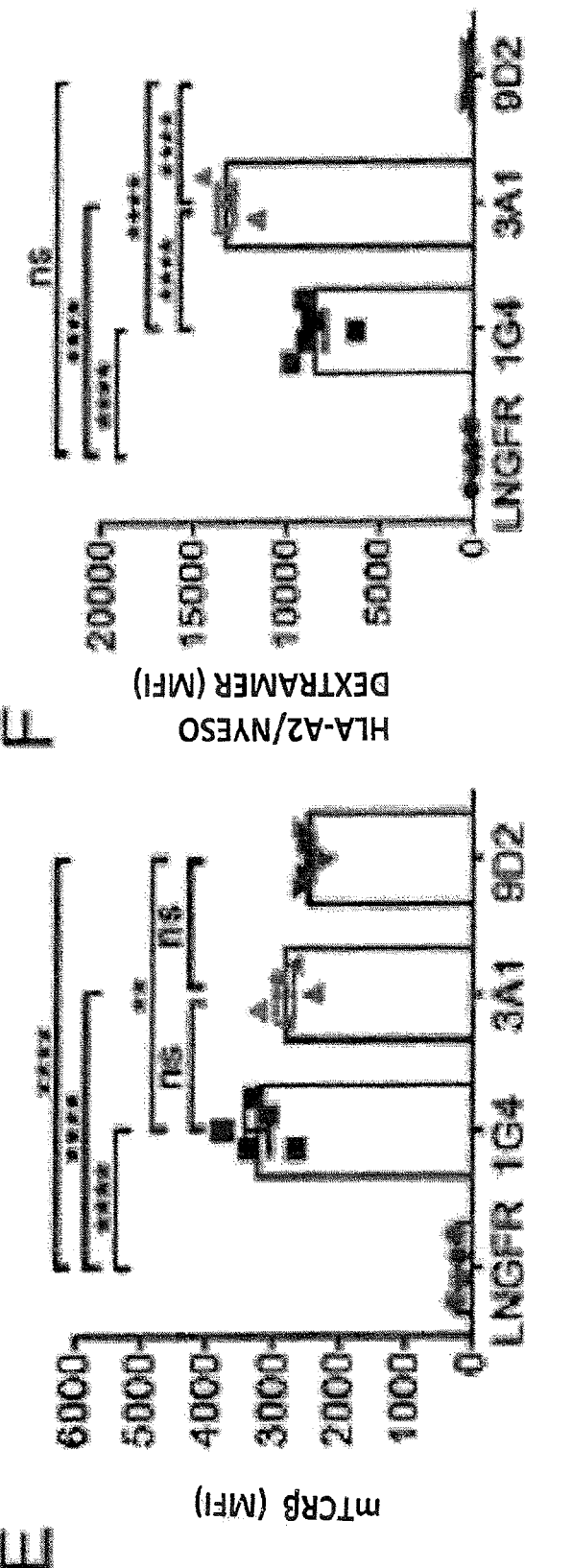
Figure 4G:
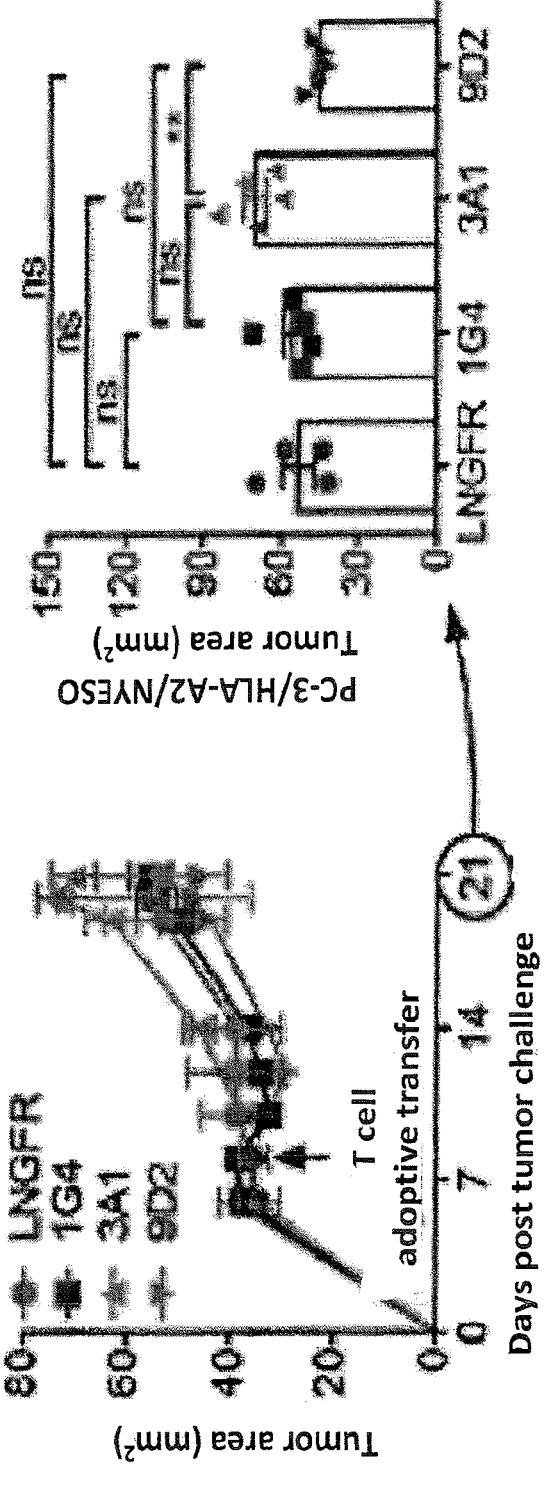
Figure 4H:
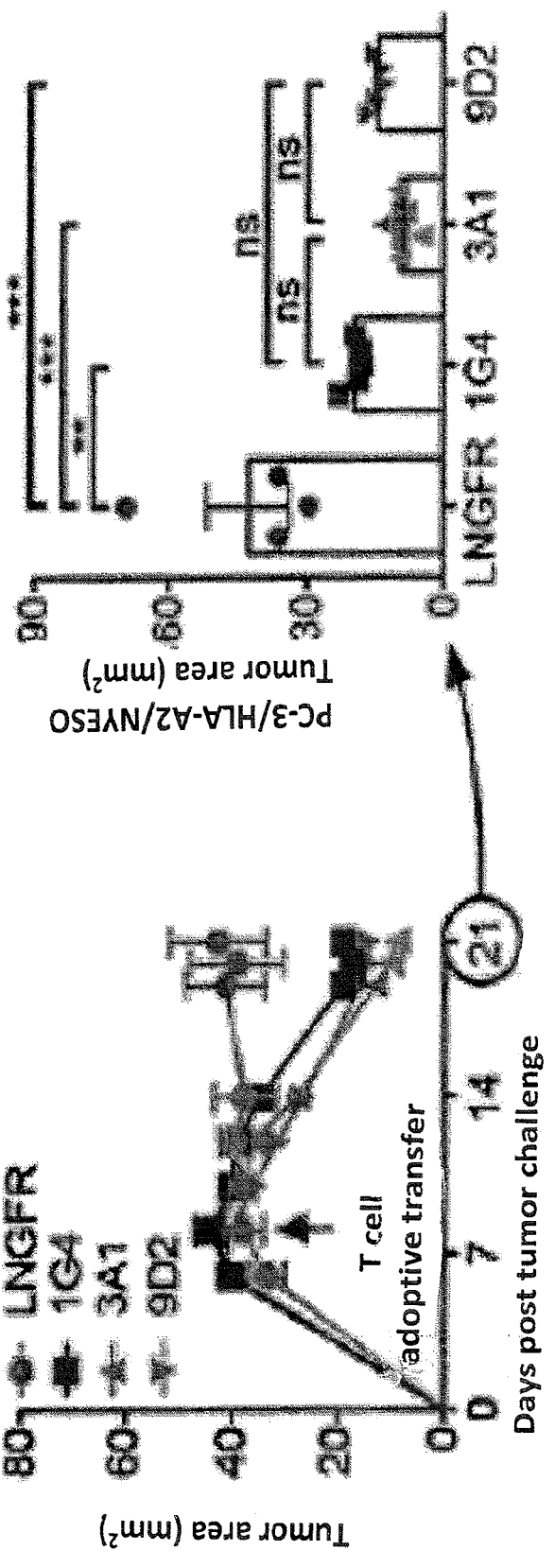

T cells transduced with 1G4 or 9D2 TCRs persisted or minimally expanded in the peripheral blood, while 3A1-transduced T cells expanded significantly (FIGS. 4C and 4D). By contrast, T cells transduced only with LNGFR contracted over the course of the experiment, suggesting the expansion of TCR-transduced T cells was antigen-driven. The expression level of murine TCR$\beta$ (mTCR$\beta$) was stable over the experimental time course and comparable between T cells transduced with different murinized TCRs (FIGS. 4C and 4E). The respective staining levels of each TCR-transduced T cell cohort with A*02:01/NY$_{157-165}$ dextramer$^+$ were also stable over time but, as expected from results in vitro, were significantly different between TCRs. Approximately 90% of human T cells transduced with 1G4 or 3A1 were dextramer$^+$ with high MFI. By contrast, only ~1% of 9D2-transduced T cells were dextramer$^+$ and the MFI of staining was not significantly different from LNGFR-transduced controls (FIGS. 4C and 4F). Nonetheless, T cells transduced with 1G4, 3A1, or 9D2 reduced tumor size comparably and in an antigen-specific manner, while LNGFR-transduced T cells failed to control tumor growth (FIGS. 4G and 4H).

Figure 4I:
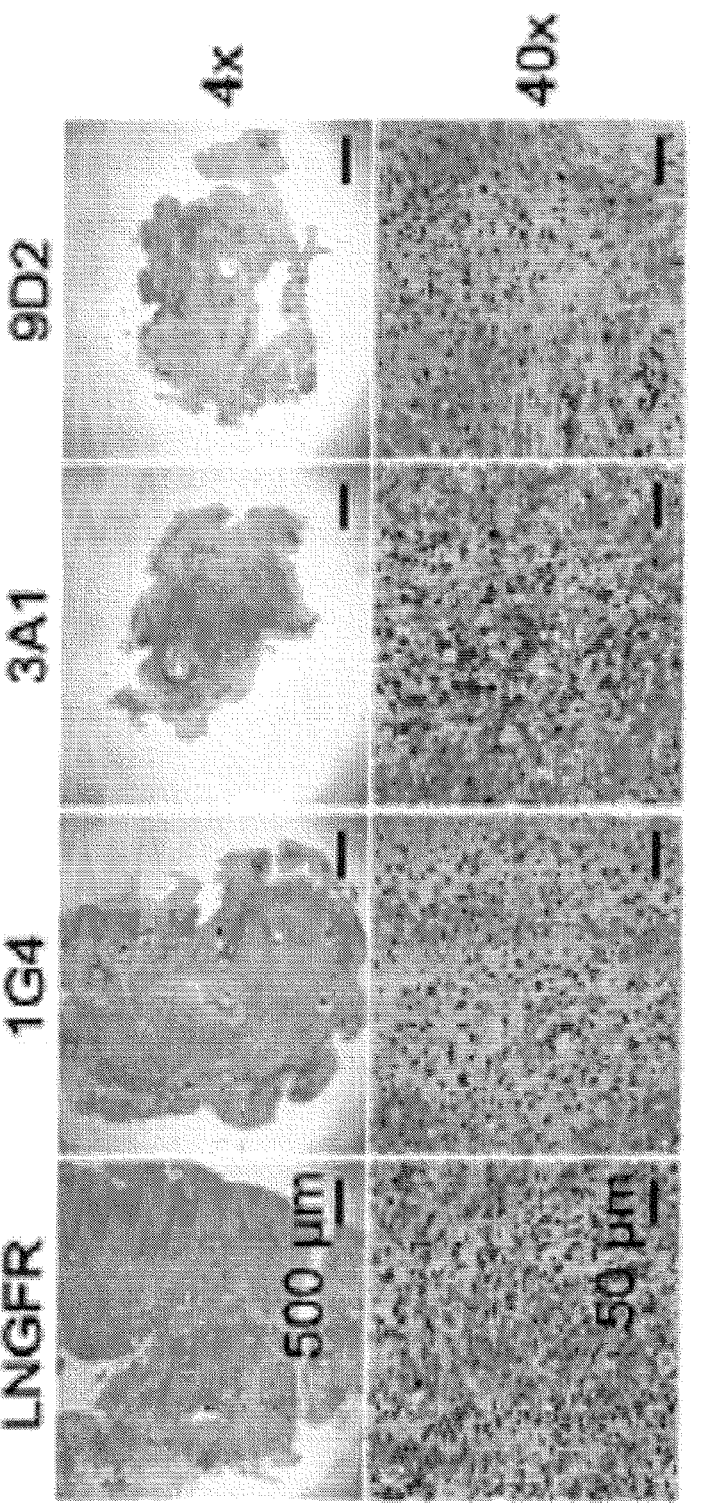
Figure 4J:
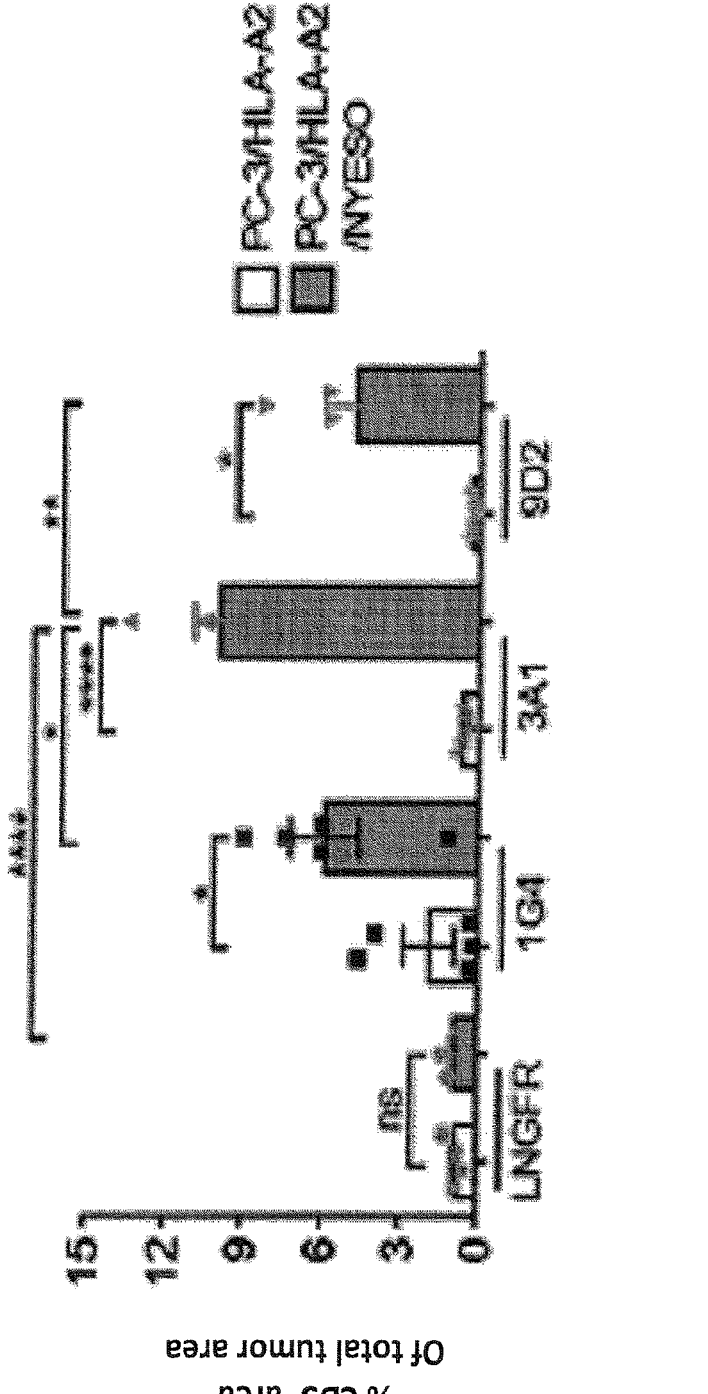

At the conclusion of the experiment, we sacrificed the mice and analyzed tumors for T cell infiltration by immunohistochemistry. Immunohistochemical staining revealed antigen-specific T cell infiltration only into target tumors in all cohorts receiving TCR-transduced T cells (FIGS. 4I and 4J). Infiltration was significantly higher in mice receiving 3A1-transduced T cells relative to mice receiving 1G4- or 9D2-transduced T cells.

Figure 5A:
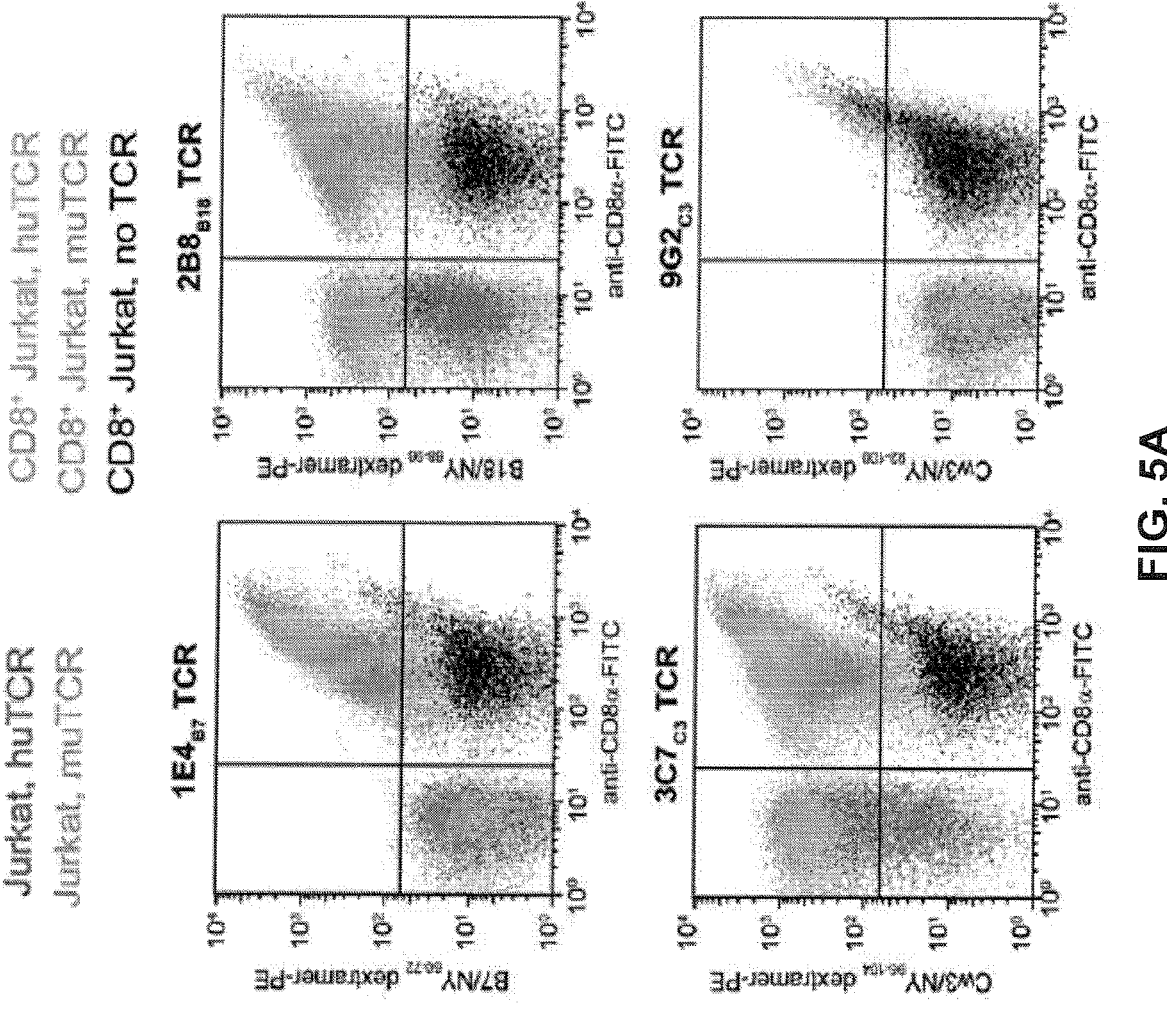
FIGS. 5A-5E provide disclosure relating to the function of NY-ESO-1-specific TCRs restricted on MHC alleles other than HLA-A2.
Figure 5B:
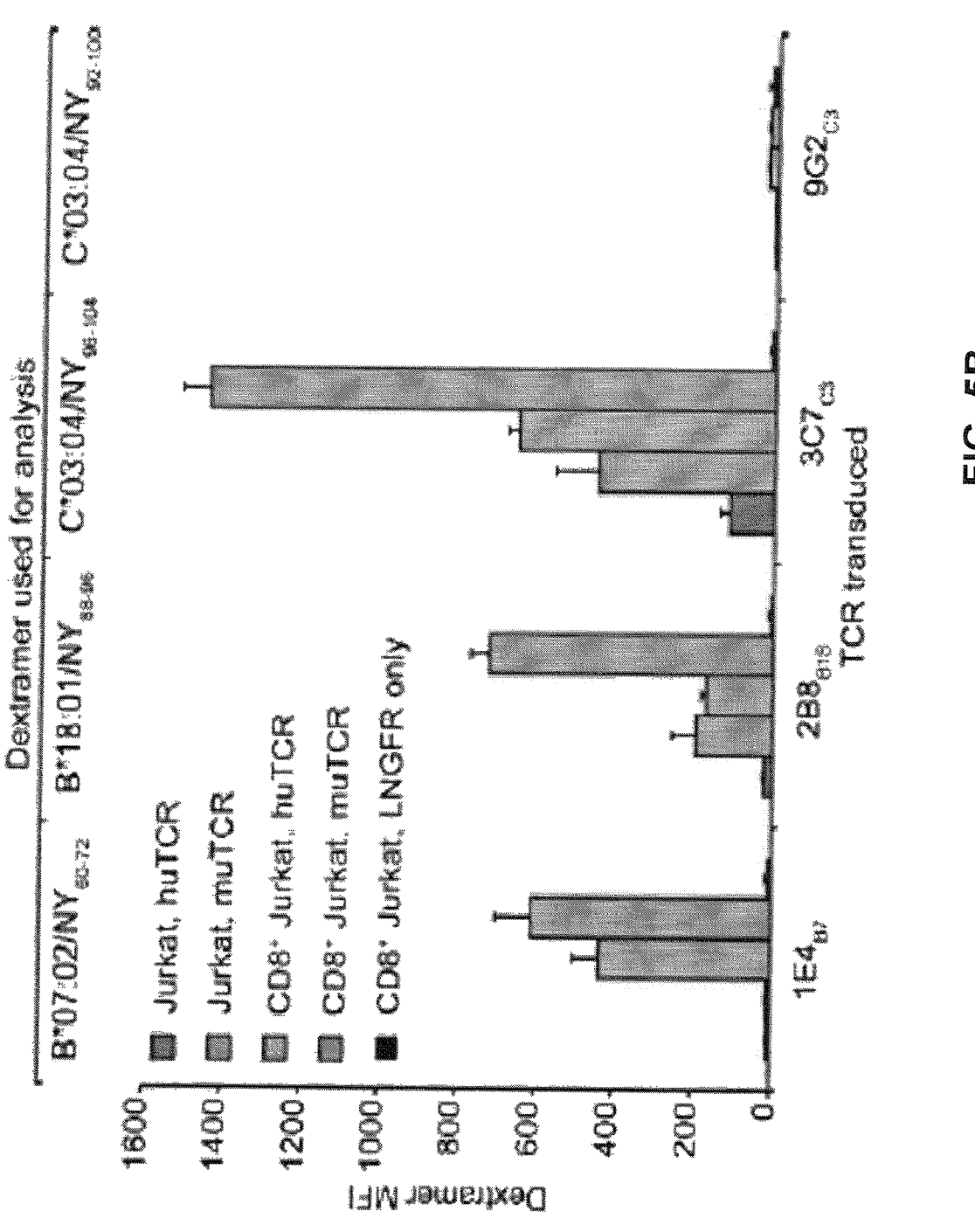
Figure 5C:
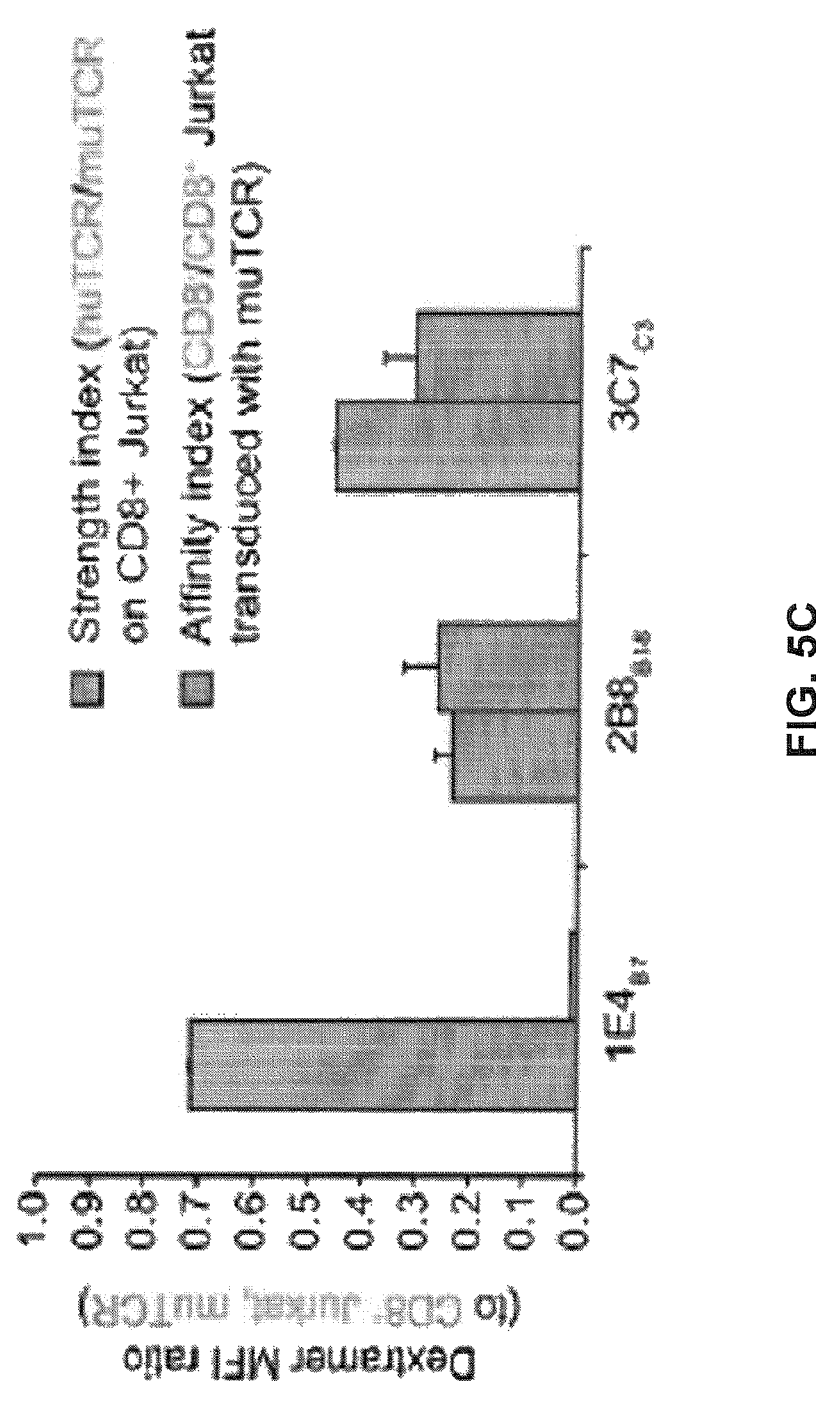

Example 4: Functional Characterization of NY-ESO-1-Specific TCRs Restricted on HLA-B and HLA-C Alleles The majority of immunotherapies targeting NY-ESO-1 have focused on the A2-restricted NY-ESO-1$_{157-165}$ epitope. To enable broader application of NY-ESO-1-targeted immunotherapies, we cloned TCRs from four non-A2-restricted T cell clones and verified NY-ESO-1-reactivity for three of these in transfected CD3$^+$ 293T (FIG. 2D). The fourth TCR—9G2, cloned from Cw3/NY-ESO-1$_{92-100}$-reactive T cells—did not impart specificity for Cw3/NY-ESO-1$_{92-100}$ on transduced Jurkat T cells even with co-expressed CD8 (FIG. 5A, 5B) and was not studied further. Comparisons of dextramer binding by the three validated TCRs expressed in Jurkat or CD8$^+$ Jurkat as human or murine TCRs revealed differences in strength and affinity (FIG. 5A, 5B, 5C). The B7/NY-ESO-1$_{60-72}$-specific 1E4 TCR exhibited high strength but low affinity, expressing comparably on the Jurkat cell surface as either a huTCR or a muTCR but binding dextramer only in the presence of CD8$^+$. Dextramer binding to these CD8$^+$, 1E4-transduced cells was steeply dependent on the level of CD8 expressed. By contrast, the B18/NY-ESO-1$_{88-96}$-specific 2B8 TCR bound dextramer in the absence of CD8$^+$, but binding was substantially higher for the murinized TCR. Finally, the Cw3/NY-ESO-1$_{96-104}$-specific 3C7 TCR exhibited intermediate strength of surface expression and an affinity index comparable to 2B8.

Figure 5D:
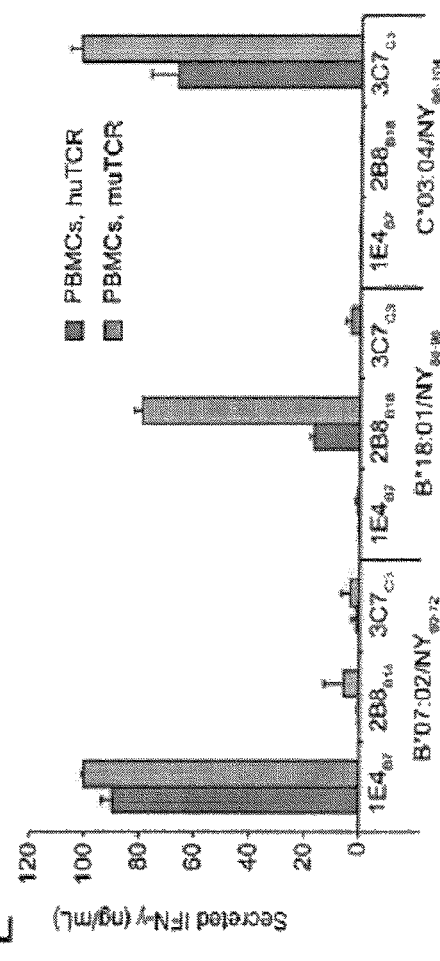
Figure 7C:
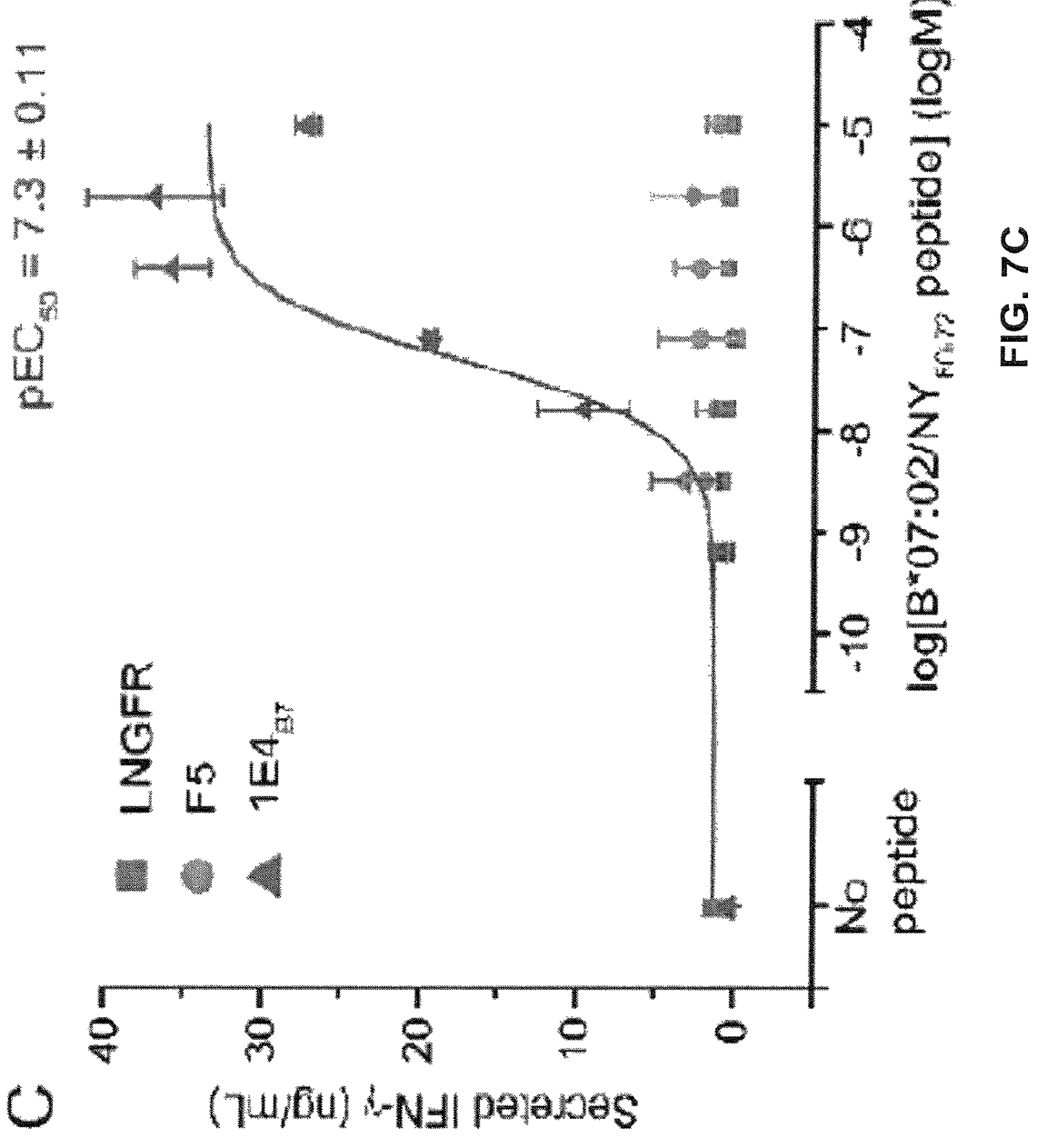
Figure 7D:
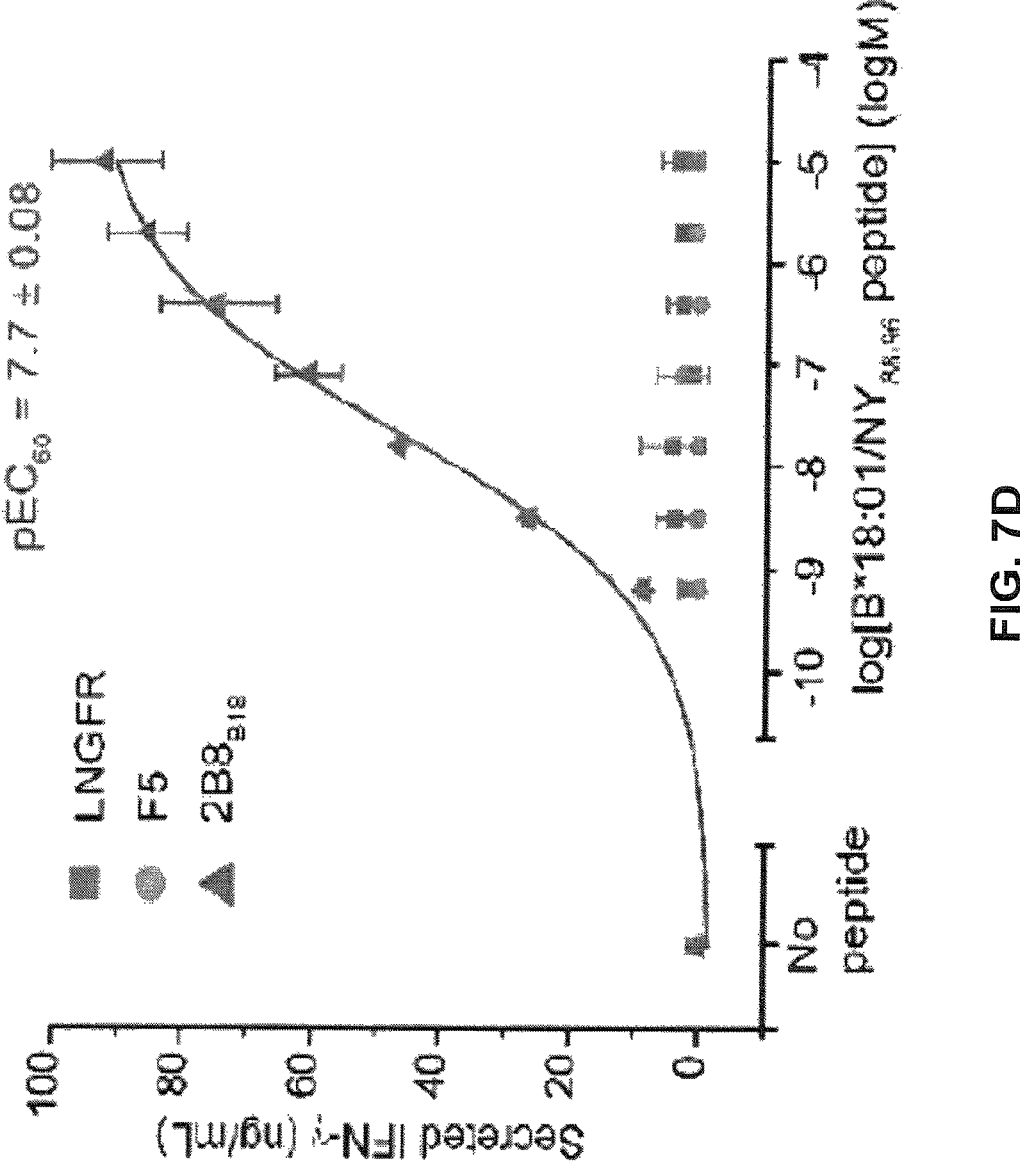
Figure 7E:
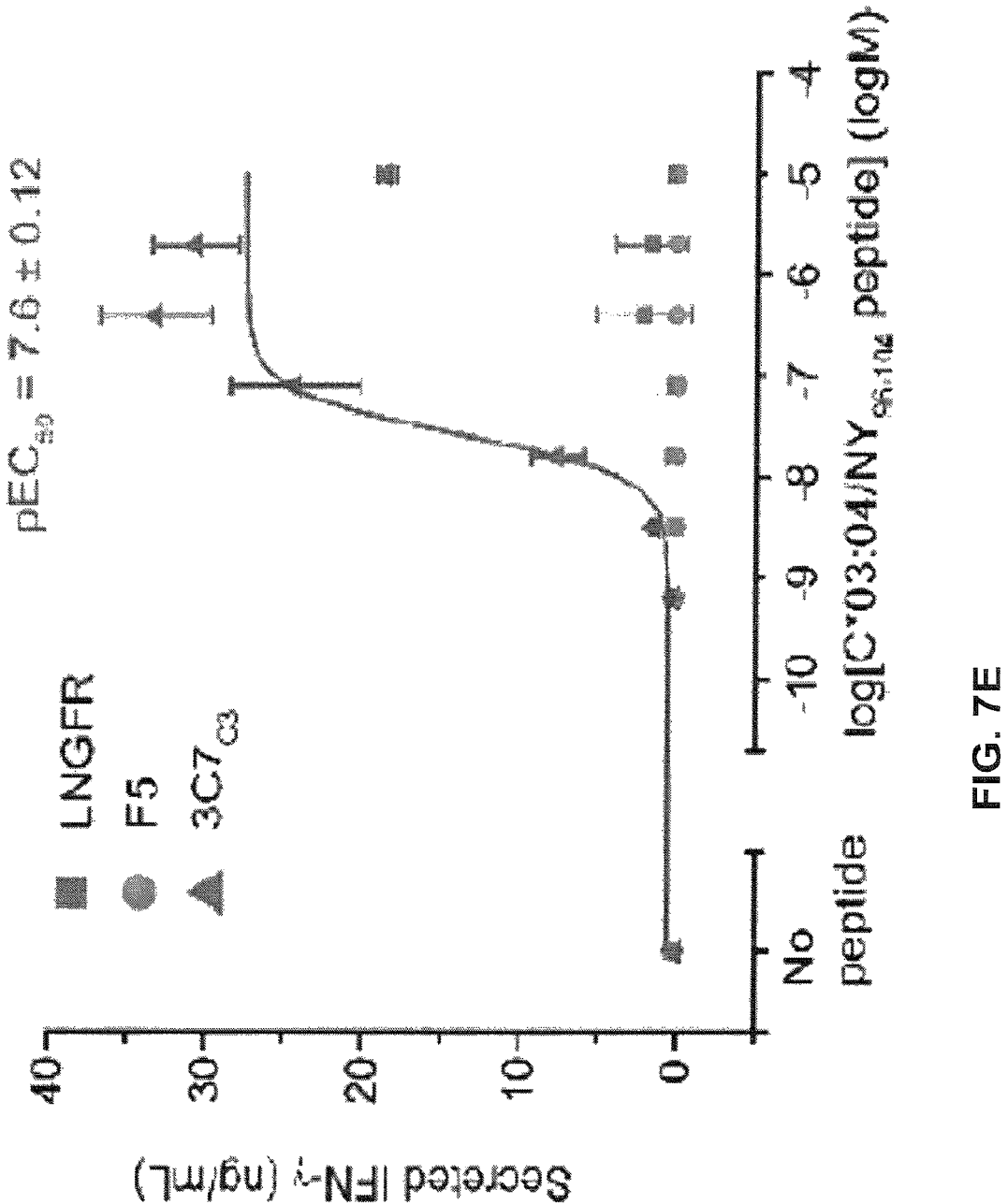

These differences in TCR strength and affinity were reflected in functional assays. For all three TCRs, murinization of the TCR constant regions increased production of IL-2 from TCR-transduced Jurkat cells co-incubated with cognate target cells. However, this increase was only 1.6- and 3.0-fold over the respective fully human TCRs for 1E4 and 3C7, but was 18.6-fold for 2B8, consistent with the latter's lower strength (FIG. 5D). In peptide titration assays, 1E4 TCR imparted lower sensitivity for cognate peptide on transduced CD8$^+$ T cells than did 3C7 or 2B8 (FIG. 7C, 7D, 7E), consistent with the presumed lower affinity of 1E4 based on its strictly CD8-dependent dextramer binding.

Figure 5E:
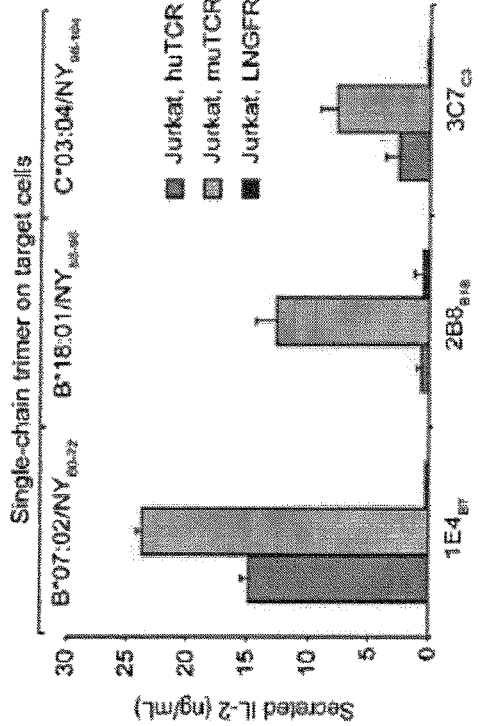

Primary PBMCs transduced with each TCR responded to the presentation of NY-ESO-1-derived epitopes in a peptide-specific and MHC-restricted manner (FIG. 5E). As such, we

Figures 6A, 6B:
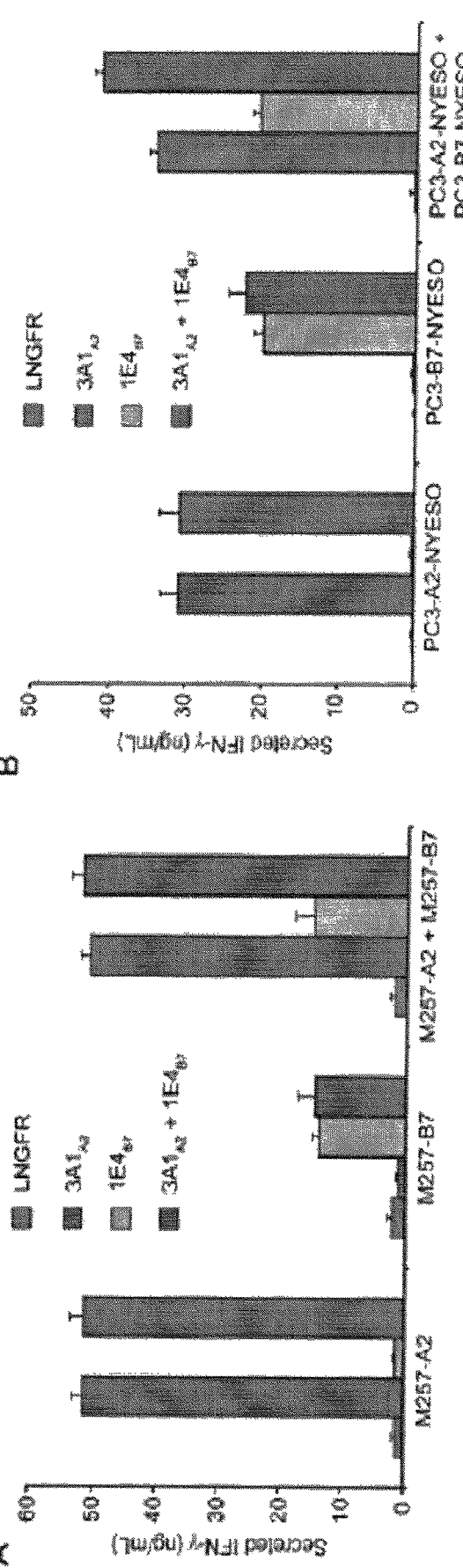
FIGS. 6A-6D provide disclosure relating to targeting NY-ESO-1 epitopes restricted on multiple MHC alleles broadens the application of TCR gene therapy and makes it robust toward loss of heterozygosity at the MHC locus. T cells transduced with LNGFR only, A2-restricted 3A1 TCR, or B7-restricted 1E4 TCR—or a 1:1 mixture of 3A1-transduced and 1E4-transduced T cells—were co-incubated for 48 hours with HLA-A2$^+$eGFP$^+$ target cells, HLA-B7$^+$ eGFP$^+$ target cells, or a 1:1 target cell mixture.
Figure 6C:
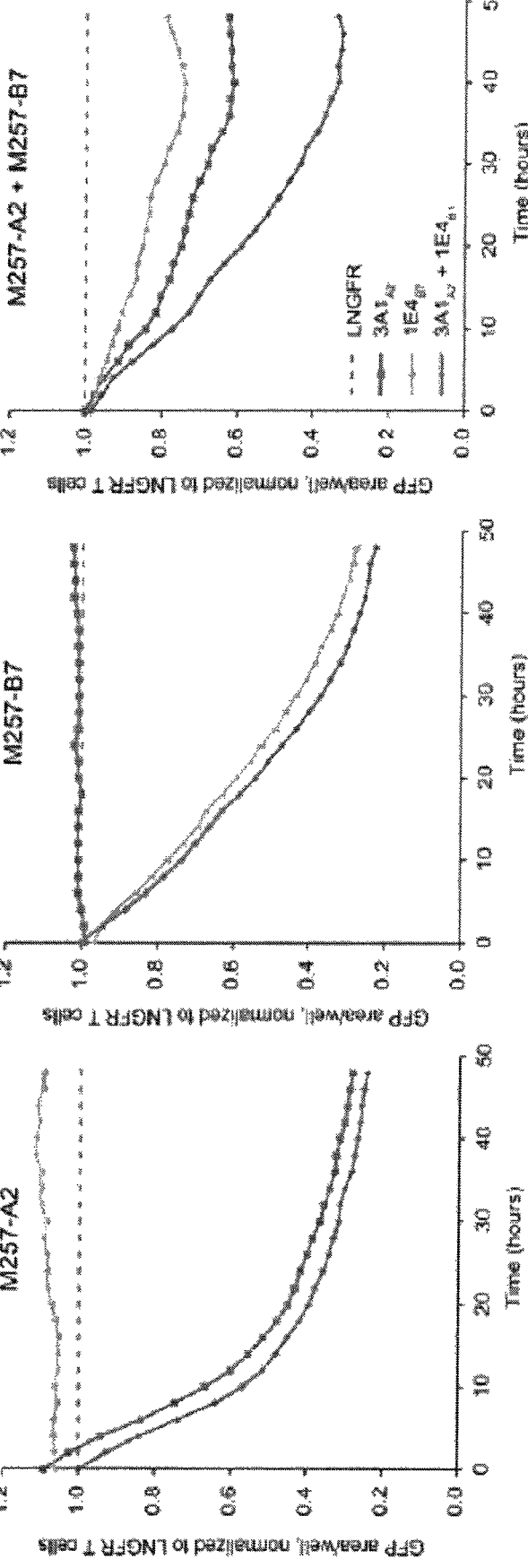
Figure 6D:
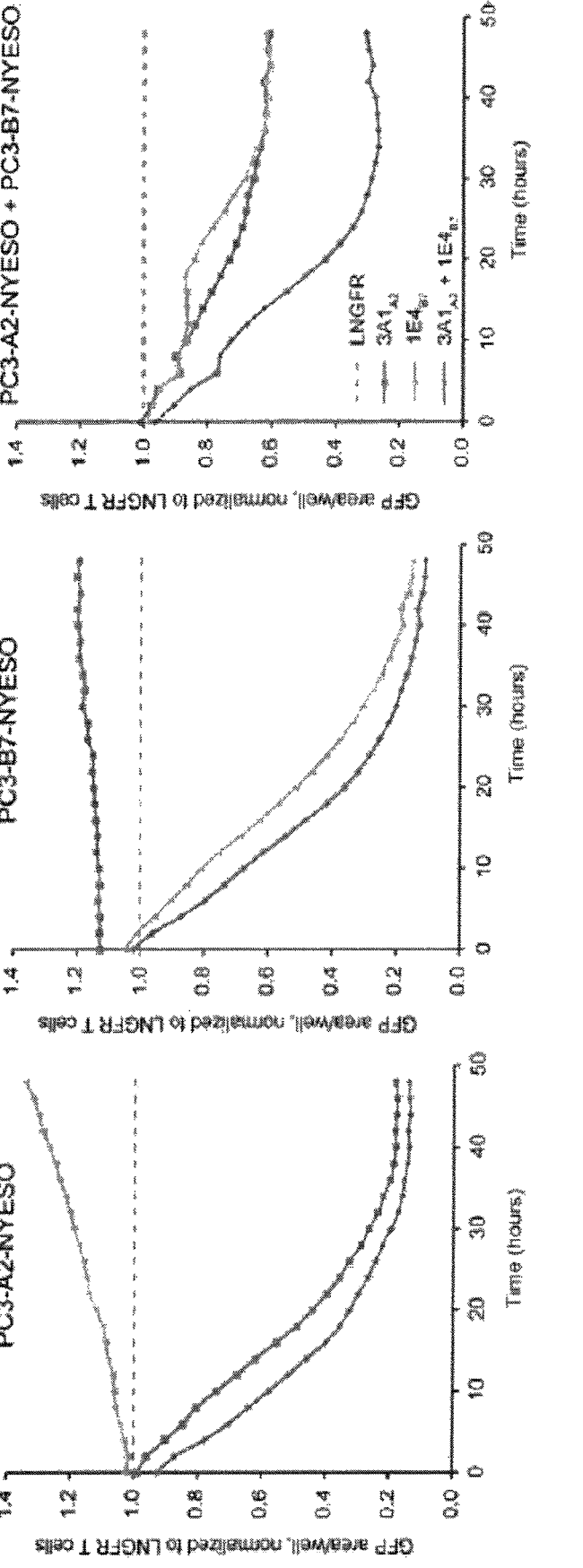

15 expect that TCR gene therapies employing NY-ESO-1 specific TCRs restricted on multiple MHCs can be applied more broadly across patient haplotypes and will be more robust toward tumor evasion via loss-of-heterozygosity at the MHCI locus. To test this, we transduced NY-ESO-1-expressing human cancer cells with HLA-A2 or HLA-B7. We then co-incubated one or both of these tumor targets with human T cells transduced with A2-restricted 3A1 TCR, with T cells transduced with B7-restricted 1E4 TCR, or with a mixture of 3A1- and 1E4-transduced T cells (FIG. 6). As expected, combination targeting using a mixture of 3A1- and 1E4-transduced T cells enabled recognition of tumor cell populations expressing both MHC alleles or either MHC allele alone (FIG. 6A, 6B). By contrast, T cells targeting a single NY-ESO-1 epitope did not respond to NY-ESO-1-expressing tumor cells that lacked the cognate MHC allele. Moreover, when tumor targets comprised a mixture of cells expressing different MHC alleles (simulating tumor heterogeneity arising from haploinsufficiency), T cells targeting both NY-ESO-1 epitopes killed tumor cells more completely than did T cells targeting either single epitope (FIG. 6C, 6D).

Discussion

T cell-mediated immunotherapies are making clinical inroads for previously refractory cancers. Two of the most successful immunotherapy modalities are checkpoint blockade and adoptive transfer of cancer-specific T cells. Checkpoint blockade elicits better clinical responses as tumor mutational burden increases (39-41), suggesting that nonsynonymous mutations go undetected by the immune system unless, fortuitously, they generate neoepitopes that are presented by the patient's complement of MHC molecules. This interpretation is bolstered by the recent finding that checkpoint blockade results in higher overall survival for melanoma patients who are heterozygous at the HLA-A, HLA-B, and HLA-C loci and thus present a more diverse array of epitopes than those who are homozygous at one or more of these MHCI loci (42). The importance of a diversely targeted anti-tumor immune response is likewise supported by results from adoptive T cell therapy, which show that loss-of-heterozygosity is a mechanism by which tumors can evade monospecific immune recognition while continuing to express an otherwise immunogenic antigen (43). Thus, a prominent narrative emerging from these studies is that diverse targeting of multiple epitopes presented by multiple MHC alleles is desirable for successful immunotherapy. A second takeaway is that targeting multiple epitopes derived from a tumor-specific public antigen may be a promising alternative to targeting neoepitopes in cancers with low mutational burden.

It has proven difficult to identify public tumor-associated antigens that mediate tumor regression without also manifesting serious morbidity or deaths resulting from on-target, off-tumor T cell reactivity. We chose to focus on NY-ESO-1 as a public antigenic target based on the criteria that it 1) is expressed exclusively in cancer cells and immunologically privileged germ cells; 2) is expressed in many patients across various tumor types; 3) harbors high-affinity ligands for multiple common MHC alleles; 4) is well-vetted, having yielded objective responses in patients across several tumor types without specificity-related adverse events; and 5) is yet underexploited, as the majority of studies have focused on mobilizing T cell responses solely against the A2-restricted NY-ESO-1$_{157-165}$ epitope.

We employed an antigen-specific expansion protocol to isolate NY-ESO-1-reactive T cells from the peripheral blood of patients with metastatic melanoma. Using this approach, we cloned several HLA-A2-restricted TCRs and compared them in terms of their strength of surface expression, affinity (i.e. dependence of target binding on CD8), and function (antigen-induced cytokine release and tumor target killing). From four candidates, we identified two that recognized and killed NY-ESO-1-expressing cancer cells as well or better than the clinically-employed 1G4 TCR. This expansion-based approach to TCR candidate identification is ideally-suited for targeting public epitopes because the speed of isolation is not a critical parameter; once identified, these TCRs can be used as off-the-shelf targeting receptors for any patient expressing the requisite MHC allele. Antigen-specific expansion of neoantigen-reactive T cells from peripheral blood has also been demonstrated (44, 45). However, on-demand isolation of private neoepitope-targeted TCRs will require more rapid approaches than that used here (e.g. direct capture of antigen-specific T cells from blood or expansion protocols optimized for rapidity). As the release of IFN-γ is strongly correlated with cytotoxicity (46), candidate evaluation can be accelerated by using IFN-γ release as a surrogate for more involved tumor xenograft assays.

One of the HLA-A2/NY-ESO-1-reactive TCRs isolated—9D2—exhibited poor staining with cognate multimer but high functional avidity toward cognate antigen-presenting target cells. This is consistent with the observation that multimer staining underestimates functional T cell subsets (47) and may be explained by the higher affinity threshold for multimer binding relative to that for T cell activation (48). However, another isolated A2-restricted TCR—4A2—exhibited robust multimer staining but poor function in cell-based assays, seemingly at odds with this affinity threshold explanation. While we do not have an explanation for this latter result, both results caution against relying overmuch on multimer staining when down-selecting immunotherapy candidates.

The HLA-A*02:01 allele is the most prevalent MHCI allele in Caucasian (45%) and Hispanic (41%) U.S. populations, but it is less common among Asian (15%) and African (16%) U.S. populations (2). These latter populations would be particularly well-served by expanding the targeting of TCR gene therapies beyond HLA-A2 to a more expansive panel of targetable MHC alleles. In addition to HLA-A2-restricted TCRs, we isolated and functionally characterized NY-ESO-1-specific TCRs restricted on various HLA-B and HLA-C alleles. In doing so, we demonstrated in principle that TCR gene therapy can be extended to a greater subset of patients/haplotypes and that, when used in combination, TCRs recognizing multiple epitopes from the same antigen can more robustly kill tumors with heterogeneous MHC expression (e.g. resulting from somatic loss-of-heterozygosity). Over 80% of people across ethnic groups express at least one allele from three MHCI supertypes (A2, A3, and B7, two of which were represented here) and >99% of people express at least one allele from nine MHCI supertypes (49). Therefore, obtaining a panel of public antigen-specific TCR reagents that enable comprehensive application of TCR gene therapy is a finite and surmountable challenge.

Materials and Methods

Materials

Peptides were purchased from Anaspec (Fremont, CA), Thermo Fisher Scientific (Waltham, MA), and Mimotopes (Victoria, Australia). Fluorescent antibodies and 7-AAD used for flow cytometry were purchased from BD Biosciences (San Jose, CA), BioLegend (San Diego, CA) or eBioscience (San Diego, CA). Fluorescent peptide-MHC multimers were purchased from TCMetrix (Epalinges, Switzerland) or prepared in-house as described (50) from biotinylated monomers (obtained from NIH Tetramer Core, Atlanta, GA, or expressed heterologously in *E. coli*, refolded, and biotinylated in-house as described(51)). Primers were purchased from Integrated DNA Technologies (Coralville, IA). KOD polymerase master mix and polybrene were purchased from EMD Millipore (Darmstadt, Germany). Sequencing was performed by Retrogen Inc (San Diego, CA). Anti-CD3 (OKT3) and anti-CD28 (CD28.2) activating antibodies were purchased from eBioscience. Cytokines were purchased from Peprotech, Inc. (Rocky Hill, NJ). BioT transfection reagent was purchased from Bioland Scientific (Paramount, CA). Cell culture media, antibiotics, and fetal bovine serum were purchased from Corning (Corning, NY). Human AB serum was purchased from Omega Scientific (Tarzana, CA). Poly-L-lysine and PHA-L (phytohaemagglutinin-L) were purchased from Sigma (St. Louis, MO).

Cells

Cell lines (293T/17, Jurkat E6-1, and K562) were purchased from the American Type Culture Collection (Manassas, VA). 293T cells were grown in Dulbecco's Modified Eagle Medium (DMEM) supplemented with antibiotics (penicillin/streptomycin) and 10% (v/v) fetal bovine serum (FBS). Jurkat and K562 cells were grown in RPMI 1640 medium supplemented with antibiotics, 10% (v/v) FBS, 10 mM HEPES, 50 $\mu$M $\beta$-mercaptoethanol, 1× MEM NEAA, and 1 mM sodium pyruvate. The cells were split every 2-3 days to maintain adherent cells sub-confluently or non-adherent cells at a density of <$10^6$ cells/mL. Jurkat and K562 cells were transduced with non-replicative viral vectors, analyzed by flow cytometry, and used directly in cell assays or sorted by FACS to establish derivative cell lines as indicated. Primary human PBMCs used in functional assays were purchased from the CFAR Virology Core Lab at the UCLA AIDS Institute, stimulated, transduced, and cultured as previously described (52). T cells were grown from PBMCs in T cell medium (AIM-V medium supplemented with 5% heat-inactivated human AB serum, 55 $\mu$M $\beta$-mercaptoethanol and 4 mM L-glutamine) with freshly added cytokines. All cells were grown and assayed at 37° C. with 5% atmospheric $CO_2$.

Generation and Culture of NY-ESO-1 Specific CD8$^+$ T-Lymphocyte Clones

CD8$^+$ T-lymphocyte clones specific for epitopes from NY-ESO-1 with various HLA restrictions (157-165/HLA-A*02:01 (53), 60-72/HLA-B*07:02 (21), 88-96/HLA-B*18:01 (23), 92-100/HLA-C*03:04 (54), 96-104/HLA-C*03:04 (22), 124-133/HLA-C*03:04 (22)) were generated from HLA-typed patients with melanoma. All selected patients had Grade III/IV metastatic melanoma and previously documented NY-ESO-1 responses to relevant T lymphocyte epitopes ex vivo (55). Patient PBMCs were stimulated in the presence of 1 $\mu$M pooled peptides (Mimotopes), comprising 28×18-mers overlapping by 12 amino acids, collectively spanning the NY-ESO-1 protein sequence and then cultured for 10 days in the presence of 25 IU/ml IL-2 (Peprotech).

On day 10, cells were restimulated with 1 $\mu$M of each individual peptide in the presence of brefeldin A and activation of CD8$^+$ T cells in response to each peptide was determined by intracellular cytokine stain (ICS). Briefly, cells were labeled with live/dead fixable violet stain (Invitrogen) according to the manufacturer's instructions, then incubated with antibodies against CD3 and CD8 for 15 min at 4° C. Samples were washed and fixed with fix/permeabilisation reagent (BD biosciences) for 20 min at 4° C. Cells were stained with anti-IFN$\gamma$ (eBiosciences) in permeabilisation/wash solution (BD biosciences) for 25 min at 4° C. The gating strategy was: SSC/LD$^-$; CD3$^+$/CD8$^+$; CD8$^+$/IFN-$\gamma^+$. Data from at least 100,000 stained cells were acquired on a FACSCanto and analyzed with FlowJo software. Data collection and analysis was in accordance with the MIATA guidelines (56).

NY-ESO-1-reactive T cells were expanded in the presence of their identified cognate 9-10-mer epitope and then labeled with a fluorescent tetramer comprising the relevant peptide and HLA molecule (TCMetrix, Epalinges, Switzerland) and single-cell sorted using a MoFlo cell sorter. Clones were re-expanded with pooled, allogeneic healthy donor PBMC as feeder cells, 1 $\mu$g/ml PHA-L and 600 IU/ml IL-2 (Cetus). After approximately 20 days, 1-10×$10^3$ clones were restimulated in the presence of allogeneic PBMC as feeder cells, PHA-L and IL-2, as described above. Clone specificity was confirmed by tetramer staining.

T-lymphocyte clones/lines were cultured in RPMI 1640 media supplemented with 2 mM Glutamax, 100 IU/ml penicillin, 100 $\mu$g/ml streptomycin, 20 mM HEPES, 1% nonessential amino acids, 1 mM sodium pyruvate, 55 $\mu$M $\beta$-mercaptoethanol, and 10% human serum (TCRPMI). IL-2 (100 IU/ml) was added and replaced every 3 days.

Cloning TCR Constructs

Single NY-ESO-1-reactive T cells were sorted for antigenic specificity on a FACS Aria II and were lysed by freeze-thaw in the presence of RNase inhibitor. Novel TCR variable genes were cloned from single, sorted T cells using a custom panel of human TCR variable region-specific primers with the Qiagen OneStep RT-PCR kit (Redwood City, CA), followed by a nested PCR amplification step. Amplified variable genes were integrated via assembly PCR and restriction enzyme-mediated cloning into a TCR expression cassette with either human or mouse TCR constant domains and a 2A ribosomal skipping peptide linking the alpha and beta genes. A P2A-linked gene encoding a truncated version of the low affinity nerve growth factor receptor (LNGFR) was also included in the cassette as an independent transfection/transduction marker. Antigenic specificity and MHC restriction of cloned TCRs were evaluated in 293T cells co-transfected with TCR and CD3 genes, as previously described (52).

Evaluation of TCR Export and Dextramer Binding on Jurkat T Cells

Jurkat T cells were transduced with MSGV-based retroviruses encoding each novel TCR in the format LNGFR$\Delta$-P2A-TCR$\alpha$-F2A-TCR$\beta$. Viruses were produced in 293T cells as described (52). For transduction, Jurkat T cells were centrifuged (1350×g for 90 minutes at 30° C.) with unconcentrated viral supernatants supplemented with 5 $\mu$g/mL polybrene. TCR-transduced Jurkat cells were stained with cognate pMHC dextramer for 15 min at room temperature and then co-stained with antibodies against LNGFR and CD8a for 15 min at 4° C. Stained cells were analyzed by flow cytometry using a FACSCanto analyzer. Data shown are gated on LNGFR$^+$ (transduced) cells. Transduction efficiency was >95%.

PBMC Activation and Transduction

Primary human PBMCs were purchased from the CFAR Virology Core Lab at the UCLA AIDS Institute. The same PBMC donor was used in all reported experiments. Primary human PBMCs were transduced with retroviruses encoding novel TCRs as described (52). Briefly, two days prior to viral transduction, 1-2×$10^6$ total thawed PBMCs were activated per well in 24-well plates with plate-coated anti-CD3 (clone OKT3), T cell medium containing 1 μg/mL soluble anti-CD28 (clone CD28.2), and 300 U/ml IL-2. After 48 hours of activation, the majority of the medium was replaced with unconcentrated retroviral supernatant supplemented with 10 μg/mL polybrene and cells were centrifuged for 90 min at 1350×g at 30° C. Following spinfection, the majority of retroviral supernatant was replaced with fresh medium containing 300 U/mL IL-2 and 1 μg/mL anti-CD28. The transduction was repeated 24 hours later, after which the cells were washed with 1×PBS and then returned to fresh medium containing final 300 U/mL IL-2 and cultured for an additional 3 to 4 days before being used in antigenic stimulation assays. One day prior to or on the day of co-culturing, PBMCs were analyzed by FACS for assessment of expression levels for LNGFR, TCR, and/or pMHC multimer binding.

Functional Co-Culture Assays—Cytokine ELISA

When Jurkat T cells were used as effectors, co-cultures were performed in RPMI supplemented with 10% FBS, 100 IU/ml penicillin, 100 μg/ml streptomycin, and 4 mM L-glutamine. Effector cells (50,000 TCR-transduced Jurat T cells) were co-incubated with target cells (50,000 K562 cells transduced with cognate or control single-chain trimers) in 96-well flat-bottom plates. Supernatants from duplicate wells were collected 44-48 h post-co-culturing and analyzed by enzyme-linked immunosorbent assay (ELISA) as described below.

When primary PBMCs were used as effectors, co-cultures were performed in T cell media containing 300 U/mL IL-2. Effector cells (50,000 TCR-transduced PBMCs) were co-incubated with target cells (50,000 M257, PC-3, or K562 cells) in 96-well flat-bottom plates. In some experiments target cells were pulsed with peptide. Supernatants from 2-8-fold replicate wells for each condition were collected 44-48 hours post-co-culturing and analyzed by enzyme-linked immunosorbent assay (ELISA) as described below.

For experiments in which target cells were titrated with pulsed peptide, lyophilized peptides were dissolved to 10 mM in DMSO and then further diluted in water to 2 mM working stocks. At point of use, the 2 mM stock was diluted to 250 μM in cell media and then 5-fold serially diluted from 250 μM down to 3.2 nM. Target cells were pulsed by adding 25 μL of each serial dilution per well on a 96-well U-bottom plate, followed by addition of 50,000 target cells in 100 μl media, yielding the final peptide concentration ranging from 50 μM to 0.64 nM. Cells were pulsed with peptides for 2 hours at 37° C., diluted with 100 μl of media per well at the end of incubation, centrifuged, and the supernatant was removed. The cells were washed with 200 ul of media and then re-suspended in 100 μl of media. Fifty thousand PBMCs prepared in 100 μl of media were then added to each well for co-culturing.

In general, ELISA results were converted to concentration (ng/mL) by interpolation relative to a standard curve and concentrations from replicate ELISA assays were averaged. Supernatants were diluted 50-100-fold for ELISA analysis. Occasionally, higher dilutions were required to place signal within the range of the standard curve. All reagents for ELISA analyses were from BD Biosciences: OptEIA Reagent Set B (550534) was used for diluent and washes and OptEIA human IFN-γ ELISA kit (555142) and OptEIA human IL-2 ELISA kit (555190) were used for measuring IFN-γ and IL-2 release, respectively.

Functional Co-Culture Assays—IncuCyte Cell Killing Assay

Prior to co-culture for IncuCyte killing assays, a 96-well flat-bottom plate was coated with 100 μl of 0.001% poly-L-Lysine in PBS for 1 hour at 37° C., washed 2 times with 200 μl PBS each, and air-dried briefly. Target cells were added and allowed to settle at RT for 3 hours before the effector cells were added. Co-cultures typically employed 25,000 PBMCs and 25,000 target cells per well of a 96-well plate. In assays where multiple effector populations (bearing different TCRs) or multiple targets (bearing different MHC) were mixed, 25,000 of each cell type was used to yield a total of 75,000 or 100,000 cells per well (for single/mixed or mixed/mixed, respectively). The total volume for all wells was adjusted to 200 μL. Total green object area (μm²/well) was quantified and its disappearance interpreted as killing of the GFP⁺ target cells. Cells were imaged at two positions per well every 2 hours and these two images were added together for one data point. Data points obtained from 4-8 replicate co-cultures for each effector/target combination were used to plot graph curves and to calculate standard deviation.

Animals

NOD.Cg-PrkdcSCIDIL-2rgtm1Wjl/SzJ (NOD/SCID/IL-2Rg$^{-/-}$, NSG) mice were purchased from the Jackson Laboratory and maintained in the animal facilities at the University of California, Los Angeles (UCLA). Adult (16 weeks old) male mice were used for in vivo tumor challenge experiments. All animal experiments were approved by the Institutional Animal Care and Use Committee of UCLA.

Human Prostate Tumor Xenograft Mouse Model

For xenograft tumor implantation, $10 \times 10^6$ PC-3/HLA-A2 cells (PC-3 cell line overexpressing HLA-A2) were s.c. injected on one flank of each mouse and $10 \times 10^6$ PC-3/HLA-A2/NY-ESO-1 cells (PC-3 cell line overexpressing HLA-A2 and NYESO) were subcutaneously injected on the other flank. Mice were allowed to develop solid tumors over the course of 1 week. On day 8 post tumor injection, mice were irradiated (100 rad) and then retro-orbitally i.v. injected with $8 \times 10^6$ purified T cells that were engineered to express LNGFR only or together with a NY-ESO-1-specific TCR (1G4, 3A1, or 9D2). Mice were bled on day 3, 7, 10 and day 14 for flow cytometry analysis. On day 14, mice were euthanized and tumors were collected for immunohistology analysis.

Immunohistology

Solid tumors dissected out from the experimental mice were fixed in 10% neutral-buffered formalin and embedded in paraffin for sectioning (4 mm thickness), followed by hematoxylin and eosin (H % E) staining or antibody staining (for human CD3E) by using standard procedures (UCLA Translational Pathology Core Laboratory). The sections were imaged using an Olympus BX51 upright microscope equipped with an Optronics Macrofire CCD camera (AU Optronics) at 4× and 40× magnifications. The images were analyzed by using Optronics PictureFrame software (AU Optronics) and Image J software (version 1.51J8). With Image J human CD3 antibody stained slides were quantified by measuring CD3*area through setting color threshold. Parameters used are as follow: thresholding method: default; threshold color: red; color space: HSB; brightness: 168-215.

Statistical Analysis

Statistical analysis of tumor xenograft experiments was performed with one-way ANOVA followed by Tukey's multiple comparison test. Data are presented as the mean f SEM. $P < 0.05$ was considered significant. ns, not significant; *, $P < 0.05$; , $P < 0.01$; *, $P < 0.001$; ****$P < 0.0001$. All statistical analyses were performed with GraphPad PRISM software (version 6.0).

TABLE 1

TCR α/β POLYNUCLEOTIDE AND POLYPEPTIDE SEQUENCES
The following disclosure provides polynucleotide sequences of various
embodiments of the invention and the variable region TCR protein sequences that they
encode (e.g. the polynucleotide sequence of SEQ ID NO: 1 encodes the variable region
TCR protein sequence of SEQ ID NO: 3).

3A1 TCR Vα DNA sequence
GGTCAACAGCTGAATCAGAGTCCTCAATCTATGTTTATCCAGGAAGGAGAAGATGTCTCCATG
AACTGCACTTCTTCAAGCATATTTAACACCTGGCTATGGTACAAGCAGGACCCTGGGGAAGGT
CCTGTCCTCTTGATAGCCTTATATAAGGCTGGTGAATTGACCTCAAATGGAAGACTGACTGCT
CAGTTTGGTATAACCAGAAAGGACAGCTTCCTGAATATCTCAGCATCCATACCTAGTGATGTA
GGCATCTACTTCTGTGCTGGATTTCTGGATAGCAACTATCAGTTAATCTGGGGCGCTGGGACC
AAGCTAATTATAAAGCCAGAT (SEQ ID NO: 1)

3A1 TCR Vβ DNA sequence
GAAGCCCAAGTGACCCAGAACCCAAGATACCTCATCACAGTGACTGGAAAGAAGTTAACAGT
GACTTGTTCTCAGAATATGAACCATGAGTATATGTCCTGGTATCGACAAGACCCAGGGCTGGG
CTTAAGGCAGATCTACTATTCAATGAATGTTGAGGTGACTGATAAGGGAGATGTTCCTGAAGG
GTACAAAGTCTCTCGAAAAGAGAAGAGGAATTTCCCCCTGATCCTGGAGTCGCCCAGCCCCA
ACCAGACCTCTCTGTACTTCTGTGCCAGCGCTAGCGGGTACCGCACAGATACGCAGTATTTTG
GCCCAGGCACCCGGCTGACAGTGCTCGAGGAC (SEQ ID NO: 2)

3A1 TCR Vα protein sequence
GQQLNQSPQSMFIQEGEDVSMNCTSSSIFNTWLWYKQDPGEGPVLLIALYKAGELTSNGRLTAQF
GITRKDSFLNISASIPSDVGIYFCAGFLDSNYQLIWGAGTKLIIKPD (SEQ ID NO: 3)

3A1 TCR Vβ protein sequence
EAQVTQNPRYLITVTGKKLTVTCSQNMNHEYMSWYRQDPGLGLRQIYYSMNVEVTDKGDVPEG
YKVSRKEKRNFPLILESPSPNQTSLYFCASASGYRTDTQYFGPGTRLTVLED (SEQ ID NO: 4)

4A2 TCR Vα DNA sequence
GCTCAGTCAGTGGCTCAGCCGGAAGATCAGGTCAACGTTGCTGAAGGGAATCCTCTGACTGTG
AAATGCACCTATTCAGTCTCTGGAAACCCTTATCTTTTTTGGTATGTTCAATACCCCAACCGAG
GCCTCCAGTTCCTTCTGAAATACATCACAGGGGATAACCTGGTTAAAGGCAGCTATGGCTTTG
AAGCTGAATTTAACAAGAGCCAAACCTCCTTCCACCTGAAGAAACCATCTGCCCTTGTGAGCG
ACTCCGCTTTGTACTTCTGTGCTGTGAGAGACAGTCGGTCTGGGGCTGGGAGTTACCAACTCA
CTTTCGGGAAGGGGACCAAACTCTCGGTCATACCAAAT (SEQ ID NO: 5)

4A2 TCR Vβ DNA sequence
GGTGCTGTCGTCTCTCAACATCCGAGCTGGGTTATCTGTAAGAGTGGAACCTCTGTGAAGATC
GAGTGCCGTTCCCTGGACTTTCAGGCCACAACTATGTTTTGGTATCGTCAGTTCCCGAAACAG
AGTCTCATGCTGATGGCAACTTCAATGAGGGCTCCAAGGCCACATACGAGCAAGGCGTCGA
GAAGGACAAGTTTCTCATCAACCATGCAAGCCTGACCTTGTCCACTCTGACAGTGACCAGTGC
CCATCCTGAAGACAGCAGCTTCTACATCTGCAGTGCTCCCCAAGGTTATGGGGGCACAGATAC
GCAGTATTTTGGCCCAGGCACCCGGCTGACAGTGCTCGAGGAC (SEQ ID NO: 6)

4A2 TCR Vα protein sequence
AQSVAQPEDQVNVAEGNPLTVKCTYSVSGNPYLFWYVQYPNRGLQFLLKYITGDNLVKGSYGFE
AEFNKSQTSFHLKKPSALVSDSALYFCAVRDSRSGAGSYQLTFGKGTKLSVIPN (SEQ ID NO: 7)

4A2 TCR Vβ protein sequence
GAVVSQHPSWVICKSGTSVKIECRSLDFQATTMFWYRQFPKQSLMLMATSNEGSKATYEQGVEK
DKFLINHASLTLSTLTVTSAHPEDSSFYICSAPQGYGGTDTQYFGPGTRLTVLED (SEQ ID NO: 37)

5G6 TCR Vα DNA sequence
GATGCTAAGACCACACAGCCAAATTCAATGGAGAGTAACGAAGAAGAGCCTGTTCACTTGCC
TTGTAACCACTCCACAATCAGTGGAACTGATTACATACATTGGTATCGACAGCTTCCCTCCCA
GGGTCCAGAGTACGTGATTCATGGTCTTACAAGCAATGTGAACAACAGAATGGCCTCTCTGGC
AATCGCTGAAGACAGAAAGTCCAGTACCTTGATCCTGCACCGTGCTACCTTGAGAGATGCTGC
TGTGTACTACTGCATCCTGAGAACCTCTGGGGCTGGGAGTTACCAACTCACTTTCGGGAAGGG
GACCAAACTCTCGGTCATACCAAAT (SEQ ID NO: 8)

5G6 TCR Vβ DNA sequence
AGTGCTGTCATCTCTCAAAAGCCAAGCAGGGATATCTGTCAACGTGGAACCTCCCTGACGATC
CAGTGTCAAGTCGATAGCCAAGTCACCATGATGTTCTGGTACCGTCAGCAACCTGGACAGAGC
CTGACACTGATCGCAACTGCAAATCAGGGCTCTGAGGCCACATATGAGAGTGGATTTGTCATT
GACAAGTTTCCCATCAGCCGCCCAAACCTAACATTCTCAACTCTGACTGTGAGCAACATGAGC
CCTGAAGACAGCAGCATATATCTCTGCAGCGCGGGAGGAGCGGGAGCGTCAGATACGCAGTA
TTTTGGCCCAGGCACCCGGCTGACAGTGCTCGAGGAC (SEQ ID NO: 9)

5G6 TCR Vα protein sequence
DAKTTQPNSMESNEEEPVHLPCNHSTISGTDYIHWYRQLPSQGPEYVIHGLTSNVNNRMASLAIAE
DRKSSTLILHRATLRDAAVYYCILRTSGAGSYQLTFGKGTKLSVIPN (SEQ ID NO: 10)

5G6 TCR Vβ protein sequence
SAVISQKPSRDICQRGTSLTIQCQVDSQVTMMFWYRQQPGQSLTLIATANQGSEATYESGFVIDKFP
ISRPNLTFSTLTVSNMSPEDSSIYLCSAGGAGASDTQYFGPGTRLTVLED (SEQ ID NO: 11)

TABLE 1-continued

TCR α/β POLYNUCLEOTIDE AND POLYPEPTIDE SEQUENCES
The following disclosure provides polynucleotide sequences of various
embodiments of the invention and the variable region TCR protein sequences that they
encode (e.g. the polynucleotide sequence of SEQ ID NO: 1 encodes the variable region
TCR protein sequence of SEQ ID NO: 3).

9D2 TCR Vα DNA sequence
CAGAAGGAGGTGGAGCAGAATTCTGGACCCCTCAGTGTTCCAGAGGGAGCCATTGCCTCTCTC
AACTGCACTTACAGTGACCGAGGTTCCCAGTCCTTCTTCTGGTACAGACAATATTCTGGGAAA
AGCCCTGAGTTGATAATGTTCATATACTCCAATGGTGACAAAGAAGATGGAAGGTTTACAGCA
CAGCTCAATAAAGCCAGCCAGTATGTTTCTCTGCTCATCAGAGACTCCCAGCCCAGTGATTCA
GCCACCTACCTCTGTGCCGTAGATGACAAGATCATCTTTGGAAAAGGGACACGACTTCATATT
CTCCCCAAT (SEQ ID NO: 12)

9D2 TCR Vβ DNA sequence
GATGCTGGAGTTATCCAGTCACCCCGGCACGAGGTGACAGAGATGGGACAAGAAGTGACTCT
GAGATGTAAACCAATTTCAGGACACGACTACCTTTTCTGGTACAGACAGACCATGATGCGGGG
ACTGGAGTTGCTCATTTACTTTAACAACAACGTTCCGATAGATGATTCAGGGATGCCCGAGGA
TCGATTCTCAGCTAAGATGCCTAATGCATCATTCTCCACTCTGAAGATCCAGCCCTCAGAACC
CAGGGACTCAGCTGTGTACTTCTGTGCCAGCAGTTTGGGACAGCCAAGCACAGATACGCAGTA
TTTTGGCCCAGGCACCCGGCTGACAGTGCTCGAGGAC (SEQ ID NO: 13)

9D2 TCR Vα protein sequence
QKEVEQNSGPLSVPEGAIASLNCTYSDRGSQSFFWYRQYSGKSPELIMFIYSNGDKEDGRFTAQLN
KASQYVSLLIRDSQPSDSATYLCAVDDKIIFGKGTRLHILPN (SEQ ID NO 14)

9D2 TCR Vβ protein sequence
DAGVIQSPRHEVTEMGQEVTLRCKPISGHDYLFWYRQTMMRGLELLIYFNNNVPIDDSGMPEDRF
SAKMPNASFSTLKIQPSEPRDSAVYFCASSLGQPSTDTQYFGPGTRLTVLED (SEQ ID NO: 15)

1E4 TCR Vα DNA sequence
AAACAGGAGGTGACGCAGATTCCTGCAGCTCTGAGTGTCCCAGAAGGAGAAAACTTGGTTCT
CAACTGCAGTTTCACTGATAGCGCTATTTACAACCTCCAGTGGTTTAGGCAGGACCCTGGGAA
AGGTCTCACATCTCTGTTGCTTATTCAGTCAAGTCAGAGAGAGCAAACAAGTGGAAGACTTAA
TGCCTCGCTGGATAAATCATCAGGACGTAGTACTTTATACATTGCAGCTTCTCAGCCTGGTGA
CTCAGCCACCTACCTCTGTGCTGTGAGTACTGCGTATTCAGGAGGAGGTGCTGACGGACTCAC
CTTTGGCAAAGGGACTCATCTAATCATCCAGCCCTAT (SEQ ID NO: 16)

1E4 TCR Vβ DNA sequence
GATACTGGAGTCTCCCAGAACCCCAGACACAAGATCACAAAGAGGGGACAGAATGTAACTTT
CAGGTGTGATCCAATTTCTGAACACAACCGCCTTTATTGGTACCGACAGACCCTGGGGCAGGG
CCCAGAGTTTCTGACTTACTTCCAGAATGAAGCTCAACTAGAAAAATCAAGGCTGCTCAGTGA
TCGGTTCTCTGCAGAGAGGCCTAAGGGATCTTTCTCCACCrrGGAGATCCAGCGCACAGAGCA
GGGGGACTCGGCCATGTATCTCTGTGCCAGCAGCCCCCCGACTGTTCGGGTCTATGGCTACAC
CTTCGGTTCGGGGACCAGGTTAACCGTTGTAGAGGAC (SEQ ID NO: 17)

1E4 TCR Vα protein sequence
KQEVTQIPAALSVPEGENLVLNCSFTDSAIYNLQWFRQDPGKGLTSLLLIQSSQREQTSGRLNASLD
KSSGRSTLYIAASQPGDSATYLCAVSTAYSGGGADGLTFGKGTHLIIQPY (SEQ ID NO 18)

1E4 TCR Vβ protein sequence
DTGVSQNPRHKITKRGQNVTFRCDPISEHNRLYWYRQTLGQGPEFLTYFQNEAQLEKSRLLSDRFS
AERPKGSFSTLEIQRTEQGDSAMYLCASSPPTVRVYGYTFGSGTRLTVVED (SEQ ID NO: 19)

2B8 TCR Vα DNA sequence
GGACAACAGGTAATGCAAATTCCTCAGTACCAGCATGTACAAGAAGGAGAAGACTTCACCAC
GTACTGCAATTCCTCAACTACTTTAAGCAATATACAGTGGTATAAGCAAAGGCCTGGTGGACA
TCCCGTTTTTTTTGATACAGTTAGTGAAGAGTGGAGAAGTGAAGAAGCAGAAAAGACTGACAT
TTCAGTTTGGAGAAGCAAAAAAGAACAGCTCCCTGCACATCACAGCCACCCAGACTACAGAT
GTAGGAACCTACTTCTGTGCGGACCCTAACTTTGGAAATGAGAAATTAACCTTTGGGACTGGA
ACAAGACTCACCATCATACCCAAT (SEQ ID NO: 20)

2B8 TCR Vβ DNA sequence
GAAGCCCAAGTGACCCAGAACCCAAGATACCTCATCACAGTGACTGGAAAGAAGTTAACAGT
GACTTGTTCTCAGAATATGAACCATGAGTATATGTCCTGGTATCGACAAGACCCAGGGCTGGG
CTTAAGGCAGATCTACTATTCAATGAATGTTGAGGTGACTGATAAGGGAGATGTTCCTGAAGG
GTACAAAGTCTCTCGAAAAGAGAAGAGGAATTTCCCCCTGATCCTGGAGTCGCCCAAGCCCCA
ACCAGACCTCTCTGTACTTCTGTGCCAGCAGTTTGAATCCCTTTGCAACTAATGAAAAACTGTT
TTTTGGCAGTGGAACCCAGCTCTCTGTCTTGGAGGAC (SEQ ID NO: 21)

2B8 TCR Vα protein sequence
GQQVMQIPQYQHVQEGEDFTTYCNSSTTLSNIQWYKQRPGGHPVFLIQLVKSGEVKKQKRLTFQF
GEAKKNSSLHITATQTTDVGTYFCADPNFGNEKLTFGTGTRLTIIPN (SEQ ID NO: 22)

2B8 TCR Vβ protein sequence
EAQVTQNPRYLITYTGKKLTVTCSQNMNHEYMSWYRQDPGLGLRQIYYSMNVEVTDKGDVPEG
YKVSRKEKRNFPLILESPSPNQTSLYFCASSLNPFATNEKLFFGSGTQLSVLED (SEQ ID NO: 23)

TABLE 1-continued

TCR α/β POLYNUCLEOTIDE AND POLYPEPTIDE SEQUENCES
The following disclosure provides polynucleotide sequences of various
embodiments of the invention and the variable region TCR protein sequences that they
encode (e.g. the polynucleotide sequence of SEQ ID NO: 1 encodes the variable region
TCR protein sequence of SEQ ID NO: 3).

3C7 TCR Vα DNA sequence
GGACAAAACATTGACCAGCCCACTGAGATGACAGCTACGGAAGGTGCCATTGTCCAGATCAA
CTGCACGTACCAGACATCTGGGTTCAACGGGCTGTTCTGGTACCAGCAACATGCTGGCGAAGC
ACCTACATTTCTGTCTTACAATGTTCTGGATGGTTTGGAGGAGAAAGGTCGTTTTTCTTCATTC
CTTAGTCGGTCTAAAGGGTACAGTTACCTCCTTTTGAAGGAGCTCCAGATGAAAGACTCTGCC
TCTTACCTCTGTGCTGTGAGAGGCGACTACAAGCTCAGCTTTGGAGCCGGAACCACAGTAACT
GTAAGAGCAAAT (SEQ ID NO: 24)

3C7 TCR Vβ DNA sequence
GATTCTGGAGTCACACAAACCCCAAAGCACCTGATCACAGCAACTGGACAGCGAGTGACGCT
GAGATGCTCCCCTAGGTCTGGAGACCTCTCTGTGTACTGGTACCAACAGAGCCTGGACCAGGG
CCTCCAGTTCCTCATTCAGTATTATAATGGAGAAGAGAGAGCAAAAGGAAACATTCTTGAACG
ATTCTCCGCACAACAGTTCCCTGACTTGCACTCTGAACTAAACCTGAGCTCTCTGGAGCTGGG
GGACTCAGCTTTGTATTTCTGTGCCAGCAGCTCGATACACGGTGTCTCTGGGGCCAACGTCCT
GACTTTCGGGGCCGGCAGCAGGCTGACCGTGCTGGAGGAC (SEQ ID NO: 25)

3C7 TCR Vα protein sequence
GQNIDQPTEMTATEGAIVQINCTYQTSGFNGLFWYQQHAGEAPTFLSYNVLDGLEEKGRFSSFLSR
SKGYSYLLLKELQMKDSASYLCAVRGDYKLSFGAGTTVTVRAN (SEQ ID NO: 26)

3C7 TCR Vβ protein sequencee
DSGVTQTPKHLITATGQRVTLRCSPRSGDLSVYWYQQSLDQGLQFLIQYYNGEERAKGNILERFSA
QQFPDLHSELNLSSLELGDSALYFCASSSIHGVSGANVLTFGAGSRLTVLED (SEQ ID NO: 27)

NY-ESO-1 protein (Homo sapiens): GenBank; CAA05908.1
MQAEGRGTGGSTGDADGPGGPGIPDGPGGNAGGPGEAGATGGRGPRGAGAARASGPGGGAPRG
PHGGAASGLNGCCRCGARGPESRLLEFYLAMPFATPMEAELARRSLAQDAPPLPVPGVLLKEFTV
SGNILTIRLTAADHRQLQLSISSCLQQLSLLMWITQCFLPVFLAQPPSGQRR (SEQ ID NO: 28)

Terminology used in the disclosure such as "A2/NY-ESO-$1_{157-165}$" refers to HLA A2 associated with a NY-ESO-1 peptide comprising amino acids 157-165 of the above protein sequence (i.e. SLLMWITQC (SEQ TD NO: 36)).

The following sequences comprise polynucleotide embodiments of the invention disposed in a vector.

pMTB1328 (MSGV-LNGFR-P2A-GB4A2 TCR Mouse Constant)

(SEQ ID NO: 29)

tgaaagacccccacctgtaggtttggcaagctagcttaagtaacgccattttgcaaggcatggaaaatacataactgagaatagagaagttcgatcaaggtta ggaacagagagacagcagaatatgggccaaacaggatatctgtggtaagcagttcctgccccggctcagggccaagaacagatggtccccagatgcgg tcccgccctcagcagtttctagagaaccatcagatgtttccagggtgccccaaggacctgaaaatgaccctgtgccttatttgaactaaccaatcagttcgctt ctcgcttagttcgcgcgcttctgaccccgagctcaataaaagagcccacaacccctcactcggcgcgccagtcaccgatagactgcgtcgcccgggta cccgtattcccaataaagcctcttgctgtttgcatccgaatcgtggactcgctgatccttgggagggtctcctcagattgattgactgcccacctcgggggtctt tcatttggaggttccaccgagatttggagacccctgcctagggaccaccgacccccccgccgggaggtaagctggccagcggtcgtttcgtgtctgtctct gtctttgtgcgtgtttgtgccggcatctaatgtttgcgcctgcgtctgtactagttagctaactagctctgtatctggcggacccgtggtggaactgacgagttc gaacacccggccgcaacccTGGGAGACGTCCCAGGGACTTCGGGGGCCGTTTTTGTGGCCCGACCTGAGTCCTAAAATCCCGATCGTTTAGGACTCTTTGGT gcacccccctTAGAGGAGGGATATGTGGTTCTGGTAGGAGACGAGAACCTAAAACAGTTCCCGCCTCCGTCTGAATTTTTGCTTCGGTTTGGGACCGAAGCC gcgccgcgcgtcttgtctgctgcagcatcgttctgtgttgtctctgtctgactgtgtttctgtatttgtctgaaaatatgggcccgggctagcctgttaccactc ccttaagtttgaccttaggtcactggaaagatgtcgagcggatcgctcacaaccagtcggtagatgtcaagaagagacgttgggttaccttctgctctgcagaat ggccaacctttaacgtcggatggccgcgagacggcacctttaaccgagacctcatcacccaggttaagatcaaggtcttttcacctggccgcatggacac ccagaccaggtcccctacatcgtgacctgggaagccttggcttttlgaccccctccctgggtcaagcccttgtacacctaagcctccgcctcctcttcctcc atccgccccgtctctcccccttgaacctcctcgttcgaccccgcctcgatcctcctttatccgccctcactccttctctaggcgcccccatatggccatatga gatcttatatggggcacccccgcccttgtaaacttccctgaccctgacatgacaagagttactaacagcccctctctccaagctcacttacaggctctctactt agtccagcacgaagtctggagaccatggcggcagcctaccaagaacaactggaccgaccggtggtacctcacccttaccgagtcggcgacacagtgtg -continued

```
ggtccgccgacaccagactaagaacctagaacctcgctggaaaggaccttacacagtcctgctgaccaccccaccgccctcaaagtagacggcatcgc agcttggatacacgccgcccacgtgaaggctgccgacccgggggtggaccatcctctagaccgccatgtcgggggcaggtgccaccggccgcgcca tggacgggccgcgcctgctgctgttgctgcttctgggggtgtcccttggaggtgccaaggaggcatgcccccacaggcctgtacacacacagcggtgagtg ctgcaaagcctgcaacctgggcgagggtgtggcccagccttgtggagccaaccagaccgtgtgtgagccctgcctggacagcgtgacgttctccgacgt ggtgagcgcgaccgagccgtgcaagccgtgcaccgagtgcgtggggctccagagcatgtcggcgccatgcgtggaggccgacgacgccgtgtgccg ctgcgcctacggctactaccaggatgagacgactgggcgctgcgaggcgtgccgcgtgtgcgaggcgggctcgggcctcgtgttctcctgccaggaca agcagaacaccgtgtgcgaggagtgccccgacggcacgtattccgacgaggccaaccacgtggacccgtgcctgccctgcaccgtgtgcgaggacac cgagcgccagctccgcgagtgcacacgctgggccgacgccgagtgcgaggagatccctggccgttggattacacggtccacaccccagagggctcg gacagcacagcccccagcacccaggagcctgaggcacctccagaacaagacctcatagccagcacggtggcaggtgtggtgaccacagtgatgggca gctcccagcccgtggtgacccgaggcaccaccgacaacctcatccctgtctattgctccatcctggctgctgtggttgtgggtcttgtggcctacatagccttc aagaggtggaacagctccggctccggagccaccaacttcagcctgctgaagcaggccggcgacgtggaggagaaccccggccccgcggccgccatg gcgacgggttcaagaacttccctacttcttgcatttggcctgctttgtttgccgtggttacaggaagcctcagcagctcagtcagtggctcagccggaagatca ggtcaacgttgctgaagggaatcctctgactgtgaaatgcacctattcagtctctggaaacccttatcttttttggtatgttcaataccccaaccgaggcctcca gttccttctgaaatacatcacaggggataacctggttaaaggcagctatggcttttgaagctgaatttaacaagagccaaacctccttccacctgaagaaaccatc tgcccttgtgagcgactccgctttgtacttctgtgctgtgagagacagtcggtctggggctgggagttaccaactcactttcgggaaggggaccaaactctcg gtcataccaaatatccagaaccccgagcccgccgtgtaccagctgaaggaccccagaagccaggacagcaccctgtgcctgttcaccgacttcgacagc cagatcaacgtgcccaagaccatggagagcggcaccttcatcaccgacaagaccgtgctggacatgaaggccatggacagcaagagcaacggcgccat cgcctggtccaaccagaccagcttcacatgccaggacatcttcaaggagaccaacgccacctaccccagcagcgacgtgccctgcgacgccaccctgac cgagaagagcttcgagaccgacatgaacctgaacttccagaacctgagcgtgatgggcctgagaatcctgctgctgaaggtggccggcttcaacctgctg atgaccctgaggctgtggagcagcagggcaaaacgttcgggttcgggtgcgccagtaaagcagacattaaactttgatttgctgaaacttgcaggtgatgta gagtcaaatccaggtccaatggcaacaggagccgaacctctctgctccttgctttcgggctcctttgcctaccgtgcctgcaggagggctcggcaggtgct gtcgtctctcaacatccgagctgggttatctgtaagagtggaacctctgtgaagatcgagtgccgttccctggactttcaggccacaactatgttttggtatcgt cagttcccgaaacagagtctcatgctgatggcaacttccaatgagggctccaaggccacatacgagcaaggcgtcgagaaggacaagtttctcatcaacca tgcaagcctgaccttgtccactctgacagtgaccagtgcccatcctgaagacagcagcttctacatctgcagtgctccccaaggttatgggggeacagatac gagtattttggcccaggcaccggctgacagtgctcgaggacctgaggaacgtgaccccccccaaggtgtccctgttcgagcccagcaaggccgagat cgccaacaagcagaaggccaccctggtgtgcctggccaggggcttcttccccgaccacgtggagctgtcttggtgggtgaacggcaaggaggtgcaca gcggcgtgagcaccgacccccaggcctacaaggagagcaactacagctactgcctgagcagcaggctgagagtgagcgccaccttctggcacaaccc caggaaccacttccgctgtcaggtgcagttccacggcctgagcgaggaggacaagtggcccgagggcagccccaagcccgtgacccagaacatcagc gccgaggcctggggcagagccgactgcggcatcaccagcgccagctaccaccagggcgtgctgtccgccaccatcctgtacgagatcctgctgggcaa ggccacactgtacgccgtgctggtgtccggcctggtgctgatggccatggtgaagaagaagaacagctaaaggatccgataaaataaaagatttatttagt ctccagaaaaagggggaatgaaagaccccacctgtaggtttggcaactagcttaagtaacgccatttttgcaaggcatggaaaatacataactgagaata gagaagttcagatcaaggttaggaacagagagacagcagaatatgggccaaacaggatatctgtggtaagcagttcctgccccggctcagggccaagaa cagatggtccccagatgcggtcccgccctcagcagtttctagagaaccatcagatgtttccaggggtgccccaaggacctgaaatgaccagtgccttatttga actaaccaatcagttcgcttctcgcttctgttcgcgcgcttctgctccccgagctcaataaaagagcccacaaccctcactcggcgcgccagtcctccgata gactgcgtcgcccgggtacccgtatccaataaaccctcttgcagttgcatccgacttgtggtctcgctgttccttgggagggtctcctctgagtgattgacta cccgtcagcgggggtctttcatgggtaacagtttcttgaagttggagaacaacattctgagggtaggagtcgaatattaagtaatcagactcaattagccact gtttgaatccacatactccaatactcctgaaatccatcgatggagttcattatggacagcgcagaaagagaggggagaattgtgaaattgttatccgctcac aattccacacaacatacgagccggaagcataaagtgtaaagcctggggtgcctaatgagtgagctaactcacattaattgcgttgcgctcactgcccgctttc cagtcgggaaacctgtcgtgccagctgcattaatgaatcggccaacgcgcggggagaggcggtttgcgtattgggcgctcttccgcttcctcgctcactga ctcgctgcgctcggtcgttcggctgcggcgagcggtatcagctcactcaaaggcggtaatacggttatccacagaatcaggggataacgcaggaaagaac atgtgagcaaaaggccagcaaaaggccaggaaccgtaaaaaggccgcgttgctggcgtttttccataggctccgcccccctgacgagcatcacaaaaatc
```

-continued gacgctcaagtcagaggtggcgaaacccgacaggactataaagataccaggcgtttcccctggaagctccctcgtgcgctctcctgttccgaccctgccg cttaccggatacctgtccgcctttctcccttcgggaagcgtggcgctttctcatagctcacgctgtaggtatctcagttcggtgtaggtcgttcgctccaagctg ggctgtgtgcacgaaccccccgttcagcccgaccgagcgccttatccggtaactatcgtcttgagtccaacccggtaagacacgacttatcgccactggca gcagccactggtaacaggattagcagagcgaggtatgtaggcggtgctacagagttcttgaagtggtggcctaactacggctacactagaaggacagtatt tggtatctgcgctctgctgaagccagttaccttcggaaaaagagttggtagctcttgatccggcaaacaaaccaccgctggtagcggtggtttttttgtttgcaa gcagcagattacgcgcagaaaaaaaggatctcaagaagatcctttgatcttttctacggggtctgacgctcagtggaacgaaaactcacgttaagggattttg gtcatgagattatcaaaaaggatcttcacctagatccttttaaattaaaaatgaagttttaaatcaatctaaagtatatatgagtaaacttgtttctgacagtta ccaatgcttaatcagtgaggcacctatctcagcgatctgtctatttcgttcatccatagttgcctgactccccgtcgtgtagataactacgatacgggagggctt accatctggccccagtgctgcaatgataccgcgagacccacgctcaccggctccagatttatcagcaataaaccagccagccggaagggccgagcgcagaagt ggtcctgcaactttatccgcctccatccagtctattaattgttgccgggaagctagagtaagtagttcgccagttaatagtttgcgcaacgttgttgccattgct acaggcatcgtggtgtcacgctcgtcgtttggtatggcttcattcagctccggttcccaacgatcaaggcgagttacatgatcccccatgttgtgcaaaaaagc ggttagctccttcggtcctccgatcgttgtcagaagtaagttggccgcagtgttatcactcatggttatggcagcactgcataattctcttactgtcatgccatc cgtaagatgcttttctgtgactggtgagtactcaaccaagtcattctgagaatagtgtatgcggcgaccgagttgctcttgcccggcgtcaatacgggataatac cgcgccacatagcagaactttaaaagtgctcatcattggaaaacgttcttcggggcgaaaactctcaaggatcttaccgctgttgagatccagttcgatgtaac ccactcgtgcacccaactgatcttcagcatcttttactttcaccagcgtttctgggtgagcaaaaacaggaaggcaaaatgccgcaaaaaagggaataaggg cgacacggaaatgttgaatactcatactcttcctttttcaatattattgaagcatttatcagggttattgtctcatgagcggatacatatttgaatgtatttaga aaaataaacaaataggggttccgcgcacatttccccgaaaagtgccacctgacgtctaagaaaccattattatcatgacattaacctataaaaataggcgtatca cgaggccctttcgtctcgcgcgtttcggtgatgacggtgaaaacctctgacacatgcagctcccggagacggtcacagcttgtctgtaagcggatgccgggagc agacaagcccgtcagggcgcgtcagcgggtgttggcgggtgtcggggctggcttaactatgcggcatcagagcagattgtactgagagtgcaccatatgc ggtgtgaaataccgcacagatgcgtaaggagaaaataccgcatcaggcgccattcgccattcaggctgcgcaactgttgggaagggcgatcggtgcggg cctcttcgctattacgccagctggcgaaagggggatgtgctgcaaggcgattaagttgggtaacgccagggttttcccagtcacgacgttgtaaaacgacg gccagtgccacgctctcccttatgcgactcctgcattaggaagcagcccagtagtaggttgaggccgttgagcaccgccgccgcaaggaatggtgcatgc aaggagatggcgcccaacagtcccccggccacggggcctgccaccatacccacgccgaaacaagcgctcatgagcccgaagtggcgagcccgatctt ccccatcggtgatgtcggcgatataggcgccagcaaccgcacctgtggcgccggtgatgccggccacgatgcgtccggcgtagaggcgatttaaagaca ggatatcagtggtccaggctctagttttgactcaacaatatcaccagctgaagcctatagagtacgagccatagataaaataaaagattttatttagtaccaga aaaagggggaa pMTB1329 (MSGV-LNGFR-P2A-GB5G6 TCR Mouse Constant)

(SEQ ID NO: 30)

tgaaagaccccacctgtaggtttggcaagctagcttaagtaacgccattttgcaaggcatggaaaatacataactgagaatagagaagttcagatcaaggtta ggaacagagagacagcagaatatgggccaaacaggatatctgtggtaagcagttcctgccccggctcagggccaagaacagatggtccccagatgcgg tcccgccctcagcagtttctagagaaccatcagatgtttccagggtgccccaaggacctgaaaatgaccctgtgccttatttgaactaaccaatcagttcgctt ctcgcttctgttcgcgcgcttctgctccccgagctcaataaaagagcccacaacccctcactcggcgcgccagtcctccgatagactgcgtcgcccgggta cccgtattcccaataaagcctcttgctgtttgcatccgaatcgtggactcgctgatccttgggagggtctcctcagattgattgactgcccacctcgggggtctt tcatttggaggttccaccgagatttggagacccctgcctaggaccaccgacccccccgccgggaggtaagctggcagcggtcgtttcgtgtctgtctct gtctttgtgcgtgtttgtgccggcatctaatgtttgcgcctgcgtctgtactagttagctaactagctctgtatctggcggacccgtggtggaactgacgagttc ggaacaccggccgcaaccctgggagacgtcccaggacttcggggccgttttgtggcccgacctgagtcctaaaatcccgatcgtttaggactctttggt gcaccccccttagaggaggatatgtggttctggtaggagacgagaacctaaaacagttcccgcctccgtctgaattttgctttcggtttgggaccgaagcc gcgccgcgcgtcttgtcgctgcagcatcgttctgtgttgtctctgtctgactgtgtttctgtatttgtctgaaaatatgggcccgggctagcctgttaccactcc cttaagtttgaccttaggtcactggaaagatgtcgagcggatcgctcacaaccagtcggtagatgtcaagaagagacgttgggttaccttctgctctgcagaat ggccaacctttaacgtcggatggccgcgagacggcacctttaaccgagacctcatcacccaggttaagatcaaggtcttttcacctggcccgcatggacac ccagaccaggtcccctacatcgtgacctgggaagccttggcttttgacccccctccctgggtcaagcccttgtacaccctaagcctccgcctcctcttcctcc -continued atccgccccgtctctcccccttgaacctcctcgttcgaccccgcctcgatcctccctttatccagccctcactccttctctaggcgcccccatatggccatatga gatcttatatggggcacccccgcccccttgtaaacttccctgaccctgacatgacaagagttactaacagccctctctccaagctcacttacaggctctctactt agtccagcacgaagtctggagacctctggcggcagcctaccaagaacaactggaccgaccggtggtacctcacccttaccgagtcggcgacacagtgtg ggtccgccgacaccagactaagaacctagaacctcgctggaaaggaccttacacagtcctgctgaccaccccaccgccctcaaagtagacggcatcgc agcttggatacacgccgcccacgtgaaggctgccgaccccggggtggaccatcctctagaccgccatgtcgggggcaggtgccaccggccgcgcca tggacgggccgcgcctgctgctgttgctgcttctgggggtgtcccttggaggtgccaaggaggcatgcccccacaggcctgtacacacacagcggtgagtg ctgcaaagcctgcaacctgggcgagggtgtggcccagccttgtggagccaaccagaccgtgtgtgagccctgcctggacagcgtgacgttctccgacgt ggtgagcgcgaccgagccgtgcaagccgtgcaccgagtgcgtggggctccagagcatgtcggcgccatgcgtggaggccgacgacgccgtgtgccg ctgcgcctacggctactaccaggatgagacgactgggcgctgcgaggcgtgccgcgtgtgcgaggcgggctcgggcctcgtgttctcctgccaggaca agcagaacaccgtgtgcgaggagtgccccgacggcacgtattccgacgaggccaaccacgtggacccgtgcctgcccctgcaccgtgtgcgaggacac cgagcgccagctccgcgagtgcacacgctgggccgacgccgagtgcgaggagatccctggccgttggattacacggtccacacccccagagggctcg gacagcacagccccagcacccaggagcctgaggcacctccagaacaagacctcatagccagcacggtggcaggtgtggtgaccacagtgatgggca gctcccagcccgtggtgacccgaggcaccaccgacaacctcatccctgtctattgctccatcctggctgctgtggttgtgggtcttgtggcctacatagccttc aagaggtggaacagctccggctccggagccaccaacttcagcctgctgaagcaggccggcgacgtggaggagaaccccggccccgcggccgccatg gcgacggtttcaagaacttccctacttcttgcatttggcctgctttgtttgccgtggttacaggaagcctcagcagatgctaagaccacacagccaaattcaat ggagagtaacgaagaagagcctgttcacttgccttgtaaccactccacaatcagtggaactgattacatacattggtatcgacagcttccctcccagggtcca gagtacgtgattcatggtcttacaagcaatgtgaacaacagaatggcctactggcaatcgctgaagacagaaagtccagtaccttgatcctgcaccgtgcta ccttgagagatgctgctgtgtactactgcatcctgagaacctaggggctgggagttaccaactcactttcgggaaggggaccaaactctcggtcataccaa atatccagaaccccgagcccgccgtgtaccagctgaaggaccccagaagccaggacagcaccctgtgcctgttcaccgacttcgacagccagatcaacg tgcccaagaccatggagagcggcacctttcatcaccgacaagaccgtgaggacatgaaggccatggacagcaagagcaacggcgccatcgcctggtcc aaccagaccagcttcacatgccaggacatcttcaaggagaccaacgccacctaccccagcagcgacgtgccctgcgacgccaccctgaccgagaagag cttcgagaccgacatgaacctgaacttccagaacctgagcgtgatgggcctgagaatcctgctgctgaaggtggccggcttcaacctgagatgaccctga ggctgtggagcagcagggcaaaacgttcgggttcgggtgcgccagtaaagcagacattaaactttgatttgctgaaacttgcaggtgatgtagagtcaaatc caggtccaatggcaacagggagccgaacctctctgctccttgctttcgggctcctttgcctaccgtgcctgcaggagggctcggcaagtgctgtcatctctca aaagccaagcagggatatctgtcaacgtggaacctccctgacgatccagtgtcaagtcgatagccaagtcaccatgatgttctggtaccgtcagcaacctg gacagagcctgacactgatcgcaactgcaaatcagggctctgaggccacatatgagagtggatttgtcattgacaagtttcccatcagccgcccaaacctaa cattctcaactctgactgtgagcaacatgagccctgaagacagcagcatatatctctgcagcgggaggagcgggagcgtcagatacgcagtattttggc ccaggcacccggctgacagtgctcgaggacctgaggaacgtgacccccccccaaggtgtccctgttcgagcccagcaaggccgagatcgccaacaagc agaaggccaccaggtgtgcctggccagggggcttcttccccgaccacgtggagctgtcttggtgggtgaacggcaaggaggtgcacagcggcgtgagc accgaccccaggcctacaaggagagcaactacagctactgcctgagcagcaggctgagagtgagcgccacccttaggcacaacccccaggaaccactt ccgctgtcaggtgcagttccacggcctgagcgaggaggacaagtggcccgagggcagcccccaagcccgtgacccagaacatcagcgccgaggcctg gggcagagccgactgcggcatcaccagcgccagctaccaccagggcgtgctgtccgccaccatcctgtacgagatcctgctgggcaaggccacactgt acgccgtgctggtgtccggcctggtgctgatggccatggtgaagaagaagaacagctaaaggatccgataaaatataaagattttatttagtctccagaaaaa gggggggaatgaaagacccacctgtaggtttggcaagctagataagtaacgccattttgcaaggcatggaaaatacataactgagaatagagaagttcag atcaaggttaggaacagagagacagcagaatatgggccaaacaggatatctgtggtaagcagttcctgccccggctcagggccaagaacagatggtccc cagatgcggtcccgccctcagcagtttctagagaaccatcagatgtttccagggtgccccaaggacctgaaatgaccctgtgccttatttgaactaaccaatc agttcgcttacgcttctgttcgcgcgcttagctccccgagctcaataaaagagcccacaaccccctcactcggcgcgccagtcaccgatagactgcgtcgc ccgggtacccgtgtatccaataaaccctcttgcagttgcatccgacttgtggtcgctgttccttgggagggtctcctctgagtgattgactacccgtcagcg gggctctttcatgggtaacagtttcttgaagttggagaacaacattctgagggtaggagtcgaatattaagtaatcctgactcaattagccactgttttgaatcc acatactccaatactcctgaaatccatcgatggagttcattatggacagcgcagaaagagctggggagaattgtgaaattgttatccgctcacaattccacaca acatacgagccggaagcataaagtgtaaagcctggggtgcctaatgagtgagctaactcacattaattgcgttgcgctcactgcccgctttccagtcgggaa -continued acctgtcgtgccagagcattaatgaatcggccaacgcgcggggagaggcggtttgcgtattgggcgctcttccgcttcctcgctcactgactcgctgcgct cggtcgttcggctgcggcgagcggtatcagctcactcaaaggcggtaatacggttatccacagaatcaggggataacgcaggaaagaacatgtgagcaa aaggccagcaaaaggccaggaaccgtaaaaaggccgcgttgagcgcgtttttccataggctccgcccccctgacgagcatcacaaaaatcgacgctcaa gtcagaggtggcgaaacccgacaggactataaagataccaggcgtttccccctggaagctccctcgtgcgctctcctgttccgaccctgccgcttaccgga tacctgtccgcctttctcccttcgggaagcgtggcgctttctcatagctcacgctgtaggtatctcagttcggtgtaggtcgttcgctccaagctgggctgtgtg cacgaacccccgttcagcccgaccgctgcgccttatccggtaactatcgtcttgagtccaacccggtaagacacgacttatcgccactggcagcagccac tggtaacaggattagcagagcgaggtatgtaggcggtgctacagagttcttgaagtggtggcctaactacggctacactagaaggacagtatttggtatctg cgctctgctgaagccagttaccttcggaaaaagagttggtagctcttgatccggcaaacaaaccaccgctggtagcggtggtttttttgtttgcaagcagcag attacgcgcagaaaaaaggatctcaagaagatcctttgatcttttctacggggtctgacgctcagtggaacgaaaactcacgttaagggattttggtcatgag attatcaaaaaggatcttcacctagatcctttttaaattaaaaatgaagttttaaatcaatctaaagtatatatgagtaaacttggtctgacagttaccaatgctt aaatcgtgaggcacctatctcagcgatctgtctatttcgttcatccatagttgcctgactccccgtcgtgtagataactacgatacgggagggcttaccatctgg ccccagtgagcaatgataccgcgagacccacgctcaccggctccagatttatcagcaataaaccagccagccggaagggccgagcgcagaagtggtcctgca actttatccgcctccatccagtctattaattgttgccgggaagctagagtaagtagttcgccagttaatagtttgcgcaacgttgttgccattgctacaggcatc gtggtgtcacgctcgtcgtttggtatggcttcattcagctccggttcccaacgatcaaggcgagttacatgatcccccatgttgtgcaaaaaagcggttagctcc ttcggtcctccgatcgttgtcagaagtaagttggccgcagtgttatcactcatggttatggcagcactgcataattctcttactgtcatgccatccgtaagatgc ttttctgtgactggtgagtactcaaccaagtcattctgagaatagtgtatgcggcgaccgagttgctcttgcccggcgtcaatacggataataccgcgccacat agcagaactttaaaagtgacatcattggaaaacgttcttcggggcgaaaactctcaaggatcttaccgagttgagatccagttcgatgtaacccactcgtgca cccaactgatcttcagcatcttttactttcaccagcgtttctgggtgagcaaaaacaggaaggcaaaatgccgcaaaaaagggaataagggcgacacggaa atgttgaatactcatactcttcctttttcaatattattgaagcatttatcagggttattgtctcatgagcggatacatatttgaatgtatttagaaaaataaaca aataggggttccgcgcacatttccccgaaaagtgccacctgacgtctaagaaaccattattatcatgacattaacctataaaaataggcgtatcacgaggcccttt tcgtctcgcgcgtttcggtgatgacggtgaaaacctctgacacatgcagctcccggagacggtcacagcttgtctgtaagcggatgccgggagcagacaagccc gtcagggcgcgtcagcgggtgttggcgggtgtcggggctggcttaactatgcggcatcagagcagattgtactgagagtgcaccatatgcggtgtgaaat accgcacagatgcgtaaggagaaaataccgcatcaggcgccattcgccattcaggctgcgcaactgttgggaagggcgatcggtgcgggcctcttcgcta ttacgccagctggcgaaagggggatgtgctgcaaggcgattaagttgggtaacgccagggttttcccagtcacgacgttgtaaaacgacggccagtgcca cgctctcccttatgcgactcctgcattaggaagcagcccagtagtaggttgaggccgttgagcaccgccgccgcaaggaatggtgcatgcaaggagatgg cgcccaacagtcccccggccacggggcctgccaccatacccacgccgaaacaagcgctcatgagcccgaagtggcgagcccgatcttccccatcggtg atgtcggcgatataggcgccagcaaccgcacctgtgtgcgccggtgatgccggccacgatgcgtccggcgtagaggcgatttaaagacaggatatcagtg gtccaggctctagttttgactcaacaatatcaccagctgaagcctatagagtacgagccatagataaaataaaagattttatttagtctccagaaaaggggggg aa:

PMTB1330 (MSGV-LNGR-P2A + HHD2 TCR Mouse Constant (SEQ ID NO: 31)

tgaaagacccccacctgtaggtttggcaagctagcttaagtaacgccattttgcaaggcatggaaaatacataactgagaatagagaagttcgatcaaggtta ggaacagagagacagcagaatatgggccaaacaggatatctgtggtaagcagttcctgccccggctcagggccaagaacagatggtccccagatgcgg tcccgccctcagcagttctagagaaccatcagatgtttccaggtgccccaaggacctgaaatgaccctgtgccttatttgaactaaccaatcagttcgctt ctcgcttctgttcgcgcgcttctgctccccgagctcaataaaagagcccacaacccctcactcggcgcgccagtcctccgatagactgcgtcgcccgggta cccgtattcccaataaagccttcttgctgtttgcatccgaatcgtggactcgctgatccttgggagggtctcctcagattgattgactgcccacctcgggggtctt tcatttggaggttccaccgagatttggagaccctgcctagggaccaccgacccccccgccgggaggtaagctggccagcggtcgtttcgtgtctgtctct gtctttgtgcgtgtttgtgccggcatctaatgtttgcgcctgcgtctgtactagttagctaactagctctgtatctggcggacccgtggtggaactgacgagttc ggaacacccggccgcaacccctgggagacgtcccagggacttcgggggccgtttttgtggcccgacctgagtcctaaaatcccgatcgtttaggactctttggt gcaccccccttagaggagggatatgtggttctggtaggagacgagaacctaaaacagttcccgcctccgtctgaattttttgctttcggtttgggaccgaagcc gcgccgcgcgtcttgtctgctgcagcatcgttctgtgttgtctctgtctgactgtgtttctgtatttgtctgaaaatatgggcccgggctagcctgttaccactc -continued

```
ccttaagtttgaccttaggtcactggaaagatgtcgagcggatcgctcacaaccagtcggtagatgtcaagaagagacgttgggttaccttctgctctgcagaat ggccaacctttaacgtcggatggccgcgagacggcacctttaaccgagacctcatcacccaggttaagatcaaggtcttttcacctggcccgcatggacac ccagaccaggtcccctacatcgtgacctgggaagccttggcttttgaccccctccctgggtcaagcccctttgtacaccctaagcctccgcctcctcttcctcc atccgccccgtctctcccccttgaacctcctcgttcgaccccgcctcgatcctccctttatccagccctcactccttctctaggcgcccccatatggccatatga gatcttatatggggcacccccgcccccttgtaaacttccctgaccctgacatgacaagagttactaacagcccctctctccaagctcacttacaggctctctactt agtccagcacgaagtctggagacctctggcggcagcctaccaagaacaactggaccgaccggtggtacctcacccttaccgagtcggcgacacagtgtg ggtccgccgacaccagactaagaacctagaacctcgctggaaaggaccttacacagtcctgctgaccaccccaccgccctcaaagtagacggcatcgc agcttggatacacgccgcccacgtgaaggctgccgacccccgggggtggaccatcctctagaccgccatgtcgggggcaggtgccaccggccgcgcca tggacgggccgcgcctgctgctgttgctgcttctgggggtgtcccttggaggtgccaaggaggcatgcccccacaggcctgtacacacacagcggtgagtg ctgcaaagcctgcaacctgggcgagggtgtggcccagccttgtggagccaaccagaccgtgtgtgagccctgcctggacagcgtgacgttctccgacgt ggtgagcgcgaccgagccgtgcaagccgtgcaccgagtgcgtggggctccagagcatgtcggcgccatgcgtggaggccgacgacgccgtgtgccg ctgcgcctacggctactaccaggatgagacgactgggcgctgcgaggcgtgccgcgtgtgcgaggcgggctcgggcctcgtgttctcctgccaggaca agcagaacaccgtgtgcgaggagtgccccgacggcacgtattccgacgaggccaaccacgtggaccgtgcctgccctgcaccgtgtgcgaggacac cgagcgccagctccgcgagtgcacacgctgggccgacgccgagtgcgaggagatccctggccgttggattacacggtccacaccccagagggctcg gacagcacagccccagcacccaggagcctgaggcacctccagaacaagacctcatagccagcacggtggcaggtgtggtgaccacagtgatgggca gctcccagcccgtggtgacccgaggcaccaccgacaacctcatccctgtctattgctccatcctggctgctgtggttgtgggtcttgtggcctacatagccttc aagaggtggaacagctccggctccggagccaccaacttcagcctgctgaagcaggccggcgacgtggaggagaacccccgcccccgcggccgccatg gcgacgggttcaagaacttccctacttcttgcatttggcctgctttgtttgccgtggttacaggaagcctcagcacagaaggaggtggagcagaattaggac ccctcagtgttccagagggagccattgcctctctcaactgcacttacagtgaccgaggttcccagtccttcttctggtacagacaatattctgggaaaagccct gagttgataatgttcatatactccaatggtgacaaagaagatggaaggtttacagcacagctcaataaagccagccagtatgtttctctgctcatcagagactc ccagcccagtgattcagccacctacctctgtgccgtagatgacaagatcatctttggaaaagggacacgacttcatattctccccaatatccagaaccccgag cccgccgtgtaccagctgaaggaccccagaagccaggacagcaccctgtgcctgttcaccgacttcgacagccagatcaacgtgcccaagaccatggag agcggcacccttcatcaccgacaagaccgtgctggacatgaaggccatggacagcaagagcaacggcgccatcgcctggtccaaccagaccagcttcac atgccaggacatcttcaaggagaccaacgccacctaccccagcagcgacgtgccctgcgacgccaccctgaccgagaagagcttcgagaccgacatga acctgaacttccagaacctgagcgtgatgggcctgagaatcctgctgctgaaggtggccggcttcaacctgctgatgaccctgaggctgtgggagcagcag ggcaaaacgttcgggttcgggtgcgccagtaaagcagacattaaactttgatttgctgaaacttgcaggtgatgtagagtcaaatccaggtccaatggcaac agggagccgaacactctgctccttgctttcgggctcctttgcctaccgtgcctgcaggagggctcggcagatgctggagttatccagtcaccccggcacga ggtgacagagatgggacaagaagtgactctgagatgtaaaccaatttcaggacacgactaccttttctggtacagacagaccatgatgcggggactggagt tgctcatttactttaacaacaacgttccgatagatgattcagggatgcccgaggatcgattctcagctaagatgcctaatgcatcattctccactctgaagatcc agccctcagaacccagggactcagctgtgtacttctgtgccagcagtttgggacagccaagcacagatacgcagtattttggcccaggcacccggctgaca gtgctcgaggacctgaggaacgtgaccccccccaaggtgtccctgttcgagcccagcaaggccgagatcgccaacaagcagaaggccaccctggtgtg cctggccagggggcttcttccccgaccacgtggagctgtcttggtgggtgaacggcaaggaggtgcacagcggcgtgagcaccgacccccaggcctaca aggagagcaactacagctactgcctgagcagcaggctgagagtgagcgccaccttctggcacaaccccaggaaccacttccgctgtcaggtgcagttcc acggcctgagcgaggaggacaagtggcccgagggcagcccccaagcccgtgacccagaacatcagcgccgaggcctggggcagagccgactgcggc atcaccagcgccagctaccaccagggcgtgctgtccgccaccatcctgtacgagatcctgctgggcaaggccacactgtacgccgtgctggtgtccggcc tggtgctgatggccatggtgaagaagaagaacagctaaaggatccgataaaataaaagattttatttagtctccagaaaaaggggggaatgaaagacccca cctgtaggtttggcaagctagcttaagtaacgccattttgcaaggcatggaaaatacataactgagaatagagaagttcagatcaaggttaggaacagagag acagcagaatatgggccaaacaggatatctgtggtaagcagttcctgccccggctcagggccaagaacagatggtccccagatgcggtcccgccctcag cagtttctagagaaccatcagatgtttccagggtgccccaaggacctgaaatgacccctgtgccttatttgaactaaccaatcagttcgcttctcgcttctgttcg cgcgcttctgctccccgagctcaataaaagagcccacaacccctcactcggcgcgccagtcctccgatagactgcgtcgcccgggtacccgtgtatccaata aaccctcttgcagttgcatccgacttgtggtctcgctgttccttgggagggtctcctctgagtgattgactacccgtcagcgggggtctttcatgggtaacagtt
```

-continued tcttgaagttggagaacaacattctgagggtaggagtcgaatattaagtaatcctgactcaattagccactgttttgaatccacatactccaatactcctgaaat ccatcgatggagttcattatggacagcgcagaaagagctggggagaattgtgaaattgttatccgctcacaattccacacaacatacgagccggaagcataaa gtgtaaagcctggggtgcctaatgagtgagctaactcacattaattgcgttgcgctcactgcccgctttccagtcgggaaacctgtcgtgccagctgcattaat gaatcggccaacgcgcggggagaggcggtttgcgtattgggcgctcttccgcttcctcgctcactgactcgctgcgctcggtcgttcggctgcggcgagc ggtatcagacactcaaaggcggtaatacggttatccacagaatcaggggataacgcaggaaagaacatgtgagcaaaaggccagcaaaaggccagga accgtaaaaaggccgcgttgctggcgtttttccataggctccgcccccctgacgagcatcacaaaaatcgacgctcaagtcagaggtggcgaaacccgac aggactataaagataccaggcgtttccccctggaagctccctcgtgcgctctcctgttccgaccctgccgcttaccggatacctgtccgcctttctcccttcgg gaagcgtggcgctttctcatagctcacgctgtaggtatctcagttcggtgtaggtcgttcgctccaagctgggctgtgtgcacgaaccccccgttcagcccga ccgctgcgccttatccggtaactatcgtcttgagtccaacccggtaagacacgacttatcgccactggcagcagccactggtaacaggattagcagagcga ggtatgtaggcggtgctacagagttcttgaagtggtggcctaactacggctacactagaaggacagtatttggtatctgcgctctgctgaagccagttaccttc ggaaaaagagttggtagctcttgatccggcaaacaaaccaccgctggtagcggtggtttttttgtttgcaagcagcagattacgcgcagaaaaaaaggatct caagaagatcctttgatcttttctacggggtctgacgctcagtggaacgaaaactcacgttaagggattttggtcatgagattatcaaaaaggatcttcacctag atcctttaaattaaaaatgaagttttaaatcaatctaaagtatatatgagtaaacttggtctgacagttaccaatgcttaatcagtgaggcacctatacagcga tctgtctatttcgttcatccatagttgcctgactccccgtcgtgtagataactacgatacgggagggcttaccatctggccccagtgctgcaatgataccgcgag acccacgctcaccggctccagatttatcagcaataaaccagccaggaagggccgagcgcagaagtggtcctgcaactttatccgcctccatccagtcta ttaattgttgccgggaagctagagtaagtagttcgccagttaatagtttgcgcaacgttgttgccattgctacaggcatcgtggtgtcacgctcgtcgtttggta tggcttcattcagctccggttcccaacgatcaaggcgagttacatgatcccccatgttgtgcaaaaaagcggttagctccttcggtcctccgatcgttgtcagaa gtaagttggccgcagtgttatcactcatggttatggcagcactgcataattctcttactgtcatgccatccgtaagatgcttttctgtgactggtgagtactcaa ccaagtcattctgagaatagtgtatgcggcgaccgagttgctcttgcccggcgtcaatacgggataataccgcgccacatagcagaactttaaaagtgctcatca ttggaaaacgttcttcggggcgaaaactctcaaggatcttaccgctgttgagatccagttcgatgtaacccactcgtgcacccaactgatcttcagcatctttta ctttcaccagcgtttctgggtgagcaaaaacaggaaggcaaaatgccgcaaaaaagggaataagggcgacacggaaatgttgaatactcatactcttcctttt ttcaatattattgaagcatttatcagggttattgtctcatgagcggatacatatttgaatgtatttagaaaaataaacaaataggggttccgcgcacatttcccc gaaaagtgccacctgacgtctaagaaaccattattatcatgacattaacctataaaaataggcgtatcacgaggccctttcgtctcgcgcgtttcggtgatgacg gtgaaaacactgacacatgcagacccggagacgtcacagcttgtctgtaagcggatgccgggagcagacaagcccgtcagggcgcgtcagcgggtgt tggcgggtgtcggggctggcttaactatgcggcatcagagcagattgtactgagagtgcaccatatgcggtgtgaaataccgcacagatgcgtaaggaga aaataccgcatcaggcgccattcgccattcaggctgcgcaactgttgggaagggcgatcggtgcgggcctcttcgctattacgccagctggcgaaagggg gatgtgctgcaaggcgattaagttgggtaacgccagggttttcccagtcacgacgttgtaaaacgacggccagtgccacgctctcccttatgcgactcctgc attaggaagcagcccagtagtaggttgaggccgttgagcaccgccgccgcaaggaatggtgcatgcaaggagatggcgcccaacagtcccccggccac ggggcctgccaccatacccacgccgaaacaagcgctcatgagcccgaagtggcgagcccgatcttccccatcggtgatgtcggcgatataggcgccag caaccgcacctgtggcgccggtgatgccggccacgatgcgtccggcgtagaggcgatttaaagacaggatatcagtggtccaggctctagttttgactcaa caatatcaccagctgaagcctatagagtacgagccatagataaaataaaagattttatttagtctccagaaaaaggggggaa pMTB1331 (MSGV-LNGFR-P2A-B07NY TCR Mouse Constant)

(SEQ ID NO: 32)
tgaagaccccacctgtaggtttggcaagctagcttaagtaacgccatttttgcaaggcatggaaaatacataactgagaatagagaagttcagatcaaggtta ggaacagagagacagcagaatatgggccaaacaggatatctgtgtaagcagttcctgcccccggctcagggccaagaacagatggtccccagatgcgg tcccgccctcagcagtttctagagaaccatcagatgtttccagggtgccccaaggacctgaaatgaccctgtgccttatttgaactaaccaatcagttcgctt ctcgcttctgttcgcgcgcttctgctccccgagctcaataaaagagcccacaacccctcactcggcgcgccagtcctccgatagactgcgtcgcccgggta cccgtattcccaataaagccttcttgctgtttgcatccgaatcgtggactcgctgatccttgggagggtctcctcagattgattgactgcccacctcgggggtctt tcatttggaggttccaccgagatttggagacccctgcctagggaccaccgacccccccgccgggaggtaagctggccagcggtcgtttcgtgtctgtctct gtctttgtgcgtgtttgtgccggcatctaatgtttgcgcctgcgtctgtactagttagctaactagctctgtatctggcggacccgtggtggaactgacgagttc ggaacacccggccgcaaccctgggagacgtcccagggacttcggggggccgtttttgtggcccgacctgagtcctaaaatcccgatcgtttaggactctttggt -continued

```
gcaccccccttagaggaggggatatgtggttctggtaggagacgagaacctaaaacagttcccgcctccgtctgaattttttgctttcggtttgggaccgaagcc gcgccgcgcgtcttgtctgctgcagcatcgttctgtgttgtctctgtagactgtgtttctgtatttgtctgaaaatatgggcccgggctagcctgttaccactcc cttaagtttgaccttaggtcactggaaagatgtcgagcggatcgctcacaaccagtcggtagatgtcaagaagagacgttgggttaccttctgctctgcagaat ggccaacctttaacgtcggatggccgcgagacggcacctttaaccgagacctcatcacccaggttaagatcaaggtcttttcacctggcccgcatggacac ccagaccaggtcccctacatcgtgacctgggaagccttggcttttgacccccctccctgggtcaagcccttttgtacaccctaagcctccgcctcctcttcctcc atccgccccgtctctcccccttgaacctcctcgttcgaccccgcctcgatcctcccttttatccagccctcactccttctctaggcgcccccatatggccatatga gatcttatatggggcaccccgcccccttgtaaacttccctgaccctgacatgacaagagttactaacagccctctctccaagctcacttacaggctctctactt agtccagcacgaagtctggagacctctggcggcagcctaccaagaacaactggaccgaccggtggtacctcacccttaccgagtcggcgacacagtgtg ggtccgccgacaccagactaagaacctagaacctcgctggaaaggaccttacacagtcctgctgaccacccccaccgccctcaaagtagacggcatcgc agcttggatacacgccgcccacgtgaaggctgccgaccccgggggtggaccatcctctagaccgccatgtcggggggcaggtgccaccggccgcgcca tggacgggccgcgcctgctgctgttgctgcttctgggggtgtcccttggaggtgccaaggaggcatgcccccacaggcctgtacacacacagcggtgagtg ctgcaaagcctgcaacctgggcgagggtgtggcccagccttgtggagccaaccagaccgtgtgtgagccctgcctggacagcgtgacgttctccgacgt ggtgagcgcgaccgagccgtgcaagccgtgcaccgagtgcgtggggctccagagcatgtcggcgccatgcgtggaggccgacgacgccgtgtgccg ctgcgcctacggctactaccaggatgagacgactgggcgctgcgaggcgtgccgcgtgtgcgaggcgggctcgggcctcgtgttctcctgccaggaca agcagaacaccgtgtgcgaggagtgccccgacggcacgtattccgacgaggccaaccacgtggacccgtgcctgccctgcaccgtgtgcgaggacac cgagcgccagaccgcgagtgcacacgagggccgacgccgagtgcgaggagatccaggccgttggattacacggtccacacccccagagggctcg gacagcacagccccagcacccaggagcctgaggcacctccagaacaagacctcatagccagcacggtggcaggtgtggtgaccacagtgatgggca gctcccagcccgtggtgacccgaggcaccaccgacaacctcatccctgtctattgctccatcctggctgctgtggttgtgggtcttgtggcctacatagccttc aagaggtggaacagctccggctccggagccaccaacttcagcctgctgaagcaggccggcgacgtggaggagaacccggcccccgcggccgccatg gcgacgggttcaagaacttccctacttcttgcatttggcctgctttgtttgccgtggttacaggaagcctcagcaaaacaggaggtgacgcagattcctgcag ctctgagtgtcccagaaggagaaaaacttggttctcaactgcagtttcactgatagcgctatttacaacctccagtggtttaggcaggaccctgggaaaggtctc acatactgttgcttattcagtcaagtcagagagagcaaacaagtggaagacttaatgcctcgctggataaatcatcaggacgtagtactttatacattgagct tctcagcctggtgactcagccacctacctctgtgctgtgagtactgcgtattcaggaggaggtgctgacggactcacctttggcaaagggactcatctaatca tccagccctatatccagaaccccgagccgccgtgtaccagctgaaggaccccagaagccaggacagcaccctgtgcctgttcaccgacttcgacagcc agatcaacgtgcccaagaccatggagagcggcaccttcatcaccgacaagaccgtgctggacatgaaggccatggacagcaagagcancggcgccatc gcctggtccaaccagaccagcttcacatgccaggacatcttcaaggagaccaacgccacctaccccagcagcgacgtgccctgcgacgccaccctgacc gagaagagcttcgagaccgacatgaacctgaacttccagaacctgagcgtgatgggcctgagaatcctgctgctgaaggtggccggcttcaacctgctga tgaccctgaggctgtggagcagcagggcaaaacgttcgggttcgggtgcgccagtaaagcagacattaaactttgatttgctgaaacttgcaggtgatgtag agtcaaatccaggtccaatggcaacagggagccgaacctctctgctccttgctttcgggctcctttgcctaccgtgcctgcaggagggctcggcagatactg gagtctcccagaaccccagacacaagatcacaaagaggggacagaatgtaactttcaggtgtgatccaatttctgaacacaaccgcctttattggtaccgac agaccctggggcagggcccagagtttctgacttacttccagaatgaagctcaactagaaaaatcaaggctgctcagtgatcggttctctgcagagaggccta agggatctttctccaccttggagatccagcgcacagagcaggggactcggccatgtatcatgtgccagcagcccccgactgttcgggtctatggctac accttcggttcggggaccaggttaaccgttgtagaggacctgaggaacgtgacccccccaaggtgtccctgttcgagcccagcaaggccgagatcgcc aacaagcagaaggccacctggtgtgcctggccaggggcttcttccccgaccacgtggagctgtcttggtgggtgaacggcaaggaggtgcacagcgg cgtgagcaccgaccccaggcctacaaggagagcaactacagctactgcctgagcagcaggctgagagtgagcgccaccttctggcacaaccccagga accacttccgctgtcaggtgcagttccacggcctgagcgaggaggacaagtggcccgagggcagccccaagcccgtgacccagaacatcagcgccga ggcctggggcagagccgactgcggcatcaccagcgccagctaccaccagggcgtgctgtccgccaccatcctgtacgagatcctgctgggcaaggcca cactgtacgccgtgctggtgtccggcctggtgctgatggccatggtgaagaagaagaacagctaaaggatccgataaaataaaagattttatttagtctccag aaaaaggggggaatgaaagaccccacctgtaggtttggcaagctagcttaagtaacgccattttgcaaggcatggaaaatacataactgagaatagagaa gttcagatcaaggttaggaacagagagacagcagaatatgggccaaacaggatatctgtggtaagcagttcctgccccggctcagggccaagaacagat ggtccccagatgcggtcccgccctcagcagtttctagagaaccatcagatgtttccagggtgccccaaggacctgaaatgaccctgtgccttatttgaactaa
```

-continued ccaatcagttcgcttctcgcttctgtttcgcgcgcgcttctgctccccgagctcaataaaagagcccacaacccctcactcggcgcgccagtcctccgatagactg cgtcgcccgggtacccgtgtatccaataaaccctcttgcagttgcatccgacttgtggtctcgctgtttccttgggagggtctcctctgagtgattgactacccg tcagcggggggtctttcatgggtaacagtacttgaagttggagaacaacattctgagggtaggagtcgaatattaagtaatcctgactcaattagccactgttttg aatccacatactccaatactcctgaaatccatcgatggagttcattatggacagcgcagaaagagctggggagaattgtgaaattgttatccgctcacaattcc acacaacatacgagccggaagcataaagtgtaaagcctggggtgcctaatgagtgagctaactcacattaattgcgttgcgctcactgcccgctttccagtc gggaaacctgtcgtgccagctgcattaatgaatcggccaacgcgcggggagaggcggtttgcgtattgggcgctcttccgcttcctcgctcactgactcgct gcgctcggtcgttcggctgcggcgagcggtatcagctcactcaaaggtaatacggttatccacagaatcaggggataacgcaggaaagaacatgtg agcaaaaggccagcaaaaggccaggaaccgtaaaaaggccgcgttgctggcgttttttccataggctccgcccccctgacgagcatcacaaaaatcgacg ctcaagtcagaggtggcgaaacccgacaggactataaagataccaggcgtttccccctggaagctccctcgtgcgctctcctgttccgaccctgccgcttac cggataccgtgtccgcctttctcccttcgggaagcgtggcgctttctcatagctcacgctgtaggtatctcagttcggtgtaggtcgttcgctccaagctgggctg tgtgcacgaaccccccgttcagcccgaccgctgcgccttatccggtaactatcgtcttgagtccaacccggtaagacacgacttatcgccactggcagcag ccactggtaacaggattagcagagcgaggtatgtaggcggtgctacagagttcttgaagtggtggcctaactacggctacactagaaggacagtatttggta tctgcgctctgctgaagccagttaccttcggaaaaagagttggtagctcttgatccggcaaacaaaccaccgctggtagcggtggtttttttgtttgcaagcag cagattacgcgcagaaaaaaaggatctcaagaagatcctttgatcttttctacggggtctgacgctcagtggaacgaaaactcacgttaagggattttggtcat gagattatcaaaaaggatcttcacctagatccttttaaattaaaaatgaagttttaaatcaatctaaagtatatatgagtaaacttggtctgacagttaccaatg cttaatcagtgaggcacctatctcagcgatctgtctatttcgttcatccatagttgcctgactccccgtcgtgtagataactacgatacgggagggcttaccatc tggccccagtgctgcaatgataccgcgagacccacgctcaccggctccagatttatcagcaataaaccagccagccggaagggccgagcgcagaagtggtc ctgcaactttatccgcctccatccagtctattaattgttgccgggaagctagagtaagtagttcgccagttaatagtttgcgcaacgttgttgccattgctacag gcatcgtggtgtcacgctcgtcgtttggtatggcttcattcagctccggttcccaacgatcaaggcgagttacatgatcccccatgttgtgcaaaaaagcggtta gctccttcggtcctccgatcgttgtcagaagtaagttggccgcagtgttatcactcatggttatggcagcactgcataattctcttactgtcatgccatccgtaa gatgcttttctgtgactggtgagtactcaaccaagtcattctgagaatagtgtatgcggcgaccgagttgctcttgcccggcgtcaatacgggataataccgcgc cacatagcagaactttaaaagtgctcatcattggaaaacgttcttcggggcgaaaactctcaaggatcttaccgctgttgagatccagttcgatgtaacccact cgtgcacccaactgatcttcagcatcttttactttcaccagcgtttctgggtgagcaaaaacaggaaggcaaaatgccgcaaaaaagggaataagggcgac acggaaatgttgaatactcatactcttcctttttcaatattattgaagcatttatcagggttattgtctcatgagcggatacatatttgaatgtatttagaaaaa taaacaaataggggttccgcgcacatttccccgaaaagtgccacctgacgtctaagaaaccattattatcatgacattaacctataaaaataggcgtatcacgag gccctttcgtctcgcgcgtttcggtgatgacggtgaaaacctctgacacatgcagctcccggagacggtcacagcttgtctgtaagcggatgccgggagcagac aagcccgtcagggcgcgtcagcgggtgttggcgggtgtcggggctggcttaactatgcggcatcagagcagattgtactgagagtgcaccatatgcggtg tgaaataccgcacagatgcgtaaggagaaaataccgcatcaggcgccattcgccattcaggctgcgcaactgttgggaagggcgatcggtgcgggcctct tcgctattacgccagctggcgaaagggggatgtgctgcaaggcgattaagttgggtaacgccagggttttcccagtcacgacgttgtaaaacgacggcca gtgccacgctctcccttatgcgactcctgcattaggaagcagcccagtagtaggttgaggccgttgagcaccgccgccgcaaggaatggtgcatgcaagg agatggcgcccaacagtcccccggccacgggcctgccaccatacccacgccgaaacaagcgctcatgagcccgaagtggcgagcccgatcttcccc atcggtgatgtcggcgatataggcgccagcaaccgcacctgtggcgccggtgatgccggccacgatgcgtccggcgtagaggcgatttaaagacaggat atcagtggtccaggctctagttttgactcaacaatatcaccagctgaagcctatagagtacgagccatagataaaataaaagattttatttagtctccagaaaaa gggggaa pMTB1332 (MSGV-LNGFR-P2A-B18NY TCR Mouse Constant (SEQ ID NO: 33)
tgaaagaccccacctgtaggtttggcaagctagcttaagtaacgccattttgcaaggcatggaaaatacataactgagaatagagaagttcagatcaaggtta ggaacagagagacagcagaatatgggccaaacaggatatctgtggtaagcagttcctgccccggctcagggccaagaacagatggtccccagatgcgg tcccgccctcagcagtttctagagaaccatcagatgtttccagggtgccccaaggacctgaaaatgaccctgtgccttatttgaactaaccaatcagttcgctt ctcgcttctgttcgcgcgcttctgctccccgagctcaataaaagagcccacaacccctcactcggcgcgccagtcctccgatagactgcgtcgcccgggta cccgtattcccaataaagcctcttgctgtttgcatccgaatcgtggactcgctgatccttgggagggtctcctcagattgattgactgcccacctcggggggtctt -continued

```
tcatttggaggttccaccgagatttggagacccctgcctagggaccaccgaccccccgccgggaggtaagctggccagcggtcgtttcgtgtctgtctct gtctttgtgcgtgtttgtgccggcatctaatgtttgcgcctgcgtctgtactagttagctaactagctctgtatctggcggacccgtggtggaactgacgagttc ggaacacccggccgcaaccctgggagacgtcccagggacttcggggggccgttttttgtggcccgacctgagtcctaaaatcccgatcgtttaggactctttggt gcaccccccttagaggagggatatgtggttctggtaggagacgagaacctaaaacagttcccgcctccgtctgaattttttgctttcggtttgggaccgaagcc gcgccgcgcgtcttgtctgctgcagcatcgttctgtgttgtctctgtctgactgtgtttctgtatttgtctgaaaatatgggcccgggctagcctgttaccactc ttaagtttgaccttaggtcactggaaagatgtcgagcggatcgctcacaaccagtcggtagatgtcaagaagagacgttgggttaccttctgactgcagaat ccggccaacctttaacgtcggatggccgcgagacggcacctttaaccgagacctcatcacccaggttaagatcaaggtcttttcacctggcccgcatggacac ccagaccaggtcccctacatcgtgacctgggaagccttggcttttgaccccctccctgggtcaagccctttgtacaccctaagcctccgcctcctcttcctcc atccgccccgtctctcccccttgaacctcctcgttcgaccccgcctcgatcctcccttttatccagccctcactccttctctaggcgcccccatatggccatatga gatcttatatggggcacccccgccccttgtaaacttccctgacctgacatgacaagagttactaacagcccctctctccaagctcacttacaggctctctactt agtccagcacgaagtaggagaccatggcggcagcctaccaagaacaactggaccgaccggtggtacctcacccttaccgagtcggcgacacagtgtg ggtccgccgacaccagactaagaacctagaacctcgctggaaaggaccttacacagtcctgctgaccaccccaccgccctcaaagtagacggcatcgc agcttggatacacgccgcccacgtgaaggctgccgaccccggggggtggaccatcctctagaccgccatgtcgggggcaggtgccaccggccgcgcca tggacgggccgcgcctgctgctgttgctgcttctgggggtgtcccttggaggtgccaaggaggcatgcccacaggcctgtacacacacagcggtgagtg ctgcaaagcctgcaacctgggcgagggtgtggcccagccttgtggagccaaccagaccgtgtgtgagccctgcctggacagcgtgacgttctccgacgt ggtgagcgcgaccgagccgtgcaagccgtgcaccgagtgcgtggggctccagagcatgtcggcgccatgcgtggaggccgacgacgccgtgtgccg ctgcgcctacggctactaccaggatgagacgactgggcgctgcgaggcgtgccgcgtgtgcgaggcgggctcgggcctcgtgttctcctgccaggaca agcagaacaccgtgtgcgaggagtgccccgacggcacgtattccgacgaggccaaccacgtggacccgtgcctgccctgcaccgtgtgcgaggacac cgagcgccgagaccgcgagtgcacacgctgggccgacgccgagtgcgaggagatccctggccgttggattacacggtccacacccccagagggctcg gacagcacagcccccagcacccaggagcctgaggcacctccagaacaagacctcatagccagcacggtggcaggtgtggtgaccacagtgatgggca gctcccagcccgtggtgacccgaggcaccaccgacaacctcatccctgtctattgctccatcctggctgctgtggttgtgggtcttgtggcctacatagccttc aagaggtggaacagctccggctccggagccaccaacttcagcctgctgaagcaggccggcgacgtggaggagaaccccggccccgcggccgccatg gcgacgggttcaagaacttccctacttcttgcatttggcctgctttgtttgccgtggttacaggaagcctcagcaggacaacaggtaatgcaaattcctcagta ccagcatgtacaagaaggagaagacttcaccacgtactgcaattcctcaactactttaagcaatatacagtggtataagcaaaggcctggtggacatcccgtt tttttgatacagttagtgaagagtggagaagtgaagaagcagaaaaagactgacatttcagtttggagaagcaaaaaagaacagctccctgcacatcacagc cacccagactacagatgtaggaacctacttctgtgcggaccctaactttggaaatgagaaattaacctttgggactggaacaagactcaccatcatacccaat atccagaaccccgagccgccgtgtaccagctgaaggaccccagaagccaggacagcaccctgtgcctgttcaccgacttcgacagccagatcaacgtg cccaagaccatggagagcggcaccttcatcaccgacaagaccgtgctggacatgaaggccatggacagcaagagcaacggcgccatcgcctggtccaa ccagaccagcttcacatgccaggacatcttcaaggagaccaacgccacctaccccagcagcgacgtgccctgcgacgccaccctgaccgagaagagctt cgagaccgacatgaacctgaacttccagaacctgagcgtgatgggcctgagaatcctgctgctgaaggtggccggcttcaacctgctgatgaccctgagg ctgtggagcagcagggcaaaacgttcgggttcgggtgcgccagtaaagcagacattaaactttgatttgctgaaacttgcaggtgatgtagagtcaaatcca ggtccaatggcaacagggagccgaacctctctgctccttgctttcgggctcctttgcctaccgtgcctgcaggagggctcggcagaagcccaagtgaccca gaacccaagatacctcatcacagtgactggaaagaagttaacagtgacttgttacagaatatgaaccatgagtatatgtcctggtatcgacaagacccagg gctgggcttaaggcagatctactattcaatgaatgttgaggtgactgataagggagatgttcctgaagggtacaaagtctctcgaaaagagaagaggaatttc cccctgatcctggagtcgcccagccccaaccagacctctctgtacttctgtgccagcagtttgaatccctttgcaactaatgaaaaactgtttttttggcagtgga acccagctctctgtcttggaggacctgaggaacgtgaccccccccaaggtgtccctgttcgagcccagcaaggccgagatcgccaacaagcagaaggcc accctggtgtgcctggccaggggcttcttccccgaccacgtggagagtcttggtgggtgaacggcaaggaggtgcacagcggcgtgagcaccgaccc caggcctacaaggagagcaactacagctactgcctgagcagcaggctgagagtgagcgccaccttctggcacaaccccaggaaccacttccgctgtcag gtgcagttccacaggcctgagcgaggaggacaagtggcccgagggcagccccaagcccgtgacccagaacatcagcgccgaggcctggggcagagc cgactgcggcatcaccagcgccagctaccaccagggcgtgctgtccgccaccatcctgtacgagatcctgctgggcaaggccacactgtacgccgtgct ggtgtccggcctggtgctgatggccatggtgaagaagaagaacagctaaaggatccgataaaatattaagattttatttagtctccagaaaaaggggggaat
```

-continued gaaagacccacctgtaggtttggcaagctagcttaagtaacgccattttgcaaggcatggaaaatacataactgagaatagagaagttcagatcaaggtta ggaacagagagacagcagaatatgggccaaacaggatatctgtggtaagcagttcctgcccggctcagggccaagaacagatggtccccagatgcgg tcccgccctcagcagtttctagagaaccatcagatgtttccagggtgccccaaggacctgaaatgaccctgtgccttatttgaactaaccaatcagttcgcttct cgcttctgttcgcgcgcttctgctccccgagctcaataaaagagcccacaacccctcactcggcgcgccagtcaccgatagactgcgtcgcccgggtacc cgtgtatccaataaaccctcttgcagttgcatccgacttgtggtctcgctgttccttgggagggtctcctctgagtgattgactaccgtcagcgggggtctttc atgggtaacagtttatgaagttggagaacaacattctgagggtaggagtcgaatattaagtaatcctgactcaattagccactgttttgaatccacatactccaa tactcctgaaatccatcgatggagttcattatggacagcgcagaaagagctggggagaattgtgaaattgttatccgctcacaattccacacaacatacgagc cggaagcataaagtgtaaagcctggggtgcctaatgagtgagctaactcacattaattgcgttgcgctcactgcccgctttccagtcgggaaacctgtcgtgc cagctgcattaatgaatcggccaacgcgcggggagaggcggtttgcgtattgggcgctcttccgcttcctcgctcactgactcgctgcgctcggtcgttcgg ctgcggcgagcggtatcagacactcaaaggcggtaatacggttatccacagaatcaggggataacgcaggaaagaacatgtgagcaaaaggccagca aaaggccaggaaccgtaaaaaggccgcgttgctggcgtttttccataggctccgcccccctgacgagcatcacaaaaatcgacgctcaagtcagaggtgg cgaaacccgacaggactataaagataccaggcgtttccccctggaagctccctcgtgcgctctcctgttccgaccctgccgcttaccggatacctgtccgcc tttaccttcgggaagcgtggcgctttctcatagctcacgctgtaggtatctcagttcggtgtaggtcgttcgctccaagctgggctgtgtgcacgaacccccc gttcagcccgaccgctgcgccttatccggtaactatcgtcttgagtccaacccggtaagacacgacttatcgccactggcagcagccactggtaacaggat tagcagagcgaggtatgtaggcggtgctacagagttcttgaagtggtggcctaactacggctacactagaaggacagtatttggtatctgcgctctgctgaa gccagttaccttcggaaaaagagttggtagctcttgatccggcaaacaaaccaccgctggtagcggtggtggtttttttgtttgcaagcagcagattacgcgcaga aaaaaaggatctcaagaagatcctttgatcttttctacggggtctgctcgctcagtggaacgaaaactcacgttaagggattttggtcatgagattatcaaaaag gatcttcacctagatccttttaaattaaaaatgaagttttaaatcaatctaaagtatatatgagtaaacttggtagacagttaccaatgcttaatcagtgaggca cctatctcagcgatctgtctatttcgttcatccatagttgcctgactccccgtcgtgtagataactacgatacgggagggcttaccatctggccccagtgctgca atgataccgcgagacccacgctcaccggctccagatttatcagcaataaaccagccagccggaagggccgagcgcagaagtggtcctgcaactttatccgc ctccatccagtctattaattgttgccgggaagctagagtaagtagttcgccagttaatagtttgcgcaacgttgttgccattgctacaggcatcgtggtgtcacg ctcgtcgtttggtatggcttcattcagctccggttcccaacgatcaaggcgagttacatgatcccccatgttgtgcaaaaaagcggttagctccttcggtcctcc gatcgttgtcagaagtaagttggccgcagtgttatcactcatggttatggcagcactgcataattacttactgtcatgccatccgtaagatgcttttctgtgact ggtgagtactcaaccaagtcattctgagaatagtgtatgcggcgaccgagttgctcttgcccggcgtcaatacgggataataccgcgccacatagcagaactt taaaagtgctcatcattggaaaacgttcttcggggcgaaaactctcaaggatcttaccgctgttgagatccagttcgatgtaacccactcgtgcacccaactga tcttcagcatcttttactttcaccagcgtttctgggtgagcaaaaacaggaaggcaaaatgccgcaaaaaagggaataagggcgacacggaaatgttgaata ctcatactcttcctttttcaatattattgaagcatttatcagggttattgtctcatgagcggatacatatttgaatgtatttagaaaaataaacaaataggggtt ccgcgcacatttccccgaaaagtgccacctgacgtctaagaaaccattattatcatgacattaacctataaaaataggcgtatcacgaggccctttcgtctcgcg cgtttcggtgatgacggtgaaaacctctgacacatgcagctcccggagacggtcacagcttgtctgtaagcggatgccgggagcagacaagcccgtcagggcg cgtcagcgggtgttggcgggtgtcggggctggcttaactatgcggcatcagagcagattgtactgagagtgcaccatatgcggtgtgaaataccgcacag atgcgtaaggagaaaataccgcatcaggcgccattcgccattcaggctgcgcaactgttgggaagggcgatcggtgcgggcctcttcgctattacgccag ctggcgaaagggggatgtgtgcaaggcgattaagttgggtaacgccagggttttcccagtcacgacgttgtaaaacgacggccagtgccacgctctccct tatgcgactcctgcattaggaagcagcccagtagtaggttgaggccgttgagcaccgccgccgcaaggaatggtgcatgcattggagatggcgcccaaca gtcccccggccacgggggcctgccaccatacccacgccgaaacaagcgctcatgagcccgaagtggcgagcccgatcttccccatcggtgatgtcggcg atataggcgccagcaaccgcacctgtggcgccggtgatgccggccacgatgcgtccggcgtagaggcgatttaaagacaggatatcagtggtccaggct ctagttttgactcaacaatatcaccagctgaagcctatagagtacgagccatagataattatataaaagattttatttagtctccagaaaaaggggggaa pMTB1333 (MSGV-LNGFR-P2A-C03NY96 TCR Mouse Constant)

(SEQ ID NO: 34)

tgaaagacccacctgtaggtttggcaagctagcttaagtaacgccattttgcaaggcatggaaaatacataactgagaatagagaagttcagatcaaggtta ggaacagagagacagcagaatatgggccattacaggatatctgtggtaagcagttcctgcccccggctcagggccaagaacagatggtccccagatgcgg tcccgccctcagcagtttctagagaaccatcagatgtttccagggtgccccaaggacctgaaatgaccagtgccttatttgaactaaccaatcagttcgctt -continued

```
ctcgcttctgttcgcgcgcttctgctccccgagctcaataaaaagagcccacaacccctcactcggcgcgccagtcctccgatagactgcgtccccgggta cccgtattcccaataaagcctcttgctgtttgcatccgaatcgtggactcgctgatccttgggagggtctcctcagattgattgactgcccacctcgggggtctt tcatttggaggttccaccgagatttggagacccctgcctagggaccaccgacccccccgccgggaggtaagctggccagcggtcgtttcgtgtctgtctct gtctttgtgcgtgtttgtgccggcatctaatgtttgcgcctgcgtctgtactagttagctaactagctctgtatctggcggacccgtggtggaactgacgagttc ggaaacccggccgcaaccctgggagacgtcccagggacttcggggcgccgtttttgtggcccgacctgagtcctaaaatcccgatcgtttaggactctttggt gcaccccccttagaggagggatatgtggttctggtaggagacgagaacctaaaacagttcccgcctccgtctgaatttttgctttcggtttgggaccgaagcc gcgccgcgcgtcttgtctgctgcagcatcgttctgtgttgtctctgtctgactgtgtttctgtatttgtctgaaaatatgggcccgggctagcctgttaccactc ccttaagtttgaccttaggtcactggaaagatgtcgagcggatcgctcacaaccagtcggtagatgtcaagaagagacgttgggttaccttctgctctgcagaat ggccaacctttaacgtcggatggccgcgagacggcacctttaaccgagacctcatcacccaggttaagatcaaggtcttttcacctggcccgcatggacac ccagaccaggtcccctacatcgtgacctgggttttgccttggcttttgacccccctccctgggtcaagccctttgtacaccctaagcctccgcctcctcttcctc catccgcccgtctctcccccttgaacctcctcgttcgaccccgcctcgatcctccctttatccagccctcactcctctctaggcgcccccatatggccatatga gatcttatatggggcaccccgcccttgtaaacttccctgaccctgacatgacaagagttactaacagcccctctctccaagctcacttacaggctctctactt agtccagcacgaagtctggagacctctggcggcagcctaccaagaacaactggaccggaccggtggtacctcacccttaccgagtcggcgacacagtgtg ggtccgccgacaccagactaagaacctagaacctcgctggaaaggaccttacacagtcctgctgaccacccccaccgccctcaaagtagacggcatcgc agcttggatacacgccgcccacgtgaaggctgccgaccccgggggtggaccatcctctagaccgccatgtcgggggcaggtgccaccggccgcgcca tggacgggccgcgcctgctgctgttgctgcttctgggggtgtcccttggaggtgccaaggaggcatgcccacaggcctgtacacacacagcggtgagtg ctgcaaagcctgcaacctgggcgagggtgtggcccagccttgtggagccaaccagaccgtgtgtgagccctgcctggacagcgtgacgttctccgacgt ggtgagcgcgaccgagccgtgcaagccgtgcaccgagtgcgtgggggctccagagcatgtcggcgccatgcgtggaggccgacgacgccgtgtgccg ctgcgcctacggctactaccaggatgagacgactgggcgctgcgaggcgtgccgctgtgtgcgaggcgggctcgggcctcgtgttctcctgccaggaca agcagaacaccgtgtgcgaggagtgccccgacggcacgtattccgacgaggccaaccacgtggacccgtgcctgccctgcaccgtgtgcgaggacac cgagcgccagctccgcgagtgcacacgctgggccgacgccgagtgcgaggagatccctggccgttggattacacggtccacacccccagagggctcg gacagcacagcccccagcacccaggagcctgaggcacctccagaacaagacctcatagccagcacggtggcaggtgtggtgaccacagtgatgggca gctcccagcccgtggtgacccgaggcaccaccgacaacctcatccctgtctattgctccatcctggctgctgtggttgtgggtcttgtggcctacatagccttc aagaggtggaacagctccggctccggagccaccaacttcagcctgctgaagcaggccggcgacgtggaggagaacccCGGCCCCGcggccgccatg gcgacgggttcaagaacttccctacttcttgcatttggcctgcttgtttgccgtggttacaggaagcctcagcaggacaaaacattgaccagcccactgagat gacagctacggaaggtgccattgtccagatcaactgcacgtaccagacatctgggttcaacgggctgttctggtaccagcaacatgctggcgaagcaccta catttctgtcttacaatgttctggatggtttggaggagaaaggtcgttttttcttcattccttagtcggtctaaagggtacagttacctccattgaaggagctcca gatgaaagactctgcctcttacctctgtgctgtgagaggcgactacaagctcagctttggagccggaaccacagtaactgtaagagcaaatatccagaacccg agcccgccgtgtaccagctgaaggaccccagaagccaggacagcaccctgtgcctgttcaccgacttcgacagccagatcaacgtgcccaagaccatgg agagcggcaccttcatcaccgacaagaccgtgctggacatgaaggccatggacagcaagagcaacggcgccatcgcctggtccaaccagaccagcttc acatgccaggacatcttcaaggagaccaacgccacctaccccagcagcgacgtgccctgcgacgccaccctgaccgagaagagcttcgagaccgacat gaacctgaacttccagaacctgagcgtgatgggcctgagaatcctgctgctgaaggtggccggcttcaacctgctgatgaccctgaggctgtggagcagc agggcaaaacgttcgggttcgggtgcgccagtaaagcagacattaaactttgatttgctgaaacttgcaggtgatgtagagtcaaatccaggtccaatggca acaggggagccgaacctctctgctccttgctttcgggctcctttgcctaccgtgcctgcaggagggctcggcagattctggagtcacacaaaccccaaagca cctgatcacagcaactggacagcgagtgacgctgagatgctccctaggtctggagttcctctctgtgtactggtaccaacagagcctggaccagggcctc cagttcctcattcagtattataatggagaagagagagcaaaaggaaacattcttgaacgattctccgcacaacagttccctgacttgcactctgaactaaacct gagctctctggagctggggactcagctttgtatttctgtgccagcagctcgatacacggtgtctctggggccaacgtcctgactttcggggccggcagcag gctgaccgtgctggaggacctgaggaacgtgacccccccaaggtgtccctgttcgagcccagcaaggccgagatcgccaacaagcagaaggccacc ctggtgtgcaggccaggggcttcttccccgaccacgtggagctgtcttggtgggtgaacggcaaggaggtgcacagcggcgtgagcaccgacccccca ggcctacaaggagagcaactacagctactgcctgagcagcaggctgagagtgagcgccacctctggcacaacccccaggaaccacttccgctgtcaggt gcagttccacggcctgagcgaggaggacaagtggcccgagggcagccccaagcccgtgacccagaacatcagcgccgaggcctggggcagagccg
```

-continued

```
actgcggcatcaccagcgccagctaccaccagggcgtgctgtccgccaccatcctgtacgagatcctgctgggcaaggccacactgtacgccgtgctggt gtccggcctggtgctgatggccatggtgaagaagaagaacagctaaaggatccgataaaataaaagattttatttagtctccagaaaaaggggggaatgaa agaccccacctgtaggtttggcaagctagcttaagtaacgccattttgcaaggcatggaaaatacataactgagaatagagaagttcagatcaaggttagga acagagagacagcagaatatgggccaaacaggatatctgtggtaagcagttcctgccccggctcagggccaagaacagatggtccccagatgcggtccc gccctcagcagtttctagagaaccatcagatgtttccagggtgccccaaggacctgaaatgaccctgtgccttatttgaactaaccaatcagttcgcactcgct tctgttcgcgcgcttctgctccccgagctcaataaaagagcccacaacccctcactcggcgcgccagtcctccgatagactgcgtcgcccgggtacccgtg tatccaataaaccctcttgcagttgcatccgacttgtggtctcgctgttccttgggagggtctcctctgagtgattgactacccgtcagcgggggtctttcatgg gtaacagtttcttgaagttggagaacaacattctgagggtaggagtcgaatattaagtaatcctgactcaattagccactgttttgaatccacatactccaatac tcctgaaatccatcgatggagttcattatggacagcgcagaaagagctggggagaattgtgaaattgttatccgctcacaattccacacaacatacgagccgg aagcataaagtgtaaagcctggggtgcctaatgagtgagctaactcacattaattgcgttgcgctcactgcccgctttccagtcgggaaacctgtcgtgccag ctgcattaatgaatcggccaacgcgcggggagaggcggtttgcgtattgggcgctcttccgcttcctcgctcactgactcgctgcgctcggtcgttcggctg cggcgagcggtatcagctcactcaaaggcggtaatacggttatccacagaatcaggggataacgcaggaaagaacatgtgagcaaaaggccagcaaaa ggccaggaaccgtaaaaaggccgcgttgctggcgtttttccataggctccgcccccctgacgagcatcacaaaaatcgacgctcaagtcagaggtggcga aacccgacaggactataaagataccaggcgtttccccctggaagctccctcgtgcgctctcctgttccgaccctgccgcttaccggatacctgtccgcctttc tcccttcgggaagcgtggcgctttctcatagctcacgagtaggtatctcagttcggtgtaggtcgttcgctccaagagggctgtgtgcacgaaccccccgtt cagcccgaccgctgcgccttatccggtaactatcgtcttgagtccaacccggtaagacacgacttatcgccactggcagcagccactggtaacaggattag cagagcgaggtatgtaggcggtgctacagagttcttgaagtggtggcctaactacggctacactagaaggacagtatttggtatctgcgctctgctgaagcc agttaccttcggaaaaagagttggtagctcttgatccggcaaacaaaccaccgctggtagcggtggtttttttgtttgcaagcagcagattacgcgcagaaaa aaaggatctcaagaagatcctttgatcttttctacggggtctgacgctcagtggaacgaaaactcacgttaagggattttggtcatgagattatcaaaaaggat cttcacctagatccttttaaattaaaaatgaagttttaaatcaatctaaagtatatatgagtaaacttggtctgacagttaccaatgcttaatcagtgaggcacc tatctcagcgatctgtctatttcgttcatccatagttgcctgactccccgtcgtgtagataactacgatacgggagggcttaccatctggccccagtgctgcaat gataccgcgagacccacgctcaccggctccagatttatcagcaataaaccagccagccggaagggccgagcgcagaagtggtcctgcaactttatccgcctc catccagtctattaattgttgccgggaagctagagtaagtagttcgccagttaatagtttgcgcaacgttgttgccattgctacaggcatcgtggtgtcacgctc gtcgtttggtatggcttcattcagctccggttcccaacgatcaaggcgagttacatgatcccccatgttgtgcaaaaaagcggttagctccttcggtcctccgat cgttgtcagaagtaagttggccgcagtgttatcactcatggttatggcagcactgcataattctcttactgtcatgccatccgtaagatgcttttctgtgactgg tgagtactcaaccaagtcattctgagaatagtgtatgcggcgaccgagttgctcttgcccggcgtcaatacgggataataccgcgccacatagcagaacttta aagtgctcatcattggaaaacgttcttcggggcgaaaactctcaaggatcttaccgctgttgagatccagttcgatgtaacccactcgtgcacccaactgatct tcagcatcttttactttcaccagcgtttctgggtgagcaaaaacaggaaggcaaaatgccgcaaaaaagggaataagggcgacacggaaatgttgaatact catactcttcctttttcaatattattgaagcatttatcagggttattgtctcatgagcggatacatatttgaatgtatttagaaaaataaacaaataggggttcc gcgcacatttccccgaaaagtgccacctgacgtctaagaaaccattattatcatgacattaacctataaaaataggcgtatcacgaggccctttcgtctcgcgcg tttcggtgatgacggtgaaaacctctgacacatgcagctcccggagacggtcacagcttgtctgtaagcggatgccgggagcagacaagcccgtcagggcgc gtcagcgggtgttggcgggtgtcggggctggcttaactatgcggcatcagagcagattgtactgagagtgcaccatatgcggtgtgaaataccgcacagat gcgtaaggagaaaataccgcatcaggcgccattcgccattcaggctgcgcaactgttgggaagggcgatcggtgcgggcctcttcgctattacgccagct ggcgaaaggggggatgtgctgcaaggcgattaagttgggtaacgccagggttttcccagtcacgacgttgtaaaacgacggccagtgccacgctctcccttA tgcgactcctgcattaggaagcagcccagtagtaggttgaggccgttgagcaccgccgccgcaaggaatggtgcatgcaaggagatggcgcccaacagt cccccggccacggggcctgccaccatacccacgccgaaacaagcgctcatgagcccgaagtggcgagcccgatcttccccatcggtgatgtcggcgat ataggcgccagcaaccgcacctgtggcgccggtgatgccggccacgatgcgtccggcgtagaggcgatttaaagacaggatatcagtggtccaggctct agttttgactcaacaatatcaccagctgaagcctatagagtacgagccatagataaaataaaagattttatttagtctccagaaaaaggggggaa
```

-continued pMTB1289 (MSGV-LNGFR-P2A-GBA1 TCR Mouse Constant)

(SEQ ID NO: 35)

```
tgaaagacccccacctgtaggtttggcaagctagcttaagtaacgccattttgcaaggcatggaaaatacataactgagaatagagaagttcagatcaaggtta ggaacagagagacagcagaatatgggccaaacaggatatctgtggtaagcagttcctgccccggctcagggccaagaacagatggtccccagatgcgg tcccgccctcagcagtttctagagaaccatcagatgtttccaggagtgccccaaggacctgaaaatgaccctgtgccttatttgaactaaccaatcagttcgctt ctcgcttctgttcgcgcgcttctgctccccgagctcaataaaagagcccacaaccccctcactcggcgcgccagtcctccgatagactgcgtcgcccgggta cccgtattcccaataaagcacttgctgtttgcatccgaatcgtggactcgctgatccttgggagggtctcctcagattgattgactgcccacctcggggggtctt tcatttggaggttccaccgagatttggagacccctgcctagggaccaccgacccccccgccgggaggtaagctggccagcggtcgtttcgtgtctgtctct gtctttgtgcgtgtttgtgccggcatctaatgtttgcgcctgcgtctgtactagttagctaactagctctgtatctggcggaccgtggtggaactgacgagttc ggaacacccggccgcaaccctgggagacgtcccagggacttcggggggccgttttgtggcccgacctgagtcctaaaatcccgatcgtttaggactctttggt gcaccccccttagaggaggggatatgtggttctggtaggagacgagaacctaaaacagttcccgcctccgtctgaatttttgctttcggtttgggaccgaagcc gcgccgcgcgtcttgtctgctgcagcatcgttctgtgttgtctctgtctgactgtgtttctgtatttgtctgaaaatatgggcccgggctagcctgttaccactc ccttaagtttgaccttaggtcactggaaagatgtcgagcggatcgctcacaaccagtcggtagatgtcaagaagagacgttgggttaccttctgctctgcagaat ggccaacctttaacgtcggatggccgcgagacggcacctttaaccgagacctcatcacccaggttaagatcaaggtcttttcacctggcccgcatggacac ccagaccaggtcccctacatcgtgacctgggaagccttggcttttgacccccctccctgggtcaagccctttgtacaccctaagcctccgcctcctcttcctcc atccgccccgtctctcccccttgaacctcctcgttcgaccccgcctcgatcctcccctttatccagccctcactccttctctaggcgcccccatatggccatatga gatcttatatggggcacccccgccccttgtaaacttccctgaccctgacatgacaagagttactaacagcccactaccaagctcacttacaggctactactt agtccagcacgaagtctggagacctctggcggcagcctaccaagaacaactggaccgaccggtggtacctcacccttaccgagtcggcgacacagtgtg ggtccgccgacaccagactaagaacctagaacctcgctggaaaggaccttacacagtcctgctgaccacccccaccgccctcaaagtagacggcatcgc agcttggatacacgccgcccacgtgaaggctgccgacccccgggggtggaccatcctctagaccgccatgtcgggggcaggtgccaccggccgcgcca tggacgggccgcgcctgctgctgttgagcttaggggggtgtcccttggaggtgccaaggaggcatgccccacaggcctgtacacacacagcggtgagtg ctgcaaagcctgcaacctgggcgagggtgtggcccagccttgtggagccaaccagaccgtgtgtgagccctgcctggacagcgtgacgttctccgacgt ggtgagcgcgaccgagccgtgcaagccgtgcaccgagtgcgtggggctccagagcatgtcggcgccatgcgtggaggccgacgacgccgtgtgccg ctgcgcctacggctactaccaggatgagacgactgggcgctgcgaggcgtgccgcgtgtgcgaggcgggctcgggcctcgtgttctcctgccaggaca agcagaacaccgtgtgcgaggagtgccccgacggcacgtattccgacgaggccaaccacgtggacccgtgcctgccctgcaccgtgtgcgaggacac cgagcgccagctccgcgagtgcacacgctgggccgacgccgagtgcgaggagatccctggccgttggattacacggtccacaccccagagggctcg gacagcacagcccccagcacccaggagcctgaggcacctccagaacaagacctcatagccagcacggtggcaggtgtggtgaccacagtgatgggca gctcccagcccgtggtgacccgaggcaccaccgacaacctcatccctgtctattgctccatcctggctgctgtggttgtgggtcttgtggcctacatagccttc aagaggtggaacagctccggctccggagccaccaacttcagcctgctgaagcaggccggcgacgtggaggagaaccccggccccgcggccgccatg gcgacgggttcaagaacttccctacttcttgcatttggcctgctttgtttgccgtggttacaggaagcctcagcaggtcaacagctgaatcagagtcctcaatct atgtttatccaggaaggagaagatgtctccatgaactgcacttcttcaagcatatatttaacacctggctatggtacaagcaggaccctggggaaggtcctgtcct cttgatagccttatataaggctggtgaattgacctcaaatggaagactgactgctcagtttggtataaccagaaaggacagcttcctgaatatctcagcatccat acctagtgatgtaggcatctacttctgtgctggatttctggatagcaactatcagttaatctggggcgctgggaccaagctaattataaagccagatatccaga accccgagcccgccgtgtaccagctgaaggaccccagaagccaggacagcacccctgtgcctgttcaccgacttcgacagccagatcaacgtgcccaag accatggagagcggcacctcatcaccgacaagaccgtgctggacatgaaggccatggacagcaagagcaacggcgccatcgcctggtccaaccagac cagcttcacatgccaggacatcttcaaggagaccaacgccacctaccccagcagcgacgtgccctgcgacgccaccctgaccgagaagagcttcgaga ccgacatgaacctgaacttccagaacctgagcgtgatgggcctgagaatcctgctgctgaaggtggccggcttcaacctgctgatgaccctgaggctgtgg agcagcagggcaaaacgttcgggttcgggtgcgccagtaaagcagacattaaactttgatttgagaaacttgcaggtgatgtagagtcaaatccaggtcca atggcaacagggagccgaacctctagctccttgattcgggacctttgcctaccgtgcctgcaggagggctcggcagaagcccaagtgaccagaacc caagatacctcatcacagtgactggaaagaagttaacagtgacttgttctcagaatatgaaccatgagtatatgtcctggtatcgacaagacccagggctggg cttaaggcagatctactattcaatgaatgttgaggtgactgataaggagatgttcctgaagggtacaaagtctctcgaaaagagaagaggaatttcccctg atcctggagtcgcccagccccaaccagacctctctgtacttctgtgccagcgctagcgggtaccgcacagatacgcagtattttggcccaggcaccggct
```

-continued gacagtgctcgaggacctgaggaacgtgacccccccccaaggtgtccctgttcgagcccagaaggccgagatcgccaacaagcagaaggccaccctg gtgtgcctggccaggggcttcttccccgaccacgtggagctgtcttggtgggtgaacggcaaggaggtgcacagcggcgtgagcaccgacccccaggc ctacaaggagagcaactacagctactgcctgagcagcaggctgagagtgagcgccaccttaggcacaaccccaggaaccacttccgctgtcaggtgca gttccacggcctgagcgaggaggacaagtggcccgagggcagccccaagcccgtgacccagaacatcagcgccgaggcctggggcagagccgact gcggcatcaccagcgccagctaccaccagggcgtgctgtccgccaccatcctgtacgagatcctgctgggcaaggccacactgtacgccgtgctggtgt ccggcctggtgctgatggccatggtgaagaagaagaacagctaaaggatccgataaaataaaagattttatttagtctccagaaaaaggggggaatgaaag accccacctgtaggtttggcaagctagcttaagtaacgccattttgcaaggcatggaaaatacataactgagaatagagaagttcagatcaaggttaggaac agagagacagcagaatatgggccaaacaggatatctgtggtaagcagttcctgccccggctcagggccaagaacagatggtccccagatgcggtcccgc cctcagcagtttctagagaaccatcagatgtttccagggtgccccaaggacctgaaatgaccctgtgccttatttgaactaaccaatcagttcgcttctcgcttc tgttcgcgcgcttctgctccccgagctcaataaaagagcccacaaccccctcactcggcgcgccagtcctccgatagactgcgtcgcccgggtacccgtgta tccaataaaccctcttgcagttgcatccgacttgtggtctcgctgttccttgggagggtctcctctgagtgattgactacccgtcagcggggggtctttcatgggt aacagtttcttgaagttggagaacaacattctgagggtaggagtcgaatattaagtaatcctgactcaattagccactgtttttgaatccacatactccaatactc ctgaaatccatcgatggagttcattatggacagcgcagaaagagctggggagaattgtgaaattgttatccgctcacaattccacacaacatacgagccggaa gcataaagtgtaaagcctggggtgcctaatgagtgagctaactcacattaattgcgttgcgctcactgcccgctttccagtcgggaaacctgtcgtgccagct gcattaatgaatcggccaacgcgcggggagaggcggtttgcgtattgggcgctcttccgcttcctcgctcactgactcgagcgctcggtcgttcggctgcg gcgagcggtatcagctcactcaaaggcggtaatacggttatccacagaatcaggggataacgcaggaaagaacatgtgagcaaaaggccagcaaaagg ccaggaaccgtaaaaaggccgcgttgctggcgtttttccataggctccgcccccctgacgagcatcacaaaaatcgacgctcaagtcagaggtggcgaaa cccgacaggactataaagataccaggcgtttccccctggaagctccctgtgcgctctcctgttccgaccctgccgcttaccggatacctgtccgcctttctc ccttcgggaagcgtggcgctttctcatagctcacgctgtaggtatctcagttcggtgtaggtcgttcgctccaagctgggctgtgtgcacgaaccccccgttc agcccgaccgctgcgccttatccggtaactatcgtcttgagtccaacccggtaagacacgacttatcgccactggcagcagccactggtattcaggattagc agagcgaggtatgtaggcggtgctacagagttcttgaagtggtggcctaactacggctacactagaaggacagtatttggtatctgcgctagagaagcca gttaccttcggaattaagagttggtagctcttgatccggcttaacaaaccaccgctggtagcggtggtttttttgtttgcaagcagcagattacgcgcagaatta aaaggatctcaagaagatcctttgatcttttctacggggtctgacgctcagtggaacgaaaactcacgttaagggattttggtcatgagattatcaaaaaggatc ttcacctagatccttttaaattaaaaatgaagttttaaatcaatctaaagtatatatgagtaaacttggtctgacagttaccaatgcttaatcagtgaggcacct atctcagcgatctgtctatttcgttcatccatagttgcctgactccccgtcgtgtagataactacgatacgggagggcttaccatctggccccagtgctgcaatg ataccgcgagacccacgctcaccggctccagatttatcagcaataaaccagccagccggaagggccgagcgcagaagtggtcctgcaactttatccgcctccat ccagtctattaattgttgccgggaagctagagtaatagttcgccagttaatagtttgcgcaacgttgttgccattgctacaggcatcgtggtgtcacgctcgtc gtttggtatggcttcattcagctccggttcccaacgatcaaggcgagttacatgatcccccatgttgtgcaaaaaagcggttagctccttcggtcctccgatcgt tgtcagaagtaagttggccgcagtgttatcactcatggttatggcagcactgcataat-
tctcttactgtcatgccatccgtaagatgcttttctgtgactggtgag tactcaaccaagtcattctgagaatagtgtatgcggcgaccgagttgctcttgcccggcgtcaatacgggataataccgcgccacatagcagaactttaaaag tgctcatcattggaaaacgttcttcggggcgaaaactctcaaggatcttaccgctgttgagatccagttcgatgtaacccactcgtgcacccaactgatcttca gcatcttttactttcaccagcgtttctgggtgagcaaaaacaggaaggcaaaatgccgcaaaaaagggaataagggcgacacggaaatgttgaatactcat actcttcctttttcaatattattgaagcatttatcagggttattgtacatgagcggatacatatttgaatgtatttagaaaaataaacaatataggggttccgcg cacatttccccgaaaagtgccacctgacgtctaagaaaccattattatcatgacattaacctataaaaataggcgtatcacgaggccctttcgtctcgcgcgttt cggtgatgacggtgaaaacctctgacacatgcagctcccggagacggtacagcttgtctgtaagcggatgccgggagcagacaagcccgtcagggcgcgtc agcgggtgttggcgggtgtcggggctggcttaactatgcggcatcagagcagattgtactgagagtgcaccatatgcggtgtgaaataccgcacagatgc gtaaggagaaaataccgcatcaggcgccattcgccattcaggctgcgcaactgttgggaagggcgatcggtgcgggcctcttcgctattacgccagctgg cgaaaggggggatgtgctgcaaggcgattaagttgggtaacgccagggttttcccagtcacgacgttgtaattacgacggccagtgccacgctctcccttatg cgactcctgcattaggaagcagcccagtagtaggttgaggccgttgagcaccgccgccgcaaggaatggtgcatgcaaggagatggcgcccaacagtc ccccggccacggggcctgccaccatacccacgccgaaacaagcgctcatgagcccgaagtggcgagcccgatcttccccatcggtgatgtcggcgatat -continued aggcgccagcaaccgcacctgtggcgccggtgatgccggccacgatgcgtccggcgtagaggcgatttaaagacaggatatcagtggtccaggctaa gttttgactcaacaatatcaccagctgaagcctatagagtacgagccatagatattaataaaagattttatttagtctccagaaaaagggggaa

Publications

All publications mentioned herein (e.g. those listed numerically herein) are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification. The following references include descriptions of methods and materials in this field of technology.

REFERENCES

1. Robinson J, et al. (2015) The IPD and IMGT/HLA database: allele variant databases. *Nucleic Acids Res* 43 (Database issue): D423-431.
2. Gonzalez-Galarza F F. et al. (2015) Allele frequency net 2015 update: new features for HLA epitopes, KIR and disease and HLA adverse drug reaction associations. *Nucleic Acids Res* 43 (Database issue): D784-788.
3. Johnson L A, et al. (2006) Gene transfer of tumor-reactive TCR confers both high avidity and tumor reactivity to nonreactive peripheral blood mononuclear cells and tumor-infiltrating lymphocytes. *J Immunol* 177(9):6548-6559.
4. Schumacher T N & Schreiber R D (2015) Neoantigens in cancer immunotherapy. *Science* 348(6230):69-74.
5. Bethune M T & Joglekar A V (2017) Personalized T cell-mediated cancer immunotherapy: progress and challenges. *Current opinion in biotechnology* 48:142-152.
6. Morgan R A, et al. (2006) Cancer regression in patients after transfer of genetically engineered lymphocytes. *Science* 314(5796):126-129.
7. Johnson L A, et al. (2009) Gene therapy with human and mouse T-cell receptors mediates cancer regression and targets normal tissues expressing cognate antigen. *Blood* 114(3):535-546.
8. Parkhurst M R, et al. (2011) T cells targeting carcinoembryonic antigen can mediate regression of metastatic colorectal cancer but induce severe transient colitis. *Molecular therapy: the journal of the American Society of Gene Therapy* 19(3):620-626.
9. Morgan R A, et al. (2010) Case report of a serious adverse event following the administration of T cells transduced with a chimeric antigen receptor recognizing ERBB2. *Molecular therapy: the journal of the American Society of Gene Therapy* 18(4):843-851.
10. Morgan R A, et al. (2013) Cancer regression and neurological toxicity following anti-MAGE-A3 TCR gene therapy. *Journal of immunotherapy* (Hagerstown, Md. 1997) 36(2):133-151.
11. Anonymous (2013) Do no harm. *Nat Biotechnol* 31(5): 365.
12. Jorritsma A, et al. (2007) Selecting highly affine and well-expressed TCRs for gene therapy of melanoma. *Blood* 110(10):3564-3572.
13. Chen Y T, et al. (1997) A testicular antigen aberrantly expressed in human cancers detected by autologous antibody screening. *Proc Natl Acad Sci USA* 94(5):1914-1918.
14. Goydos J S, Patel M, & Shih W (2001) NY-ESO-1 and CTp11 expression may correlate with stage of progression in melanoma. *The Journal of surgical research* 98(2):76-80.
15. Sharma P, et al. (2003) Frequency of NY-ESO-1 and LAGE-1 expression in bladder cancer and evidence of a new NY-ESO-1 T-cell epitope in a patient with bladder cancer. *Cancer immunity* 3:19.
16. Li M. et al. (2005) Expression profile of cancer-testis genes in 121 human colorectal cancer tissue and adjacent normal tissue. *Clinical cancer research: an official journal of the American Association for Cancer Research* 11(5):1809-1814.
17. Gure A O, et al. (2005) Cancer-testis genes are coordinately expressed and are markers of poor outcome in non-small cell lung cancer. *Clinical cancer research: an official journal of the American Association for Cancer Research* 11(22):8055-8062.
18. Jungbluth A A, et al. (2001) Monophasic and biphasic synovial sarcomas abundantly express cancer/testis antigen NY-ESO-1 but not MAGE-A1 or CT7. *International journal of cancer* 94(2):252-256.
19. Aung P P, et al. (2014) Expression of New York esophageal squamous cell carcinoma-1 in primary and metastatic melanoma. *Human pathology* 45(2):259-267.
20. Ademuyiwa F O, et al. (2012) NY-ESO-1 cancer testis antigen demonstrates high immunogenicity in triple negative breast cancer. *PloS one* 7(6):e38783.
21. Ebert L M, et al. (2009) A long, naturally presented immunodominant epitope from NY-ESO-1 tumor antigen: implications for cancer vaccine design. *Cancer research* 69(3):1046-1054.
22. Jackson H, et al. (2006) Striking immunodominance hierarchy of naturally occurring CD8+ and CD4+ T cell responses to tumor antigen NY-ESO-1. *J. Immunol* 176 (10):5908-5917.
23. Zhao R Y, et al. (2012) A novel HLA-B18 restricted CD8+ T cell epitope is efficiently cross-presented by dendritic cells from soluble tumor antigen. *PloS one* 7(9):e44707.
24. Robbins P F, et al. (2011) Tumor regression in patients with metastatic synovial cell sarcoma and melanoma using genetically engineered lymphocytes reactive with NY-ESO-1. *J Clin Oncol* 29(7):917-924.
25. Robbins P F, et al. (2015) A pilot trial using lymphocytes genetically engineered with an NY-ESO-1-reactive T-cell receptor: long-term follow-up and correlates with response. *Clinical cancer research: an official journal of the American Association for Cancer Research* 21(5): 1019-1027.
26. Rapoport A P, et al. (2015) NY-ESO-1-specific TCR-engineered T cells mediate sustained antigen-specific antitumor effects in myeloma. *Nat Med* 21(8):914-921.
27. Klippel Z K, et al. (2014) Immune escape from NY-ESO-1-specific T-cell therapy via loss of heterozygosity in the MHC. *Gene therapy* 21(3):337-342.

28. Zhao Y, et al. (2007) High-affinity TCRs generated by phage display provide CD4+ T cells with the ability to recognize and kill tumor cell lines. *J Immunol* 179(9): 5845-5854.

29. Cameron B J, et al. (2013) Identification of a Titin-derived HLA-A1-presented peptide as a cross-reactive target for engineered MAGE A3-directed T cells. *Science translational medicine* 5(197):197ra103.

30. Linette G P. et al. (2013) Cardiovascular toxicity and titin cross-reactivity of affinity-enhanced T cells in myeloma and melanoma. *Blood* 122(6):863-871.

31. Andreatta M & Nielsen M (2016) Gapped sequence alignment using artificial neural networks: application to the MHC class I system. *Bioinformatics* 32(4):511-517.

32. Wooldridge L, et al. (2005) Interaction between the CD8 coreceptor and major histocompatibility complex class I stabilizes T cell receptor-antigen complexes at the cell surface. *J Biol Chem* 280(30):27491-27501.

33. Aleksic M, et al. (2012) Different affinity windows for virus and cancer-specific T-cell receptors: implications for therapeutic strategies. *European journal of immunology* 42(12):3174-3179.

34. Sommermeyer D, et al. (2006) Designer T cells by T cell receptor replacement. *European journal of immunology* 36(11):3052-3059.

35. Klausner R D, Lippincott-Schwartz J, & Bonifacino J S (1990) The T cell antigen receptor: insights into organelle biology. *Annual review of cell biology* 6:403-431.

36. Cohen C J, Zhao Y, Zheng Z, Rosenberg S A, & Morgan R A (2006) Enhanced antitumor activity of murine-human hybrid T-cell receptor (TCR) in human lymphocytes is associated with improved pairing and TCR/CD3 stability. *Cancer research* 66(17):8878-8886.

37. Robbins P F, et al. (2008) Single and dual amino acid substitutions in TCR CDRs can enhance antigen-specific T cell functions. *J Immunol* 180(9):6116-6131.

38. Hansen T, Yu Y Y, & Fremont D H (2009) Preparation of stable single-chain trimers engineered with peptide, beta2 microglobulin, and MHC heavy chain. *Current protocols in immunology/edited by John E. Coligan . . . [et al.]* Chapter 17: Unit 17 15.

39. Snyder A, et al. (2014) Genetic basis for clinical response to CTLA-4 blockade in melanoma. *The New England journal of medicine* 371(23):2189-2199.

40. Van Allen E M, et al. (2015) Genomic correlates of response to CTLA-4 blockade in metastatic melanoma. *Science* 350(6257):207-211.

41. Rizvi N A, et al. (2015) Cancer immunology. Mutational landscape determines sensitivity to PD-1 blockade in non-small cell lung cancer. *Science* 348(6230):124-128.

42. Chowell D, et al. (2018) Patient HLA class I genotype influences cancer response to checkpoint blockade immunotherapy. *Science* 359(6375):582-587.

43. Tran E, et al. (2016) T-Cell Transfer Therapy Targeting Mutant KRAS in Cancer. *New England Journal of Medicine* 375(23):2255-2262.

44. Gros A, et al (2016) Prospective identification of neoantigen-specific lymphocytes in the peripheral blood of melanoma patients. *Nat Med* 22(4):433-438.

45. Stronen E, et al (2016) Targeting of cancer neoantigens with donor-derived T cell receptor repertoires. *Science* 352(6291):1337-1341.

46. Ioannidou K, et al. (2017) Heterogeneity assessment of functional T cell avidity. *Scientific reports* 7:44320.

47. Rius C, et al. (2018) Peptide-MHC Class I Tetramers Can Fail To Detect Relevant Functional T Cell Clonotypes and Underestimate Antigen-Reactive T Cell Populations. *J Immunol* 200(7):2263-2279.

48. Laugel B, et al. (2007) Different T cell receptor affinity thresholds and CD8 coreceptor dependence govern cytotoxic T lymphocyte activation and tetramer binding properties. *J Biol Chem* 282(33):23799-23810.

49. Sette A & Sidney J (1999) Nine major HLA class I supertypes account for the vast preponderance of HLA-A and -B polymorphism. *Immunogenetics* 50(3-4): 201-212.

50. Bethune M T, Comin-Anduix B, Hwang Fu Y H, Ribas A, & Baltimore D (2017) Preparation of peptide-MHC and T-cell receptor dextramers by biotinylated dextran doping. *BioTechniques* 62(3):123-130.

51. Toebes M, et al. (2006) Design and use of conditional MHC class I ligands. *Nat Med* 12(2):246-251.

52. Bethune M T, et al. (2016) Domain-swapped T cell receptors improve the safety of TCR gene therapy. *eLife* 5.

53. Chen J L, et al. (2000) Identification of NY-ESO-1 peptide analogues capable of improved stimulation of tumor-reactive CTL. *J Immunol* 165(2):948-955.

54. Gnjatic S, et al. (2000) Strategy for monitoring T cell responses to NY-ESO-1 in patients with any HLA class I allele. *Proc Natl Acad Sci USA* 97(20):10917-10922.

55. Davis I D, et al. (2004) Recombinant NY-ESO-1 protein with ISCOMATRIX adjuvant induces broad integrated antibody and CD4(+) and CD8(+) T cell responses in humans. *Proc Natl Acad Sci USA* 101(29):10697-10702.

56. Britten C M, et al. (2012) T cell assays and MIATA: the essential minimum for maximum impact. *Immunity* 37(1): 1-2.

CONCLUSION

This concludes the description of the illustrative embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A polynucleotide disposed in a vector, wherein:
   the polynucleotide encodes a Vα T cell receptor polypeptide and a Vβ T cell receptor polypeptide; and
   when a Vα/Vβ T cell receptor comprising the Vα T cell receptor polypeptide and/or the Vβ T cell receptor polypeptide is expressed in a CD 8$^+$ T cell, the Vα/Vβ T cell receptor recognizes a NY-ESO-1 peptide associated with:
   human leukocyte antigen A2; and
   the vector comprises:
   (a) a polynucleotide encoding a 3A1 Vα polypeptide (SEQ ID NO: 3); and
   (b) a polynucleotide encoding a 3A1 Vβ polypeptide (SEQ ID NO: 4);
   wherein the vector comprises a polynucleotide sequence that modulates expression of the polypeptide within CD 8$^+$ T cells.

2. The polynucleotide of claim 1, wherein the vector is a Sendai viral vector, an adenoviral vector, an adeno-associated virus vector, a retroviral vector, or a lentiviral vector.

3. A composition of matter comprising a host cell transduced with a vector comprising a polynucleotide, wherein:
   the polynucleotide encodes a Vα T cell receptor polypeptide and a Vβ T cell receptor polypeptide; and
   when a Vα/Vβ T cell receptor comprising the Vα T cell receptor polypeptide and/or the Vβ T cell receptor polypeptide is expressed in a CD 8$^+$ T cell, the Vα/Vβ

T cell receptor recognizes a NY-ESO-1 peptide associated with:
   human leukocyte antigen A2; and
   the vector comprises:
   (a) a polynucleotide encoding a 3A1 Vα polypeptide (SEQ ID NO: 3); and
   (b) a polynucleotide encoding a 3A1 Vβ polypeptide (SEQ ID NO: 4).

4. The composition of claim 3, wherein the host cell is a human CD 8$^+$ T cell.

5. The composition of claim 4, wherein the composition is a pharmaceutical composition comprising one more pharmaceutically acceptable excipients selected from the group consisting of buffering agents, antimicrobial agents, tonicity adjusting agents, wetting agents, detergents and pH adjusting agents.

6. The composition of claim 5, wherein:
   the CD8$^+$ T cell is obtained from an individual diagnosed with a cancer that expresses a NY-ESO-1 antigen; and
   the CD8$^+$ T cell is transduced with a vector comprising a polynucleotide encoding a TCR Vα polypeptide in combination with a polynucleotide encoding a TCR Vβ polypeptide such that a heterologous TCR is expressed on a surface of the CD8$^+$ T cell, wherein the heterologous TCR recognizes a NY-ESO-1 peptide associated with a human leukocyte antigen expressed on the surface of cells of the cancer.

7. The composition of claim 6, wherein the vector is a retroviral vector.

* * * * *